(12) United States Patent
Rashid et al.

(10) Patent No.: US 12,377,294 B2
(45) Date of Patent: Aug. 5, 2025

(54) ANTI-CD3 ANTIBODY FOLATE BIOCONJUGATES AND THEIR USES

(71) Applicant: Ambrx, Inc., La Jolla, CA (US)

(72) Inventors: Md Harunur Rashid, La Jolla, CA (US); Ying Sun, La Jolla, CA (US); Feng Tian, La Jolla, CA (US); Sung Ju Moon, La Jolla, CA (US)

(73) Assignee: Ambrx, Inc., La Jolla, CA (US)

( * ) Notice: Subject to any disclaimer, the term of this patent is extended or adjusted under 35 U.S.C. 154(b) by 1162 days.

(21) Appl. No.: 17/272,241

(22) PCT Filed: Aug. 28, 2019

(86) PCT No.: PCT/US2019/048677
§ 371 (c)(1),
(2) Date: Feb. 26, 2021

(87) PCT Pub. No.: WO2020/047176
PCT Pub. Date: Mar. 5, 2020

(65) Prior Publication Data
US 2021/0317213 A1    Oct. 14, 2021

Related U.S. Application Data

(60) Provisional application No. 62/723,793, filed on Aug. 28, 2018.

(51) Int. Cl.
| | | |
|---|---|---|
| *A61P 35/00* | (2006.01) | |
| *A61K 31/519* | (2006.01) | |
| *A61K 39/00* | (2006.01) | |
| *A61K 47/60* | (2017.01) | |
| *A61K 47/68* | (2017.01) | |
| *C07K 16/28* | (2006.01) | |

(52) U.S. Cl.
CPC ........ *A61K 47/6869* (2017.08); *A61K 31/519* (2013.01); *A61K 47/60* (2017.08); *A61K 47/6803* (2017.08); *A61P 35/00* (2018.01); *C07K 16/2809* (2013.01); *A61K 2039/505* (2013.01)

(58) Field of Classification Search
CPC ............ C07K 16/2809; C07K 2317/31; C07K 2317/732; C07K 2317/92; C07K 2317/94; C07K 2319/55; C07K 2317/32; C07K 2317/55; A61K 31/519; A61K 47/60; A61K 47/6803; A61K 47/6869; A61K 2039/505; A61K 39/395; A61K 39/39558; A61P 35/00; A61P 3/10; A61P 31/14
See application file for complete search history.

(56) References Cited

FOREIGN PATENT DOCUMENTS

| | | | | |
|---|---|---|---|---|
| WO | 2004043344 A2 | 5/2004 | | |
| WO | WO-2015184203 A1 * | 12/2015 | ................ | A61P 1/04 |
| WO | WO-2017009442 A1 * | 1/2017 | .............. | A61P 31/00 |
| WO | WO2017/079272 A2 | 5/2017 | | |
| WO | WO-2017136659 A2 * | 8/2017 | ......... | A61K 47/6803 |

OTHER PUBLICATIONS

Sela-Culang, et al., Front. in Immunol. 2013; vol. 4 Article 302 (Year: 2013).*
Wermuth, C., Drug Discovery Today Apr. 2006; 11(7-8):348-54 (Year: 2006).*
Goodwin, et al. J. Biol. Chem. Jan. 2009; 284(5): 2979-2989 (Year: 2009).*
Kularatne Sumith A et al : "Recruiting cytotoxic T cells to folate-receptor-positive cancer cells", Angewandte Chemie (International Edition), Wiley-VCH Verlag GMBH & Co, DE vol. 52, No. 46; Nov. 11, 2013.
Kranz D M et al : "Conjugates of Folate and Anti-T-Cell-Receptor Antibodies Specifically Target Folate-Receptor-Positive Tumor Cells for Lysis", Proceedings of the National Academy of Sciences, National Academy of Sciences, vol. 92, Sep. 1, 1995, pp. 9057-9061.
Ma, H. et al. (2008). "PEG-Modified Mouse Anti-Human CD3 Monoclonal Antibody," Chin. J. Cell. Mo. Immunol. 24(11):1096-1097, with English Abstract, 6 pages.

* cited by examiner

*Primary Examiner* — Anne M. Gussow
*Assistant Examiner* — Sydney Van Druff
(74) *Attorney, Agent, or Firm* — Morrison & Foerster LLP

(57) ABSTRACT

Described herein are novel anti-CD3 Folate antibodies and uses thereof in the treatment of diseases or conditions that would benefit from such.

21 Claims, 30 Drawing Sheets
Specification includes a Sequence Listing.

FIG. 13A

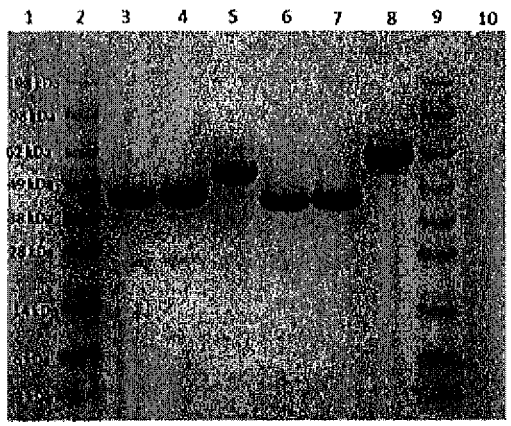

Lane 1: empty
Lane 2: Molecular Weight Marker
Lane 3: Fab1-HK129 pAF
Lane 4: Fab1-HK129-Folate
Lane 5: Fab1-HK129-Folate-5KPE
Lane 6: Fab1-HK129-LL157 pAF
Lane 7: Fab1-HK129-LL157-BiFolate
Lane 8: Fab1-HK129-LL157-BiFolate-Bi5KPEG
Lane 9: Molecular Weight Marker
Lane 10: empty

FIG. 13B

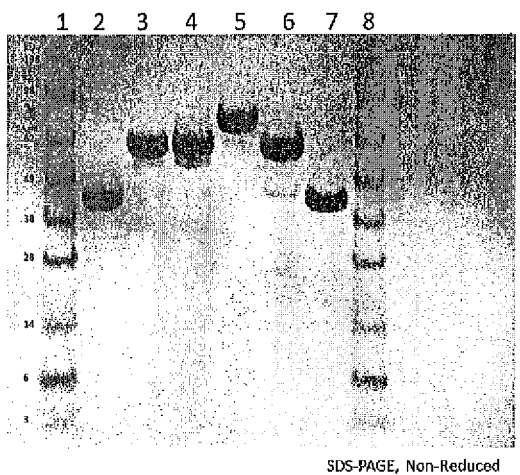

SDS-PAGE, Non-Reduced

Lane 1: Mol. Wt. Markers
Lane 2: CD3 (HK129pAF-LL157pAF) - unconjugated
Lane 3: CD3 (HK129pAF-LL157pAF) – BiFolate-Bi5KPEG
Lane 4: CD3 (HK129pAF-LL157pAF) – BiFolate-Bi5KPEG
Lane 5: CD3 (HK129pAF-LL157pAF) – BiFolate-Bi10KPEG
Lane 6: CD3 (HK129pAF) – Folate-10KPEG
Lane 7: CD3 (HK129pAF-LL157pAF) - unconjugated
Lane 8: Mol. Wt. Markers

- G1:Fab1-HK129-pAF control (0.05 mpk)
- G2:Fab1-HK129-LL157-BiFolate-Bi5KPEG (0.01 mpk)
- G3:Fab1-HK129-LL157-BiFolate-Bi5KPEG (0.05 mpk)
- G4:Fab9-HK129-LL157-BiFolate-Bi5KPEG (0.125 mpk)
- G5:Fab1-HK129-Folate-control (0.025 mpk)

- G1:Fab1-HK129-pAF control (0.05 mpk)
- G2:Fab1-HK129-LL157-BiFolate-Bi5KPEG (0.01 mpk)
- G2:Fab1-HK129-LL157-BiFolate-Bi5KPEG (0.05 mpk)
- G4:Fab9-HK129-LL157-BiFolate-Bi5KPEG (0.125 mpk)
- G5:Fab1-HK129-Folate-control (0.025 mpk)

FIG. 21C

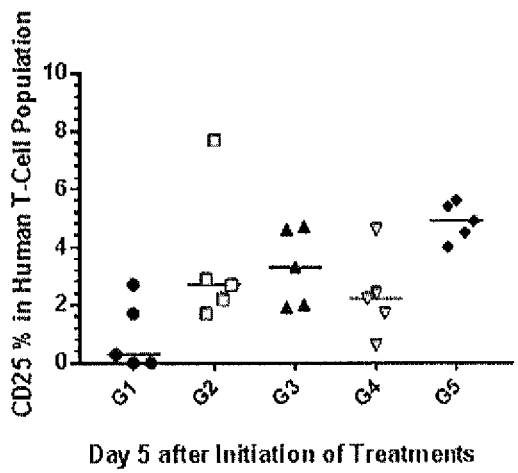

Day 5 after Initiation of Treatments

FIG. 21D

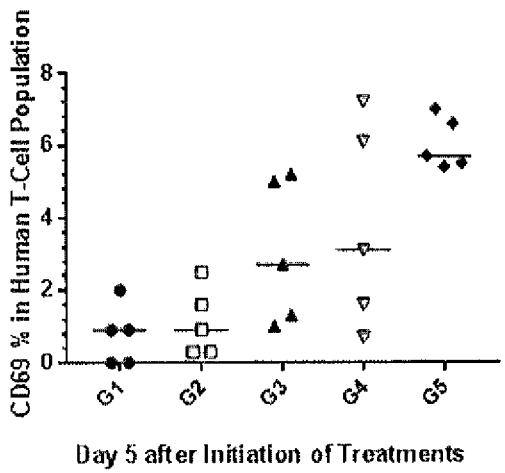

Day 5 after Initiation of Treatments

- G1:Fab1-HK129-pAF control (0.0125 mpk)
- G2:Fab1-HK129-LL157-Bifolate (0.0025 mpk)
- G3:Fab1-HK129-LL157-Bifolate (0.0125 mpk)
- G4:Fab1-HK129-LL157-Bifolate-B5KPEG (0.0025 mpk)
- G5:Fab1-HK129-LL157-Bifolate-B5KPEG (0.0125 mpk)

FIG. 21E

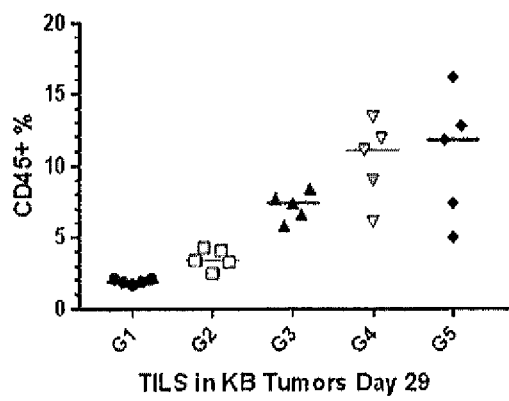

TILS in KB Tumors Day 29

FIG. 21F

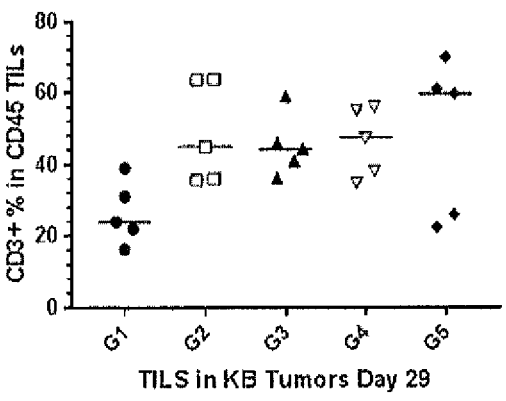

TILS in KB Tumors Day 29

G1:Fab1-HK129-pAF control (0.0125 mpk)
G2:Fab1-HK129-LL157-Bifolate (0.0025 mpk)
G3:Fab1-HK129-LL157-Bifolate (0.0125 mpk)
G4:Fab1-HK129-LL157-Bifolate-B5KPEG (0.0025 mpk)
G5:Fab1-HK129-LL157-Bifolate-B5KPEG (0.0125 mpk)

SEQUENCE LISTING

<160> NUMBER OF SEQ ID NOS: 62

<210> SEQ ID NO 1
<211> LENGTH: 228
<212> TYPE: PRT
<213> ORGANISM: Artificial Sequence
<220> FEATURE:
<223> OTHER INFORMATION: HC (vH1.2+CH1)

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys
225

<210> SEQ ID NO 2
<211> LENGTH: 228
<212> TYPE: PRT
<213> ORGANISM: Artificial Sequence
<220> FEATURE:
<223> OTHER INFORMATION: HC (VH1.1+CH1)

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

```
Ser Val Lys Asp Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
                115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Leu Gly Thr Gln Thr Tyr Ile Cys
                195                 200                 205

Asn Val Asn His Lys Pro Ser Asn Thr Lys Val Asp Lys Lys Val Glu
    210                 215                 220

Pro Lys Ser Cys
225

<210> SEQ ID NO 3
<211> LENGTH: 228
<212> TYPE: PRT
<213> ORGANISM: Artificial Sequence
<220> FEATURE:
<223> OTHER INFORMATION: HC (vH1.0+CH1)

<400> SEQUENCE: 3

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Asn Thr Tyr
                 20                  25                  30

Ala Met Asn Trp Val Arg Gln Ala Pro Gly Lys Gly Leu Glu Trp Val
                 35                  40                  45

Gly Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
                115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190
```

```
Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys
225
```

<210> SEQ ID NO 4
<211> LENGTH: 233
<212> TYPE: PRT
<213> ORGANISM: Artificial Sequence
<220> FEATURE:
<223> OTHER INFORMATION: HC (vH1.2+CH1-DKTHT)

<400> SEQUENCE: 4

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr
225                 230
```

<210> SEQ ID NO 5
<211> LENGTH: 233
<212> TYPE: PRT
<213> ORGANISM: Artificial Sequence
<220> FEATURE:
<223> OTHER INFORMATION: HC (vH1.1+CH1-DKTHT)

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30
```

```
Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
50                      55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                    85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
                115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                    165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
                195                 200                 205

Asn Val Asn His Lys Pro Ser Asn Thr Lys Val Asp Lys Lys Val Glu
        210                 215                 220

Pro Lys Ser Cys Asp Lys Thr His Thr
225                 230

<210> SEQ ID NO 6
<211> LENGTH: 233
<212> TYPE: PRT
<213> ORGANISM: Artificial Sequence
<220> FEATURE:
<223> OTHER INFORMATION: HC (vH1.0+CH1-DKTHT)

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
50                  55                      60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                    85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
                115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160
```

Pro Val Thr Val Ser Trp Asn Ser Gly Ala Leu Thr Ser Gly Val His
              165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
    210                 215                 220

Pro Lys Ser Cys Asp Lys Thr His Thr
225                 230

<210> SEQ ID NO 7
<211> LENGTH: 217
<212> TYPE: PRT
<213> ORGANISM: Artificial Sequence
<220> FEATURE:
<223> OTHER INFORMATION: LC (vL1.2+CL)

<400> SEQUENCE: 7

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Gly Thr Pro Ala Arg Phe
50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 8
<211> LENGTH: 217
<212> TYPE: PRT
<213> ORGANISM: Artificial Sequence
<220> FEATURE:
<223> OTHER INFORMATION: LC (vL1.0+CL)

<400> SEQUENCE: 8

Gln Ala Val Val Thr Gln Glu Pro Ser Leu Thr Val Ser Pro Gly Gly

```
1               5                   10                  15
Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
                35                  40                  45

Leu Ile Gly Gly Thr Asn Lys Arg Ala Pro Gly Val Pro Ala Arg Phe
            50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Arg Thr
                100                 105                 110

Val Ala Ala Pro Ser Val Phe Ile Phe Pro Pro Ser Asp Glu Gln Leu
                115                 120                 125

Lys Ser Gly Thr Ala Ser Val Val Cys Leu Leu Asn Asn Phe Tyr Pro
            130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
                195                 200                 205

Thr Lys Ser Phe Asn Arg Gly Glu Cys
            210                 215

<210> SEQ ID NO 9
<211> LENGTH: 217
<212> TYPE: PRT
<213> ORGANISM: Artificial Sequence
<220> FEATURE:
<223> OTHER INFORMATION: LC (vL1.0+CL)

<400> SEQUENCE: 9

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Phe Gln Gln Lys Pro Gly Gln Ala Pro Arg Thr
                35                  40                  45

Leu Ile Tyr Gly Thr Asn Lys Arg Ala Pro Trp Thr Pro Ala Arg Phe
            50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Arg Thr
                100                 105                 110

Val Ala Ala Pro Ser Val Phe Ile Phe Pro Pro Ser Asp Glu Gln Leu
                115                 120                 125

Lys Ser Gly Thr Ala Ser Val Val Cys Leu Leu Asn Asn Phe Tyr Pro
            130                 135                 140

Arg Glu Ala Lys Val Gln Trp Lys Val Asp Asn Ala Leu Gln Ser Gly
```

```
                145                 150                 155                 160
Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
                195                 200                 205

Thr Lys Ser Phe Asn Arg Gly Glu Cys
    210                 215

<210> SEQ ID NO 10
<211> LENGTH: 230
<212> TYPE: PRT
<213> ORGANISM: Artificial Sequence
<220> FEATURE:
<223> OTHER INFORMATION: HC (vH1.2+CH1-HS115pAF)

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Pro Ala Phe
            115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
                195                 200                 205

Ile Cys Asn Val Asn His Lys Pro Ser Asn Thr Lys Val Asp Lys Lys
    210                 215                 220

Val Glu Pro Lys Ser Cys
225                 230

<210> SEQ ID NO 11
<211> LENGTH: 230
<212> TYPE: PRT
<213> ORGANISM: Artificial Sequence
<220> FEATURE:
<223> OTHER INFORMATION: HC (vH1.2+CH1- HS115pAF)

<400> SEQUENCE: 11
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Pro Ala
            115                 120                 125

Phe Thr Lys Gly Pro Ser Val Phe Pro Leu Ala Pro Ser Ser Lys Ser
        130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
            195                 200                 205

Ile Cys Asn Val Asn His Lys Pro Ser Asn Thr Lys Val Asp Lys Lys
210                 215                 220

Val Glu Pro Lys Ser Cys
225                 230

<210> SEQ ID NO 12
<211> LENGTH: 230
<212> TYPE: PRT
<213> ORGANISM: Artificial Seuence
<220> FEATURE:
<223> OTHER INFORMATION: HC (vH1.2+CH1- HK129pAF)

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
            115                 120                 125
```

```
Lys Gly Pro Ser Val Phe Pro Leu Ala Pro Ser Ser Pro Ala Phe Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Leu Gly Thr Gln Thr Tyr
                195                 200                 205

Ile Cys Asn Val Asn His Lys Pro Ser Asn Thr Lys Val Asp Lys Lys
    210                 215                 220

Val Glu Pro Lys Ser Cys
225                 230

<210> SEQ ID NO 13
<211> LENGTH: 230
<212> TYPE: PRT
<213> ORGANISM: Artificial Sequence
<220> FEATURE:
<223> OTHER INFORMATION: HC (vH1.2+CH1- HT160pAF)

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Pro Ala Phe Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Leu Gly Thr Gln Thr Tyr
                195                 200                 205

Ile Cys Asn Val Asn His Lys Pro Ser Asn Thr Lys Val Asp Lys Lys
    210                 215                 220

Val Glu Pro Lys Ser Cys
225                 230

<210> SEQ ID NO 14
<211> LENGTH: 235
```

```
<212> TYPE: PRT
<213> ORGANISM: Artificial Sequence
<220> FEATURE:
<223> OTHER INFORMATION: HC (vH1.2+CH1- HA114pAF+ DKTHT)

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Pro Ala Phe
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr
225                 230                 235

<210> SEQ ID NO 15
<211> LENGTH: 235
<212> TYPE: PRT
<213> ORGANISM: Artificial Sequence
<220> FEATURE:
<223> OTHER INFORMATION: HC (vH1.2+CH1- HS115pAF+ DKTHT)

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95
```

```
Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Pro Ala
            115                 120                 125

Phe Thr Lys Gly Pro Ser Val Phe Pro Leu Ala Pro Ser Ser Lys Ser
        130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
210                 215                 220

Val Glu Pro Lys Ser Cys Asp Lys Thr His Thr
225                 230                 235

<210> SEQ ID NO 16
<211> LENGTH: 235
<212> TYPE: PRT
<213> ORGANISM: Artificial Sequence
<220> FEATURE:
<223> OTHER INFORMATION: HC (vH1.2+CH1- HK129pAF-DKTHT)

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Pro Ala Phe Ser
        130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
210                 215                 220
```

```
Val Glu Pro Lys Ser Cys Asp Lys Thr His Thr
225                 230                 235

<210> SEQ ID NO 17
<211> LENGTH: 235
<212> TYPE: PRT
<213> ORGANISM: Artificial Sequence
<220> FEATURE:
<223> OTHER INFORMATION: HC (vH1.2+CH1- HT160pAF+ DKTHT)

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Pro Ala Phe Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr
225                 230                 235

<210> SEQ ID NO 18
<211> LENGTH: 219
<212> TYPE: PRT
<213> ORGANISM: Artificial Sequence
<220> FEATURE:
<223> OTHER INFORMATION: LC (vL1.2+CL- LL157pAF)

<400> SEQUENCE: 18

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
```

```
            50                  55                  60
Ser Gly Ser Leu Leu Gly Gly Lys Ala Ala Leu Thr Leu Ser Gly Ala
 65                  70                  75                  80
Gln Pro Glu Asp Glu Ala Glu Tyr Tyr Cys Ala Leu Trp Tyr Ser Asn
                 85                  90                  95
Leu Trp Val Phe Gly Gly Gly Thr Lys Leu Thr Val Leu Gly Arg Thr
                100                 105                 110
Val Ala Ala Pro Ser Val Phe Ile Phe Pro Pro Ser Asp Glu Gln Leu
                115                 120                 125
Lys Ser Gly Thr Ala Ser Val Val Cys Leu Leu Asn Asn Phe Tyr Pro
    130                 135                 140
Arg Glu Ala Lys Val Gln Trp Lys Val Asp Asn Ala Pro Ala Phe Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
                180                 185                 190
Lys His Lys Val Tyr Ala Cys Glu Val Thr His Gln Gly Leu Ser Ser
                195                 200                 205
Pro Val Thr Lys Ser Phe Asn Arg Gly Glu Cys
    210                 215

<210> SEQ ID NO 19
<211> LENGTH: 219
<212> TYPE: PRT
<213> ORGANISM: Artificial Sequence
<220> FEATURE:
<223> OTHER INFORMATION: LC (vL1.2+CL- LK172pAF)

<400> SEQUENCE: 19

Gln Ala Val Val Thr Gln Glu Pro Ser Leu Thr Val Ser Pro Gly Gly
 1                   5                  10                  15
Thr Val Thr Leu Thr Cys Arg Ser Ser Thr Gly Ala Val Thr Thr Ser
                 20                  25                  30
Asn Tyr Ala Asn Trp Val Gln Gln Lys Pro Gly Gln Ala Pro Arg Gly
             35                  40                  45
Leu Ile Gly Gly Thr Asn Lys Arg Ala Pro Gly Thr Pro Ala Arg Phe
    50                  55                  60
Ser Gly Ser Leu Leu Gly Gly Lys Ala Ala Leu Thr Leu Ser Gly Ala
 65                  70                  75                  80
Gln Pro Glu Asp Glu Ala Glu Tyr Tyr Cys Ala Leu Trp Tyr Ser Asn
                 85                  90                  95
Leu Trp Val Phe Gly Gly Gly Thr Lys Leu Thr Val Leu Gly Arg Thr
                100                 105                 110
Val Ala Ala Pro Ser Val Phe Ile Phe Pro Pro Ser Asp Glu Gln Leu
                115                 120                 125
Lys Ser Gly Thr Ala Ser Val Val Cys Leu Leu Asn Asn Phe Tyr Pro
    130                 135                 140
Arg Glu Ala Lys Val Gln Trp Lys Val Asp Asn Ala Leu Gln Ser Gly
145                 150                 155                 160
Asn Ser Gln Glu Ser Val Thr Glu Gln Asp Ser Pro Ala Phe Asp Ser
                165                 170                 175
Thr Tyr Ser Leu Ser Ser Thr Leu Thr Leu Ser Lys Ala Asp Tyr Glu
                180                 185                 190
Lys His Lys Val Tyr Ala Cys Glu Val Thr His Gln Gly Leu Ser Ser
```

```
                    195                 200                 205
Pro Val Thr Lys Ser Phe Asn Arg Gly Glu Cys
    210                 215

<210> SEQ ID NO 20
<211> LENGTH: 219
<212> TYPE: PRT
<213> ORGANISM: Artificial Sequence
<220> FEATURE:
<223> OTHER INFORMATION: LC (vL1.2+CL- LS205pAF)

<400> SEQUENCE: 20

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Pro Ala Phe Ser
        195                 200                 205

Pro Val Thr Lys Ser Phe Asn Arg Gly Glu Cys
    210                 215

<210> SEQ ID NO 21
<211> LENGTH: 233
<212> TYPE: PRT
<213> ORGANISM: Artificial Sequence
<220> FEATURE:
<223> OTHER INFORMATION: HC (vH2.3+CH1-DKTHT)

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60
```

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr
225                 230

<210> SEQ ID NO 22
<211> LENGTH: 233
<212> TYPE: PRT
<213> ORGANISM: Artificial Sequence
<220> FEATURE:
<223> OTHER INFORMATION: HC (vH2.2+CH1-DKTHT)

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

```
Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys Asp Lys Thr His Thr
225                 230

<210> SEQ ID NO 23
<211> LENGTH: 233
<212> TYPE: PRT
<213> ORGANISM: Artificial Sequence
<220> FEATURE:
<223> OTHER INFORMATION: HC (vH2.1+CH1-DKTHT)

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr
225                 230

<210> SEQ ID NO 24
<211> LENGTH: 233
<212> TYPE: PRT
<213> ORGANISM: Artificial Sequence
<220> FEATURE:
<223> OTHER INFORMATION: HC (vH2.4+CH1-DKTHT)

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30
```

```
Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
 50                      55                  60

Ser Val Lys Asp Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                    165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
                195                 200                 205

Asn Val Asn His Lys Pro Ser Asn Thr Lys Val Asp Lys Lys Val Glu
    210                 215                 220

Pro Lys Ser Cys Asp Lys Thr His Thr
225                 230

<210> SEQ ID NO 25
<211> LENGTH: 233
<212> TYPE: PRT
<213> ORGANISM: Artificial Sequence
<220> FEATURE:
<223> OTHER INFORMATION: HC (vH2.5+CH1-DKTHT)

<400> SEQUENCE: 25

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
 50                      55                  60

Ser Val Lys Asp Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160
```

```
Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys Asp Lys Thr His Thr
225                 230

<210> SEQ ID NO 26
<211> LENGTH: 233
<212> TYPE: PRT
<213> ORGANISM: Artificial Sequence
<220> FEATURE:
<223> OTHER INFORMATION: HC (vH2.6+CH1-DKTHT)

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys Asp Lys Thr His Thr
225                 230

<210> SEQ ID NO 27
<211> LENGTH: 233
<212> TYPE: PRT
<213> ORGANISM: Artificial Sequence
<220> FEATURE:
<223> OTHER INFORMATION: HC (vH3.1+CH1-DKTHT)
```

```
<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met His Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
        180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
        210                 215                 220

Pro Lys Ser Cys Asp Lys Thr His Thr
225                 230

<210> SEQ ID NO 28
<211> LENGTH: 233
<212> TYPE: PRT
<213> ORGANISM: Artificial Sequence
<220> FEATURE:
<223> OTHER INFORMATION: HC (vH3.2+CH1-DKTHT)

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
```

```
                115                 120                 125
Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Leu Gly Thr Gln Thr Tyr Ile Cys
                195                 200                 205

Asn Val Asn His Lys Pro Ser Asn Thr Lys Val Asp Lys Lys Val Glu
                210                 215                 220

Pro Lys Ser Cys Asp Lys Thr His Thr
225                 230

<210> SEQ ID NO 29
<211> LENGTH: 233
<212> TYPE: PRT
<213> ORGANISM: Artificial Sequence
<220> FEATURE:
<223> OTHER INFORMATION: HC (vH3.3+CH1-DKTHT)

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met His Trp Val Arg Gln Ala Pro Gly Lys Gly Leu Glu Trp Val
            35                  40                  45

Ala Arg Ile Arg Ser Lys Ser Asn Asn Tyr Ala Thr Tyr Tyr Ala Asp
        50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
                195                 200                 205

Asn Val Asn His Lys Pro Ser Asn Thr Lys Val Asp Lys Lys Val Glu
                210                 215                 220

Pro Lys Ser Cys Asp Lys Thr His Thr
225                 230
```

```
<210> SEQ ID NO 30
<211> LENGTH: 228
<212> TYPE: PRT
<213> ORGANISM: Artificial Sequence
<220> FEATURE:
<223> OTHER INFORMATION: HC  (vH2.3+CH1)

<400> SEQUENCE: 30
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys
225

```
<210> SEQ ID NO 31
<211> LENGTH: 228
<212> TYPE: PRT
<213> ORGANISM: Artificial Sequence
<220> FEATURE:
<223> OTHER INFORMATION: HC (vH2.2+CH1)

<400> SEQUENCE: 31
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

```
Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys
225
```

<210> SEQ ID NO 32
<211> LENGTH: 228
<212> TYPE: PRT
<213> ORGANISM: Artificial Sequence
<220> FEATURE:
<223> OTHER INFORMATION: HC (vH2.1+CH1)

<400> SEQUENCE: 32

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205
```

Asn Val Asn His Lys Pro Ser Asn Thr Lys Val Asp Lys Lys Val Glu
            210                 215                 220

Pro Lys Ser Cys
225

<210> SEQ ID NO 33
<211> LENGTH: 228
<212> TYPE: PRT
<213> ORGANISM: Artificial Sequence
<220> FEATURE:
<223> OTHER INFORMATION: HC (vH2.4+CH1)

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys
225

<210> SEQ ID NO 34
<211> LENGTH: 228
<212> TYPE: PRT
<213> ORGANISM: Artificial Sequence
<220> FEATURE:
<223> OTHER INFORMATION: HC (vH2.5+CH1)

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
            50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
    210                 215                 220

Pro Lys Ser Cys
225

<210> SEQ ID NO 35
<211> LENGTH: 228
<212> TYPE: PRT
<213> ORGANISM: Artificial Sequence
<220> FEATURE:
<223> OTHER INFORMATION: HC (vH2.6+CH1)

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
            50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

```
Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
            195                 200                 205

Asn Val Asn His Lys Pro Ser Asn Thr Lys Val Asp Lys Lys Val Glu
        210                 215                 220

Pro Lys Ser Cys
225

<210> SEQ ID NO 36
<211> LENGTH: 228
<212> TYPE: PRT
<213> ORGANISM: Artificial Sequence
<220> FEATURE:
<223> OTHER INFORMATION: HC (vH3.1+CH1)

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met His Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
            195                 200                 205

Asn Val Asn His Lys Pro Ser Asn Thr Lys Val Asp Lys Lys Val Glu
        210                 215                 220

Pro Lys Ser Cys
225

<210> SEQ ID NO 37
<211> LENGTH: 228
<212> TYPE: PRT
<213> ORGANISM: Artificial Sequence
<220> FEATURE:
<223> OTHER INFORMATION: HC (vH3.2+CH1)

<400> SEQUENCE: 37

Glu Val Gln Leu Val Glu Ser Gly Gly Gly Leu Val Gln Pro Gly Gly
```

```
1               5                   10                  15
Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
                35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
                115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
                195                 200                 205

Asn Val Asn His Lys Pro Ser Asn Thr Lys Val Asp Lys Lys Val Glu
                210                 215                 220

Pro Lys Ser Cys
225
```

<210> SEQ ID NO 38
<211> LENGTH: 228
<212> TYPE: PRT
<213> ORGANISM: Artificial Sequence
<220> FEATURE:
<223> OTHER INFORMATION: HC (vH3.3+CH1)

<400> SEQUENCE: 38

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met His Trp Val Arg Gln Ala Pro Gly Lys Gly Leu Glu Trp Val
                35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
                115                 120                 125

Lys Gly Pro Ser Val Phe Pro Leu Ala Pro Ser Ser Lys Ser Thr Ser
```

```
                130              135              140
Gly Gly Thr Ala Ala Leu Gly Cys Leu Val Lys Asp Tyr Phe Pro Glu
145              150              155              160

Pro Val Thr Val Ser Trp Asn Ser Gly Ala Leu Thr Ser Gly Val His
                165              170              175

Thr Phe Pro Ala Val Leu Gln Ser Ser Gly Leu Tyr Ser Leu Ser Ser
                180              185              190

Val Val Thr Val Pro Ser Ser Ser Leu Gly Thr Gln Thr Tyr Ile Cys
                195              200              205

Asn Val Asn His Lys Pro Ser Asn Thr Lys Val Asp Lys Lys Val Glu
        210              215              220

Pro Lys Ser Cys
225

<210> SEQ ID NO 39
<211> LENGTH: 217
<212> TYPE: PRT
<213> ORGANISM: Artificial Sequence
<220> FEATURE:
<223> OTHER INFORMATION: LC (vL2.3+CL)

<400> SEQUENCE: 39

Gln Ala Val Val Thr Gln Glu Pro Ser Leu Thr Val Ser Pro Gly Gly
1               5               10              15

Thr Val Thr Leu Thr Cys Arg Ser Ser Thr Gly Ala Val Thr Thr Ser
                20              25              30

Asn Tyr Ala Asn Trp Val Gln Gln Lys Pro Gly Gln Ala Pro Arg Gly
            35              40              45

Leu Ile Tyr Gly Thr Asn Lys Arg Ala Pro Gly Val Pro Ala Arg Phe
    50              55              60

Ser Gly Ser Leu Leu Gly Gly Lys Ala Ala Leu Thr Leu Ser Gly Ala
65              70              75              80

Gln Pro Glu Asp Glu Ala Glu Tyr Tyr Cys Ala Leu Trp Tyr Ser Asn
                85              90              95

Leu Trp Val Phe Gly Gly Gly Thr Lys Leu Thr Val Leu Gly Arg Thr
            100             105             110

Val Ala Ala Pro Ser Val Phe Ile Phe Pro Pro Ser Asp Glu Gln Leu
        115             120             125

Lys Ser Gly Thr Ala Ser Val Val Cys Leu Leu Asn Asn Phe Tyr Pro
    130             135             140

Arg Glu Ala Lys Val Gln Trp Lys Val Asp Asn Ala Leu Gln Ser Gly
145             150             155             160

Asn Ser Gln Glu Ser Val Thr Glu Gln Asp Ser Lys Asp Ser Thr Tyr
                165             170             175

Ser Leu Ser Ser Thr Leu Thr Leu Ser Lys Ala Asp Tyr Glu Lys His
            180             185             190

Lys Val Tyr Ala Cys Glu Val Thr His Gln Gly Leu Ser Ser Pro Val
        195             200             205

Thr Lys Ser Phe Asn Arg Gly Glu Cys
    210             215

<210> SEQ ID NO 40
<211> LENGTH: 235
<212> TYPE: PRT
<213> ORGANISM: Artificial Sequence
<220> FEATURE:
<223> OTHER INFORMATION: HC (vH2.3+CH1- HK129pAF-DKTHT)
```

<400> SEQUENCE: 40

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ala Ser Thr
        115                 120                 125

Lys Gly Pro Ser Val Phe Pro Leu Ala Pro Ser Ser Pro Ala Phe Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr
225                 230                 235

<210> SEQ ID NO 41
<211> LENGTH: 235
<212> TYPE: PRT
<213> ORGANISM: Artificial Sequence
<220> FEATURE:
<223> OTHER INFORMATION: HC (vH2.2+CH1- HK129pAF-DKTHT)

<400> SEQUENCE: 41

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Pro Ala Phe Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
            195                 200                 205

Ile Cys Asn Val Asn His Lys Pro Ser Asn Thr Lys Val Asp Lys Lys
            210                 215                 220

Val Glu Pro Lys Ser Cys Asp Lys Thr His Thr
225                 230                 235

<210> SEQ ID NO 42
<211> LENGTH: 235
<212> TYPE: PRT
<213> ORGANISM: Artificial Sequence
<220> FEATURE:
<223> OTHER INFORMATION: HC (vH1.0+CH1- HK129pAF-DKTHT)

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Pro Ala Phe Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
            195                 200                 205

Ile Cys Asn Val Asn His Lys Pro Ser Asn Thr Lys Val Asp Lys Lys
            210                 215                 220

Val Glu Pro Lys Ser Cys Asp Lys Thr His Thr
225                 230                 235

```
<210> SEQ ID NO 43
<211> LENGTH: 235
<212> TYPE: PRT
<213> ORGANISM: Artificial Sequence
<220> FEATURE:
<223> OTHER INFORMATION: HC (vH2.1+CH1- HK129pAF-DKTHT)

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Pro Ala Phe Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr
225                 230                 235

<210> SEQ ID NO 44
<211> LENGTH: 235
<212> TYPE: PRT
<213> ORGANISM: Artificial Sequence
<220> FEATURE:
<223> OTHER INFORMATION: HC (vH2.4+CH1- HK129pAF-DKTHT)

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80
```

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Pro Ala Phe Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Lys
        210                 215                 220

Val Glu Pro Lys Ser Cys Asp Lys Thr His Thr
225                 230                 235

<210> SEQ ID NO 45
<211> LENGTH: 235
<212> TYPE: PRT
<213> ORGANISM: Artificial Sequence
<220> FEATURE:
<223> OTHER INFORMATION: HC (vH2.5+CH1- HK129pAF-DKTHT)

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Pro Ala Phe Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

```
Ile Cys Asn Val Asn His Lys Pro Ser Asn Thr Lys Val Asp Lys Lys
    210                 215                 220

Val Glu Pro Lys Ser Cys Asp Lys Thr His Thr
225                 230                 235
```

<210> SEQ ID NO 46
<211> LENGTH: 235
<212> TYPE: PRT
<213> ORGANISM: Artificial Sequence
<220> FEATURE:
<223> OTHER INFORMATION: HC (vH2.6+CH1- HK129pAF-DKTHT)

<400> SEQUENCE: 46

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Ala Phe Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
            195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr
225                 230                 235
```

<210> SEQ ID NO 47
<211> LENGTH: 235
<212> TYPE: PRT
<213> ORGANISM: Artificial Sequence
<220> FEATURE:
<223> OTHER INFORMATION: HC (vH3.1+CH1- HK129pAF-DKTHT)

<400> SEQUENCE: 47

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met His Trp Val Arg Gln Ala Pro Gly Lys Gly Leu Glu Trp Val
```

```
                35                  40                  45
Ala Arg Ile Arg Ser Lys Tyr Asn Asn Tyr Ala Thr Tyr Tyr Ala Asp
            50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
                115                 120                 125

Lys Gly Pro Ser Val Phe Pro Leu Ala Pro Ser Ser Pro Ala Phe Ser
            130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                    165                 170                 175

Val His Thr Phe Pro Ala Val Leu Gln Ser Ser Gly Leu Tyr Ser Leu
                180                 185                 190

Ser Ser Val Val Thr Val Pro Ser Ser Ser Leu Gly Thr Gln Thr Tyr
                195                 200                 205

Ile Cys Asn Val Asn His Lys Pro Ser Asn Thr Lys Val Asp Lys Lys
            210                 215                 220

Val Glu Pro Lys Ser Cys Asp Lys Thr His Thr
225                 230                 235

<210> SEQ ID NO 48
<211> LENGTH: 235
<212> TYPE: PRT
<213> ORGANISM: Artificial Sequence
<220> FEATURE:
<223> OTHER INFORMATION: HC (vH3.2+CH1- HK129pAF-DKTHT)

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Ser Asn Asn Tyr Ala Thr Tyr Tyr Ala Asp
            50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
                115                 120                 125

Lys Gly Pro Ser Val Phe Pro Leu Ala Pro Ser Ser Pro Ala Phe Ser
            130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
```

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Lys
210                 215                 220

Val Glu Pro Lys Ser Cys Asp Lys Thr His Thr
225                 230                 235

<210> SEQ ID NO 49
<211> LENGTH: 230
<212> TYPE: PRT
<213> ORGANISM: Artificial Sequence
<220> FEATURE:
<223> OTHER INFORMATION: HC (vH2.3+CH1- HK129pAF)

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Pro Ala Phe Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Lys
210                 215                 220

Val Glu Pro Lys Ser Cys
225                 230

<210> SEQ ID NO 50
<211> LENGTH: 230
<212> TYPE: PRT
<213> ORGANISM: Artificial Sequence
<220> FEATURE:
<223> OTHER INFORMATION: HC (vH2.2+CH1- HK129pAF)

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Pro Ala Phe Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Lys
210                 215                 220

Val Glu Pro Lys Ser Cys
225                 230

<210> SEQ ID NO 51
<211> LENGTH: 230
<212> TYPE: PRT
<213> ORGANISM: Artificial Sequence
<220> FEATURE:
<223> OTHER INFORMATION: HC (vH1.0+CH1- HK129pAF)

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Pro Ala Phe Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Ser Leu Gly Thr Gln Thr Tyr
                195                 200                 205

Ile Cys Asn Val Asn His Lys Pro Ser Asn Thr Lys Val Asp Lys Lys
210                 215                 220

Val Glu Pro Lys Ser Cys
225                 230

<210> SEQ ID NO 52
<211> LENGTH: 230
<212> TYPE: PRT
<213> ORGANISM: Artificial Sequence
<220> FEATURE:
<223> OTHER INFORMATION: HC (vH2.1+CH1- HK129pAF)

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Pro Ala Phe Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Ser Leu Gly Thr Gln Thr Tyr
                195                 200                 205

Ile Cys Asn Val Asn His Lys Pro Ser Asn Thr Lys Val Asp Lys Lys
210                 215                 220

Val Glu Pro Lys Ser Cys
225                 230

<210> SEQ ID NO 53
<211> LENGTH: 230

```
<212> TYPE: PRT
<213> ORGANISM: Artificial Sequence
<220> FEATURE:
<223> OTHER INFORMATION: HC (vH2.4+CH1- HK129pAF)

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
            85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala Ser Thr
            115                 120                 125

Lys Gly Pro Ser Val Phe Pro Leu Ala Pro Ser Ser Pro Ala Phe Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Lys
210                 215                 220

Val Glu Pro Lys Ser Cys
225                 230

<210> SEQ ID NO 54
<211> LENGTH: 230
<212> TYPE: PRT
<213> ORGANISM: Artificial Sequence
<220> FEATURE:
<223> OTHER INFORMATION: HC (vH2.5+CH1- HK129pAF)

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
            85                  90                  95
```

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Pro Ala Phe Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Lys
210                 215                 220

Val Glu Pro Lys Ser Cys
225                 230

<210> SEQ ID NO 55
<211> LENGTH: 230
<212> TYPE: PRT
<213> ORGANISM: Artificial Sequence
<220> FEATURE:
<223> OTHER INFORMATION: HC (vH2.6+CH1- HK129pAF)

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
            85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Pro Ala Phe Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Lys
210                 215                 220

Val Glu Pro Lys Ser Cys
225                 230

<210> SEQ ID NO 56
<211> LENGTH: 230
<212> TYPE: PRT
<213> ORGANISM: Artificial Sequence
<220> FEATURE:
<223> OTHER INFORMATION: HC (vH3.1+CH1- HK129pAF)

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met His Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ile
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Pro Ala Phe Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys
225                 230

<210> SEQ ID NO 57
<211> LENGTH: 230
<212> TYPE: PRT
<213> ORGANISM: Artificial Sequence
<220> FEATURE:
<223> OTHER INFORMATION: HC (vH3.2+CH1- HK129pAF)

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp

```
                50                  55                  60
Ser Val Lys Asp Arg Phe Thr Ile Ser Arg Asp Asp Ser Lys Asn Ile
 65                  70                  75                  80

Leu Tyr Leu Gln Met Asn Ser Leu Lys Thr Glu Asp Thr Ala Val Tyr
                 85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
                115                 120                 125

Lys Gly Pro Ser Val Phe Pro Leu Ala Pro Ser Ser Pro Ala Phe Ser
            130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Lys
210                 215                 220

Val Glu Pro Lys Ser Cys
225                 230

<210> SEQ ID NO 58
<211> LENGTH: 217
<212> TYPE: PRT
<213> ORGANISM: Artificial Sequence
<220> FEATURE:
<223> OTHER INFORMATION: LC (vL2.4+CL )

<400> SEQUENCE: 58

Gln Ala Val Val Thr Gln Glu Pro Ser Leu Thr Val Ser Pro Gly Gly
 1               5                  10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
             35                  40                  45

Leu Ile Gly Gly Thr Asn Lys Arg Ala Pro Trp Val Pro Ala Arg Phe
         50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Gly Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
```

```
                  180                 185                 190
Lys Val Tyr Ala Cys Glu Val Thr His Gln Gly Leu Ser Ser Pro Val
            195                 200                 205
Thr Lys Ser Phe Asn Arg Gly Glu Cys
            210                 215

<210> SEQ ID NO 59
<211> LENGTH: 217
<212> TYPE: PRT
<213> ORGANISM: Artificial Sequence
<220> FEATURE:
<223> OTHER INFORMATION: LC (VL2.1+CL)

<400> SEQUENCE: 59

Gln Ala Val Val Thr Gln Glu Pro Ser Leu Thr Val Ser Pro Gly Gly
1               5                   10                  15
Thr Val Thr Leu Thr Cys Arg Ser Ser Thr Gly Ala Val Thr Thr Ser
            20                  25                  30
Asn Tyr Ala Asn Trp Phe Gln Gln Lys Pro Gly Gln Ala Pro Arg Gly
            35                  40                  45
Leu Ile Gly Gly Thr Asn Lys Arg Ala Pro Gly Val Pro Ala Arg Phe
        50                  55                  60
Ser Gly Ser Leu Leu Gly Gly Lys Ala Ala Leu Thr Leu Ser Gly Ala
65                  70                  75                  80
Gln Pro Glu Asp Glu Ala Glu Tyr Tyr Cys Ala Leu Trp Tyr Ser Asn
                85                  90                  95
Leu Trp Val Phe Gly Gly Gly Thr Lys Leu Thr Val Leu Gly Arg Thr
            100                 105                 110
Val Ala Ala Pro Ser Val Phe Ile Phe Pro Pro Ser Asp Glu Gln Leu
        115                 120                 125
Lys Ser Gly Thr Ala Ser Val Val Cys Leu Leu Asn Asn Phe Tyr Pro
    130                 135                 140
Arg Glu Ala Lys Val Gln Trp Lys Val Asp Asn Ala Leu Gln Ser Gly
145                 150                 155                 160
Asn Ser Gln Glu Ser Val Thr Glu Gln Asp Ser Lys Asp Ser Thr Tyr
                165                 170                 175
Ser Leu Ser Ser Thr Leu Thr Leu Ser Lys Ala Asp Tyr Glu Lys His
            180                 185                 190
Lys Val Tyr Ala Cys Glu Val Thr His Gln Gly Leu Ser Ser Pro Val
        195                 200                 205
Thr Lys Ser Phe Asn Arg Gly Glu Cys
    210                 215

<210> SEQ ID NO 60
<211> LENGTH: 217
<212> TYPE: PRT
<213> ORGANISM: Artificial Sequence
<220> FEATURE:
<223> OTHER INFORMATION: LC (vL2.5+CL)

<400> SEQUENCE: 60

Gln Ala Val Val Thr Gln Glu Pro Ser Leu Thr Val Ser Pro Gly Gly
1               5                   10                  15
Thr Val Thr Leu Thr Cys Arg Ser Ser Thr Gly Ala Val Thr Thr Ser
            20                  25                  30
Asn Tyr Ala Asn Trp Phe Gln Gln Lys Pro Gly Gln Ala Pro Arg Gly
            35                  40                  45
```

Leu Ile Gly Gly Thr Asn Lys Arg Ala Pro Trp Val Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 61
<211> LENGTH: 217
<212> TYPE: PRT
<213> ORGANISM: Artificial Sequence
<220> FEATURE:
<223> OTHER INFORMATION: LC (vL2.2+CL)

<400> SEQUENCE: 61

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Thr
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

```
Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 62
<211> LENGTH: 217
<212> TYPE: PRT
<213> ORGANISM: Artificial Sequence
<220> FEATURE:
<223> OTHER INFORMATION: LC (vL3.1+CL)

<400> SEQUENCE: 62

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Asn Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

ANTI-CD3 ANTIBODY FOLATE BIOCONJUGATES AND THEIR USES

CROSS-REFERENCE TO RELATED APPLICATIONS

This application is a U.S. National Stage entry under 35 U.S.C. § 371 of International Application No. PCT/US2019/048677, filed on Aug. 28, 2019, which is incorporated by reference herein in its entirety and claims priority to and the benefit of U.S. Provisional Application Ser. No. 62/723,793 filed on Aug. 28, 2018, the specification and contents of which is incorporated by reference herein in its entirety for all purposes.

SEQUENCE LISTING

The instant application contains a Sequence Listing which has been submitted in ASCII format via EFS-Web and is hereby incorporated by reference in its entirety. The ASCII copy was created on Aug. 28, 2019 is named AMBX_0228_00PCT_Sequence_Listing.txt and is 128,417 bytes in size.

FIELD OF THE INVENTION

The present invention disclosure pertains to the field of immune-oncology. More particularly the invention relates to anti-CD3 antibodies and fragments or variants thereof conjugated to-one or more folate molecules. The invention also relates to anti-CD3 Fab-Folate antibodies and variants thereof conjugated to-polyethylene glycol (PEG).

BACKGROUND OF THE INVENTION

Ovarian cancer is one of the most common cancer worldwide in women. Annually about 250,000 women, will be diagnosed with ovarian cancer and approximately 140,000 women each year succumb to this disease. The five-year survival rate for ovarian cancer varies depending on the type and stage of the cancer with the trend being, the more advanced ovarian cancers have the worst five-year survival rates. The current treatment options for ovarian cancer includes chemotherapy, surgery, radiation or a combination of these therapies. The response rates for advanced ovarian cancer after surgical debulking followed by platinum-based chemotherapy is 80% with 40-60% being complete responses. Unfortunately, approximately 70% of these patients will relapse with a median progression free survival being 18 months.

Currently, there is a deficiency in the field for therapies targeting ovarian cancers and types of ovarian cancer including epithelial, stromal and germ cell tumors and including fallopian tube cancer and primary peritoneal carcinoma. Although surgery, radiation and a variety of chemotherapeutics are commonly used to treat ovarian cancer patients, the Food and Drug Administration (FDA) has recently accepted a supplemental biologics license application (sBLA) for bevacizumab (Avastin) for the treatment of advanced ovarian cancer as first line therapy.

Immunotherapy is being evaluated as a new treatment option for cancer patients, which uses a biologic or an engineered T-cells to stimulate the patient's immune system to attack their cancer. Several immunotherapeutics have shown great promise and have been approved to treat various types of cancer. Immune checkpoint inhibitors, Chimeric Antigen Receptor T-cells (CAR-T), Bispecific T-cell Engagers (BiTEs), various designs of T-cell Dependent Bispecific antibodies (TDBs), NK-cell dependent bispecific antibodies, macrophage-dependent bispecific antibodies, and autologous antigen presenting cells (APC)/cancer vaccines are some of the immunotherapeutics used to treat cancer patients.

Some biologics undergoing clinical evaluation for ovarian cancer patients include an antibody drug conjugate against the folate receptor alpha (Mirvetuximab soravtansine (IMGN853)), the EpCAM-CD3 bispecific antibody (Catumaxomab), a DLL4-VEGF bispecific, vaccines targeting NY-ESO-1 and a CAR-T targeting folate receptor alpha (FOLR1).

Ovarian cancer has been reported to have an immunosuppressive environment, which makes developing certain types of immunotherapeutics, like checkpoint inhibitors, a challenge. Currently no immunotherapeutics have been approved to treat ovarian cancer patients, although several are being evaluated in clinical trials.

Folate receptors are expressed in a number of cancers including, but not limited to epithelial cancers such as breast, cervical, colorectal, renal, nasopharyngeal, ovarian, and endometrial. Folate receptor (FR) family in humans includes FRalpha, FRbeta, and FRgamma. Folate receptor-alpha (FOLR1) is a GPI anchored receptor that is highly expressed in approximately 80-90% of ovarian cancer. FOLR1 binds to folic acid, also known as Vitamin B9, and folic acid's primary metabolite 5-methyl-tetrahydrofolate (5-MTHF). High expression of FOLR1 is observed in approximately 76% of high grade serous ovarian cancer, which the predominant histotype, as compared to 11% in mucinous ovarian cancer. FOLR1 has low and restricted expression in normal tissues, which makes it a preferred target for oncology drug development efforts.

To overcome the deficiencies in the art, the inventors have developed an antibody conjugate in an anti-CD3 antibody having one or more non-naturally encoded amino acids incorporated and further comprising one or more folate molecules. The bispecific antibody can comprise or consist of an anti-CD3 antibody, that has been engineered to have one or more non-naturally encoded amino acids on the heavy or light chain of the Fab. The bispecific antibody or antibody fragment can comprise an anti-CD3 antibody, that has been engineered to have one or more non-naturally encoded amino acids on the heavy and/or light chains.

BRIEF SUMMARY OF THE INVENTION

Anti-CD3 bispecific antibodies recruiting cytotoxic T cells to cancer cells are a promising new approach for the treatment of various liquid and solid tumors. The present invention provides anti-CD3 antibodies. In some embodiments, the anti-CD3 antibody is a bispecific antibody. In some embodiments the anti-CD3 antibody comprises an anti-CD3 Fab. In some embodiments, the anti-CD3 antibody includes a non-naturally encoded amino acid in the heavy or light chain of the Fab, preferably in the heavy chain. In some embodiments, the non-naturally encoded amino acid is para-acetyl-phenylalanine (pAF). In some embodiments, the anti-CD3 antibody includes two or more non-naturally encoded amino acids in the heavy and/or light chain(s) of the Fab, e.g. two, three, or four non-naturally encoded amino acids, optionally wherein the two or more non-naturally encoded amino acids are pAF. In some embodiments, the anti-CD3 Fab is conjugated to folate. In some embodiments the anti-CD3 Fab is conjugated to a water-soluble polymer, such as polyethylene glycol (PEG). In some embodiments the anti-CD3 Fab is conjugated to both folate and polyethylene glycol (PEG), optionally using bi-functional linkers. In some embodiments the anti-CD3 Fab is conjugated to two folate and two polyethylene glycol (PEG) molecules. In some embodiments, conjugation is via the side chain of a non-naturally encoded amino acid, such as pAF. In some embodiments, the anti-CD3 antibody recruits cytotoxic T cells to folate receptor positive (FR+) tumor cells. In some embodiments, the anti-CD3 antibody has improved efficacy, reduced toxicity, improved pharmacokinetic (PK) properties, improved affinity, improved tumor-associated antigen (TAA) binding, an improved in-vivo half life (T½), improved in vitro activity, improved serum half-life, and/or improved in vivo activity. In some embodiments, the anti-CD3 antibody has improved efficacy. In some embodiments, the anti-CD3 antibody has reduced toxicity. In some embodiments, the anti-CD3 antibody has improved PK properties. In some embodiments, the anti-CD3 antibody has improved affinity. In some embodiments, the anti-CD3 antibody has improved TAA binding. In some embodiments, the anti-CD3 antibody has an improved in-vivo T½. In some embodiments, the anti-CD3 antibody has improved in vitro activity. In some embodiments, the anti-CD3 antibody has improved serum half-life. In some embodiments, the anti-CD3 antibody has improved in vivo activity. The present invention provides optimization of an anti-CD3 Fab-Folate conjugate that targets cytotoxic T cells to folate receptor positive (FR+) tumor cells for optimal efficacy, reduced toxicity and optimal pharmacokinetic (PK) properties. For example, the present invention provides an optimized anti-CD3 Fab-folate conjugate that targets cytotoxic T cells to folate receptor positive (FR+) tumor cells for optimal efficacy, reduced toxicity and optimal pharmacokinetic (PK) properties. To strike an optimal balance between efficacy and toxicity due to cytokine release syndrome (CRS), the inventors fine-tuned the affinity of the anti-CD3 antibody as well as optimized the tumor-associated antigen (TAA) binding. To increase the in-vivo half-life (T½), both Folate and PEG molecules of various sizes were simultaneously conjugated by the use of bi-functional linkers. The optimized conjugates showed potent and selective in vitro activity, good serum half-life, and potent in vivo activity in xenograft mouse models. This semi-synthetic approach is likely to be applicable for the generation of additional anti-CD3 bispecific agents using small molecule ligands selective for other TAAs.

This invention provides anti-CD3 antibodies and conjugates thereof to folate. This invention also provides anti-CD3 antibodies and conjugates thereof to PEG. This invention also provides anti-CD3 antibodies and conjugates thereof to folate and PEG. In some embodiments, the novel anti-CD3 antibodies of the present invention comprise one or more non-naturally encoded amino acids. In some embodiments, the anti-CD3 antibody comprises a complete antibody heavy chain. In some embodiments, the anti-CD3 antibody comprises a complete antibody light chain. In some embodiments, the anti-CD3 antibody comprises a complete antibody heavy chain and a complete antibody light chain. In some embodiments, the anti-CD3 antibody comprises a variable region of an antibody light chain. In some embodiments, the anti-CD3 antibody comprises a variable region of an antibody heavy chain. In some embodiments, the anti-CD3 antibody comprises a variable region of a light chain and a variable region of a heavy chain. In some embodiments, the anti-CD3 antibody comprises at least one CDR of an antibody light chain. In some embodiments, the anti-CD3 antibody comprises at least one CDR of an anti-CD3 antibody heavy chain. In some embodiments, the anti-CD3 antibody comprises at least one CDR of a light chain and at least one CDR of a heavy chain. In some embodiments, the anti-CD3 antibody comprises three CDRs of a light chain. In some embodiments, the anti-CD3 antibody comprises three CDRs of a heavy chain. In some embodiments, the anti-CD3 antibody comprises three CDRs of a light chain and three CDRs of a heavy chain. In some embodiments, the anti-CD3 antibody comprises a Fab. In some embodiments, the anti-CD3 antibody comprises two Fabs. In some embodiments, the anti-CD3 antibody comprises two or more Fabs. In some embodiments, the anti-CD3 antibody comprises a scFv. In some embodiments, the anti-CD3 antibody comprises two scFvs. In some embodiments, the anti-CD3 antibody comprises two or more scFv. In some embodiments, the anti-CD3 antibody comprises a minibody. In some embodiments, the anti-CD3 antibody comprises two minibodies. In some embodiments, the anti-CD3 antibody comprises two or more minibodies. In some embodiments, the anti-CD3 antibody comprises a diabody. In some embodiments, the anti-CD3 antibody comprises two diabodies. In some embodiments, the anti-CD3 antibody comprises two or more diabodies. In some embodiments, the anti-CD3 antibody comprises a BiTE. In some embodiments, the anti-CD3 antibody comprises two BiTEs. In some embodiments, the anti-CD3 antibody comprises two or more BiTEs. In some embodiments, the anti-CD3 antibody comprises a DART. In some embodiments, the anti-CD3 antibody comprises two DARTs. In some embodiments, the anti-CD3 antibody comprises two or more DARTs. In some embodiments, the anti-CD3 antibody comprises a TandAb. In some embodiments, the anti-CD3 antibody comprises two TandAbs. In some embodiments, the anti-CD3 antibody comprises two or more TandAbs. In some embodiments, the anti-CD3 antibody comprises a variable region of a light chain and a variable region of a heavy chain. In some embodiments, the anti-CD3 antibody comprises a complete light chain and a complete heavy chain. In some embodiments, the anti-CD3 antibody comprises one or more Fc domain or portion thereof. In some embodiments, the anti-CD3 antibody comprises a combination of any of the above embodiments. In some embodiments, the anti-CD3 antibody comprises a homodimer, heterodimer, homomultimer or heteromultimer of any of the above embodiments. In some embodiments, the anti-CD3 antibody comprises a polypeptide that binds to a binding partner wherein the binding partner comprises an antigen, a polypeptide, a nucleic acid molecule, a polymer, or other molecule or substance. In some embodiments, the anti-CD3 antibody is associated with a non-antibody scaffold molecule or substance.

In some embodiments, the anti-CD3 antibody comprises one or more post-translational modifications. In some embodiments, the anti-CD3 antibody is linked to a linker, polymer, or biologically active molecule. In some embodiments, the anti-CD3 antibody is linked to a bifunctional polymer, bifunctional linker, or at least one additional anti-CD3 antibody. In some embodiments, the anti-CD3 antibody is linked to a polypeptide that is not an anti-CD3 antibody. In some embodiments, an antigen-binding polypeptide comprising a non-naturally encoded amino acid is linked to one or more additional antigen-binding polypeptides which may also comprise a non-naturally encoded amino acid. In some embodiments, an antigen-binding polypeptide comprising a non-naturally encoded amino acid is linked to one or more polypeptide small molecule conjugates which may also comprise a non-naturally encoded amino acid. In some embodiments, an anti-CD3 antibody comprising a nonnaturally encoded amino acid is linked to one or more additional antigen-binding polypeptides which may also comprise a non-naturally encoded amino acid.

In some embodiments, the non-naturally encoded amino acid is linked to a small molecule ligand. In some embodiments, the non-naturally encoded amino acid is linked to two small molecule ligands. In some embodiments, the non-naturally encoded amino acid is linked to two or more small molecule ligands. In some embodiments, the small molecule ligand comprises a folate or DUPA molecule. In some embodiments, the small molecule ligand comprises two folate or two DUPA molecules. In some embodiments, the small molecule ligand comprises two or more folate or two or more DUPA molecules. In some embodiments, the non-naturally encoded amino acid is linked to a water-soluble polymer. In some embodiments, the water-soluble polymer comprises a poly(ethylene glycol) moiety. In some embodiments, the poly(ethylene glycol) molecule is a bifunctional polymer. In some embodiments, the bifunctional polymer is linked to a second polypeptide. In some embodiments, the second polypeptide is an antigen-binding polypeptide. In some embodiments, the second polypeptide is an anti-CD3 antibody. In some embodiments, a small molecule ligand is linked to a water-soluble polymer. In some embodiments, two small molecule ligands are linked to two water-soluble polymers. In some embodiments, two or more small molecule ligands are linked to two or more water-soluble polymers. In some embodiments, a folate is linked to a PEG molecule. In some embodiments, two folate molecules are linked to two water-soluble polymers. In some embodiments, two or more folate molecules are linked to two or more PEG molecules.

In some embodiments the amino acid substitutions in the anti-CD3 antibody may be with naturally occurring or non-naturally occurring amino acids, provided that at least one substitution is with a non-naturally encoded amino acid.

In some embodiments, the non-naturally encoded amino acid comprises a carbonyl group, an acetyl group, an aminooxy group, a hydrazine group, a hydrazide group, a semicarbazide group, an azide group, or an alkyne group.

In some embodiments, the poly(ethylene glycol) molecule has an average molecular weight of between about 0.1 kDa and about 100 kDa. In some embodiments, the poly(ethylene glycol) molecule has an average molecular weight of between 0.1 kDa and 50 kDa. In some embodiments, the poly(ethylene glycol) has an average molecular weight of between 1 kDa and 25 kDa, or between 2 and 22 kDa, or between 5 kDa and 20 kDa. For example, the average molecular weight may be about 5 kDa, or about 10 kDa, or about 20 kDa. For example, the average molecular weight of the poly(ethylene glycol) polymer may be 5 kDa or 10 kDa or 20 kDa. In certain embodiments, the molecular weight is determined by appropriate methods such as SDS/PAGE analysis, RP-HPLC, SEC, mass spectrometry, and capillary electrophoresis.

In some embodiments, the poly(ethylene glycol) molecule is a branched polymer. In some embodiments, each branch of the poly(ethylene glycol) branched polymer has a molecular weight of between 1 kDa and 100 kDa, or between 1 kDa and 50 kDa. In some embodiments, each branch of the poly(ethylene glycol) branched polymer has a molecular weight of between 1 kDa and 25 kDa, or between 2 and 22 kDa, or between 5 kDa and 20 kDa. For example, the molecular weight of each branch of the poly(ethylene glycol) branched polymer may be about 5 kDa, or about 10 kDa, or about 20 kDa. For example, the molecular weight of each branch of the poly(ethylene glycol) branched polymer may be 5 kDa or 10 kDa or 20 kDa.

The present invention also provides an anti-CD3 antibody polypeptide comprising a linker, polymer, or biologically active molecule that is attached to one or more non-naturally encoded amino acids wherein said non-naturally encoded amino acid is ribosomally incorporated into the polypeptide at pre-selected sites.

Embodiments of the invention provide an anti-CD3 antibody comprising at least one of SEQ ID NOs: 1-62. The anti-CD3 antibody comprising two of SEQ ID NOs: 1-62. Embodiments of the invention provide an anti-CD3 antibody comprising two of SEQ ID NOs: 1-62. The anti-CD3 antibody comprising any one of SEQ ID NOs: 1-6 and any one of SEQ ID NOs: 7-9. Embodiments of the invention provide an anti-CD3 Fab antibody comprising two of SEQ ID NOs: 1-5. In other embodiments the invention provides a bispecific binding molecule comprising i) a first binding domain and ii) a second binding domain wherein the second binding domain is selected from the group consisting of SEQ ID NOs: 1-62. In other embodiments the invention provides a bispecific binding molecule comprising i) a first binding domain and ii) a second binding domain wherein the second binding domain comprises an anti-CD3 comprising any one of SEQ ID NOs: 1, 2, 3, 4, 5, 6, 10, 11, 12, 13, 14, 15, 16, 17, 21, 22, 23, 24, 25, 26, 27, 28, 29, 30, 31, 32, 33, 34, 35, 36, 37, 38, 40, 41, 42, 43, 44, 45, 46, 47, 48, 49, 50, 50, 51, 52, 53, 54, 55, 56, and 57, and any one of SEQ ID NOs: 7, 8, 9, 18, 19, 20, 39, 58, 59, 60, 61, and 62. In other embodiments the invention provides a bispecific binding molecule comprising i) a first binding domain and ii) a second binding domain wherein the second binding domain comprises an anti-CD3 Fab comprising any one of SEQ ID NOs: 1, 2, 3, 4, 5, 6, 10, 11, 12, 13, 14, 15, 16, 17, 21, 22, 23, 24, 25, 26, 27, 28, 29, 30, 31, 32, 33, 34, 35, 36, 37, 38, 40, 41, 42, 43, 44, 45, 46, 47, 48, 49, 50, 50, 51, 52, 53, 54, 55, 56, and 57. In other embodiments the invention provides a bispecific binding molecule comprising i) a first binding domain and ii) a second binding domain wherein the second binding domain comprises an anti-CD3 Fab comprising any one SEQ ID NOs: 1, 2, 3, 4, 5, 6, 10, 11, 12, 13, 14, 15, 16, 17, 21, 22, 23, 24, 25, 26, 27, 28, 29, 30, 31, 32, 33, 34, 35, 36, 37, 38, 40, 41, 42, 43, 44, 45, 46, 47, 48, 49, 50, 50, 51, 52, 53, 54, 55, 56, and 57; and any one of SEQ ID NOs: 7, 8, 9, 18, 19, 20, 39, 58, 59, 60, 61, and 62. In other embodiments the invention provides a cytotoxically active CD3 specific binding construct comprising the amino acid sequence set forth in one or more of SEQ ID NOs: 1-62. In other embodiments the invention provides a cytotoxically active CD3 specific binding construct comprising the amino acid sequence set forth in two of SEQ ID NO: 1-62. In other embodiments the invention provides a cytotoxically active CD3 specific binding construct comprising an anti-CD3 comprising any one of SEQ ID NOs: 1, 2, 3, 4, 5, 6, 10, 11, 12, 13, 14, 15, 16, 17, 21, 22, 23, 24, 25, 26, 27, 28, 29, 30, 31, 32, 33, 34, 35, 36, 37, 38, 40, 41, 42, 43, 44, 45, 46, 47, 48, 49, 50, 50, 51, 52, 53, 54, 55, 56, and 57. In other embodiments the invention provides a cytotoxically active CD3 Fab specific binding construct comprising an anti-CD3 Fab comprising any one of SEQ ID NOs: 7, 8, 9, 18, 19, 20, 39, 58, 59, 60, 61, and 62. In other embodiments the invention provides a cytotoxically active CD3 specific binding construct comprising an anti-CD3 comprising any one SEQ ID NOs: 1, 2, 3, 4, 5, 6, 10, 11, 12, 13, 14, 15, 16, 17, 21, 22, 23, 24, 25, 26, 27, 28, 29, 30, 31, 32, 33, 34, 35, 36, 37, 38, 40, 41, 42, 43, 44, 45, 46, 47, 48, 49, 50, 50, 51, 52, 53, 54, 55, 56, and 57; and any one of SEQ ID NOs: 7, 8, 9, 18, 19, 20, 39, 58, 59, 60, 61, and 62. Another embodiment of the invention provides anti-CD3 Fab antibody, wherein the anti-CD3 antibody comprises a binding domain comprising (a) a VH domain comprising an amino acid sequence selected from the group consisting of SEQ ID NO: 1-6 and (b) a VL domain comprising an amino acid sequence selected from the group consisting of SEQ ID NO: 7-9.

Another embodiment of the invention provides an anti-CD3 antibody wherein the antibody comprises one or more post-translational modifications. Embodiments of the invention provide an anti-CD3 Fab antibody wherein the antibody is linked to a linker, polymer, or biologically active molecule. Another embodiment of the invention provides an anti-CD3 antibody wherein the biologically active molecule is folate. Embodiments of the invention provide an anti-CD3 antibody comprising one or more folate. Embodiments of the invention provide an anti-CD3 antibody comprising two folates. Another embodiment of the invention provides anti-CD3 antibody wherein the biologically active molecule is DUPA. Embodiments of the invention provides anti-CD3 antibody comprising one or more DUPA. Embodiments of the invention provides anti-CD3 antibody comprising two DUPA.

In certain embodiments, the anti-CD3 antibody comprises a heavy chain amino acid sequence of any one of SEQ. ID. NOs: 1, 2, 3, 4, 5, 6, 10, 11, 12, 13, 14, 15, 16, 17, 21, 22, 23, 24, 25, 26, 27, 28, 29, 30, 31, 32, 33, 34, 35, 36, 37, 38, 40, 41, 42, 43, 44, 45, 46, 47, 48, 49, 50, 50, 51, 52, 53, 54, 55, 56, and 57; and a light chain amino acid sequence of any one of SEQ. ID. NOs: 7, 8, 9, 18, 19, 20, 39, 58, 59, 60, 61, and 62.

In some embodiments, the anti-CD3 antibody comprises an anti-CD3 comprising any one of SEQ ID NOs: 1, 2, 3, 4, 5, 6, 10, 11, 12, 13, 14, 15, 16, 17, 21, 22, 23, 24, 25, 26, 27, 28, 29, 30, 31, 32, 33, 34, 35, 36, 37, 38, 40, 41, 42, 43, 44, 45, 46, 47, 48, 49, 50, 50, 51, 52, 53, 54, 55, 56, and 57. In some embodiments, the anti-CD3 antibody comprises an anti-CD3 comprising any one of SEQ ID NOs: 7, 8, 9, 18, 19, 20, 39, 58, 59, 60, 61, and 62.

In some embodiments, the anti-CD3 antibody comprises an anti-CD3 Fab comprising any one of SEQ ID NOs: 1, 2, 3, 4, 5, 6, 10, 11, 12, 13, 14, 15, 16, 17, 21, 22, 23, 24, 25, 26, 27, 28, 29, 30, 31, 32, 33, 34, 35, 36, 37, 38, 40, 41, 42, 43, 44, 45, 46, 47, 48, 49, 50, 50, 51, 52, 53, 54, 55, 56, and 57; and any one of SEQ ID NOs: 7, 8, 9, 18, 19, 20, 39, 58, 59, 60, 61, and 62. Another embodiment of the invention provides anti-CD3 variant comprising a heavy chain of SEQ ID NO: 1-5 and a light chain of SEQ ID NO: 7-9. In some embodiments, the anti-CD3 antibody comprises an anti-CD3 Fab comprising SEQ ID NOs: 7 and 10, or 7 and 14, or 7 and 11, or 7 and 15, or 7 and 12, or 7 and 16, or 7 and 13, or 7 and 17, or 7 and 1, or 7 and 18, or 7 and 19, or 12 and 18, or 12 and 19, or 12 and 16. In some embodiments the anti-CD3 antibody comprises an anti-CD3 Fab comprising SEQ ID NOs: 7 and 10, or 7 and 14, or 7 and 11, or 7 and 15, or 7 and 12, or 7 and 16, or 7 and 13, or 7 and 17, or 7 and 1, or 7 and 18, or 7 and 19, or 12 and 18, or 12 and 19, or 12 and 16 each comprising at least one non-natural amino acid. In some embodiments the anti-CD3 antibody comprises an anti-CD3 Fab comprising SEQ ID NOs: 7 and 10, or 7 and 14, or 7 and 11, or 7 and 15, or 7 and 12, or 7 and 16, or 7 and 13, or 7 and 17, or 7 and 1, or 7 and 18 or 7 and 19, or 12 and 18, or 12 and 19, or 12 and 16 each comprising two non-natural amino acid. In some embodiments the anti-CD3 antibody comprises an anti-CD3 Fab comprising SEQ ID NO: 7 comprising at least one non-natural amino acid; and one of SEQ ID NOs: 10, or 14, or 11, or 15, or 12, or 16, or 13, or 17, or 1, or 18 or 19 comprising at least one non-natural amino acid. In some embodiments the anti-CD3 antibody comprises an anti-CD3 Fab comprising SEQ ID NO:12 comprising at least one non-natural amino acid; and one of SEQ ID NOs: 18, or 19, or 16 comprising at least one non-natural amino acid. In some embodiments the anti-CD3 antibody comprises an anti-CD3 Fab comprising SEQ ID NOs: 58 and 49, or 58 and 40, or 59 and 50, or 59 and 41, or 59 and 42, or 59 and 52, or 59 and 43, or 59 and 44, or 59 and 45, or 59 and 54 or 59 and 55, or 59 and 46, or 9 and 44, or 9 and 53, or 60 and 44, or 60 and 53, or 60 and 42, or 60 and 51, 60 and 50, or 60 and 41, or 61 and 45, or 61 and 54, or 62 and 56, or 62 and 47, or 62 and 48, or 62 and 57, or 7 and 47, or 7 and 56. In some embodiments the anti-CD3 antibody comprises an anti-CD3 Fab comprising two non-natural amino acids the antibody comprising SEQ ID NOs: 18 and 16, or 18 and 59, or 18 and 43.

In some embodiments, the anti-CD3 antibody comprises an anti-CD3 Fab comprising SEQ ID NOs: 1 and 7, or 1 and 8, or 1 and 9. In some embodiments, the anti-CD3 antibody comprises an anti-CD3 Fab comprising SEQ ID NOs: 2 and 7, or 2 and 8, or 2 and 9. In some embodiments, the anti-CD3 antibody comprises an anti-CD3 Fab comprising SEQ ID NOs: 3 and 7, or 3 and 8, or 3 and 9. In some embodiments, the anti-CD3 antibody comprises an anti-CD3 Fab comprising SEQ ID NOs: 4 and 7, or 4 and 8, or 4 and 9. In some embodiments, the anti-CD3 antibody comprises an anti-CD3 Fab comprising SEQ ID NOs: 5 and 7, or 5 and 8, or 5 and 9. In some embodiments, the anti-CD3 antibody comprises an anti-CD3 Fab comprising SEQ ID NOs: 6 and 7, or 6 and 8, or 6 and 9. The anti-CD3 antibody can be a bispecific antibody comprising i) a first binding domain and ii) a second binding domain wherein the second binding domain comprises said anti-CD3 Fab. Other embodiments of the invention provide anti-CD3 Fab antibody selected from SEQ. ID. NOs.: 1 to 62 having a non-naturally encoded amino acid incorporated. In some embodiments the non-naturally encoded amino acid is site-specifically incorporated into the antibody.

In other embodiments the invention provides anti-CD3 Fab antibody wherein the non-naturally encoded amino acid is selected from the group consisting of: an O-methyl-L-tyrosine, an L-3-(2-naphthyl)alanine, a 3-methyl-phenylalanine, an O-4-allyl-L-tyrosine, a 4-propyl-L-tyrosine, p-propargyloxy-L-phenylalanine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, or an isopropyl-L-phenylalanine.

Another embodiment of the invention provides anti-CD3 Fab antibody wherein the non-naturally encoded amino acid is site specifically incorporated. Embodiments of the invention provide an anti-CD3 Fab antibody wherein the non-naturally encoded amino acid is site specifically incorporated at any one of positions H114, H115, H129, L157, H160, L172, and L205 (according to Kabat numbering, as well know to the skilled artisan). Embodiments of the invention provide anti-CD3 Fab antibody wherein the non-naturally encoded amino acid is site specifically incorporated at position H114, H115, H129, L157, H160, L172, and L205 according to Kabat numbering. Embodiments of the invention provide an anti-CD3 Fab antibody wherein the non-naturally encoded amino acid is site specifically incorporated at position 114. Embodiments of the invention provide an anti-CD3 Fab antibody wherein the non-naturally encoded amino acid is site specifically incorporated at position 115. Embodiments of the invention provide an anti-CD3 Fab antibody wherein the non-naturally encoded amino acid is site specifically incorporated at position 129. Embodiments of the invention provide an anti-CD3 Fab antibody wherein the non-naturally encoded amino acid is site specifically incorporated at position 157. Embodiments of the invention provide an anti-CD3 Fab antibody wherein the non-naturally encoded amino acid is site specifically incorporated at position 160. Embodiments of the invention provide an anti-CD3 Fab antibody wherein the non-naturally encoded amino acid is site specifically incorporated at position 172. Embodiments of the invention provide an anti-CD3 Fab antibody wherein the non-naturally encoded amino acid is site specifically incorporated at position 205. Another embodiment of the invention provides anti-CD3 Fab antibody wherein at least one non-naturally encoded amino acid is incorporated. Another embodiment of the invention provides anti-CD3 Fab antibody wherein two non-naturally encoded amino acids are incorporated. Other embodiments of the invention provide an anti-CD3 Fab variant comprising at least one non-naturally encoded amino acid in the heavy or light chain. Other embodiments of the invention provide an anti-CD3 Fab antibody comprising one non-naturally encoded amino acid in the light chain. Other embodiments of the invention provide an anti-CD3 Fab antibody comprising one non-naturally encoded amino acid in the heavy chain. Another embodiment of the invention provides an anti-CD3 Fab variant comprising two non-naturally encoded amino acids.

Another embodiment of the invention provides an anti-CD3 Fab variant wherein the heavy chain further comprises an amino acid extension at the C-terminus. Embodiments of the invention provide an anti-CD3 Fab variant wherein the amino acid extension comprises amino acids DKTHT. Another embodiment of the invention provides an anti-CD3 Fab variant further comprising an amino acid extension in the heavy chain at the C-terminus. Other embodiments of the invention provide an anti-CD3 Fab variant wherein the amino acid extension comprises amino acids DKTHT.

Another embodiment of the invention provides anti-CD3 Fab antibody wherein the heavy chain sequence comprises mouse framework residues at one or more positions for antigen binding. Other embodiments of the invention provide anti-CD3 Fab antibody wherein the heavy chain sequence comprises mouse framework residues at positions 30, 49, 77 or 93 (according to Kabat numbering). Another embodiment of the invention provides anti-CD3 Fab antibody wherein the light chain sequence comprises mouse framework residues at one or more positions. Other embodiment of the invention provides anti-CD3 Fab antibody wherein the light chain sequence comprises framework residues at positions 36, 46, 49, 57 or 58 (according to Kabat numbering).

In some embodiments of the invention the anti-CD3 Fab antibody includes a linker. In another embodiment the invention provides an anti-CD3 Fab antibody wherein the linker is a water-soluble polymer. Another embodiment of the invention provides an anti-CD3 Fab antibody wherein the water-soluble polymer comprises poly(ethylene glycol). Other embodiments of the invention provide an anti-CD3 Fab antibody wherein the water-soluble polymer is linear or branched. Another embodiment of the invention provides anti-CD3 Fab antibody wherein the water-soluble polymer is linked to a non-naturally encoded amino acid present in the antibody. In some embodiments, the linker is attached to the anti-CD3 Fab antibody via the side chain of the non-natural amino acid. Embodiments of the invention provide an anti-CD3 Fab antibody comprising at least two amino acids linked to a water-soluble polymer comprising a poly(ethylene glycol). Another embodiment of the invention provides an anti-CD3 Fab antibody wherein at least one amino acid linked to said water-soluble polymer is a non-naturally encoded amino acid. Another embodiment of the invention provides an anti-CD3 Fab antibody comprising one or more a poly(ethylene glycol). Another embodiment of the invention provides anti-CD3 Fab antibody wherein the poly(ethylene glycol) is between 1 kDa and 100 kDa. Another embodiment of the invention provides an anti-CD3 Fab antibody comprising one or more folate and one or more poly(ethylene glycol). Another embodiment of the invention provides an anti-CD3 Fab antibody comprising two folate and two poly(ethylene glycol).

In another embodiment the invention provides a method for optimizing cell kill in a cell expressing high folate receptor numbers comprising an anti-CD3 Fab antibody wherein the antibody comprises one or more folate; and wherein one or more non-naturally encoded amino acid is incorporated into the antibody. In another embodiment the invention provides a method for optimizing tumor cell killing which express high folate receptor numbers by the redirected T cells comprising an anti-CD3 Fab antibody wherein the antibody comprises one or more folate; and wherein one or more non-naturally encoded amino acid is incorporated into the antibody. In another embodiment method further comprising one or more of a water-soluble polymer. Another embodiment of the invention provides the method wherein the water-soluble polymer comprises poly(ethylene glycol). In another is provided a method wherein the water-soluble polymer is linear or branched. The poly(ethylene glycol) is between 1 kDa and 100 kDa. The poly(ethylene glycol) is 5, 10, 20, 30, 40, 50 or 60 kDa. In another embodiment the folate receptor number is equal or greater than 10,000.

Another embodiment of the invention provides a method for reducing cytotoxicity in a cell. Another embodiment of the invention provides a method for reducing cytotoxicity in a cell by optimizing or reducing affinity of the anti-CD3 antibody for its target for T cell recruitment. Another embodiment of the invention provides a method for increasing cytotoxicity of the tumor cells by conjugating more than one Folate to preferentially bind to tumor cells prior to T-cell binding. Another embodiment of the invention provides a method for improving serum half-life of an anti CD3 Fab antibody. Another embodiment of the invention provides a method for improving serum half-life of an anti CD3 Fab antibody by conjugating the Fab to a pharmacokinetic (PK) extending molecule including but not limited to HSA, C12-C16 acyl chains, XTEN, or water-soluble polymers such as PEG. Another embodiment provides a method for recruiting cytotoxic T cells to FR+ tumor cells. Another embodiment provides a method for improving efficacy, reducing toxicity, improving PK properties, improving affinity, improving TAA binding, improving in-vivo T½, improving in vitro activity, improving serum half-life, and/or improving in vivo activity. Another embodiment provides a method for improving efficacy. Another embodiment provides a method for reducing toxicity. Another embodiment provides a method for improving PK properties. Another embodiment provides a method for improving affinity. Another embodiment provides a method for improving TAA binding. Another embodiment provides a method for improving in-vivo TI/2. Another embodiment provides a method for improving in vitro activity. Another embodiment provides a method for improving in vivo activity.

Another embodiment of the invention provides an anti-CD3 Fab antibody wherein the heavy chain or light chain sequence comprises human germline mutations at one or more positions. Embodiments of the invention provide an anti-CD3 Fab antibody wherein the heavy chain sequence human germline mutation is at positions 35 or 52 (according to Kabat numbering). Another embodiment of the invention provides an anti-CD3 Fab antibody wherein the light chain sequence human germline mutation is at position 53 (according to Kabat numbering).

Another embodiment of the invention provides an anti-CD3 Fab antibody comprising a PEG folate linker having the structure according to compound 29A, 29B, 29C, 29D, 29E, 30A, 30B, 30C, 30D and 30E.

In another embodiment is provided a method of treating a patient having a disease or condition in a cell expressing high folate receptor number comprising administering to the patient a therapeutically-effective amount of the anti-CD3 Fab antibody disclosed herein. In another embodiment of the invention is provided a bispecific anti-CD3 Fab comprising two folate and two PEGylated molecules. In another embodiment the bispecific anti-CD3 Fab antibody further comprising a non-naturally encoded amino acid site specifically incorporated. The invention provides a method of treating cancer by administering to a patient a therapeutically-effective amount of an anti-CD3 antibody of the invention. In some embodiments, the cancer is ovarian cancer. In some embodiments the ovarian cancer is an epithelial, stromal and germ cell tumor. In some embodiments the ovarian cancer comprises fallopian tube cancer and primary peritoneal carcinoma. In some embodiments, the cancer is characterized by high expression of folate receptor-alpha (FOLR1), such as ovarian cancer. In some embodiments, the cancer is treated by recruiting cytotoxic T cells to folate receptor positive (FR+) tumor cells. The invention provides a method of treating inherited diseases by administering to a patient a therapeutically-effective amount of an anti-CD3 antibody of the invention. The invention provides a method of treating AIDs by administering to a patient a therapeutically-effective amount of an anti-CD3 antibody of the invention. The invention provides a method of treating diabetes by administering to a patient a therapeutically-effective amount of an anti-CD3 antibody of the invention. Said anti-CD3 antibody of the invention can be a bispecific antibody comprising an anti-CD3 Fab antibody, optionally wherein the anti-CD3 Fab antibody is conjugated to two folate and two PEGylated molecules. In a further embodiment, a non-naturally encoded amino acid is site specifically incorporated into said anti-CD3 Fab antibody and conjugation to the two folate and two PEGylated molecules is via the side chain of the non-natural amino acid.

The anti-CD3 antibodies of the invention are for use in treating a disease or condition in a cell expressing high folate receptor number. The anti-CD3 antibodies of the invention are for use in treating cancer. In some embodiments, the cancer is ovarian cancer. In some embodiments ovarian cancer is an epithelial, stromal and germ cell tumor. In some embodiments the ovarian cancer comprises fallopian tube cancer and primary peritoneal carcinoma. In some embodiments, the cancer is characterized by high expression of folate receptor-alpha (FOLR1), such as ovarian cancer. In some embodiments, the cancer is treated by recruiting cytotoxic T cells to folate receptor positive (FR+) tumor cells. The anti-CD3 antibodies of the invention are for use in treating inherited diseases. The anti-CD3 antibodies of the invention are for use in treating AIDS. The anti-CD3 antibodies of the invention are for use in treating diabetes. Said anti-CD3 antibody of the invention can be a bispecific antibody comprising an anti-CD3 Fab antibody, optionally wherein the anti-CD3 Fab antibody is conjugated to two folate and two PEGylated molecules. In a further embodiment, a non-naturally encoded amino acid is site specifically incorporated into said anti-CD3 Fab antibody and conjugation to the two folate and two PEGylated molecules is via the side chain of the non-natural amino acid. The anti-CD3 antibodies of the invention can be used in the manufacture of a medicament for treating a disease or condition in a cell expressing high folate receptor number. The anti-CD3 antibodies of the invention can be used in the manufacture of a medicament for treating cancer. In some embodiments, the cancer is ovarian cancer. In some embodiments ovarian cancer is an epithelial, stromal and germ cell tumor. In some embodiments the ovarian cancer comprises fallopian tube cancer and primary peritoneal carcinoma. In some embodiments, the cancer is characterized by high expression of folate receptor-alpha (FOLR1), such as ovarian cancer. In some embodiments, the cancer is treated by recruiting cytotoxic T cells to folate receptor positive (FR+) tumor cells. The anti-CD3 antibodies of the invention can be used in the manufacture of a medicament for treating inherited diseases. The anti-CD3 antibodies of the invention can be used in the manufacture of a medicament for treating AIDS. The anti-CD3 antibodies of the invention can be used in the manufacture of a medicament for treating diabetes. Said anti-CD3 antibody of the invention can be a bispecific antibody comprising an anti-CD3 Fab antibody, optionally wherein the anti-CD3 Fab antibody is conjugated to two folate and two PEGylated molecules. In a further embodiment, a non-naturally encoded amino acid is site specifically incorporated into said anti-CD3 Fab antibody and conjugation to the two folate and two PEGylated molecules is via the side chain of the non-natural amino acid.

The invention disclosure provides an anti-CD3 antibody or antibody fragment or variant having one or more non-naturally encoded amino acids incorporated into the antibody or fragment or variant. The anti-CD3 antibody or antibody fragment or variant can be include but are not limited to Fv, Fc, Fab, and (Fab')$_2$, single chain Fv (scFv), diabodies, triabodies, tetrabodies, bifunctional hybrid antibodies, CDR1, CDR2, CDR3, combinations of CDRs, variable regions, framework regions, constant regions, heavy chains, light chains, alternative scaffold non-antibody molecules, bispecific antibodies and the like. In some embodiments, the anti-CD3 antibody or antibody fragment or variant is an anti-CD3 Fab antibody, fragment or variant.

The invention disclosure provides bispecific antibody conjugates comprising anti-CD3 antibody or antibody fragment. The present invention discloses herein bispecific antibody conjugates comprising anti-CD3 Fab antibody or antibody fragment having one or more non-naturally encoded amino acids incorporated. Further disclosed herein are bispecific antibody conjugates comprising anti-CD3 Fab antibody or antibody fragment and one or more Folate molecules, wherein one or more non-naturally encoded amino acids is site-specifically incorporated into the anti-CD3 Fab antibody. Disclosed herein are bispecific antibody conjugates comprising anti-CD3 Fab antibody or antibody fragment, one or more Folate molecules, and one or more PEG molecules, wherein one or more non-naturally encoded amino acids is site-specifically incorporated into the anti-CD3 Fab antibody. Disclosed herein is an anti-CD3 Fab bispecific antibody comprising: an antibody or antibody fragment; one or more small molecules; and one or more linkers, wherein the antibody or antibody fragment is linked to the one or more small molecules by the one or more linkers and wherein the small molecules is a one or more Folate or one or more DUPA molecule or analog or derivative. The antibody or antibody fragment may be site-specifically linked to the one or more Folate or one or more DUPA molecules by the one or more linkers. The antibody or antibody fragment may comprise one or more non-natural amino acids. The antibody or antibody fragment may be linked to the one or more Folate or one or more DUPA molecules by the one or more linkers to the one or more non-natural amino acids. The non-natural amino acid may be site-specifically incorporated into the antibody. The antibody or antibody fragment may be linked to the one or more Folate or DUPA molecules by one or more PEG molecules to the one or more non-natural amino acids. The antibody or antibody fragment may alternatively be linked to the one or more Folate or one or more DUPA molecules by the one or more linkers to a natural amino acid. The antibody or antibody fragment may be an anti-CD3 Fab.

Disclosed herein are bispecific antibody conjugates comprising: an anti-CD3 Fab; one or more Folate molecules; and one or more linkers, wherein the anti-CD3 Fab is linked to the one or more Folate molecules by the one or more linkers. The anti-CD3 Fab may comprise one or more non-natural amino acids. The one or more non-natural amino acids may replace a natural amino acid of the anti-CD3 Fab. Disclosed herein are bispecific antibody conjugates comprising: an anti-CD3 Fab; one or more DUPA molecules; and one or more linkers, wherein the anti-CD3 Fab is linked to the one or more DUPA molecules by the one or more linkers. The anti-CD3 Fab may comprise one or more non-natural amino acids. The one or more non-natural amino acids may replace a natural amino acid of the anti-CD3 Fab.

BRIEF DESCRIPTION OF THE DRAWINGS

The novel features of the invention are set forth with particularity in the appended claims. A better understanding of the features and advantages of the present invention disclosure will be obtained by reference to the following detailed description that sets forth illustrative embodiments, in which the principles of the invention are utilized, and the accompanying drawings provided.

(FIG. 2A), Fab1 titration; (FIG. 2B), Fab 2 titration; (FIG. 2C), Fab 3 titration; (FIG. 2D), Fab 4 titration; (FIG. 2E), Fab 5 titration; and (FIG. 2F), Fab 6 titration.

FIG. 6A shows binding of Round 1 and FIG. 6B shows binding of Round 2 low-affinity variants of anti-CD3 Fab-HK129-Folate molecules purified from E. coli cells to human CD3. Fab1-HK129-Folate, parent control, is included as a positive control.

FIG. 7A shows binding of Round 1 and FIG. 7B shows binding of Round 2 low-affinity variants of anti-CD3 Fab-HK129-Folate molecules purified from E. coli cells to cyno CD3. Fab1-HK129-Folate, parent control, is included as a positive control.

FIG. 10A shows activation of T cell markers CD25 and CD69 without SKOV-3 cells by various low affinity anti-CD3 Fab-HK129-Folate molecules. FIG. 10(B) shows activation of T cell markers CD25 and CD69 with SKOV-3 cells by various low affinity anti-CD3 Fab-HK129-Folate molecules.

FIG. 12A is a representative example of Folate-PEG ligands; FIG. 12B is a representative example of Folate-Branched PEG ligands; FIGS. 12C-12D are representative illustrations of the CD3-Folate bispecifics with PEG conjugates; FIG. 12E is a representative illustration of CD3-Folate bispecific with C-terminal PEGylation; and FIG. 12F is a representative illustration of CD3-Folate bispecific with C-terminal PEGylation by CD3-Fab cross-linking.

FIGS. 13A-13D depict CD3 Fab-Folate conjugates in the presence and absence of PEGylation. 13A and 13B show SDS-PAGE gel electrophoresis analysis of single and dual conjugated anti-CD3 Fab compositions; FIG. 13C shows SDS-PAGE gel electrophoresis analysis of anti-CD3 Fab-Folate C-terminal PEG conjugates; FIG. 13D shows in vitro cytotoxicity of anti-CD3 Fab-Folate C-terminal PEG conjugates in KB, OV-90 and SKOV-3 cells.

FIG. 15A shows the anti-CD3 Fab-Folate bispecific antibodies selectively kill FOLRα expressing SKOV3 cells in the presence of 20 nM folic acid and FIG. 15B shows selective kill at 50 nM folic acid.

FIG. 18A shows in vitro macrophage cytotoxicity by single folate containing anti-CD3 Fab-Folate bispecific antibodies. The arrow and number denote $IC_{50}$ fold differences between M1 and M2 macrophages. The dotted lines indicate Fab1-HK129-Folate in M1 and M2 and solid lines indicate Fab1-HK129-5KPEG-Folate in M1 and M2. FIG. 18B shows in vitro macrophage cytotoxicity by double folate containing anti-CD3 Fab-Folate bispecific antibodies. The arrow and number denote $IC_{50}$ fold differences between M1 and M2 macrophages. The dotted lines indicate Fab1-HK129-LL157-BiFolate in M1 and M2 and solid lines indicate Fab1-HK129-LL157-BiFolate-Bi5KPEG in M1 and M2.

FIG. 19A shows tumor volume and FIG. 19B shows mass/body weight; expression of human CD45 and induction of TILs are shown in FIGS. 19C and 19D, respectively.

FIG. 20A shows tumor volume and FIG. 20B shows 0 mass/body weight; expression of human CD45 and induction of TILs are shown in FIGS. 20C and 20D, respectively.

FIGS. 21A-21F depict anti-tumor efficacy by multiple dose administration of CD3-Folate bispecific antibodies in human cervical tumors derived from the KB cell line (FIG. 21A shows tumor growth, FIG. 21B shows body weight), and expression of T-cell activation markers CD25 (FIG. 21C), CD69 (FIG. 21D), CD45 (FIG. 21E), and CD3 (FIG. 21F).

FIG. 22A shows tumor growth and FIG. 22B shows body weight.

FIG. 23A shows tumor growth and FIG. 23B shows body weight.

DEFINITIONS

Figure 1:
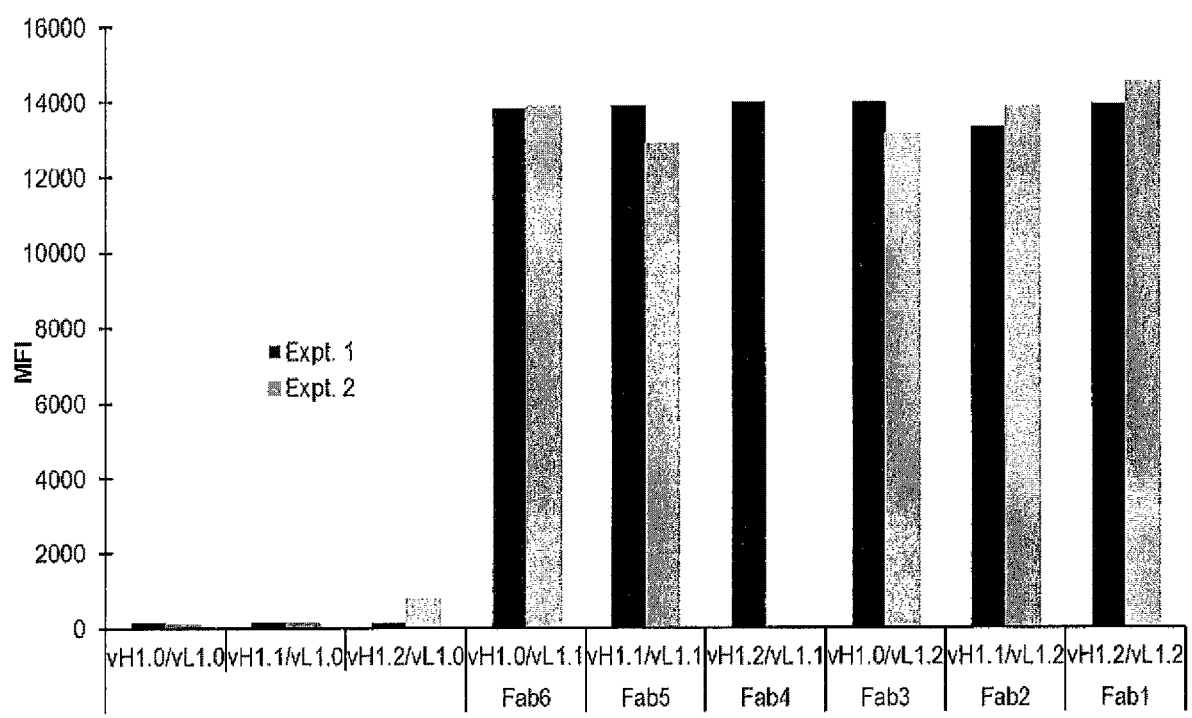
FIG. 1 depicts humanized anti-CD3 Fab binding to human PBMC. Binding of humanized anti-CD3 Fabs expressed in HEK293 cells to human PBMC (2 experiments) is shown. A total of 9 Fabs were tested by combining 3 vH and 3 vL chain sequences. 3 Fabs containing vL1.0 chain lost binding to human CD3 with any vH chain combinations.
Figure 2A:
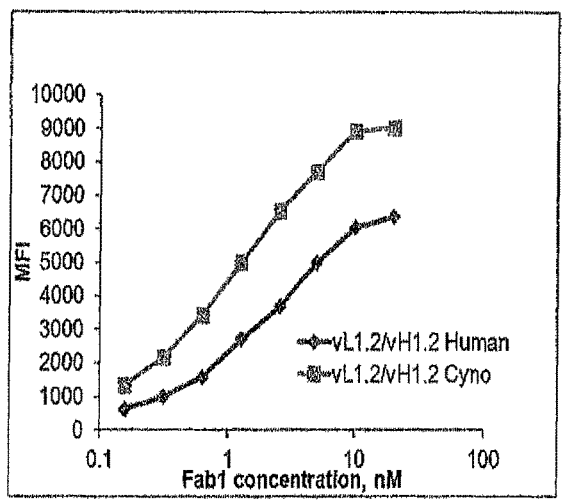
FIGS. 2A-2F depict titration of humanized anti-CD3 Fab binding to human and cyno PBMCs.
Figure 2B:
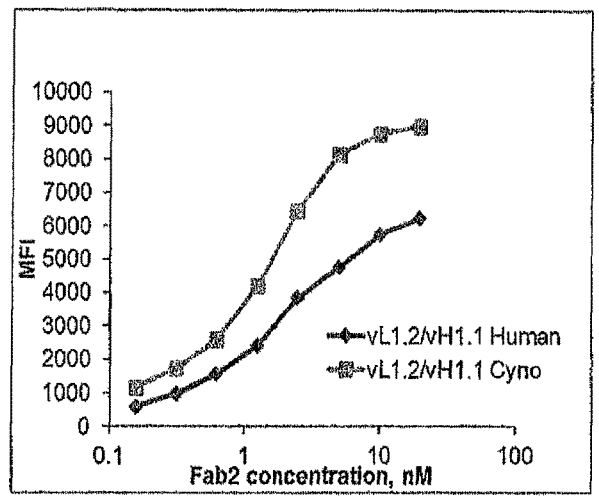
Figure 2C:
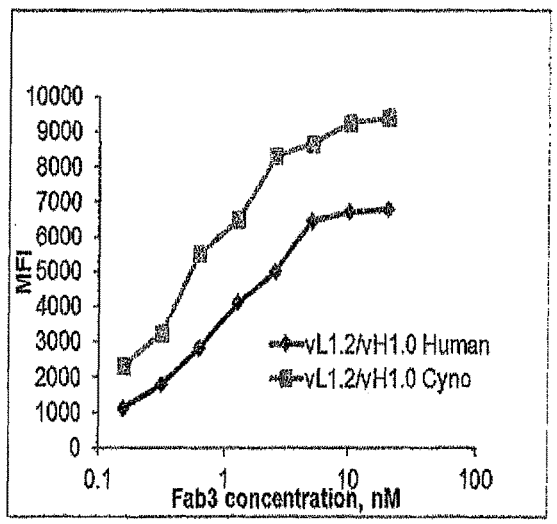
Figure 2D:
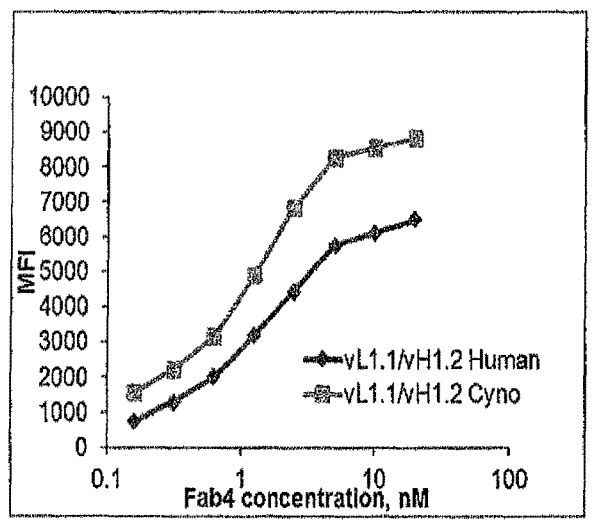
Figure 2E:
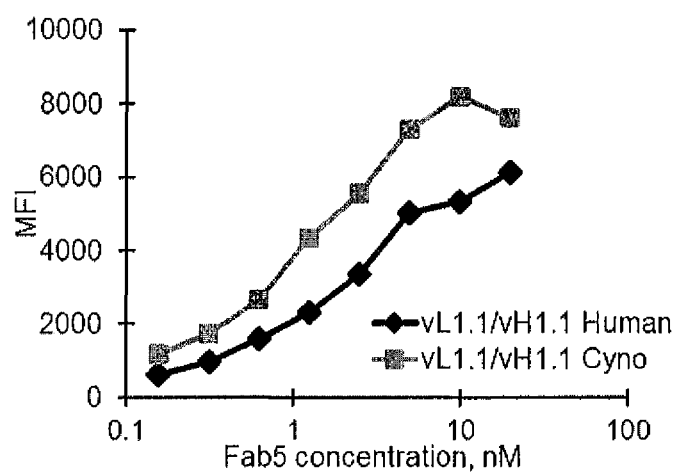
Figure 2F:
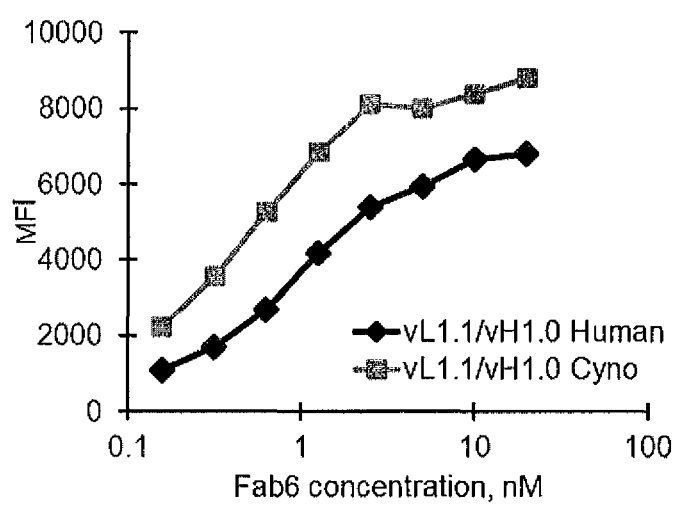

It is to be understood that this invention is not limited to the particular methodology, protocols, cell lines, constructs, and reagents described herein and as such may vary. It is also to be understood that the terminology used herein is for the purpose of describing particular embodiments only and is not intended to limit the scope of the present invention, which will be limited only by the appended claims.

As used herein and in the appended claims, the singular forms "a," "an," and "the" include plural reference unless the context clearly indicates otherwise. Thus, for example, reference to an "anti-CD3 Fab" or "anti-CD3 Fab-Folate antibody" is a reference to one or more such proteins and includes equivalents thereof known to those skilled in the art, and so forth. The terms "PEG-Folate" or "Folate-PEG" and the terms "BiPEG-BiFolate" or "BiFolate-BiPEG" are used interchangeably herein.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

The term "substantially purified" refers to anti-CD3 Fab antibody that may be substantially or essentially free of components that normally accompany or interact with the protein as found in its naturally occurring environment, i.e. a native cell, or host cell in the case of recombinantly produced anti-CD3 antibody. Anti-CD3 antibody that may be substantially free of cellular material includes preparations of protein having less than about 30%, less than about 25%, less than about 20%, less than about 15%, less than about 10%, less than about 5%, less than about 4%, less than about 3%, less than about 2%, or less than about 1% of contaminating protein. When the anti-CD3 antibody or variant thereof is recombinantly produced by the host cells, the protein may be present at about 300, about 25%, about 20%, about 15%, about 10%, about 5%, about 4%, about 3%, about 2%, or about 1% or less of the dry weight of the cells. When the anti-CD3 antibody or variant thereof is recombinantly produced by the host cells, the protein may be present in the periplasm and/or culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. Thus, "substantially purified" anti-CD3 antibody as produced by the methods of the present invention may have a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

A "recombinant host cell" or "host cell" refers to a cell that includes an exogenous polynucleotide, regardless of the method used for insertion, for example, direct uptake, transformation, transduction, f-mating, or other methods known in the art to create recombinant host cells. The exogenous polynucleotide may be maintained as a nonintegrated vector, for example, a plasmid, or alternatively, may be integrated into the host genome.

Antibodies are proteins, which exhibit binding specificity to a specific antigen. Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in three segments called Complementarity Determining Regions (CDRs) both in the light chain and the heavy chain variable domains. The more highly conserved portions of the variable domains are called the framework regions (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al., Sequences of Proteins of Immunological Interest, 5th Ed. Public Health Service, National Institutes of Health, Bethesda, MD. (1991)).

The constant domains are not involved directly in binding an antibody to an antigen but exhibit various effector functions. Depending on the amino acid sequence of the constant region of their heavy chains, antibodies or immunoglobulins can be assigned to different classes. There are five major classes of immunoglobulins: IgA, IgD, IgE, IgG and IgM, and several of these may be further divided into subclasses (isotypes), e.g. IgG as IgG1, IgG2, IgG3, and IgG4; IgA as IgA1 and IgA2. The heavy chain constant regions that correspond to the different classes of immunoglobulins are called α, δ, ε, γ and μ, respectively. The light chain constant regions that correspond to the different classes of immunoglobulins are called κ, and λ, respectively. Of the various human immunoglobulin classes, only human IgG1, IgG2, IgG3 and IgM are known to activate complement. The immunoglobulin may be selected from an IgG, IgA, IgD, IgE, IgM or a fragment or a modification thereof.

In vivo, affinity maturation of antibodies is driven by antigen selection of higher affinity antibody variants which are made primarily by somatic hypermutagenesis. A "repertoire shift" also often occurs in which the predominant germline genes of the secondary or tertiary response are seen to differ from those of the primary or secondary response.

The affinity maturation process of the immune system may be replicated by introducing mutations into antibody genes in vitro and using affinity selection to isolate mutants with improved affinity. Such mutant antibodies can be displayed on the surface of filamentous bacteriophage or microorganisms such as E. coli, yeast, and antibodies can be selected by their affinity for antigen or by their kinetics of dissociation (off-rate) from antigen. Hawkins et al. J. Mol. Biol. 226:889-896 (1992). CDR walking mutagenesis has been employed to affinity mature human antibodies which bind the human envelope glycoprotein gp120 of human immunodeficiency virus type 1 (HIV-1) (Barbas III et al. PNAS (USA) 91: 3809-3813 (1994); and Yang et al. J. Mol. Biol. 254:392-403 (1995)); and an anti-c-erbB-2 single chain Fv fragment (Schier et al. J. Mol. Biol. 263:551567 (1996)). Antibody chain shuffling and CDR mutagenesis were used to affinity mature a high-affinity human antibody directed against the third hypervariable loop of HIV (Thompson et al. J. Mol. Biol. 256:77-88 (1996)). Balint and Larrick Gene 137:109-118 (1993) describe a computer-assisted oligodeoxyribonucleotide-directed scanning mutagenesis whereby all CDRs of a variable region gene are simultaneously and thoroughly searched for improved variants. An αvβ3-specific humanized antibody was affinity matured using an initial limited mutagenesis strategy in which every position of all six CDRs was mutated followed by the expression and screening of a combinatorial library including the highest affinity mutants (Wu et al. PNAS (USA) 95: 6037-6-42 (1998)). Phage displayed antibodies are reviewed in Chiswell and McCafferty TIBTECH 10:80-84 (1992); and Rader and Barbas III Current Opinion in Biotech. 8:503-508 (1997). In each case where mutant antibodies with improved affinity compared to a parent antibody are reported in the above references, the mutant antibody has amino acid substitutions in a CDR.

By "affinity maturation" herein is meant the process of enhancing the affinity of an antibody for its antigen. Methods for affinity maturation include but are not limited to computational screening methods and experimental methods.

By "antibody" herein is meant a protein consisting of one or more polypeptides substantially encoded by all or part of the antibody genes. The immunoglobulin genes include, but are not limited to, the kappa, lambda, alpha, gamma (IgG1, IgG2, IgG3, and IgG4), delta, epsilon and mu constant region genes, as well as the myriad immunoglobulin variable region genes. Antibody herein is meant to include full-length antibodies and antibody fragments and include antibodies that exist naturally in any organism or are engineered (e.g. are variants). Antibody disclosed herein may be human, humanized, engineered, non-human, and/or chimeric antibody. Humanized antibodies and methods of making such as well know in the art. (See, for example, U.S. Pat. Nos. 5,821,337; 7,527,791; 6,982,321; 7,087,409; 5,766, 886). Generally, a humanized antibody comprises one or more variable domains in which CDRs or portions thereof are derived from a non-human antibody, and framework regions or portions thereof are derived from human antibody sequences. A humanized antibody can optionally comprise at least a portion of a human constant region. In some embodiments, framework residues in a humanized antibody can be substituted with corresponding residues from a non-human antibody—the antibody from which the CDR residues are derived—to restore or improve antibody specificity or affinity, for example. Chimeric antibodies may refer to antibodies generated through combining or joining two or more antibody genes originally encoded for separate antibodies. For example, chimeric antibodies may be generated through combining or joining two or more antibody genes, (or fragments therefrom), from human, bovine or murine species. In some embodiments, at least a portion of the antibody or antibody fragment may be from a human. or cynomolgus monkey but is not limited to such. In certain embodiments, the antibodies disclosed herein may be cross-species reactive, for example an antibody may recognize a human antigen and a cynomolgus monkey antigen (e.g., a human/cyno antibody).

By "antibody fragment" is meant any form of an antibody other than the full-length form. Antibody fragments herein include antibodies that are smaller components that exist within full-length antibodies, and antibodies that have been engineered. Antibody fragments include but are not limited to Fv, Fc, Fab, and (Fab')$_2$, single chain Fv (scFv), diabodies, triabodies, tetrabodies, bifunctional hybrid antibodies, CDR1, CDR2, CDR3, combinations of CDRs, variable regions, framework regions, constant regions, heavy chains, light chains, alternative scaffold non-antibody molecules, bispecific antibodies and the like (Maynard & Georgiou, 2000, Annu. Rev. Biomed. Eng. 2:339-76; Hudson, 1998, Curr. Opin. Biotechnol. 9:395-402). Unless specifically noted otherwise, statements and claims that use the term "antibody" or "antibodies" may specifically include "antibody fragment" and "antibody fragments". In certain embodiments the 'anti-CD3 antibody', 'anti-CD3 Fab', 'anti-CD3 Fab antibody' and 'anti-CD3 Fab variant' are antibody fragments as defined herein.

By "computational screening method" herein is meant any method for designing one or more mutations in a protein, wherein said method utilizes a computer to evaluate the energies of the interactions of potential amino acid side chain substitutions with each other and/or with the rest of the protein.

By "full-length antibody" herein is meant the structure that constitutes the natural biological form of an antibody H and/or L chain. In most mammals, including humans and mice, this form is a tetramer and consists of two identical pairs of two immunoglobulin chains, each pair having one light and one heavy chain, each light chain comprising immunoglobulin domains $V_L$ and $C_L$, and each heavy chain comprising immunoglobulin domains $V_H$, C$\gamma$1, C$\gamma$2, and C$\gamma$3. In each pair, the light and heavy chain variable regions ($V_L$ and $V_H$) are together responsible for binding to an antigen, and the constant regions ($C_L$, C$\gamma$1, C$\gamma$2, and C$\gamma$3, particularly C$\gamma$2, and C$\gamma$3) are responsible for antibody effector functions. In some mammals, for example in camels and llamas, full-length antibodies may consist of only two heavy chains, each heavy chain comprising immunoglobulin domains $V_H$, C$\gamma$2, and C$\gamma$3.

By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full-length antibodies, antibody fragments, and individual immunoglobulin domains including but not limited to $V_H$, C$\gamma$1, C$\gamma$2, C$\gamma$3, $V_L$, and $C_L$.

By "immunoglobulin (Ig) domain" herein is meant a protein domain consisting of a polypeptide substantially encoded by an immunoglobulin gene. Ig domains include but are not limited to $V_H$, C$\gamma$1, C$\gamma$2, C$\gamma$3, $V_L$, and $C_L$.

By "variant protein sequence" as used herein is meant a protein sequence that has one or more residues that differ in amino acid identity from another similar protein sequence. Said similar protein sequence may be the natural wild type protein sequence, or another variant of the wild type sequence. In general, a starting sequence is referred to as a "parent" sequence and may either be a wild type or variant sequence. For example, preferred embodiments of the present invention may utilize humanized parent sequences upon which computational analyses are done to make variants.

By "variable region" of an antibody herein is meant a polypeptide or polypeptides composed of the $V_H$ immunoglobulin domain, the $V_L$ immunoglobulin domains, or the $V_H$ and $V_L$ immunoglobulin domains including variants. Variable region may refer to such polypeptides in isolation, as an Fv fragment, as a scFv fragment, as this region in the context of a larger antibody fragment, or as this region in the context of a full-length antibody or an alternative, non-antibody scaffold molecule.

With respect to anti-CD3 Fab antibody of the invention, the term "antigenically specific" or "specifically binds" refers to anti-CD3 antibody that binds to one or more epitopes of an antigen or binding partner of interest, but which do not substantially recognize and bind other molecules in a sample containing a mixed population of antigens.

The term "bispecific anti-CD3 antibody" or "multispecific anti-CD3 antibody" as used herein refers to an anti-CD3 antibody comprising two or more antigen-binding sites or binding partner binding sites, a first binding site having affinity for a first antigen or epitope and a second binding site having binding affinity for a second antigen or epitope distinct from the first. In some embodiments, the bispecific anti-CD3 antibody has a binding site which binds to CD3 and a binding site or binding sites which have binding affinity for a different antigen or epitope.

The term "epitope" as used herein refers to a site on an antigen or binding partner that is recognized by anti-CD3 Fab antibody. An epitope may be a linear or conformationally formed sequence or shape of amino acids, if the antigen comprises a polypeptide. An epitope may also be any location on any type of antigen where an anti-CD3 antibody binds to the antigen.

As used herein, "antigen-binding polypeptide" or "anti-CD3 Fab antibody" shall include those polypeptides and proteins that have at least the biological activity of specific binding to a particular binding partner such as antigen, as well as CD3 analogs, CD3 isoforms, CD3 mimetics, CD3 fragments, hybrid CD3 proteins, fusion proteins, oligomers and multimers, homologues, glycosylation pattern variants, and muteins, thereof, regardless of the biological activity of same, and further regardless of the method of synthesis or manufacture thereof including, but not limited to, recombinant (whether produced from cDNA, genomic DNA, synthetic DNA or other form of nucleic acid), in vitro, in vivo, by microinjection of nucleic acid molecules, synthetic, transgenic, and gene activated methods. Specific examples of anti-CD3 antibody include, but are not limited to, antibody molecules, heavy chain, light chain, variable region, CDR, Fab, scFv, alternative scaffold non-antibody molecules, ligands, receptors, peptides, or any amino acid sequence that binds to an antigen.

Antigen-binding polypeptides include the pharmaceutically acceptable salts and prodrugs, and prodrugs of the salts, polymorphs, hydrates, solvates, biologically-active fragments, biologically-active variants and stereoisomers of the naturally-occurring human anti-CD3 antibody as well as agonist, mimetic, and antagonist variants of the naturally-occurring human anti-CD3 antibody and polypeptide fusions thereof. Fusions comprising additional amino acids at the amino terminus, carboxyl terminus, or both, are encompassed by the term "antigen-binding polypeptide." Exemplary fusions include, but are not limited to, e.g., methionyl anti-CD3 antibody in which a methionine is linked to the N-terminus of anti-CD3 antibody resulting from the recombinant expression, fusions for the purpose of purification (including but not limited to poly-histidine or affinity epitopes), fusions for the purpose of linking anti-CD3 antibody's to other biologically active molecules, fusions with serum albumin binding peptides, and fusions with serum proteins such as serum albumin.

The term "antigen" or "binding partner" refers to a substance that is the target for the binding activity exhibited by the anti-CD3 antibody. Virtually any substance may be an antigen or binding partner for an anti-CD3 Fab antibody.

A naturally produced antibody (Ab) is a tetrameric structure consisting of two identical immunoglobulin (Ig) heavy chains and two identical light chains. The heavy and light chains of an Ab consist of different domains. Each light chain has one variable domain (VL) and one constant domain (CL), while each heavy chain has one variable domain (VH) and three constant domains (CH). Each domain, consisting of about 110 amino acid residues, is folded into a characteristic β-sandwich structure formed from two β-sheets packed against each other, the immunoglobulin fold. The VL domains each have three complementarity determining regions (CDR1-3) and the VH domains each have up to three complementarity determining regions (CDR1-3), that are loops, or turns, connecting β-strands at one end of the domains. The variable regions of both the light and heavy chains generally contribute to antigen specificity, although the contribution of the individual chains to specificity is not necessarily equal. Antibody molecules have evolved to bind to a large number of molecules by using randomized CDR loops.

Functional substructures of Abs can be prepared by proteolysis and by recombinant methods. They include the Fab fragment, which comprises the VH-CH1 domains of the heavy chain and the VL-CL1 domains of the light chain joined by a single interchain disulfide bond, and the Fv fragment, which comprises only the VH and VL domains, and the Fe portion which comprises the non-antigen binding region of the molecule. In some cases, a single VH domain retains significant affinity for antigen (Ward et al., Nature 341, 554-546, 1989). It has also been shown that a certain monomeric κ light chain will specifically bind to its antigen. (L. Masa et al., PNAS 91:893-8%, 1994). Separated light or heavy chains have sometimes been found to retain some antigen-binding activity as well (Ward et al., Nature 341, 554-546, 1989).

Another functional substructure is a single chain Fv (scFv), comprised of the variable regions of the immunoglobulin heavy and light chain, covalently connected by a peptide linker (S-z Hu et al., Cancer Research, 56, 3055-3061, 1996). These small (Mr 25,000 Da) proteins generally retain specificity and affinity for antigen in a single polypeptide and can provide a convenient building block for larger, antigen-specific molecules. The short half-life of scFvs in the circulation limits their therapeutic utility in many cases.

A small protein scaffold called a "minibody" was designed using a part of the Ig VH domain as the template (Pessi et al., Nature 362, 367-369, 1993). Minibodies with high affinity (dissociation constant ($K_d$) about $10^{-7}$ M) to interleukin-6 were identified by randomizing loops corresponding to CDR1 and CDR2 of VH and then selecting mutants using the phage display method (Martin et al., EMBO J. 13, 5303-5309, 1994).

Camels often lack variable light chain domains when IgG-like material from their serum is analyzed, suggesting that sufficient antibody specificity and affinity can be derived from VH domains (three or four CDR loops) alone. "Camelized" VH domains with high affinity have been made, and high specificity can be generated by randomizing only the CDR3.

An alternative to the "minibody" is the "diabody." Diabodies are small bivalent and bispecific antibody fragments, having two antigen-binding sites. The fragments comprise a heavy-chain variable domain ($V_H$) connected to a light-chain variable domain ($V_L$) on the same polypeptide chain ($V_H$-$V_L$). Diabodies are similar in size to the Fab fragment. By using a linker that is too short to allow pairing between the two domains on the same chain, the domains are forced to pair with the complementary domains of another chain and create two antigen-binding sites. These dimeric antibody fragments, or "diabodies," are bivalent and bispecific. (See, P. Holliger et al., PNAS 90:6444-6448, 1993).

CDR peptides and organic CDR mimetics have been made (Dougall et al., 1994, Trends Biotechnol. 12, 372-379). CDR peptides are short, typically cyclic, peptides which correspond to the amino acid sequences of CDR loops of antibodies. CDR loops are responsible for antibody-antigen interactions. CDR peptides and organic CDR mimetics have been shown to retain some binding affinity (Smyth & von Itzstein, J. Am. Chem. Soc. 116, 2725-2733, 1994). Mouse CDRs have been grafted onto the human Ig framework without the loss of affinity (Jones et al., Nature 321, 522-525, 1986; Riechmann et al., 1988).

In the human body, specific Abs are selected and amplified from a large library (affinity maturation). The processes can be reproduced in vitro using combinatorial library technologies. The successful display of Ab fragments on the surface of bacteriophage has made it possible to generate and screen a vast number of CDR mutations (McCafferty et al., Nature 348, 552-554, 1990; Barbas et al., Proc. Natl. Acad. Sci. USA 88, 7978-7982, 1991; Winter et al., Annu. Rev. Immunol. 12, 433-455, 1994). An increasing number of Fabs and Fvs (and their derivatives) are produced by this technique. The combinatorial technique can be combined with Ab mimics.

A number of protein domains that could potentially serve as protein scaffolds have been expressed as fusions with phage capsid proteins. Review in Clackson & Wells, Trends Biotechnol. 12:173-184, 1994. Several of these protein domains have already been used as scaffolds for displaying random peptide sequences, including bovine pancreatic trypsin inhibitor (Roberts et al., PNAS 89:2429-2433 1992), human growth hormone (Lowman et al., Biochemistry 30:10832-10838, 1991), (Venturini et al., Protein Peptide Letters 1:70-75 1994), and the IgG binding domain of *Streptococcus* (O'Neil et al., Techniques in Protein Chemistry V (Crabb, L,. ed.) pp. 517-524, Academic Press, San Diego, 1994). These scaffolds have displayed a single randomized loop or region. Tendamistat has been used as a presentation scaffold on the filamentous phage M13 (McConnell and Hoess, J. Mol. Biol. 250:460-470, 1995).

Covalent attachment of the hydrophilic polymer poly (ethylene glycol), abbreviated PEG, is a method of increasing water solubility, bioavailability, increasing serum half-life, increasing therapeutic half-life, modulating immunogenicity, modulating biological activity, or extending the circulation time of many biologically active molecules, including proteins, peptides, and particularly hydrophobic molecules. PEG has been used extensively in pharmaceuticals, on artificial implants, and in other applications where biocompatibility, lack of toxicity, and lack of immunogenicity are of importance. In order to maximize the desired properties of PEG, the total molecular weight and hydration state of the PEG polymer or polymers attached to the biologically active molecule must be sufficiently high to impart the advantageous characteristics typically associated with PEG polymer attachment, such as increased water solubility and circulating half life, while not adversely impacting the bioactivity of the parent molecule.

PEG derivatives are frequently linked to biologically active molecules through reactive chemical functionalities, such as lysine, cysteine and histidine residues, the N-terminus and carbohydrate moieties. Proteins and other molecules often have a limited number of reactive sites available for polymer attachment. Often, the sites most suitable for modification via polymer attachment play a significant role in receptor binding and are necessary for retention of the biological activity of the molecule. As a result, indiscriminate attachment of polymer chains to such reactive sites on a biologically active molecule often leads to a significant reduction or even total loss of biological activity of the polymer-modified molecule. (R. Clark et al., J. Biol. Chem., 271:21969-21977, 1996). To form conjugates having sufficient polymer molecular weight for imparting the desired advantages to a target molecule, prior art approaches have typically involved random attachment of numerous polymer arms to the molecule, thereby increasing the risk of a reduction or even total loss in bioactivity of the parent molecule.

Reactive sites that form the loci for attachment of PEG derivatives to proteins are dictated by the protein's structure. Proteins, including enzymes, are composed of various sequences of alpha-amino acids, which have the general structure $H_2N$—CHR—COOH. The alpha amino moiety ($H_2N$—) of one amino acid joins to the carboxyl moiety (—COOH) of an adjacent amino acid to form amide linkages, which can be represented as —(NH—CHR—CO)$_n$—, where the subscript "n" can equal hundreds or thousands. The fragment represented by R can contain reactive sites for protein biological activity and for attachment of PEG derivatives.

For example, in the case of the amino acid lysine, there exists an —$NH_2$ moiety in the epsilon position as well as in the alpha position. The epsilon —$NH_2$ is free for reaction under conditions of basic pH. Much of the art in the field of protein derivatization with PEG has been directed to developing PEG derivatives for attachment to the epsilon —$NH_2$ moiety of lysine residues present in proteins. ("Polyethylene Glycol and Derivatives for Advanced PEGylation", Nektar Molecular Engineering Catalog, pp. 1-17, 2003). These PEG derivatives all have the common limitation, however, that they cannot be installed selectively among the numerous lysine residues present on the surfaces of proteins. This can be a significant limitation in instances where a lysine residue is important to protein activity, existing in an enzyme active site for example, or in cases where a lysine residue plays a role in mediating the interaction of the protein with other biological molecules, as in the case of receptor binding sites.

A second and equally important complication of existing methods for protein PEGylation is that the PEG derivatives can undergo undesired side reactions with residues other than those desired. Histidine contains a reactive imino moiety, represented structurally as —N(H)—, but many chemically reactive species that react with epsilon —$NH_2$ can also react with —N(H)—. Similarly, the side chain of the amino acid cysteine bears a free sulfhydryl group, represented structurally as —SH. In some instances, the PEG derivatives directed at the epsilon —$NH_2$ group of lysine also react with cysteine, histidine or other residues. This can create complex, heterogeneous mixtures of PEG-derivatized bioactive molecules and risks destroying the activity of the bioactive molecule being targeted. It would be desirable to develop PEG derivatives that permit a chemical functional group to be introduced at a single site within the protein that would then enable the selective coupling of one or more PEG polymers to the bioactive molecule at specific sites on the protein surface that are both well-defined and predictable.

In addition to lysine residues, considerable effort in the art has been directed toward the development of activated PEG reagents that target other amino acid side chains, including cysteine, histidine and the N-terminus. See, e.g., U.S. Pat. No. 6,610,281, which is incorporated by reference herein, and "Polyethylene Glycol and Derivatives for Advanced PEGylation", Nektar Molecular Engineering Catalog, pp. 1-17, 2003. A cysteine residue can be introduced site-selectively into the structure of proteins using site-directed mutagenesis and other techniques known in the art, and the resulting free sulfhydryl moiety can be reacted with PEG derivatives that bear thiol-reactive functional groups. This approach is complicated, however, in that the introduction of a free sulfhydryl group can complicate the expression, folding and stability of the resulting protein. Thus, it would be desirable to have a means to introduce a chemical functional group into bioactive molecules that enables the selective coupling of one or more PEG polymers to the protein while simultaneously being compatible with (i.e., not engaging in undesired side reactions with) sulfhydryls and other chemical functional groups typically found in proteins.

As noted in the art, many of these derivatives that have been developed for attachment to the side chains of proteins, in particular, the —$NH_2$ moiety on the lysine amino acid side chain and the —SH moiety on the cysteine side chain, have proven problematic in their synthesis and use. Some form unstable linkages with the protein that are subject to hydrolysis and therefore decompose, degrade, or are otherwise unstable in aqueous environments, such as in the bloodstream. Some form more stable linkages but are subject to hydrolysis before the linkage is formed, which means that the reactive group on the PEG derivative may be inactivated before the protein can be attached. Some are somewhat toxic and are therefore less suitable for use in vivo. Some are too slow to react to be practically useful. Some result in a loss of protein activity by attaching to sites responsible for the protein's activity. Some are not specific in the sites to which they will attach, which can also result in a loss of desirable activity and in a lack of reproducibility of results. In order to overcome the challenges associated with modifying proteins with poly(ethylene glycol) moieties, PEG derivatives have been developed that are more stable (e.g., U.S. Pat. No. 6,602,498, which is incorporated by reference herein) or that react selectively with thiol moieties on molecules and surfaces (e.g., U.S. Pat. No. 6,610,281, which is incorporated by reference herein). There is clearly a need in the art for PEG derivatives that are chemically inert in physiological environments until called upon to react selectively to form stable chemical bonds.

Recently, an entirely new technology in the protein sciences has been reported, which promises to overcome many of the limitations associated with site-specific modifications of proteins. Specifically, new components have been added to the protein biosynthetic machinery of the prokaryote *Escherichia coli* (*E. coli*) (e.g., L. Wang, et al., Science 292:498-500, 2001) and the eukaryote *Saccharomyces cerevisiae* (*S. cerevisiae*) (e.g., J. Chin et al., Science 301:964-7, 2003), which has enabled the incorporation of non-genetically encoded amino acids to proteins in vivo. A number of new amino acids with novel chemical, physical or biological properties, including photoaffinity labels and photoisomerizable amino acids, keto amino acids, and glycosylated amino acids have been incorporated efficiently and with high fidelity into proteins in *E. coli* and in yeast in response to the amber codon, TAG, using this methodology. See, e.g., J. W. Chin et al., Journal of the American Chemical Society 124:9026-9027, 2002; J. W. Chin, & P. G. Schultz, (2002), ChemBioChem 11:1135-1137; J. W. Chin, et al., PNAS United States of America 99:11020-11024, 2002; and, L.

Wang, & P. G. Schultz, Chem. Comm., 1-10, 2002. These studies have demonstrated that it is possible to selectively and routinely introduce chemical functional groups, such as ketone groups, alkyne groups and azide moieties, that are not found in proteins, that are chemically inert to all of the functional groups found in the 20 common, genetically-encoded amino acids and that may be used to react efficiently and selectively to form stable covalent linkages.

The ability to incorporate non-genetically encoded amino acids into proteins permits the introduction of chemical functional groups that could provide valuable alternatives to the naturally-occurring functional groups, such as the epsilon $-NH_2$ of lysine, the sulfhydryl $-SH$ of cysteine, the imino group of histidine, etc. Certain chemical functional groups are known to be inert to the functional groups found in the 20 common, genetically-encoded amino acids but react cleanly and efficiently to form stable linkages. Azide and acetylene groups, for example, are known in the art to undergo a Huisgen [3+2] cycloaddition reaction in aqueous conditions in the presence of a catalytic amount of copper. See, e.g., Tomoe, et al., (2002) Org. Chem. 67:3057-3064; and, Rostovtsev, et al., (2002) Angew. Chem. Int. Ed. 41:2596-2599. By introducing an azide moiety into a protein structure, for example, one is able to incorporate a functional group that is chemically inert to amines, sulfhydryls, carboxylic acids, hydroxyl groups found in proteins, but that also reacts smoothly and efficiently with an acetylene moiety to form a cycloaddition product. Importantly, in the absence of the acetylene moiety, the azide remains chemically inert and unreactive in the presence of other protein side chains and under physiological conditions.

Various references disclose modification of polypeptides by polymer conjugation or glycosylation. The term "anti-CD3 antibody" or "antigen-binding polypeptide" refers to an anti-CD3 antibody as described above, as well as a polypeptide that retains at least one biological activity of a naturally-occurring antibody, including but not limited to, activities other than antigen binding. Activities other than antigen binding include, but are not limited to, any one or more of the activities associated with the Fc. The term "anti-CD3 antibody" or "antigen-binding polypeptide" includes, but is not limited to, polypeptides conjugated to a polymer such as PEG and may be comprised of one or more additional derivatizations of cysteine, lysine, N or C-terminal amino acids, or other residues. In addition, the anti-CD3 antibody may comprise a linker, polymer or biologically active molecule, wherein the amino acid to which the linker, polymer, or biologically active molecule is conjugated may be a non-natural amino acid according to the present invention or may be conjugated to a naturally encoded amino acid utilizing techniques known in the art such as coupling to lysine or cysteine. U.S. Pat. No. 4,904,584 discloses PEGylated lysine depleted polypeptides, wherein at least one lysine residue has been deleted or replaced with any other amino acid residue. WO 99/67291 discloses a process for conjugating a protein with PEG, wherein at least one amino acid residue on the protein is deleted and the protein is contacted with PEG under conditions sufficient to achieve conjugation to the protein. WO 99/03887 discloses PEGylated variants of polypeptides belonging to the growth hormone superfamily, wherein a cysteine residue has been substituted with a non-essential amino acid residue located in a specified region of the polypeptide. WO 00/26354 discloses a method of producing a glycosylated polypeptide variant with reduced allergenicity, which as compared to a corresponding parent polypeptide comprises at least one additional glycosylation site.

The term "antigen-binding polypeptide" also includes glycosylated anti-CD3 antibodies, such as but not limited to, polypeptides glycosylated at any amino acid position, N-linked or O-linked glycosylated forms of the polypeptide. Variants containing single nucleotide changes are also considered as biologically active variants of anti-CD3 antibody. In addition, splice variants are also included. The term "antigen-binding polypeptide" also includes anti-CD3 antibody heterodimers, homodimers, heteromultimers, or homomultimers of any one or more anti-CD3 antibody or any other polypeptide, protein, carbohydrate, polymer, small molecule, linker, ligand, or other biologically active molecule of any type, linked by chemical means or expressed as a fusion protein, as well as polypeptide analogues containing, for example, specific deletions or other modifications yet maintain biological activity.

In some embodiments, the antigen-binding polypeptides further comprise an addition, substitution or deletion that modulates biological activity of the anti-CD3 antibody. For example, the additions, substitutions or deletions may modulate one or more properties or activities of the anti-CD3 antibody, including but not limited to, modulating affinity for the antigen, modulate (including but not limited to, increases or decreases) antigen conformational or other secondary, tertiary or quaternary structural changes, stabilize antigen conformational or other secondary, tertiary or quaternary structural changes, induce or cause antigen conformational or other secondary, tertiary or quaternary structural changes, modulate circulating half-life, modulate therapeutic half-life, modulate stability of the polypeptide, modulate dose, modulate release or bio-availability, facilitate purification, or improve or alter a particular route of administration. Similarly, antigen-binding polypeptides may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide.

The term "antigen-binding polypeptide" also encompasses anti-CD3 antibody homodimers, heterodimers, homomultimers, and heteromultimers that are linked, including but not limited to those linked directly via non-naturally encoded amino acid side chains, either to the same or different non-naturally encoded amino acid side chains, to naturally-encoded amino acid side chains, as fusions, or indirectly via a linker. Exemplary linkers include but are not limited to, small organic compounds, water-soluble polymers of a variety of lengths such as poly(ethylene glycol) or polydextran, or polypeptides of various lengths.

Those of skill in the art will appreciate that amino acid positions corresponding to positions in a particular antigen-binding polypeptide sequence can be readily identified in a fragment of the antigen-binding polypeptide or related antigen-binding polypeptide, etc. For example, sequence alignment programs such as BLAST can be used to align and identify a particular position in a protein that corresponds with a position in a related sequence.

The term "antigen-binding polypeptide" encompasses antigen-binding polypeptides comprising one or more amino acid substitutions, additions or deletions. Antigen-binding polypeptides of the present invention may be comprised of modifications with one or more natural amino acids in conjunction with one or more non-natural amino acid modification. Exemplary substitutions in a wide variety of amino acid positions in naturally-occurring anti-CD3 antibody polypeptides have been described, including but not limited to substitutions that modulate one or more of the biological activities of the antigen-binding polypeptide, such as but not limited to, increase agonist activity, increase solubility of the polypeptide, convert the polypeptide into an antagonist, etc. and are encompassed by the term "anti-CD3 antibody."

A "non-naturally encoded amino acid" refers to an amino acid that is not one of the 20 common amino acids or pyrolysine or selenocysteine. Other terms that may be used synonymously with the term "non-naturally encoded amino acid" are "non-natural amino acid," "unnatural amino acid," "non-naturally-occurring amino acid," "non-canonical amino acid", and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine. In some embodiments, non-natural amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like. Specific examples of unnatural amino acids include, but are not limited to, a p-acetyl-L-phenylalanine, a p-propargyloxyphenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include, but are not limited to, various water-soluble polymers, peptides or proteins such as serum albumin, or other moieties that increase serum half-life of peptides.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "linkage" or "linker" is used herein to refer to groups or bonds that normally are formed as the result of a chemical reaction and typically are covalent linkages. Hydrolytically stable linkages mean that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide. Branched linkers may be used in antigen-binding polypeptides of the invention.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include, but are not limited to, any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, hard drugs, soft drugs, dyes, lipids, nucleosides, oligonucleotides, toxins, cells, viruses, liposomes, microparticles and micelles. Classes of biologically active agents that are suitable for use with the invention include, but are not limited to, drugs, prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins, and the like.

The anti-CD3 Fab-Folate antibodies of the invention may be conjugated to molecules such as PEG to improve in vivo delivery and pharmacokinetic profiles. Leong et al. describe site-specific PEGylation of a Fab' fragment of an anti-IL-8 antibody with a decreased clearance rate over the non-PEGylated form and little or no loss of antigen binding activity (Leong, S. R. et al. (2001) *Cytokine* 16:106-119).

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis.

U.S. Pat. No. 4,671,958, for example, includes a description of immunoconjugates comprising linkers which are cleaved at the target site in vivo by the proteolytic enzymes of the patient's complement system. The length of the linker may be predetermined or selected depending upon a desired spatial relationship between the anti-CD3 antibody and the molecule linked to it. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an anti-CD3 antibody or other polypeptide.

A "bifunctional polymer" refers to a polymer comprising two discrete functional groups that are capable of reacting specifically with other moieties (including but not limited to, amino acid side groups) to form covalent or non-covalent linkages. A bifunctional linker having one functional group reactive with a group on a particular biologically active component, and another group reactive with a group on a second biological component, may be used to form a conjugate that includes the first biologically active component, the bifunctional linker and the second biologically active component. Many procedures and linker molecules for attachment of various compounds to peptides are known. See, e.g., European Patent Application No. 188,256; U.S. Pat. Nos. 4,671,958, 4,659,839, 4,414,148, 4,699,784; 4,680,338; 4,569,789; and 4,589,071 which are incorporated by reference herein. A "multi-functional polymer" refers to a polymer comprising two or more discrete functional groups that are capable of reacting specifically with other moieties (including but not limited to, amino acid side groups) to form covalent or non-covalent linkages. A bi-functional polymer or multi-functional polymer may be any desired molecular length or molecular weight and may be selected to provide a particular desired spacing or conformation between one of molecules linked to the anti-CD3 antibody.

As used herein, the term "water-soluble polymer" refers to any polymer that is soluble in aqueous solvents. Linkage of water-soluble polymers to anti-CD3 antibody can result in changes including, but not limited to, increased or modulated serum half-life, or increased or modulated therapeutic half-life relative to the unmodified form, modulated immunogenicity, modulated physical association characteristics such as aggregation and multimer formation, altered receptor binding and altered receptor dimerization or multimerization. The water-soluble polymer may or may not have its own biological activity and may be utilized as a linker for attaching an anti-CD3 antibody to other substances, including but not limited to one or more anti-CD3 antibody, or one or more biologically active molecules. Suitable polymers include, but are not limited to, polyethylene glycol, polyethylene glycol propionaldehyde, mono C1-C10 alkoxy or aryloxy derivatives thereof (described in U.S. Pat. No. 5,252,714 which is incorporated by reference herein), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. Examples of such water-soluble polymers include, but are not limited to, polyethylene glycol and serum albumin.

As used herein, the term "polyalkylene glycol" or "poly (alkene glycol)" refers to polyethylene glycol (poly(ethylene glycol)), polypropylene glycol, polybutylene glycol, and derivatives thereof. The term "polyalkylene glycol" encompasses both linear and branched polymers and average molecular weights of between 0.1 kDa and 100 kDa. In some embodiments the "polyalkylene glycol" or "poly(alkene glycol)" can be from about or between 5K to 50K. Other exemplary embodiments are listed, for example, in commercial supplier catalogs, such as Shearwater Corporation's catalog "Polyethylene Glycol and Derivatives for Biomedical Applications" (2001). As used herein, poly(ethylene glycol) with a molecular weight of 5 kDa, 10 kDa, 20 kDa etc., is referred to herein as "5K PEG", "10K PEG", "20K PEG etc.", respectively.

As used herein, the term "modulated serum half-life" means the positive or negative change in circulating half-life of a modified anti-CD3 antibody relative to its non-modified form. Serum half-life is measured by taking blood samples at various time points after administration of anti-CD3 antibody and determining the concentration of that molecule in each sample. Correlation of the serum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, at least about ten-fold, at least about fifteen-fold, at least about twenty-fold, at least about twenty-five-fold, at least about thirty-fold, at least about forty-fold, or at least about fifty-fold or greater The term "modulated therapeutic half-life" as used herein means the positive or negative change in the half-life of the therapeutically effective amount of an anti-CD3 antibody or anti-CD3 antibody comprising a modified biologically active molecule, relative to its non-modified form. Therapeutic half-life is measured by measuring pharmacokinetic and/or pharmacodynamic properties of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, or an increase or decrease in another parameter or mechanism of action of the non-modified molecule.

The term "isolated," when applied to a nucleic acid or protein, denotes that the nucleic acid or protein is substantially free of other cellular components with which it is associated in the natural state. It can be in a homogeneous state. Isolated substances can be in either a dry or semi-dry state, or in solution, including but not limited to, an aqueous solution. Purity and homogeneity are typically determined using analytical chemistry techniques such as polyacrylamide gel electrophoresis or high-performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to substantially one band in an electrophoretic gel. Particularly, it means that the nucleic acid or protein is at least 85% pure, at least 90% pure, at least 95% pure, at least 99% or greater pure.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081, 1991; Ohtsuka et al., *J. Biol. Chem.* 260:2605-2608, 1985; and Cassol et al., 1992; Rossolini et al., *Mol. Cell. Probes* 8:91-98, 1994).

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins (i.e., antigens), wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M); (see, e.g., Creighton, *Proteins: Structures and Molecular Properties* (W H Freeman & Co.; 2nd edition (December 1993).

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, optionally about 65%, about 70%, about 75%, about 80%, about 85%, about 90%, or about 95% identity over a specified region), when compared and aligned for maximum correspondence over a comparison window, or designated region as measured using one of the following sequence comparison algorithms or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence or a polynucleotide or polypeptide.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "subject" as used herein, refers to an animal, preferably a mammal, most preferably a human, who is the object of treatment, observation or experiment.

The term "effective amount" as used herein refers to that amount of the (modified) non-natural amino acid polypeptide being administered which will relieve to some extent one or more of the symptoms of the disease, condition or disorder being treated. Compositions containing the (modified) non-natural amino acid polypeptide described herein can be administered for prophylactic, enhancing, and/or therapeutic treatments.

The terms "enhance" or "enhancing" means to increase or prolong either in potency or duration of a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition, previous therapy, the patient's health status and response to the drugs, and the judgment of the treating physician.

The term "modified," as used herein refers to the presence of a post-translational modification on a polypeptide. The form "(modified)" term means that the polypeptides being discussed are optionally modified, that is, the polypeptides under discussion can be modified or unmodified.

The term "post-translationally modified" and "modified" refers to any modification of a natural or non-natural amino acid that occurs to such an amino acid after it has been incorporated into a polypeptide chain. The term encompasses, by way of example only, co-translational in vivo modifications, post-translational in vivo modifications, and post-translational in vitro modifications.

In prophylactic or therapeutic applications, compositions containing the (modified) non-natural amino acid polypeptide are administered to a patient already suffering from a disease, condition or disorder, in an amount sufficient to cure or at least partially arrest the symptoms of the disease, disorder or condition. Such an amount is defined to be a "prophylactically effective amount," or "therapeutically effective amount," and will depend on the severity and course of the disease, disorder or condition, previous therapy, the patient's health status and response to the drugs, and the judgment of the treating physician. It is considered well within the skill of the art for one to determine such therapeutically effective amounts by routine experimentation (e.g., a dose escalation clinical trial).

The term "treating" is used to refer to either prophylactic and/or therapeutic treatments.

Unless otherwise indicated, conventional methods of mass spectroscopy, NMR, HPLC, protein chemistry, biochemistry, recombinant DNA techniques and pharmacology, within the skill of the art are employed.

DETAILED DESCRIPTION

Introduction

The inventors have developed a bispecific antibody comprising a biologically active molecule or agent in the absence or presence of a water-soluble polymer molecule. In certain embodiments, the invention provides a bispecific antibody comprising an anti-CD3 antibody, fragment or variant comprising one or more folate molecules in the absence or presence of one or more PEG molecules. The one or more PEG molecules may be a single or double PEG, for example, a single or double 5K PEG, 10K PEG, 20K PEG or greater. The one or more PEG molecules may be linear or branched. The anti-CD3 antibody, fragment or variant comprises an anti-CD3 Fab antibody that has been engineered to have one, or more non-naturally encoded amino acids, such as, for example, para-acetyl-phenylalanine (pAF), at any suitable position in the heavy or light chain amino acid sequence, including, but not limited to, in the heavy chain at positions 114, 115, 129, or 160 (according to Kabat numbering), and in the light chain at positions 157, 172, 205 (according to Kabat numbering), of the Fab. The bispecific antibody may comprise an anti-CD3 Fab that has been engineered to have one, or more non-naturally encoded amino acids, such as, for example, para-acetyl-phenylalanine (pAF) on the heavy (K129; Kabat numbering) and light chains (L157; Kabat numbering) of the Fab. The bispecific antibody may consist of an anti-CD3 Fab that has been engineered to have one, or more non-naturally encoded amino acids, such as, for example, pam-acetyl-phenylalanine (pAF) on the heavy (K129; Kabat numbering) and light chains (L157; Kabat numbering) of the Fab. In some embodiments of the invention, one or more PEG molecules may be conjugated or linked to one or more folate molecules conjugated to one or more non-natural amino acids, for example pAF, incorporated into the anti-CD3 antibody using proprietary oxime chemistry, resulting in, for example, one or two PEG and/or Folate molecule stably conjugated to the anti-CD3 Fab. The addition of one or more PEG molecule, for example 5K, 10K, or 20K PEG, provide significant improvements in the pharmacokinetic properties of the bispecific antibody, while maintaining the specific cytotoxicity against FOLR1 expressing cells both in vitro and in vivo. Pro-tumorigenic macrophages (M2) and MDSCs cells were observed to be preferentially depleted with the PEGylated anti-CD3 Fab-Folate compositions disclosed herein. The results suggest that the improved pharmacokinetic properties will require less frequent dosing and can obviate administration using an infusion pump. As used herein the terms "PEG-Folate" or "Folate-PEG" and "BiPEG-BiFolate" or "BiFolate-BiPEG" are used interchangeably.

Antibodies, Antibody Fragments and Variants Thereof

Antibody or antibody fragments or variants of the invention may be human, humanized, engineered, non-human, and/or chimeric antibody or antibody fragments. An antibody or antibody fragment or variant provided herein may comprise two or more amino acid sequences. A first amino acid sequence may comprise a first antibody chain and a second amino acid sequence may comprise a second antibody chain. A first antibody chain may comprise a first amino acid sequence, and a second antibody chain may comprise a second amino acid sequence. A chain of an antibody may refer to an antibody heavy chain, an antibody light chain, or a combination of a region or all of an antibody heavy chain and a region or all of an antibody light chain. As a non-limiting example, an antibody provided herein comprises a heavy chain or fragment or variant thereof, and a light chain or fragment or variant thereof. Two amino acid sequences of an antibody, including two antibody chains, may be connected by one or more disulfide bonds, a chemical linker, a peptide linker, or a combination thereof. A chemical linker includes a linker via a non-natural amino acid. A chemical linker includes a linker via one or more non-natural amino acids. A chemical linker can include a chemical conjugate. A peptide linker includes any amino acid sequence joining the two amino acid sequences. The peptide linker may comprise 1 or more, 5 or more, 10 or more, 15 or more, 20 or more, 25 or more, 30 or more, 35 or more, 40 or more, 45 or more, 50 or more, 55 or more, 60 or more, 65 or more, 70 or more, 75 or more, 80 or more, 85 or more, 90 or more, 95 or more, 100 or more amino acids. The peptide linker may be a portion of any antibody, including a domain of an antibody, such as a variable domain, CH1, CH2, CH3, and/or CL domain. In some embodiments a heavy and a light chain are connected, for example, via a peptide linker. In some cases, a heavy chain and a light chain are connected, for example, by one or more disulfide bonds.

Antibodies, antibody fragments and antibody variants of the invention disclosure may interact or engage with an antigen on an effector cell. The effector cell can include, but is not limited to, an immune cell, a genetically modified cell having increase or decrease cytotoxic activity, a cell involve in the host defense mechanism, an anti-inflammatory cell, a leukocyte, a lymphocyte, a macrophage, an erythrocyte, a thrombocyte, a neutrophil, a monocyte, an eosinophil, a basophil, a mast cell, a NK cell, a B-cell, or a T-cell. In some embodiments the immune cell may be a T cell such as a cytotoxic T cell or natural killer T cell. The antibody or antibody fragment may interact with a receptor on a T-cell such as, but not limited to a T-cell receptor (TCR). The TCR may comprise TCR alpha, TCR beta, TCR gamma, and/or TCR delta or TCR zeta. Antibody or antibody fragments of the disclosure may bind to a receptor on a lymphocyte, dendritic cell, B-cell, macrophage, monocytes, neutrophils and/or NK cells. Antibody or antibody fragments of the disclosure may bind to a cell surface receptor. Antibody or antibody fragments of the disclosure may bind to a folate receptor. Antibody or antibody fragments of the disclosure can be conjugated to a T-cell surface antigen, for example, but not limited to 2-[3-(1,3-dicarboxy propyl)-ureido] pentanedioic acid (DUPA) or analogs or derivatives thereof. See for example, U.S. Pat. No. 6,479,470; WO2017/136659 and WO2014/153164 each incorporated herein by reference in its entirety.

In certain embodiments antibody or antibody fragments disclosed herein are anti-CD3 antibodies or antibody fragments or variants thereof. In certain embodiments, the anti-CD3 antibodies or antibody fragments or variants disclosed herein can be humanized. Anti-CD3 antibodies or antibody fragments or variants disclosed herein include, but are not limited to, CD3 analogs, isoforms, mimetics, fragments, or hybrids. Anti-CD3 antibodies or antibody fragments or variants of the present invention include but are not limited to Fv, Fc, Fab, and (Fab')₂, single chain Fv (scFv), diabodies, triabodies, tetrabodies, bifunctional hybrid antibodies, CDR1, CDR2, CDR3, combinations of CDRs, variable regions, framework regions, constant regions, heavy chains, light chains, alternative scaffold non-antibody molecules, bispecific antibodies and the like. The anti-CD3 antibodies or antibody fragments or variants of the present invention comprise a sequence of SEQ. ID. NOs: 1 to 62. The antibodies, fragments or variants of the present invention can be an anti-CD3 Fab antibody, fragment or variant. The antibodies, fragments or variants of the present invention can comprise one or more anti-CD3 Fabs. The antibodies, fragments or variants of the present invention can comprise two anti-CD3 Fabs. In certain embodiments, the anti-CD3 antibody comprises a heavy chain and/or light chain amino acid sequence selected from a sequence of SEQ. ID. NOs: 1 to 62. In certain embodiments, the anti-CD3 antibody consists of a heavy chain and/or light chain amino acid sequence selected from a sequence of SEQ. ID. NOs: 1 to 62. In certain embodiments, the anti-CD3 antibody comprises a heavy chain amino acid sequence of any one of SEQ. ID. NOs: 1, 2, 3, 4, 5, 6, 10, 11, 12, 13, 14, 15, 16, 17, 21, 22, 23, 24, 25, 26, 27, 28, 29, 30, 31, 32, 33, 34, 35, 36, 37, 38, 40, 41, 42, 43, 44, 45, 46, 47, 48, 49, 50, 50, 51, 52, 53, 54, 55, 56, and 57; and a light chain amino acid sequence of any one of SEQ. ID. NOs: 7, 8, 9, 18, 19, 20, 39, 58, 59, 60, 61, and 62.

Anti-CD3 bispecific antibodies comprising non-natural amino acids are also disclosed herein. In certain embodiments, the anti-CD3 bispecific antibody or antibody fragments or variants include but are not limited to Fv, Fc, Fab, and (Fab')₂, single chain Fv (scFv), diabodies, triabodies, tetrabodies, bifunctional hybrid antibodies, CDR1, CDR2, CDR3, combinations of CDRs, variable regions, framework regions, constant regions, heavy chains, light chains, alternative scaffold non-antibody molecules, bispecific antibodies and the like. In some embodiments, the anti-CD3 bispecific antibody or antibody fragments or variants is an anti-CD3 Fab bispecific antibody, fragment, or variant comprising one or more non-naturally encoded amino acids. Anti-CD3 Fab bispecific antibodies or antibody fragments or variants of the present invention may comprise one or more sequences of SEQ. ID. NOs: 1 to 62. The bispecific antibodies, fragments or variants of the present invention can be an anti-CD3 Fab antibody, fragment or variant. The anti-CD3 bispecific antibody may comprise a heavy chain and/or light chain amino acid sequence selected from a sequence of SEQ. ID. NOs: 1 to 62. In some embodiments, the anti-CD3 antibody consists of a heavy chain and/or light chain amino acid sequence selected from a sequence of SEQ. ID. NOs: 1 to 62. In certain embodiments, the anti-CD3 bispecific antibody comprises a heavy chain amino acid sequence of any one of SEQ. ID. NOs: 1, 2, 3, 4, 5, 6, 10, 11, 12, 13, 14, 15, 16, 17, 21, 22, 23, 24, 25, 26, 27, 28, 29, 30, 31, 32, 33, 34, 35, 36, 37, 38, 40, 41, 42, 43, 44, 45, 46, 47, 48, 49, 50, 50, 51, 52, 53, 54, 55, 56, and 57; and a light chain amino acid sequence of any one of SEQ. ID. NOs: 7, 8, 9, 18, 19, 20, 39, 58, 59, 60, 61, and 62. In some embodiments, the bispecific antibody, fragments or variants disclosed herein specifically binds CD3. The bispecific antibody, fragments or variants can be cross-species reactive. The bispecific antibody, fragments or variants can be cross-species reactive with human and monkey antigens. In some embodiments, the antibody comprises a cross-species reactive CDR. The bispecific antibody can be a humanized antibody.

TABLE 1

Novel amino acid sequences of humanized anti-CD3 variants with and without HC-DKTHT extension with the location of non-natural amino acid pAF incorporation underlined in heavy and light chains. Also disclosed are all of the sequences in the table below, where pAF is replaced by any other non-natural amino acid

| SEQ. ID. NO. | CHAIN | SEQUENCE |
|---|---|---|
| 1 | HC (vH1.2 + CH1) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSC |

TABLE 1-continued

Novel amino acid sequences of humanized anti-CD3 variants with and without HC-DKTHT extension with the location of non-natural amino acid pAF incorporation underlined in heavy and light chains. Also disclosed are all of the sequences in the table below, where pAF is replaced by any other non-natural amino acid

| SEQ. ID. NO. | CHAIN | SEQUENCE |
|---|---|---|
| 2 | HC (vH1.1 + CH1) | EVQLVESGGGLVQPGGSLRLSCAASGFTFNTYAMNWVRQAPGKGLEWVARIRSKYNNYATYYADSVKDRFTISRDDSKNSLYLQMNSLKTEDTAVYYCVRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 3 | HC (vH1.0 + CH1) | EVQLVESGGGLVQPGGSLRLSCAASGFTFNTYAMNWVRQAPGKGLEWVGRIRSKYNNYATYYADSVKDRFTISRDDSKNSLYLQMNSLKTEDTAVYYCVRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 4 | HC (vH1.2 + CH1-DKTHT) | EVQLVESGGGLVQPGGSLRLSCAASGFTFNTYAMNWVRQAPGKGLEWVARIRSKYNNYATYYADSVKDRFTISRDDSKNILYLQMNSLKTEDTAVYYCVRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT |
| 5 | HC (vH1.1 + CH1-DKTHT) | EVQLVESGGGLVQPGGSLRLSCAASGFTFNTYAMNWVRQAPGKGLEWVARIRSKYNNYATYYADSVKDRFTISRDDSKNSLYLQMNSLKTEDTAVYYCVRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT |
| 6 | HC (vH1.0 + CH1-DKTHT) | EVQLVESGGGLVQPGGSLRLSCAASGFTFNTYAMNWVRQAPGKGLEWVGRIRSKYNNYATYYADSVKDRETISRDDSKNSLYLQMNSLKTEDTAVYYCVRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT |
| 7 | LC (vL1.2 + CL) | QAVVTQEPSLTVSPGGTVTLTCRSSTGAVTTSNYANWVQQKPGQAPRGLIGGTNKRAPGTPARFSGSLLGGKAALTLSGAQPEDEAEYYCALWYSNLWVFGGGTKLTVLGRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 8 | LC (vL1.1 + CL) | QAVVTQEPSLTVSPGGTVTLTCRSSTGAVTTSNYANWVQQKPGQAPRGLIGGTNKRAPGVPARFSGSLLGGKAALTLSGAQPEDEAEYYCALWYSNLWVFGGGTKLTVLGRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 9 | LC (vL1.0 + CL) | QAVVTQEPSLTVSPGGTVTLTCRSSTGAVTTSNYANWFQQKPGQAPRTLIYGTNKRAPWTPARFSGSLLGGKAALTLSGAQPEDEAEYYCALWYSNLWVFGGGTKLTVLGRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 10 | HC (vH1.2 + CH1-HA114pAF) | EVQLVESGGGLVQPGGSLRLSCAASGFTFNTYAMNWVRQAPGKGLEWVARIRSKYNNYATYYADSVKDRFTISRDDSKNILYLQMNSLKTEDTAVYYCVRHGNFGNSYVSWFAYWGQGTLVTVSSpAFSTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 11 | HC (vH1.2 + CH1-HS115pAF) | EVQLVESGGGLVQPGGSLRLSCAASGFTFNTYAMNWVRQAPGKGLEWVARIRSKYNNYATYYADSVKDRFTISRDDSKNILYLQMNSLKTEDTAVYYCVRHGNFGNSYVSWFAYWGQGTLVTVSSApAFTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |

TABLE 1-continued

Novel amino acid sequences of humanized anti-CD3 variants with and without HC-DKTHT extension with the location of non-natural amino acid pAF incorporation underlined in heavy and light chains. Also disclosed are all of the sequences in the table below, where pAF is replaced by any other non-natural amino acid

| SEQ. ID. NO. | CHAIN | SEQUENCE |
|---|---|---|
| 12 | HC (vH1.2 + CH1-HK129pAF) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSC |
| 13 | HC (vH1.2 + CH1-HT160pAF) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALpAFSGVHTFPAVLQSSGLYSLSSVVTVPS SSLGTQTYICNVNHKPSNTKVDKKVEPKSC |
| 14 | HC (vH1.2 + CH1-HA114pAF + DKTHT) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSpAFSTKGPSVFPLAPSSKSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 15 | HC (vH1.2 + CH1-HS115pAF + DKTHT) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSApAFTKGPSVFPLAPSSKSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 16 | HC (vH1.2 + CH1-HK129pAF-DKTHT) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 17 | HC (vH1.2 + CH1-HT160pAF + DKTHT) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALpAFSGVHTFPAVLQSSGLYSLSSVVTVPS SSLGTQTYICNVNHKPSNTKVDKKVEPKSCDKTHT |
| 18 | LC (vL1.2 + CL-LL157pAF) | QAVVTQEPSLTVSPGGTVTLTCRSSTGAVTTSNYANWVQQ KPGQAPRGLIGGTNKRAPGTPARFSGSLLGGKAALTLSGA QPEDEAEYYCALWYSNLWVFGGGTKLTVLGRTVAAPSVFI FPPSDEQLKSGTASVVCLLNNFYPREAKVQWKVDNApAFQ SGNSQESVTEQDSKDSTYSLSSTLTLSKADYEKHKVYACE VTHQGLSSPVTKSFNRGEC |
| 19 | LC (vL1.2 + CL-LK172pAF) | QAVVTQEPSLTVSPGGTVTLTCRSSTGAVTTSNYANWVQQ KPGQAPRGLIGGTNKRAPGTPARFSGSLLGGKAALTLSGA QPEDEAEYYCALWYSNLWVFGGGTKLTVLGRTVAAPSVFI FPPSDEQLKSGTASVVCLLNNFYPREAKVQWKVDNALQSG NSQESVTEQDSpAFDSTYSLSSTLTLSKADYEKHKVYACE VTHQGLSSPVTKSFNRGEC |
| 20 | LC (vL1.2 + CL-LS205pAF) | QAVVTQEPSLTVSPGGTVTLTCRSSTGAVTTSNYANWVQQ KPGQAPRGLIGGTNKRAPGTPARFSGSLLGGKAALTLSGA QPEDEAEYYCALWYSNLWVFGGGTKLTVLGRTVAAPSVFI FPPSDEQLKSGTASVVCLLNNFYPREAKVQWKVDNALQSG NSQESVTEQDSKDSTYSLSSTLTLSKADYEKHKVYACEVT HQGLpAFSPVTKSFNRGEC |
| 21 | HC (vH2.3 + CH1-DKTHT) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCARHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHT |

TABLE 1-continued

Novel amino acid sequences of humanized anti-CD3 variants with and without HC-DKTHT extension with the location of non-natural amino acid pAF incorporation underlined in heavy and light chains. Also disclosed are all of the sequences in the table below, where pAF is replaced by any other non-natural amino acid

| SEQ. ID. NO. | CHAIN | SEQUENCE |
|---|---|---|
| 22 | HC (vH2.2 + CH1-DKTHT) | EVQLVESGGGLVQPGGSLRLSCAASGFTFNTYAMNWVRQA PGKGLEWVGRIRSKYNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHT |
| 23 | HC (vH2.1 + CH1-DKTHT) | EVQLVESGGGLVQPGGSLRLSCAASGFTFSTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHT |
| 24 | HC (vH2.4 + CH1-DKTHT) | EVQLVESGGGLVQPGGSLRLSCAASGFTFSTYAMNWVRQA PGKGLEWVGRIRSKYNNYATYYADSVKDRFTISRDDSKNS LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHT |
| 25 | HC (vH2.5 + CH1-DKTHT) | EVQLVESGGGLVQPGGSLRLSCAASGFTFNTYAMNWVRQA PGKGLEWVGRIRSKYNNYATYYADSVKDRFTISRDDSKNS LYLQMNSLKTEDTAVYYCARHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHT |
| 26 | HC (vH2.6 + CH1-DKTHT) | EVQLVESGGGLVQPGGSLRLSCAASGFTFSTYAMNWVRQA PGKGLEWVGRIRSKYNNYATYYADSVKDRFTISRDDSKNS LYLQMNSLKTEDTAVYYCARHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHT |
| 27 | HC (vH3.1 + CH1-DKTHT) | EVQLVESGGGLVQPGGSLRLSCAASGFTFNTYAMHWVRQA PGKGLEWVARIRSKYNNYATYYADSVKDRFTISRDDSKNI LYLQMNSLKTEDTAVYYCVREGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHT |
| 28 | HC (vH3.2 + CH1-DKTHT) | EVQLVESGGGLVQPGGSLRLSCAASGFTFNTYAMNWVRQA PGKGLEWVARIRSKSNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHT |
| 29 | HC (vH3.3 + CH1-DKTHT) | EVQLVESGGGLVQPGGSLRLSCAASGFTFNTYAMHWVRQA PGKGLEWVARIRSKSNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHT |
| 30 | HC (vH2.3 + CH1) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCARHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSC |
| 31 | HC (vH2.2 + CH1) | EVQLVESGGGLVQPGGSLRLSCAASGFTFNTYAMNWVRQA PGKGLEWVGRIRSKYNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSC |

TABLE 1-continued

Novel amino acid sequences of humanized anti-CD3 variants with and without HC-DKTHT extension with the location of non-natural amino acid pAF incorporation underlined in heavy and light chains. Also disclosed are all of the sequences in the table below, where pAF is replaced by any other non-natural amino acid

| SEQ. ID. NO. | CHAIN | SEQUENCE |
|---|---|---|
| 32 | HC (vH2.1 + CH1) | EVQLVESGGGLVQPGGSLRLSCAASGFTFSTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSC |
| 33 | HC (vH2.4 + CH1) | EVQLVESGGGLVQPGGSLRLSCAASGFTFSTYAMNWVRQA PGKGLEWVGRERSKYNNYATYYADSVKDRFTISRDDSKNS LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSC |
| 34 | HC (vH2.5 + CH1) | EVQLVESGGGLVQPGGSLRLSCAASGFTFNTYAMNWVRQA PGKGLEWVGRIRSKYNNYATYYADSVKDRFTISRDDSKNS LYLQMNSLKTEDTAVYYCARHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSC |
| 35 | HC (vH2.6 + CH1) | EVQLVESGGGLVQPGGSLRLSCAASGFTFSTYAMNWVRQA PGKGLEWVGRIRSKYNNYATYYADSVKDRFTISRDDSKNS LYLQMNSLKTEDTAVYYCARHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSC |
| 36 | HC (vH3.1 + CH1) | EVQLVESGGGLVQPGGSLRLSCAASGFTFNTYAMHWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSC |
| 37 | HC (vH3.2 + CH1) | EVQLVESGGGLVQPGGSLRLSCAASGFTFNTYAMNWVRQA PGKGLEWVARIRSKSNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSC |
| 38 | HC (vH3.3 + CH1) | EVQLVESGGGLVQPGGSLRLSCAASGFTFNTYAMHWVRQA PGKGLEWVARIRSKSNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSC |
| 39 | LC (vL2.3 + CL) | QAVVTQEPSLTVSPGGTVTLTCRSSTGAVTTSNYANWVQQ KPGQAPRGLIYGTNKRAPGVPARFSGSLLGGKAALTLSGA QPEDEAEYYCALWYSNLWVFGGGTKLTVLGRTVAAPSVFI FPPSDEQLKSGTASVVCLLNNFYPREAKVQWKVDNALQSG NSQESVTEQDSKDSTYSLSSTLTLSKADYEKHKVYACEVT HQGLSSPVTKSFNRGEC |
| 40 | HC (vH2.3 + CH1-HK129pAF-DKTHT) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCARHGNFGNSYVSWFAYWGQGTL VTVSSASTKGPSVFPLAPSS<u>pAF</u>STSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 41 | HC (vH2.2 + CH1-HK129pAF-DKTFIT) | EVQLVESGGGLVQPGGSLRLSCAASGFTFNTYAMNWVRQA PGKGLEWVGRIRSKYNNYATYYADSVKDRFTISRDDSKNI LYLQMNSLKTEDTAVYYCVRHGNFGNSYVSWFAYWGQGTL VTVSSASTKGPSVFPLAPSS<u>pAF</u>STSGGTAALGCLVKDYF PEPVTVSWNSGALTSGVHTFPAVLQSSGLYSLSSVVTVPS SSLGTQTYICNVNHKPSNTKVDKKVEPKSCDKTHT |

TABLE 1-continued

Novel amino acid sequences of humanized anti-CD3 variants with and without HC-DKTHT extension with the location of non-natural amino acid pAF incorporation underlined in heavy and light chains. Also disclosed are all of the sequences in the table below, where pAF is replaced by any other non-natural amino acid

| SEQ. ID. NO. | CHAIN | SEQUENCE |
|---|---|---|
| 42 | HC (vH1.0 + CH1-HK129pAF-DKTHT) | EVQLVESGGGLVQPGGSLRLSCAASGFTFNTYAMNWVRQA PGKGLEWVGRIRSKYNNYATYYADSVKDRFTISRDDSKNS LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 43 | HC (vH2.1 + CH1-HK129pAF-DKTHT) | EVQLVESGGGLVQPGGSLRLSCAASGFTFSTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 44 | HC (vH2.4 + CH1-HK129pAF-DKTHT) | EVQLVESGGGLVQPGGSLRLSCAASGFTFSTYAMNWVRQA PGKGLEWVGRIRSKYNNYATYYADSVKDRFTISRDDSKNS LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 45 | HC (vH2.5 + CH1-HK129pAF-DKTHT) | EVQLVESGGGLVQPGGSLRLSCAASGFTFNTYAMNWVRQA PGKGLEWVGRIRSKYNNYATYYADSVKDRFTISRDDSKNS LYLQMNSLKTEDTAVYYCARHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 46 | HC (vH2.6 + CH1-HK129pAF-DKTHT) | EVQLVESGGGLVQPGGSLRLSCAASGFTFSTYAMNWVRQA PGKGLEWVGRIRSKYNNYATYYADSVKDRFTISRDDSKNS LYLQMNSLKTEDTAVYYCARHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 47 | HC (vH3.1 + CH1-HK129pAF-DKTHT) | EVQLVESGGGLVQPGGSLRLSCAASGFTFNTYAMHWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 48 | HC (vH3.2 + CH1-HK129pAF-DKTHT) | EVQLVESGGGLVQPGGSLRLSCAASGFTFNTYAMNWVRQA PGKGLEWVARIRSKSNNYATYYADSVKDRFTISRDDSKNI LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 49 | HC (vH2.3 + CH1-HK129pAF) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCARHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSC |
| 50 | HC (vH2.2 + CH1-HK129pAF) | EVQLVESGGGLVQPGGSLRLSCAASGFTFNTYAMNWVRQA PGKGLEWVGRIRSKYNNYATYYADSVKDRFTISRDDSKNI LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSC |
| 51 | HC (vH1.0 + CH1-HK129pAF) | EVQLVESGGGLVQPGGSLRLSCAASGFTFNTYAMNWVRQA PGKGLEWVGRIRSKYNNYATYYADSVKDRFTISRDDSKNS LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSC |

TABLE 1-continued

Novel amino acid sequences of humanized anti-CD3 variants with and without HC-DKTHT extension with the location of non-natural amino acid pAF incorporation underlined in heavy and light chains. Also disclosed are all of the sequences in the table below, where pAF is replaced by any other non-natural amino acid

| SEQ. ID. NO. | CHAIN | SEQUENCE |
|---|---|---|
| 52 | HC (vH2.1 + CH1-HK129pAF) | EVQLVESGGGLVQPGGSLRLSCAASGFTFSTYAMNWVRQAPGKGLEWVARIRSKYNNYATYYADSVKDRFTISRDDSKNILYLQMNSLKTEDTAVYYCVRHGNFGNSYVSWFAYWGQGTLVTVSSASTKGPSVFPLAPSSpAFSTSGGTAALGCLVKDYFPEPVTVSWNSGALTSGVHTFPAVLQSSGLYSLSSVVTVPSSSLGTQTYICNVNHKPSNTKVDKKVEPKSC |
| 53 | HC (vH2.4 + CH1-HK129pAF) | EVQLVESGGGLVQPGGSLRLSCAASGFTFSTYAMNWVRQAPGKGLEWVGRIRSKYNNYATYYADSVKDRFTISRDDSKNSLYLQMNSLKTEDTAVYYCVRHGNFGNSYVSWFAYWGQGTLVTVSSASTKGPSVFPLAPSSpAFSTSGGTAALGCLVKDYFPEPVTVSWNSGALTSGVHTFPAVLQSSGLYSLSSVVTVPSSSLGTQTYICNVNHKPSNTKVDKKVEPKSC |
| 54 | HC (vH2.5 + CH1-HK129pAF) | EVQLVESGGGLVQPGGSLRLSCAASGFTFNTYAMNWVRQAPGKGLEWVGRIRSKYNNYATYYADSVKDRFTISRDDSKNSLYLQMNSLKTEDTAVYYCARHGNFGNSYVSWFAYWGQGTLVTVSSASTKGPSVFPLAPSSpAFSTSGGTAALGCLVKDYFPEPVTVSWNSGALTSGVHTFPAVLQSSGLYSLSSVVTVPSSSLGTQTYICNVNHKPSNTKVDKKVEPKSC |
| 55 | HC (vH2.6 + CH1-HK129pAF) | EVQLVESGGGLVQPGGSLRLSCAASGFTFSTYAMNWVRQAPGKGLEWVGRIRSKYNNYATYYADSVKDRFTISRDDSKNSLYLQMNSLKTEDTAVYYCARHGNFGNSYVSWFAYWGQGTLVTVSSASTKGPSVFPLAPSSpAFSTSGGTAALGCLVKDYFPEPVTVSWNSGALTSGVHTFPAVLQSSGLYSLSSVVTVPSSSLGTQTYICNVNHKPSNTKVDKKVEPKSC |
| 56 | HC (vH3.1 + CH1-HK129pAF) | EVQLVESGGGLVQPGGSLRLSCAASGFTFNTYAMHWVRQAPGKGLEWVARIRSKYNNYATYYADSVKDRFTISRDDSKNILYLQMNSLKTEDTAVYYCVRHGNFGNSYVSWFAYWGQGTLVTVSSASTKGPSVFPLAPSSpAFSTSGGTAALGCLVKDYFPEPVTVSWNSGALTSGVHTFPAVLQSSGLYSLSSVVTVPSSSLGTQTYICNVNHKPSNTKVDKKVEPKSC |
| 57 | HC (vH3.2 + CH1-HK129pAF) | EVQLVESGGGLVQPGGSLRLSCAASGFTENTYAMNWVRQAPGKGLEWVARIRSKSNNYATYYADSVKDRFTISRDDSKNILYLQMNSLKTEDTAVYYCVRHGNFGNSYVSWFAYWGQGTLVTVSSASTKGPSVFPLAPSSpAFSTSGGTAALGCLVKDYFPEPVTVSWNSGALTSGVHTFPAVLQSSGLYSLSSVVTVPSSSLGTQTYICNVNHKPSNTKVDKKVEPKSC |
| 58 | LC (vL2.4 + CL) | QAVVTQEPSLTVSPGGTVTLTCRSSTGAVTTSNYANWVQQKPGQAPRGLIGGTNKRAPWVPARFSGSLLGGKAALTLSGAQPEDEAEYYCALWYSNLWVFGGGTKLTVLGRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 59 | LC (VL2.1 + CL) | QAVVTQEPSLTVSPGGTVTLTCRSSTGAVTTSNYANWFQQKPGQAPRGLIGGTNKRAPGVPARFSGSLLGGKAALTLSGAQPEDEAEYYCALWYSNLWVEGGGTKLTVLGRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 60 | LC (vL2.5 + CL) | QAVVTQEPSLTVSPGGTVTLTCRSSTGAVTTSNYANWFQQKPGQAPRGLIGGTNKRAPWVPARFSGSLLGGKAALTLSGAQPEDEAEYYCALWYSNLWVEGGGTKLTVLGRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 61 | LC (vL2.2 + CL) | QAVVTQEPSLTVSPGGTVTLTCRSSTGAVTTSNYANWVQQKPGQAPRTLIGGTNKRAPGVPARFSGSLLGGKAALTLSGAQPEDEAEYYCALWYSNLWVFGGGTKLTVLGRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 1-continued

Novel amino acid sequences of humanized anti-CD3 variants with and without HC-DKTHT extension with the location of non-natural amino acid pAF incorporation underlined in heavy and light chains. Also disclosed are all of the sequences in the table below, where pAF is replaced by any other non-natural amino acid

| SEQ.<br>ID. NO. | CHAIN | SEQUENCE |
|---|---|---|
| 62 | LC<br>(vL3.1 + CL) | QAVVTQEPSLTVSPGGTVTLTCRSSTGAVTTSNYANWVQQ<br>KPGQAPRGLIGGTNNRAPGTPARFSGSLLGGKAALTLSGA<br>QPEDEAEYYCALWYSNLWVFGGGTKLTVLGRTVAAPSVFI<br>FPPSDEQLKSGTASVVCLLNNFYPREAKVQWKVDNALQSG<br>NSQESVTEQDSKDSTYSLSSTLTLSKADYEKHKVYACEVT<br>HQGLSSPVTKSFNRGEC |

Non-Natural Amino Acids

The present invention provides anti-CD3 antibodies, antibody fragments or variants comprising at least one non-naturally encoded amino acid. Introduction of at least one non-naturally encoded amino acid into an anti-CD3 antibody can allow for the application of conjugation chemistries that involve specific chemical reactions with one or more non-naturally encoded amino acids while not reacting with the commonly occurring 20 amino acids.

In some embodiments disclosed herein are anti-CD3 antibodies comprising one or more non-naturally encoded amino acids. The one or more non-natural amino acids may be encoded by a codon that does not code for one of the twenty natural amino acids. The one or more non-natural amino acids may be encoded by a nonsense codon (stop codon). The stop codon may be an amber codon. The amber codon may comprise a UAG sequence. The stop codon may be an ochre codon. The ochre codon may comprise a UAA sequence. The stop codon may be an opal or umber codon. The opal or umber codon may comprise a UGA sequence. The one or more non-natural amino acids may be encoded by a four-base codon.

The one or more non-natural amino acids may include, but are not limited to, p-azidophenylalanine (pAz), p-benzoylphenylalanine (pBpF), p-propargyloxyphenylalanine (pPrF), p-iodophenylalanine (pIF), p-cyanophenylalanine (pCNF), p-carboxylmethylphenylalanine (pCmF), 3-(2-naphthyl)alanine (NapA), p-boronophenylalanine (pBoF), o-nitrophenylalanine (oNiF), (8-hydroxyquinolin-3-yl)alanine (HQA), and (2,2'-bipyridin-5-yl)alanine (BipyA). The one or more non-natural amino acids may be β-amino acids (β3 and β2), homo-amino acids, proline and pyruvic acid derivatives, 3-substituted alanine derivatives, glycine derivatives, ring-substituted phenylalanine and tyrosine derivatives, linear core amino acids, diamino acids, D-amino acids, N-methyl amino acids, or a combination thereof. Non-natural amino acids may also include, but are not limited to, 1) various substituted tyrosine and phenylalanine analogues such as O-methyl-L-tyrosine, p-amino-L-phenylalanine, 3-nitro-L-tyrosine, p-nitro-L-phenylalanine, m-methoxy-L-phenylalanine and p-isopropyl-L-phenylalanine; 2) amino acids with aryl azide and benzophenone groups that may be photo-cross-linked; 3) amino acids that have unique chemical reactivity including acetyl-L-phenylalanine and m-acetyl-L-phenylalanine, O-allyl-L-tyrosine, O-(2-propynyl)-L-tyrosine, p-ethylthiocarbonyl-L-phenylalanine and p-(3-oxobutanoyl)-L-phenylalanine; 4) heavy-atom-containing amino acids for phasing in X-ray crystallography including p-iodo and p-bromo-L-phenylalanine; 5) the redox-active amino acid dihydroxy-L-phenylalanine; 6) glycosylated amino acids including b-N-acetylglucosamine-O-serine and a-N-acetylgalactosamine-O-threonine; 7) fluorescent amino acids with naphthyl, dansyl, and 7-aminocoumarin side chains; 8) photocleavable and photoisomerizable amino acids with azobenzene and nitrobenzyl Cys, Ser, and Tyr side chains; 9) the phosphotyrosine mimetic p-carboxymethyl-L-phenylalanine; 10) the glutamine homologue homoglutamine; and 11) 2-aminooctanoic acid. In some embodiments non-natural amino acid is N-acetylglucosaminyl-L-serine, N-acetylglucosaminyl-L-threonine, and O-phosphotyrosine. In some embodiments, non-natural amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like. Specific examples of non-natural amino acids include, but are not limited to, a p-acetyl-L-phenylalanine, a p-propargyloxyphenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like. Additional non-natural amino acids are disclosed in Liu et al., Annu Rev Biochem, 79:413-44, 2010; Wang et al., Angew Chem Int Ed, 44:34-66, 2005; and International Application NOs.: PCT/US2012/039472, PCT/US2012/039468, PCT/US2007/088009, PCT/US2009/058668, PCT/US2007/089142, PCT/US2007/088011, PCT/US2007/001485, PCT/US2006/049397, PCT/US2006/047822 and PCT/US2006/044682, each of which is incorporated herein by reference in its entirety. In some embodiments, the one or more non-natural amino acids may be p-acetylphenylalanine (pAF).

In certain embodiments of the invention, an anti-CD3 antibody with at least one non-natural amino acid includes at least one post-translational modification. In one embodiment, the at least one post-translational modification comprises attachment of a molecule including but not limited to, a water-soluble polymer, a derivative of polyethylene glycol, a drug, a second protein or polypeptide or polypeptide analog, an antibody or antibody fragment, a biologically active agent, a small molecule, or any combination of the above or any other desirable compound or substance, comprising a second reactive group to at least one non-natural amino acid comprising a first reactive group utilizing chemistry methodology that is known to one of ordinary skill in the art to be suitable for the particular reactive groups. For example, the first reactive group is an alkynyl moiety (including but not limited to, the non-natural amino acid p-propargyloxyphenylalanine, where the propargyl group is also sometimes referred to as an acetylene moiety) and the second reactive group is an azido moiety, and [3+2] cycloaddition chemistry methodologies are utilized. In another example, the first reactive group is the azido moiety (including but not limited to, the non-natural amino acid p-azido-L-phenylalanine) and the second reactive group is the alkynyl moiety. In certain embodiments of the modified anti-CD3 antibody polypeptide of the present invention at least one non-natural amino acid, (including but not limited to, non-natural amino acid containing a keto functional group), comprising at least one post-translational modification is used where the at least one post-translational modification comprises a saccharide moiety. In certain embodiments, the post-translational modification is made in vivo in a eukaryotic cell or in a non-eukaryotic cell. In other embodiments the post-translational modification is made in vitro. In another embodiment, the post-translational modification is made in vitro and in vivo.

In some embodiments, the non-natural amino acid may be modified to incorporate a chemical group. In some embodiments the non-natural amino acid may be modified to incorporate a ketone group. The one or more non-natural amino acids may comprise at least one oxime, carbonyl, dicarbonyl, hydroxylamine group or a combination thereof. The one or more non-natural amino acids may comprise at least one carbonyl, dicarbonyl, alkoxy-amine, hydrazine, acyclic alkene, acyclic alkyne, cyclooctyne, aryl/alkyl azide, norbornene, cyclopropene, trans-cyclooctene, or tetrazine functional group or a combination thereof.

In some embodiments disclosed herein the non-natural amino acid is site-specifically incorporated into the antibody, antibody fragment or variant. In some embodiments the non-natural amino acid is site-specifically incorporated into an anti-CD3 antibody, antibody fragment or variant. Methods for incorporating a non-natural amino acid into a molecule, for example, proteins, polypeptides or peptides, are disclosed in U.S. Pat. Nos. 7,332,571; 7,928,163; 7,696,312; 8,008,456; 8,048,988; 8,809,511; 8,859,802; 8,791,231; 8,476,411; or 9,637,411, (each of which is incorporated herein by reference in its entirety), and in the Examples herein. The one or more non-natural amino acids may be incorporated by methods known in the art. For example, cell-based or cell-free systems may be used, and auxotrophic strains may also be used in place of engineered tRNA and synthetase. In certain embodiments, orthogonal tRNA synthetase are used as disclosed in for example, PCT/US2002/012465; PCT/US2002/012635; PCT/US2003/032576; PCT/US2005/044041; PCT/US2005/043603; PCT/US2005/046618, each incorporated herein by reference in its entirety. Incorporating one or more non-natural amino acids into the antibody or antibody fragment or variant may comprise modifying one or more amino acid residues in the antibody or antibody fragment or variant. Modifying the one or more amino acid residues in the antibody or antibody fragment or variant may comprise mutating one or more nucleotides in the nucleotide sequence encoding the antibody or antibody fragment or variant. Mutating the one or more nucleotides in the nucleotide sequence encoding the antibody or antibody fragment or variant may comprise altering a codon encoding an amino acid to a nonsense codon. Incorporating one or more non-natural amino acids into the antibody or antibody fragment or variant may comprise modifying one or more amino acid residues in the antibody or antibody fragment or variant to produce one or more amber codons in the antibody or antibody fragment or variant. The one or more non-natural amino acids may be incorporated into the antibody or antibody fragment or variant in response to an amber codon. The one or more non-natural amino acids may be site-specifically incorporated into the antibody or antibody fragment or variant. Incorporating one or more non-natural amino acids into the antibody or antibody fragment or variant may comprise one or more genetically encoded non-natural amino acids with orthogonal chemical reactivity relative to the canonical twenty amino acids to site-specifically modify the biologically active molecule or targeting agent. Incorporating the one or more non-natural amino acids may comprise use of a tRNA/aminoacyl-tRNA synthetase pair to site-specifically incorporate one or more non-natural amino acids at defined sites in the biologically active molecule or targeting agent in response to one or more amber nonsense codon. Additional methods for incorporating non-natural amino acids include, but are not limited to, methods disclosed in Chatterjee et al., A Versatile Platform for Single- and Multiple-Unnatural Amino Acid Mutagenesis in *Escherichia coli*, Biochemistry, 2013; Kazane et al., J Am Chem Soc, 135(1):340-6, 2013; Kim et al., J Am Chem Soc, 134(24):9918-21, 2012; Johnson et al., Nat Chem Biol, 7(11):779-86, 2011; and Hutchins et al., J Mol Biol, 406(4): 595-603, 2011. The one or more non-natural amino acids may be produced through selective reaction of one or more natural amino acids. The selective reaction may be mediated by one or more enzymes. In non-limiting examples, the selective reaction of one or more cysteines with formylglycine generating enzyme (FGE) may produce one or more formylglycines as described in Rabuka et al., Nature Protocols 7: 1052-1067, 2012. The one or more non-natural amino acids may involve a chemical reaction to form a linker. The chemical reaction to form the linker may include a bioorthogonal reaction. The chemical reaction to form the linker may include click chemistry. See for example WO2006/050262 incorporated herein by reference in its entirety.

Biologically Active Molecules/Agents

Disclosed herein are anti-CD3 antibodies or antibody fragments or variant thereof comprising a biologically active molecule linked to the antibody or fragment or variant via a non-natural amino acid. Biologically active molecules include but are not limited to a small molecule or agent, a non-peptide compound, a drug, a second protein or polypeptide or polypeptide analog or derivative, an antibody or antibody fragment or variant, a second biologically active agent, a targeting agent, or any combination of the above or any other desirable compound or substance. In some embodiments the biologically active agent is involved in recruiting cytotoxic T cells to a cell, including but not limited to a cancer or tumor cell. In some embodiments the biologically active molecule is a small molecule such as, but not limited to, folic acid or a derivative or analog thereof or 2-[3-(1,3-dicarboxypropy)ureidol] pentanedioic acid (DUPA) or a derivative or analog thereof. In some embodiments the biologically active molecule is folate or a derivative or analog thereof. The biologically active molecule may be selected from a cell-targeting molecule, a ligand, a protein, a peptide, a peptoid, a DNA aptamer, a peptide nucleic acid, a vitamin, a substrate or a substrate analog, a cholecystokinin B receptor, a gonadotropin-releasing hormone receptor, a somatostatin receptor 2, an avb3 integrin, a gastrin-releasing peptide receptor, a neurokinin 1 receptor, a melanocortin 1 receptor, a neurotensin receptor, neuropeptide Y receptor and C-type lectin like molecule 1, a receptor, a co-receptor, a trans-membrane protein or a cell marker or cell surface protein. The biologically active molecule may bind a target cell. The biologically active molecule may bind a cell surface protein or a cell surface marker or a cell surface molecule on a cell. The biologically active molecule may bind a cell surface molecule on a cell including but limited to a cancer or tumor cell or immune suppressive cell. The cell surface molecule may be a folate receptor molecule. The biologically active molecule may be an agent that binds prostate-specific membrane antigen (PSMA) such as, but not limited to, DUPA or an analog or derivative thereof. The biologically active molecule or agent may bind to a cell overexpressing or highly expressing a cell surface marker, protein or receptor.

In some embodiments, the biologically active molecule may be a folate or folate ligand or analog or derivative thereof. The biologically active molecule may bind a folate receptor protein (FR). Such biologically active molecule may be N-(4-{[(2-amino-4-oxo-1,4-dihydropteridin-6-yl)methyl]amino}benzoyl)-L-glutamic acid (folic acid), or an analog or derivative thereof. An analog thereof may be a moiety that is based on folic acid and preserves FR binding. The folic acid analog may preserve a significant portion of the structure of folic acid. Moreover, the folic acid analog may be a slightly modified form of folic acid because of its conjugation to a linker or an antibody or antibody fragment or variant. For example, the folic acid analog may be slightly modified due to conjugation of a folate carboxyl group to the linker or antibody or antibody fragment or variant. In addition, folic acid may be slightly modified because of its conjugation to a linker or an antibody or antibody fragment but maintain its FR binding properties. In some embodiments the folate molecule targets folate receptor alpha. In some embodiments the folate molecule targets folate receptor beta. In some embodiments folic acid or folate is used as a biologically active molecule or targeting agent to bind to the folate receptor (FR) antigen, which is overexpressed or highly expressed on FR+ cell lines. In some embodiments the cell is a cancer cell or an immune suppressive cell but is not limited to such.

The biologically active molecule or agent may be site-specifically linked by the one or more linkers to the one or more non-natural amino acids of the antibody or antibody fragment or variant. The linker may be a chemical linker, a peptide linker, or a combination thereof. A chemical linker includes a linker via a non-natural amino acid. A chemical linker includes a linker via one or more non-natural amino acids. A chemical linker can include a chemical conjugate. A peptide linker includes any amino acid sequence joining the two amino acid sequences. The peptide linker may comprise 1 or more, 5 or more, 10 or more, 15 or more, 20 or more, 25 or more, 30 or more, 35 or more, 40 or more, 45 or more, 50 or more, 55 or more, 60 or more, 65 or more, 70 or more, 75 or more, 80 or more, 85 or more, 90 or more, 95 or more, 100 or more amino acids. The peptide linker may be a portion of any antibody, including a domain of an antibody, such as a variable domain, CH1, CH2, CH3, and/or CL domain. The antibody or antibody fragment or variant may be conjugated to a biologically active molecule.

The antibody or antibody fragment or variant may be conjugated to a biologically active molecule via a chemical and/or a peptide linker. In some embodiments, the invention provides an anti-CD3 antibody or antibody fragments or variant conjugated to one or more biologically active molecule or agent. In some embodiments the one or more biologically active molecules or agents is one or more small molecules. In some embodiments, the invention provides an anti-CD3 Fab antibody or antibody fragments or variant conjugated to one or more small molecule. In some embodiments the invention provides an anti-CD3 Fab antibody or antibody fragments or variant conjugated to one or more folate molecules. In some embodiments the invention provides an anti-CD3 Fab antibody or antibody fragments or variant conjugated to one or more DUPA molecules. In some embodiments one or more folate molecules and/or one or more DUPA molecules may be conjugated to an anti-CD Fab antibody via a chemical an/or peptide linker.

PEG Linkers/Ligands/Conjugates

An anti-CD3 antibody or an antigen-binding polypeptide and a small molecule may be joined by a linker, polymer or covalent bond. The linker, polymer, or small molecule itself may comprise a functional group that is unreactive toward the 20 common amino acids. The linker or polymer may be bifunctional linker or polymer. The bifunctional linker or polymer is a branched linker or polymer. One or more bonds involved in joining an anti-CD3 antibody or an antigen-binding polypeptide via the linker, polymer, or covalent bond to the biologically active molecule may be irreversible, reversible or labile under desired conditions. One or more bonds involved in joining an anti-CD3 antibody or a antigen-binding polypeptide via the linker, polymer, or covalent bond to a molecule may allow modulated release of the antigen-binding polypeptide or other molecule. A diversity of small molecules may be generated by one skilled in the art by chemical means, isolation as natural products, or other means.

Disclosed herein are anti-CD3 antibodies or antibody fragments or variants comprising one or more non-naturally encoded amino acids linked to one or more water-soluble polymer, such as polyethylene glycol (PEG) molecule or ligands. The anti-CD3 antibody or antibody fragment or variant comprising the non-naturally encoded amino acid can be linked to two water-soluble polymer, such as two polyethylene glycol (PEG) molecules or ligands. The antibody or antibody fragment or variant comprising the non-naturally encoded amino acid and one or more biologically active molecules can be linked to one or more water-soluble polymer, such as polyethylene glycol (PEG) molecule or linker. In some embodiments, the antibody or antibody fragment or variant comprising the non-naturally encoded amino acid and two biologically active molecules is linked to two water-soluble polymers, such as polyethylene glycol (PEG) molecule or linker.

The methods may comprise linking the antibody or antibody fragment to a biologically active molecule, or a water-soluble polymer, or a conjugate comprising a biologically active molecule and a water-soluble polymer. The method may comprise conjugating one or more linkers to a biologically active molecule to produce a biologically active molecule-linker intermediate and conjugating the intermediate to the antibody or antibody fragment. The method may comprise conjugating one or more linkers to a PEG molecule to produce a PEG-linker intermediate and conjugating the PEG-linker-intermediate to the antibody or antibody fragment. The method may comprise conjugating one or more linkers to the antibody or antibody fragment to produce an antibody-linker intermediate or antibody fragment-linker intermediate and conjugating the antibody-linker intermediate or antibody-fragment-linker intermediate to another biologically active molecule, or a water-soluble polymer, or a conjugate comprising a biologically active molecule and a water-soluble polymer. The methods disclosed herein may comprise conjugating one or more linkers to one or more antibodies or antibody fragments, one or more biologically active molecules, or combinations thereof to produce one or more intermediates such as an antibody-linker intermediate, an antibody fragment-linker intermediate and/or a biologically active molecule antibody conjugate-linker intermediate. The methods may comprise conjugating a first linker to an antibody or antibody fragment to produce an antibody-linker intermediate or antibody fragment-linker intermediate. The methods may comprise conjugating a linker to a biologically active molecule to produce a biologically active molecule-linker intermediate.

The method of producing a bispecific anti-CD3 antibody conjugate of the invention may comprise (a) conjugating a first linker to the antibody or antibody fragment comprising one or more non-natural amino acids incorporated into the antibody or antibody fragment (b) conjugating a second linker to the biologically active molecule to produce a biologically active molecule-linker intermediate; and (c) linking the two intermediates together to produce the anti-CD3 antibody-biological active molecule conjugate; the biologically active molecule can be small molecule including but not limited to a folate or a DUPA molecule or an analog or derivative thereof. In certain embodiments, the method of producing a bispecific anti-CD3 antibody conjugate of the invention may comprise (a) conjugating a first linker to the antibody or antibody fragment comprising one or more non-natural amino acids incorporated into the antibody or antibody fragment to produce an antibody-linker intermediate or antibody fragment-linker intermediate; (b) conjugating a second linker to the biologically active molecule to produce a biologically active molecule-linker intermediate; and (c) linking the two intermediates together to produce the anti-CD3 antibody-biological active molecule conjugate; the biologically active molecule can be small molecule including but not limited to a folate or a DUPA molecule or an analog or derivative thereof. The method of producing a bispecific anti-CD3 Fab antibody-folate conjugate of the invention may comprise (a) conjugating a first linker to the anti-CD3 Fab antibody or antibody fragment comprising one or more non-natural amino acids incorporated into the antibody or antibody fragment to produce an antibody-linker intermediate or antibody fragment-linker intermediate; (b) conjugating a second linker to the biologically active molecule to produce a biologically active molecule-linker intermediate; and (c) linking the two intermediates together to produce the anti-CD3 Fab antibody-biological active molecule conjugate; the biologically active molecule comprising one or more folate or DUPA molecules or analogs or derivatives; the linker comprising one or more chemical and/or peptide linkers; the linker comprising one or more PEG molecules. The one or more PEG molecule is a linear or branched PEG molecule. The one or more branched PEG molecule is a bifunctional linker. The PEG molecule has an average molecular weight of 5 kDa, 10 kDa, 20 kDa, 30 kDa 40 kDa, 50 kDa or greater. The PEG molecule has an average molecular weight of 5K, 10K or 20K.

Conjugating of the one or more linkers to the antibody or antibody fragment, or biologically active molecule may occur simultaneously. Conjugating of the one or more linkers to the antibody or antibody fragment, or biologically active molecule may occur sequentially. Conjugating of the one or more linkers to the antibody or antibody fragment, or biologically active molecule may occur in a single step process such as an enzymatic conjugation, or a chemical step, or process or reaction. Conjugating of the one or more linkers to the antibody or antibody fragment, or biologically active molecule may occur in two step process such as two enzymatic conjugations, or two chemical steps, or two processes or two reactions. Conjugating of the one or more linkers to the antibody or antibody fragment, or biologically active molecule may occur in two or more steps processes such as two or more enzymatic conjugations, or chemical steps, or processes or reactions.

Conjugating an intermediate to an antibody or antibody fragment, or biologically active molecule, or a water-soluble polymer may comprise oxime chemistry to form an oxime bond and/or click chemistry, as well known to the skilled artisan. The antibody or antibody fragment may comprise one or more non-natural amino acids. Linking the antibody or antibody fragment to an intermediate may comprise forming an oxime between the non-natural amino acid and the linker intermediate. Conjugating a linker to an antibody or antibody fragment, or biologically active molecule or water-soluble molecule may comprise an ionic bond, a covalent bond, a non-covalent bond, or a combination thereof between the linker and the antibody or antibody fragment, or biologically active molecule or water-soluble molecule. Conjugation of a linker to an antibody or antibody fragment or biologically active molecule or water-soluble molecule is known in the art. See for example Roberts et al., Advanced Drug Delivery Reviews 54:459-476 (2002).

Conjugating one or more linkers to the antibody or antibody fragment and/or biologically active molecule may comprise forming one or more oximes between the linker and the antibody or antibody fragment or biological active molecule. Conjugating one or more linkers to the antibody or antibody fragment and/or biologically active molecule may comprise forming one or more stable bonds between linker and the antibody or antibody fragment or biologically active molecule. Conjugating one or more linkers to the antibody or antibody fragment and/or biologically active molecule may comprise forming one or more covalent bonds between linker and the antibody or antibody fragment or biologically active molecule. Conjugating one or more linkers to the antibody or antibody fragment and/or biologically active molecule may comprise forming one or more non-covalent bonds between linker and the antibody, antibody fragment or biologically active molecule. Conjugating one or more linkers to the antibody or antibody fragment and/or ligand may comprise forming one or more ionic bonds between linker and the antibody or antibody fragment or biologically active molecule.

Conjugating one or more linkers to the antibody or antibody fragment may comprise site specifically conjugating one or more linkers to the antibody or antibody fragment. Site-specific conjugation may comprise linking the one or more linkers to the non-natural amino acid of the antibody or antibody fragment. Linking the one or more linkers to the non-natural amino acid of the antibody or antibody fragment may comprise formation of an oxime. Linking the one or more linkers to the non-natural amino acid of the antibody or antibody fragment may comprise formation of a sulfide. Linking the one or more linkers to the non-natural amino acid of the antibody or antibody fragment may comprise, by way of non-limiting example, reacting a hydroxylamine of the one or more linkers with an aldehyde or ketone of an amino acid. The amino acid may be a non-natural amino acid. Linking the one or more linkers to the non-natural amino acid of the antibody or antibody fragment may comprise, by way of non-limiting example, reacting a bromo derivative of the one or more linkers with a thiol of an amino acid. The amino acid may be a non-natural amino acid.

One or more PEG or linkers may comprise a disulfide bridge that connects two cysteine residues using conjugation chemistry as known by the skilled artisan. (See also, for example ThioBridge™ technology, Abzena). Two or more PEG molecules or linkers may comprise a maleimide bridge that connects two amino acid residues. The two amino acids may be at the C-terminal of the antibody or antibody fragment. One or more linkers may comprise a maleimide bridge that connects two cysteine residues. The two cysteine residues may be C-terminal of the antibody or antibody fragment. In some embodiments, one or more PEG may be a C-terminal PEG conjugation. In some embodiments a C-terminal PEG molecule may not involve covalent disulfide link or attachment between the heavy and light chain antibody or antibody fragments. In some embodiments two or more C-terminal located PEG molecules may be covalently attached or crosslinked between the heavy and light chains of the antibody or antibody fragment. Such PEG conjugates or linkers are described herein.

In some embodiments disclosed herein are Folate-PEG linkers comprising one or more folate and one or more PEG molecules. The one or more PEG molecules can be 5 kDa, 10 kDa, 15 kDa, 20 kDa or more. PEG molecules encompass both linear and branched polymers and average molecular weights of between 0.1 kDa and 100 kDa. In some embodiments, the poly(ethylene glycol) molecule or a linker has a molecular weight of between about 0.1 kDa and about 100 kDa. In some embodiments, the poly(ethylene glycol) molecule or a linker has a molecular weight of between 0.1 kDa and 50 kDa. In some embodiments, the poly(ethylene glycol) molecule or a linker is a branched polymer or linker. In some embodiments, each branch of the poly(ethylene glycol) branched polymer or linker has a molecular weight of between 1 kDa and 100 kDa, or between 1 kDa and 50 kDa. PEG molecules are well known in the art, for example, see Shearwater Corporation's catalog "Polyethylene Glycol and Derivatives for Biomedical Applications" (2001).

In certain embodiments disclosed herein are anti-CD3 Fab-Folate PEGylated conjugates comprising one or more PEG molecules. In certain embodiments disclosed herein are anti-CD3 Fab-Folate PEGylated conjugates comprising one or more C-terminal PEG molecules. In some embodiments a C-terminal PEG molecule may not involve covalent disulfide linkage or attachment between the heavy and light chain antibody or antibody fragments. In some embodiments a C-terminal PEG molecule may be attached separately to the heavy chain and the light chain of the antibody or antibody fragment. In some embodiments two or more C-terminal PEG molecules may be covalently attached or crosslinked between the heavy and light chains of the antibody or antibody fragments. In some embodiments two or more PEG molecules may be covalently attached or crosslinked via a maleimide bridge that connects two cysteine residues.

PEGylation can be used to improve pharmacokinetics and modulate cytotoxicity of a composition. PEGylation of a protein can increase its serum half-life by retarding renal clearance, since the PEG moiety adds considerable hydrodynamic radius to the protein. Covalent attachment of the hydrophilic polymer poly(ethylene glycol), abbreviated PEG, is a method of increasing water solubility, bioavailability, increasing serum half-life, increasing therapeutic half-life, modulating immunogenicity, modulating biological activity, or extending the circulation time of many biologically active molecules, including proteins, peptides, and particularly hydrophobic molecules. PEG has been used extensively in pharmaceuticals, on artificial implants, and in other applications where biocompatibility, lack of toxicity, and lack of immunogenicity are of importance. Preferably the PEGylation does not alter, or only minimally alters, the activity of the biologically active molecule. Preferably, the increase in half-life is greater than any decrease in biological activity. Rader et al. in Proc Natl Acad Sci USA. 2003 Apr. 29; 100(9):5396-400, which is incorporated by reference herein, describe a method to provide effector function and extended serum half-life to small synthetic molecules via reacting them with a generic antibody molecule. The complex described was created by a reversible covalent bond between mAb 38C2, a catalytic antibody that mimics natural aldolase enzymes, and a diketone derivative of an integrin targeting Arg-Gly-Asp peptidomimetic via a reactive lysine residue on the antibody. In addition to an increase in half-life of the peptidomimetic, the complex showed selective retargeting of the antibody to the surface of integrin $\alpha_v\beta_3$ and $\alpha_v\beta_5$ expressing cells.

In some embodiments, the anti-CD3 antibody comprising the non-naturally encoded amino acid is linked to a water-soluble polymer, such as polyethylene glycol (PEG), via the side chain of the non-naturally encoded amino acid. In some embodiments, the anti-CD3 antibody comprising the non-naturally encoded amino acid is linked to folate, where said link is via the side chain of the non-naturally encoded amino acid. In some embodiments, the anti-CD3 antibody comprising the non-naturally encoded amino acid is linked to a folate derivative via the side chain of the non-naturally encoded amino acid. In some embodiments, the anti-CD3 antibody comprising the non-naturally encoded amino acid is linked to a water-soluble polymer, such as polyethylene glycol (PEG), where said link is via the side chain of the non-naturally encoded amino acid. In some embodiments, the anti-CD3 antibody comprising the non-naturally encoded amino acid is linked to a water-soluble polymer derivative, such as polyethylene glycol (PEG) derivative, where said link is via the side chain of the non-naturally encoded amino acid. In some embodiments, water-soluble polymer-folate linkers are provided, and the anti-CD3 antibody comprising the at least one or more non-naturally encoded amino acids is linked to the folate and/or to the water-soluble polymer and/or to the linker via the side chain of the one or more non-naturally encoded amino acids.

In some embodiments, the folate moiety is derived from the following structure including the structure illustrated in FIGS. 12A-12F:

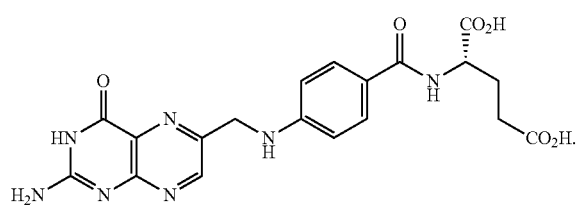 [SMILES: Nc1nc2ncc(CNc3ccc(C(=O)N[C@@H](CCC(=O)O)C(=O)O)cc3)nc2c(=O)[nH]1]

In some embodiments, the water-soluble polymer is poly (ethylene glycol). In some embodiments, the term poly (ethylene glycol) includes poly(ethylene glycol) in any form, including linear poly(ethylene glycol), branched poly (ethylene glycol), bifunctional poly(ethylene glycol), multiarmed poly(ethylene glycol), derivatized poly(ethylene glycol) and forked poly(ethylene glycol).

The molecular weight of the poly(ethylene glycol) may be from between 1 kDa and 100 kDa. The molecular weight of the poly(ethylene glycol) may be 5, 10, 15, 20, 25, 30, 35, 40, 45, 50, 55 or 60 kDa. The molecular weight of the poly(ethylene glycol) may be between about 1 kDa and about 25 kDa, or between about 5 kDa and 20 kDa. The molecular weight of the poly(ethylene glycol) may be about 5 kDa, or about 10 kDa, or about 20 kDa. The molecular weight of the poly(ethylene glycol) may be 5 kDa or 10 kDa or 20 kDa. The molecular weight of the poly(ethylene glycol) may be 5 kDa.

In some embodiments, the bifunctional water-soluble polymer-folate linker has the following structure:

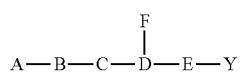

wherein:

A has the structure of:

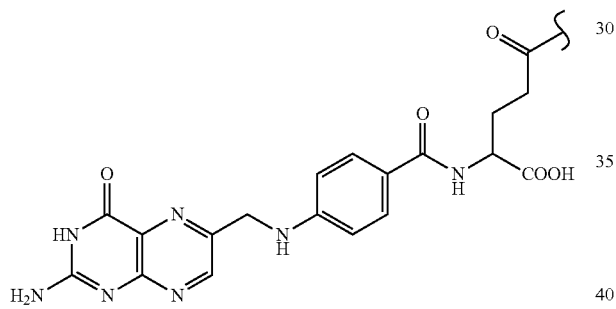

B is a bivalent group connecting A and C;

C and E are each independently selected from the group consisting of -alkylene-, alkylene-(O)—, -(alkylene-O)$_{n'}$-alkylene-, -(alkylene-O)$_{n'}$-alkylene-C(O)—, -(alkylene-O)$_{n'}$—(CH$_2$)$_{n'}$—NHC(O)—(CH$_2$)—C(Me)$_2$—S—S—(CH$_2$)$_{n'}$—NHC(O)-(alkylene-O)$_{n'}$-alkylene-, -(alkylene-O)$_{n'}$-alkylene-U-alkylene-C(O)—, and -(alkylene-O)$_{n'}$-alkylene-U-alkylene-, where n' is independently an integer greater than or equal to one;

D is a trivalent group connecting C, F and E;

F is a water-soluble polymer, such as polyethylene glycol (PEG); and where

Y is selected from the group consisting of an hydroxylamine, methyl, aldehyde, protected aldehyde, ketone, protected ketone, thioester, ester, dicarbonyl, hydrazine, amidine, imine, diamine, azide, ketoamine, keto-alkyne, alkyne, cycloalkyne, and enedione.

In some embodiments, B is a substituted bivalent heterohydrocarbyl residue. In some embodiments, the substituents include one or mom carboxyl, ketone and/or amide functional groups. In some embodiments, the heteroatoms are selected from N, O and S.

In some embodiments, B has the following structure:

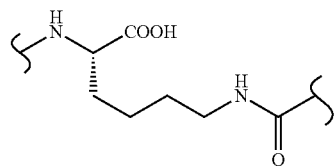

In some embodiments, D is substituted trivalent heterohydrocarbyl residue. In some embodiments, the substituents include one or more carboxyl, ketone and/or amide functional groups. In some embodiments, the heteroatoms are selected from N, O and S.

In some embodiments, D has the following structure:

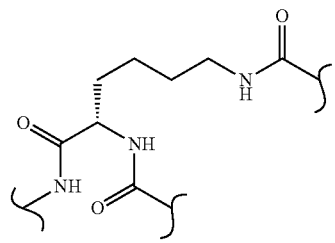 [SMILES: CNC(=O)[C@H](CCCCNC(C)=O)NC(C)=O]

In some embodiments, C and E are each -(alkylene-O)$_{n'}$-alkylene-. In some embodiments, each alkylene is —CH$_2$CH$_2$—.

In some embodiments, n' is 1 to 20, or 1 to 10, or 1 to 5.

In some embodiments, F has the structure:

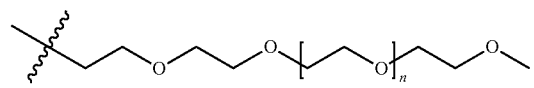

wherein n is between 2 and 10,000. In some embodiments, n is chosen such that the molecular weight of the poly(ethylene glycol) (PEO) is from between 1 kDa and 100 kDa. For example, the molecular weight may be 5, 10, 15, 20, 25, 30, 35, 40, 45, 50, 55 or 60 kDa. For example, the molecular weight may be between about 1 kDa and about 25 kDa, or between about 5 kDa and 20 kDa. For example, the molecular weight may be about 5 kDa, or about 10 kDa, or about 20 kDa. For example, the molecular weight may be 5 kDa or 10 kDa or 20 kDa. For example, the molecular weight may be 5 kDa.

In some embodiments, the bifunctional water-soluble polymer-folate linker has the following structure:

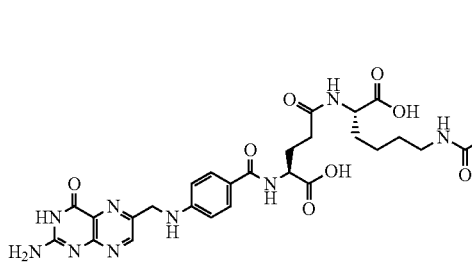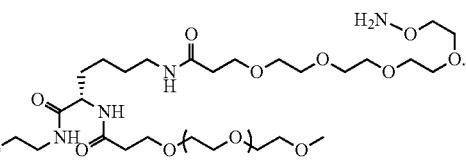

In some embodiments, the anti-CD3 antibody comprising the at least one non-naturally encoded amino acid is linked to the water-soluble polymer bifunctional PEG-folate linker, and accordingly has the following structure:

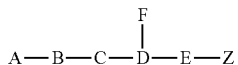

wherein A, B, C, D, E and F are as defined in any of the embodiments above and Z is an oxime or cyclic linkage connected via a non-natural amino acid to the anti-CD3 antibody.

In some embodiments, Z has the structure of:

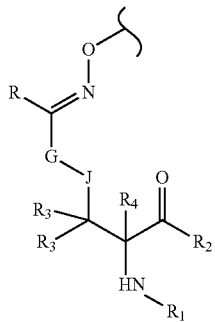

wherein:

J is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

G is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$ (alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N—, —C(R')$_2$—N=N—, and —C(R')$_2$—N(R')—N(R')—, where each R' is independently H, alkyl, or substituted alkyl;

R is H, alkyl, substituted alkyl, cycloalkyl, or substituted cycloalkyl;

R$_1$ is H, an amino protecting group, resin, at least one amino acid, polypeptide, or polynucleotide;

R$_2$ is OH, an ester protecting group, resin, at least one amino acid, polypeptide, or polynucleotide;

wherein R$_1$ and/or R$_2$ is the anti-CD3 antibody; and

R$_3$ and R$_4$ are each independently H, halogen, lower alkyl, or substituted lower alkyl, or R$_3$ and R$_4$ or two R$_3$ groups optionally form a cycloalkyl or a heterocycloalkyl.

In some embodiments, Z has the structure of

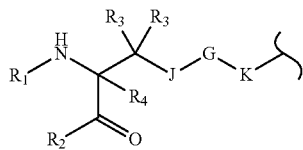

where J, G, R$_1$, R$_2$, R$_3$ and R$_4$ are as defined above, and where D has the structure of:

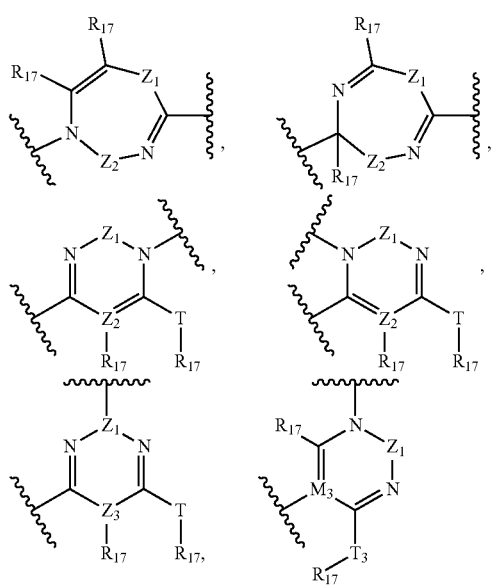

-continued

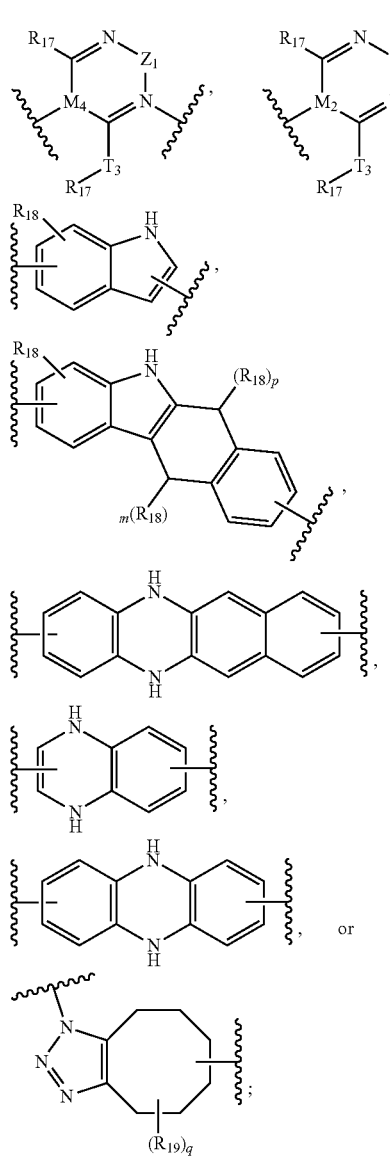

where each $R_{17}$ is independently selected from the group consisting of H, alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, aryl, substituted aryl, heteroaryl, substituted heteroaryl, alkaryl, substituted alkaryl, aralkyl, substituted aralkyl, -(alkylene or substituted alkylene)-ON(R")$_2$, -(alkylene or substituted alkylene)-C(O)SR", -(alkylene or substituted alkylene)-S—S-(aryl or substituted aryl), —C(O)R", —C(O)$_2$R", or —C(O)N(R")$_2$, wherein each R" is independently hydrogen, alkyl, substituted alkyl, alkenyl, substituted alkenyl, alkoxy, substituted alkoxy, aryl, substituted aryl, heteroaryl, alkaryl, substituted alkaryl, aralkyl, or substituted aralkyl;

each $Z_1$ is a bond, $CR_{17}R_{17}$, O, S, NR', $CR_{17}R_{17}$—$CR_{17}R_{17}$, $CR_{17}R_{17}$—O, O—$CR_{17}R_{17}$, $CR_{17}R_{17}$—S, S—$CR_{17}R_{17}$, $CR_{17}R_{17}$—NR', or NR'—$CR_{17}R_{17}$;

each R' is H, alkyl, or substituted alkyl;

each $Z_2$ is selected from the group consisting of a bond, —C(O)—, —C(S)—, optionally substituted $C_1$-$C_3$ alkylene, optionally substituted $C_1$-$C_3$ alkenylene, and optionally substituted heteroalkyl;

each $Z_3$ are independently selected from the group consisting of a bond, optionally substituted $C_1$-$C_4$ alkylene, optionally substituted $C_1$-$C_4$ alkenylene, optionally substituted heteroalkyl, —O—, —S—, —C(O)—, —C(S)—, and —N(R')—;

each $T_3$ is a bond, C(R")(R"), O, or S; with the proviso that when $T_3$ is O or S, R" cannot be halogen;

each R" is H, halogen, alkyl, substituted alkyl, cycloalkyl, or substituted cycloalkyl;

m and p are 0, 1, 2, or 3, provided that at least one of m or p is not 0;

$M_2$ is

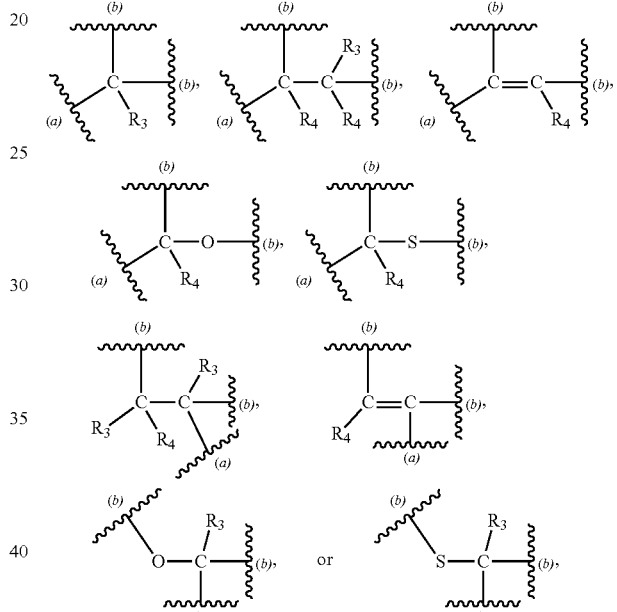

where (a) indicates bonding to the B group and (b) indicates bonding to respective positions within the heterocycle group;

$M_3$ is

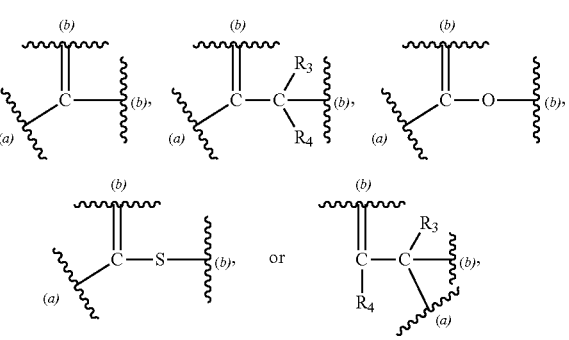

where (a) indicates bonding to the B group and (b) indicates bonding to respective positions within the heterocycle group;

M4 is

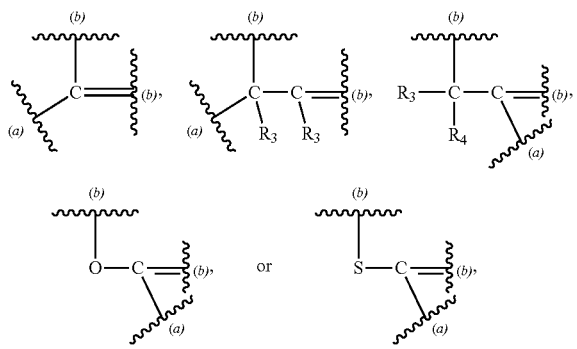

where (a) indicates bonding to the B group and (b) indicates bonding to respective positions within the heterocycle group;

each $R_{19}$ is independently selected from the group consisting of $C_1$-$C_6$ alkyl, $C_1$-$C_6$ alkoxy, ester, ether, thioether, aminoalkyl, halogen, alkyl ester, aryl ester, amide, aryl amide, alkyl halide, alkyl amine, alkyl sulfonic acid, alkyl nitro, thioester, sulfonyl ester, halosulfonyl, nitrile, alkyl nitrile, and nitro;

q is 0, 1, 2, 3, 4, 5, 6, 7, 8, 9, 10 or 11; and each $R_{16}$ is independently selected from the group consisting of hydrogen, halogen, alkyl, $NO_2$, CN, and substituted alkyl.

This invention provides a highly efficient method for the selective modification of proteins with PEG derivatives, which involves the selective incorporation of non-genetically encoded amino acids, including but not limited to, those amino acids containing functional groups or substituents not found in the 20 naturally incorporated amino acids, including but not limited to a ketone, an azide or acetylene moiety, into proteins in response to a selector codon and the subsequent modification of those amino acids with a suitably reactive PEG derivative. Once incorporated, the amino acid side chains can then be modified by utilizing chemistry methodologies known to those of ordinary skill in the art to be suitable for the particular functional groups or substituents present in the naturally encoded amino acid. Known chemistry methodologies of a wide variety are suitable for use in the present invention to incorporate a water-soluble polymer into the protein. Such methodologies include but are not limited to a Huisgen [3+2] cycloaddition reaction (see, e.g., Padwa, A. in Comprehensive Organic Synthesis, Vol. 4, Ed. Trost, B. M., Pergamon, Oxford, p. 1069-1109, 1991; and, Huisgen, R. in 1,3-Dipolar Cycloaddition Chemistry, Ed. Padwa, A., Wiley, New York, p. 1-176, 1984) with, including but not limited to, acetylene or azide derivatives, respectively.

Because the Huisgen [3+2] cycloaddition method involves a cycloaddition rather than a nucleophilic substitution reaction, proteins can be modified with extremely high selectivity. The reaction can be carried out at room temperature in aqueous conditions with excellent regioselectivity, (1,4>1,5), by the addition of catalytic amounts of Cu(I) salts to the reaction mixture. (See, e.g., Tornoe, et al., Org. Chem. 67:3057-3064, 2002; and, Rostovtsev, et al., Angew. Chem. Int. Ed. 41:2596-2599, 2002; and WO 03/101972). A molecule that can be added to a protein of the invention through a [3+2] cycloaddition includes virtually any molecule with a suitable functional group or substituent including but not limited to an azido or acetylene derivative. These molecules can be added to an unnatural amino acid with an acetylene group, including but not limited to, p-propargyloxyphenylalanine, or azido group, including but not limited to p-azido-phenylalanine, respectively.

The five-membered ring that results from the Huisgen [3+2] cycloaddition is not generally reversible in reducing environments and is stable against hydrolysis for extended periods in aqueous environments. Consequently, the physical and chemical characteristics of a wide variety of substances can be modified under demanding aqueous conditions with the active PEG or PEG derivatives of the present invention. Even more important, because the azide and acetylene moieties are specific for one another (and do not, for example, react with any of the 20 common, genetically-encoded amino acids), proteins can be modified in one or more specific sites with extremely high selectivity.

The invention also provides water-soluble and hydrolytically stable derivatives of PEG derivatives and related hydrophilic polymers having one or more acetylene or azide moieties. The PEG polymer derivatives that contain acetylene moieties are highly selective for coupling with azide moieties that have been introduced selectively into proteins in response to a selector codon. Similarly, PEG polymer derivatives that contain azide moieties are highly selective for coupling with acetylene moieties that have been introduced selectively into proteins in response to a selector codon.

More specifically, the azide moieties comprise, but are not limited to, alkyl azides, aryl azides and derivatives of these azides. The derivatives of the alkyl and aryl azides can include other substituents so long as the acetylene-specific reactivity is maintained. The acetylene moieties comprise alkyl and aryl acetylenes and derivatives of each. The derivatives of the alkyl and aryl acetylenes can include other substituents so long as the azide-specific reactivity is maintained.

An anti-CD3 antibody therefore is intended to include any polypeptide that demonstrates an ability to specifically bind to a target molecule or antigen. Any known antibody or antibody fragment is an anti-CD3 antibody.

In one embodiment, compositions of anti-CD3 antibody that include an unnatural amino acid (such as p-(propargyloxy)-phenylalanine) are provided. Various compositions comprising p-(propargyloxy)-phenylalanine and, including but not limited to, proteins and/or cells, are also provided. In one aspect, a composition that includes the p-(propargyloxy)-phenylalanine unnatural amino acid, further includes an orthogonal tRNA. The unnatural amino acid can be bonded (including but not limited to, covalently) to the orthogonal tRNA, including but not limited to, covalently bonded to the orthogonal tRNA though an amino-acyl bond, covalently bonded to a 3'OH or a 2'OH of a terminal ribose sugar of the orthogonal tRNA, etc.

Measurement of Anti-CD3 Antibody Activity and Affinity of Anti-CD3 Antibody for its Antigen or Binding Partner Anti-CD3 antibody activity can be determined using standard in vitro or in vivo assays. For example, cells or cell lines that bind anti-CD3 antibody (including but not limited to, cells containing native anti-CD3 antibody antigen or binding partner or recombinant anti-CD3 antibody antigen or binding partner producing cells) can be used to monitor anti-CD3 antibody binding. For a non-PEGylated or PEGylated antigen-binding polypeptide comprising a non-natural amino acid, the affinity of the anti-CD3 antibody for its antigen or binding partner can be measured by using techniques known in the art such as a BIAcore™ biosensor (Pharmacia) or Octet (ForteBio).

Regardless of which methods are used to create the anti-CD3 antibody, the anti-CD3 antibody are subject to assays for biological activity. Tritiated thymidine assays may be conducted to ascertain the degree of cell division, if appropriate. Other biological assays, however, may be used to ascertain the desired activity. Biological assays such as measuring the ability to inhibit an antigen's biological activity, such as an enzymatic, proliferative, or metabolic activity also provides an indication of anti-CD3 antibody activity. Other in vitro assays well known to one of skill in the art may be used to ascertain biological activity. In general, the test for biological activity should provide analysis for the desired result, such as increase or decrease in biological activity (as compared to non-altered anti-CD3 antibody), different biological activity (as compared to non-altered anti-CD3 antibody), receptor affinity analysis, conformational or structural changes, or serum half-life analysis, as appropriate for the antigen's biological activity. Those skilled in the art will recognize other assays useful for testing for the desired end results.

Measurement of Potency, Functional In Vivo Half-Life, and Pharmacokinetic Parameters An important aspect of the invention is the prolonged biological half-life that is obtained by construction of anti-CD3 antibody with or without conjugation of the anti-CD3 antibody to a water-soluble polymer moiety. The rapid decrease of anti-CD3 antibody serum concentrations has made it important to evaluate biological responses to treatment with conjugated and non-conjugated anti-CD3 antibody and variants thereof. Preferably, the conjugated and non-conjugated anti-CD3 antibody and variants thereof of the present invention have prolonged serum half-lives also after i.v. administration, making it possible to measure by, e.g. ELISA method or by a primary screening assay. Measurement of in vivo biological half-life is carried out as described herein.

Pharmacokinetic parameters for an antigen-binding polypeptide comprising a non-naturally encoded amino acid can be evaluated in normal Sprague-Dawley male rats). Pharmacokinetic data for anti-CD3 antibody is well-studied in several species and can be compared directly to the data obtained for anti-CD3 antibody comprising a non-naturally encoded amino acid.

The specific activity of anti-CD3 antibody in accordance with this invention can be determined by various assays known in the art. The biological activity of the anti-CD3 antibody muteins, or fragments thereof, obtained and purified in accordance with this invention can be tested by methods described or referenced herein or known to those skilled in the art.

Administration and Pharmaceutical Compositions

The polypeptides or proteins of the invention (including but not limited to, anti-CD3 antibody, synthetases, proteins comprising one or more unnatural amino acid, etc.) are optionally employed for therapeutic uses, including but not limited to, in combination with a suitable pharmaceutical carrier. Such compositions, for example, comprise a therapeutically effective amount of the compound, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are well known in the art and can be applied to administration of the polypeptides of the invention.

Therapeutic compositions comprising one or more polypeptide of the invention are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of unnatural herein to natural amino acid homologues (including but not limited to, comparison of an anti-CD3 antibody modified to include one or more unnatural amino acids to a natural amino acid anti-CD3 antibody), i.e., in a relevant assay.

Administration is by any of the routes normally used for introducing a molecule into ultimate contact with blood or tissue cells. The unnatural amino acid polypeptides of the invention are administered in any suitable manner, optionally with one or more pharmaceutically acceptable carriers. Suitable methods of administering such polypeptides in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Polypeptide compositions can be administered by a number of routes including, but not limited to oral, intravenous, intraperitoneal, intramuscular, transdermal, subcutaneous, topical, sublingual, or rectal means. Compositions comprising non-natural amino acid polypeptides, modified or unmodified, can also be administered via liposomes. Such administration routes and appropriate formulations are generally known to those of skill in the art.

The anti-CD3 antibody comprising a non-natural amino acid, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged anti-CD3 antibody can be presented in unit-dose or multi-dose sealed containers, such as ampules and vials.

Parenteral administration and intravenous administration are preferred methods of administration. In particular, the routes of administration already in use for natural amino acid homologue therapeutics (including but not limited to, those typically used for EPO, GH, anti-CD3 antibody, G-CSF, GM-CSF, IFNs, interleukins, antibodies, and/or any other pharmaceutically delivered protein), along with formulations in current use, provide preferred routes of administration and formulation for the polypeptides of the invention.

The dose administered to a patient, in the context of the present invention, is sufficient to have a beneficial therapeutic response in the patient over time, or, including but not limited to, to inhibit infection by a pathogen, or other appropriate activity, depending on the application. The dose is determined by the efficacy of the particular vector, or formulation, and the activity, stability or serum half-life of the unnatural amino acid polypeptide employed and the condition of the patient, as well as the body weight or surface area of the patient to be treated. The size of the dose is also determined by the existence, nature, and extent of any adverse side-effects that accompany the administration of a particular vector, formulation, or the like in a particular patient.

In determining the effective amount of the vector or formulation to be administered in the treatment or prophylaxis of disease (including but not limited to, cancers, inherited diseases, diabetes, AIDS, or the like), the physician evaluates circulating plasma levels, formulation toxicities, progression of the disease, and/or where relevant, the production of anti-unnatural amino acid polypeptide antibodies.

The dose administered, for example, to a 70 kilogram patient, is typically in the range equivalent to dosages of currently-used therapeutic proteins, adjusted for the altered activity or serum half-life of the relevant composition. The vectors of this invention can supplement treatment conditions by any known conventional therapy, including antibody administration, vaccine administration, administration of cytotoxic agents, natural amino acid polypeptides, nucleic acids, nucleotide analogues, biologic response modifiers, and the like.

For administration, formulations of the present invention are administered at a rate determined by the LD-50 or ED-50 of the relevant formulation, and/or observation of any side-effects of the unnatural amino acids at various concentrations, including but not limited to, as applied to the mass and overall health of the patient. Administration can be accomplished via single or divided doses.

If a patient undergoing infusion of a formulation develops fevers, chills, or muscle aches, he/she receives the appropriate dose of aspirin, ibuprofen, acetaminophen or other pain/fever controlling drug. Patients who experience reactions to the infusion such as fever, muscle aches, and chills are premedicated 30 minutes prior to the future infusions with either aspirin, acetaminophen, or, including but not limited to, diphenhydramine. Meperidine is used for more severe chills and muscle aches that do not quickly respond to antipyretics and antihistamines. Cell infusion is slowed or discontinued depending upon the severity of the reaction.

Human antigen-binding polypeptides of the invention can be administered directly to a mammalian subject. Administration is by any of the routes normally used for introducing anti-CD3 antibody to a subject. The anti-CD3 antibody compositions according to embodiments of the present invention include those suitable for oral, rectal, topical, inhalation (including but not limited to, via an aerosol), buccal (including but not limited to, sub-lingual), vaginal, parenteral (including but not limited to, subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration, although the most suitable route in any given case will depend on the nature and severity of the condition being treated. Administration can be either local or systemic. The formulations of compounds can be presented in unit-dose or multi-dose sealed containers, such as ampoules and vials. Anti-CD3 antibody of the invention can be prepared in a mixture in a unit dosage injectable form (including but not limited to, solution, suspension, or emulsion) with a pharmaceutically acceptable carrier. Anti-CD3 antibody of the invention can also be administered by continuous infusion (using, including but not limited to, minipumps such as osmotic pumps), single bolus or slow-release depot formulations.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. Solutions and suspensions can be prepared from sterile powders, granules, and tablets of the kind previously described.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions (including optional pharmaceutically acceptable carriers, excipients, or stabilizers) of the present invention (see, e.g., Remington's Pharmaceutical Sciences, 17$^{th}$ ed. 1985).

Suitable carriers include buffers containing phosphate, borate, HEPES, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates, including glucose, mannose, or dextrins; chelating agents such as EDTA; divalent metal ions such as zinc, cobalt, or copper; sugar alcohols such as mannitol or sorbitol; salt-forming counter ions such as sodium; and/or nonionic surfactants such as Tween™, Pluronics™, or PEG.

The anti-CD3 antibodies of the invention, including those linked to water-soluble polymers such as PEG can also be administered by or as part of sustained-release systems. Sustained-release compositions include, including but not limited to, semi-permeable polymer matrices in the form of shaped articles, including but not limited to, films, or microcapsules. Sustained-release matrices include from biocompatible materials such as poly(2-hydroxyethyl methacrylate) (Langer et al., J. Biomed. Mater. Res., 15: 167-277 1981; Langer, Chem. Tech., 12: 98-105, 1982), ethylene vinyl acetate (Langer et al., supra) or poly-D-(–)-3-hydroxybutyric acid (EP 133,988), polylactides (polylactic acid) (U.S. Pat. No. 3,773,919; EP 58,481), polyglycolide (polymer of glycolic acid), polylactide co-glycolide (copolymers of lactic acid and glycolic acid) polyanhydrides, copolymers of L-glutamic acid and gamma-ethyl-L-glutamate (U. Sidman et al., Biopolymers, 22, 547-556. 1983), poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Sustained-release compositions also include a liposomally entrapped compound. Liposomes containing the compound are prepared by methods known per se: DE 3,218,121; (Epstein et al., Proc. Natl. Acad. Sci. U.S.A., 82: 3688-3692, 1985; Hwang et al., Proc. Natl. Acad. Sci. U.S.A., 77: 4030-4034, 1980; EP 52,322; EP 36,676; EP 88,046; EP 143,949; EP 142,641; Japanese Pat. Appln. 83-118008; U.S.

Pat. Nos. 4,485,045 and 4,544,545; and EP 102,324). All references and patents cited are incorporated by reference herein.

Liposomally entrapped anti-CD3 antibody can be prepared by methods described in, e.g., DE 3,218,121; Epstein et al., Proc. Natl. Acad. Sci. U.S.A., 82: 3688-3692, 1985; Hwang et al., Proc. Natl. Acad. Sci. U.S.A., 77: 4030-4034, 1980; EP 52,322; EP 36,676; EP 88,046; EP 143,949; EP 142,641; Japanese Pat. Appln. 83-118008; U.S. Pat. Nos. 4,485,045 and 4,544,545; and EP 102,324. Composition and size of liposomes are well known or able to be readily determined empirically by one skilled in the art. Some examples of liposomes as described in, e.g., Park J W, et al., Proc. Natl. Acad. Sci. USA 92:1327-1331, 1995; Lasic D and Papahadjopoulos D (eds): MEDICAL APPLICATIONS OF LIPOSOMES, 1998; Drummond D C, et al., Liposomal drug delivery systems for cancer therapy, in Teicher B (ed): CANCER DRUG DISCOVERY AND DEVELOPMENT, 2002; Park J W, et al., Clin. Cancer Res. 8:1172-1181, 2002; Nielsen U B, et al., Biochim. Biophys. Acta 1591(1-3):109-118, 2002; Mamot C, et al., Cancer Res. 63: 3154-3161, 2003. All references and patents cited are incorporated by reference herein.

The dose administered to a patient in the context of the present invention should be sufficient to cause a beneficial response in the subject over time. Generally, the total pharmaceutically effective amount of the anti-CD3 antibody of the present invention administered parenterally per dose is in the range of about 0.01 µg/kg/day to about 100 µg/kg, or about 0.05 mg/kg to about 1 mg/kg, of patient body weight, although this is subject to therapeutic discretion. The frequency of dosing is also subject to therapeutic discretion and may be more frequent or less frequent than the commercially available anti-CD3 antibody products approved for use in humans. Generally, a bispecific antigen-binding polypeptide of the invention can be administered by any of the routes of administration described above.

Therapeutic Uses of Anti-CD3 Antibody Bioconjugates of the Invention

The anti-CD3 antibody polypeptides of the invention are useful for treating a wide range of disorders. Anti-CD3 antibody compositions disclosed herein may be used to modulate an immune response. Modulation of an immune response may comprise stimulating, activating, increasing, enhancing, or up-regulating an immune response. Modulation of an immune response may comprise suppressing, inhibiting, preventing, reducing, or downregulating an immune response. The anti-CD3 antibody-Folate compositions disclosed may have advantages in penetrating solid tumors while the natural folate ligand targets the folate receptor alpha on tumors, for example, and folate receptor beta on immune suppressive cells. In some embodiments, the tumor is a liquid or solid tumor.

Disclosed herein are methods of treating a subject for a condition with an anti-CD3 conjugate or pharmaceutical composition of the invention. In some cancers, overexpression of specific cell surface receptors can allow selective targeting of cancerous cells with small molecules or drugs, while minimizing effects on healthy cells. For example, prostate cancer-specific membrane antigen (PMSA)-targeting 2-[3-(1,3-dicarboxy propyl)-ureido] pentanedioic acid (DUPA) can be conjugated to a T-cell surface antigen (anti-CD3) binding antibody to selectively recruit or target cytotoxic T-cells to kill prostate cancer cells. N-(4-{[(2-amino-4-oxo-1,4-dihydropteridin-6-yl)methyl]amino}benzoyl)-L-glutamic acid (folic acid) can also be used as a biological active molecule to bind to the folate receptor (FR) antigen, which is overexpressed on FR+ cancer cell lines.

The invention provides a method of treating cancer by administering to a patient a therapeutically-effective amount of an anti-CD3 antibody of the invention. The cancer may be ovarian cancer including, but not limited to, an epithelial, stromal and germ cell tumor. The ovarian cancer may comprise a fallopian tube cancer or primary peritoneal carcinoma. The cancer may be characterized by high expression of folate receptor-alpha (FOLR1), such as ovarian cancer, for example. The cancer may be treated by recruiting cytotoxic T cells to folate receptor positive (FR+) tumor cells. In some embodiments, the invention provides a method of treating inherited diseases, AIDs or diabetes by administering to a patient a therapeutically-effective amount of an anti-CD3 antibody of the invention. In some embodiments the anti-CD3 antibody or therapeutic can be a bispecific antibody comprising an anti-CD3 Fab antibody, optionally wherein the anti-CD3 Fab antibody comprises a site specifically incorporated non-naturally encoded amino acid optionally conjugated to two folate and two PEGylated molecules. In a further embodiment, into said anti-CD3 Fab antibody and conjugation to the two folate and two PEGylated molecules is via the side chain of the non-natural amino acid.

The invention provides anti-CD3 antibodies for use in treating a disease or condition in a cell expressing high folate receptor number. The anti-CD3 antibodies of the invention are for use in treating cancer including, but not limited to, ovarian cancer ovarian cancer including, but not limited to, an epithelial, stromal and germ cell tumor. The ovarian cancer may comprise a fallopian tube cancer or primary peritoneal carcinoma. The cancer may be characterized by high expression of folate receptor-alpha (FOLR1), such as ovarian cancer, for example. The cancer may be treated by recruiting cytotoxic T cells to folate receptor positive (FR+) tumor cells. The anti-CD3 antibodies of the invention are for use in treating inherited diseases, AIDS, or diabetes but is not limited to such. The anti-CD3 antibodies of the invention can be used in the manufacture of a medicament for treating a disease or condition in a cell expressing high folate receptor number. The anti-CD3 antibodies of the invention can be used in the manufacture of a medicament for treating cancer including, but not limited to, ovarian cancer ovarian cancer including, but not limited to, an epithelial, stromal and germ cell tumor. The ovarian cancer may comprise a fallopian tube cancer or primary peritoneal carcinoma. The cancer may be characterized by high expression of folate receptor-alpha (FOLR1), such as ovarian cancer, for example. The cancer may be treated by recruiting cytotoxic T cells to folate receptor positive (FR+) tumor cells. The anti-CD3 antibodies of the invention can be used in the manufacture of a medicament for treating inherited diseases, AIDS or diabetes but is not limited to such.

In some embodiments the condition to be treated is a cancer. The cancer may be, but is non-limited to, a breast cancer, a brain cancer, a pancreatic cancer, a skin cancer, a lung cancer, a liver cancer, a gall bladder cancer, a colon cancer, an ovarian cancer, a prostate cancer, a uterine cancer, a bone cancer, and a blood cancer (leukemic) cancer or a cancer or disease or conditions related to any of these cancers. Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some instances, the cancer is a skin cancer, such as a basal cell carcinoma, squamous, melanoma, nonmelanoma, or actinic (solar) keratosis. In some embodiments the cancer is any cancer with highly expressed folate receptor alpha or beta. In some embodiments the condition to be treated is a disease or condition. The disease or condition may be a pathogenic infection. The pathogenic infection may be a bacterial infection. The pathogenic infection may be a viral infection. The disease or condition may be an inflammatory disease. The disease or condition may be an autoimmune disease. The autoimmune disease may be diabetes. The disease or condition may be a cancer. In some embodiments the disease or condition is any disease or condition with highly expressed folate receptor alpha or beta. The disease or condition may be a pathogenic infection. The biologically active molecule may interact with a cell surface molecule on an infected cell. The biologically active molecule may interact with a molecule on a bacterium, a virus, or a parasite. Pathogenic infections may be caused by one or more pathogens. In some instances, the pathogen is a bacterium, fungi, virus, or protozoan. Exemplary pathogens include but are not limited to: *Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* or *Yersinia*. The pathogen may be a virus. Examples of viruses include, but are not limited to, adenovirus, coxsackievirus, Epstein-Barr virus, Hepatitis virus (e.g., Hepatitis A, B, and C), herpes simplex virus (type 1 and 2), cytomegalovirus, herpes virus, HIV, influenza virus, measles virus, mumps virus, papillomavirus, parainfluenza virus, poliovirus, respiratory syncytial virus, rubella virus, and varicella-zoster virus. Examples of diseases or conditions caused by viruses include, but are not limited to, cold, flu, hepatitis, AIDS, chicken pox, rubella, mumps, measles, warts, and poliomyelitis. The disease or condition may be an autoimmune disease or autoimmune related disease. An autoimmune disorder may be a malfunction of the body's immune system that causes the body to attack its own tissues. Examples of autoimmune diseases and autoimmune related diseases include, but are not limited to, Addison's disease, alopecia areata, ankylosing spondylitis, antiphospholipid syndrome (APS), autoimmune aplastic anemia, autoimmune hemolytic anemia, autoimmune hepatitis, autoimmune myocarditis, Behcet's disease, celiac sprue, Crohn's disease, dermatomyositis, eosinophilic fasciitis, erythema nodosum, giant cell arteritis (temporal arteritis), Goodpasture's syndrome, Graves' disease, Hashimoto's disease, idiopathic thrombocytopenic purpura (ITP), IgA nephropathy, juvenile arthritis, diabetes, juvenile diabetes, Kawasaki syndrome, Lambert-Eaton syndrome, lupus (SLE), mixed connective tissue disease (MCTD), multiple sclerosis, myasthenia gravis, pemphigus, polyarteritis nodosa, type I, II, & III autoimmune polyglandular syndromes, polymyalgia rheumatica, polymyositis, psoriasis, psoriatic arthritis, Reiter's syndrome, relapsing polychondritis, rheumatoid arthritis, sarcoidosis, scleroderma, Sjogren's syndrome, sperm & testicular autoimmunity, stiff person syndrome, Takayasu's arteritis, temporal arteritis/giant cell arteritis, ulcerative colitis, uveitis, vasculitis, vitiligo, and Wegener's granulomatosis.

The disease or condition may be an inflammatory disease. Examples of inflammatory diseases include, but are not limited to, alveolitis, amyloidosis, angiitis, ankylosing spondylitis, avascular necrosis, Basedow's disease, Bell's palsy, bursitis, carpal tunnel syndrome, celiac disease, cholangitis, chondromalacia patella, chronic active hepatitis, chronic fatigue syndrome, Cogan's syndrome, congenital hip dysplasia, costochondritis, Crohn's Disease, cystic fibrosis, De Quervain's tendinitis, diabetes associated arthritis, diffuse idiopathic skeletal hyperostosis, discoid lupus, Ehlers-Danlos syndrome, familial mediterranean fever, fascitis, fibrositis/fibromyalgia, frozen shoulder, ganglion cysts, giant cell arteritis, gout, Graves' Disease, HIV-associated rheumatic disease syndromes, hyperparathyroid associated arthritis, infectious arthritis, inflammatory bowel syndrome/irritable bowel syndrome, juvenile rheumatoid arthritis, lyme disease, Marfan's Syndrome, Mikulicz's Disease, mixed connective tissue disease, multiple sclerosis, myofascial pain syndrome, osteoarthritis, osteomalacia, osteoporosis and corticosteroid-induced osteoporosis, Paget's Disease, palindromic rheumatism, Parkinson's Disease, Plummer's Disease, polymyalgia rheumatica, polymyositis, pseudogout, psoriatic arthritis, Raynaud's Phenomenon/Syndrome, Reiter's Syndrome, rheumatic fever, rheumatoid arthritis, sarcoidosis, sciatica (lumbar radiculopathy), scleroderma, scurvy, sickle cell arthritis, Sjogren's Syndrome, spinal stenosis, spondyloisthesis, Still's Disease, systemic lupus erythematosis, Takayasu's (Pulseless) Disease, Tendinitis, tennis elbow/golf elbow, thyroid associated arthritis, trigger finger, ulcerative colitis, Wegener's Granulomatosis, and Whipple's Disease.

The pharmaceutical compositions containing the anti-CD3 antibody may be formulated at a strength effective for administration by various means to a human patient experiencing disorders that may be affected by anti-CD3 antibody agonists or antagonists, such as but not limited to, anti-proliferatives, anti-inflammatory, or anti-virals are used, either alone or as part of a condition or disease. Average quantities of anti-CD3 antibody may vary and in particular should be based upon the recommendations and prescription of a qualified physician. The exact amount of anti-CD3 antibody is a matter of preference subject to such factors as the exact type of condition being treated, the condition of the patient being treated, as well as the other ingredients in the composition. The invention also provides for administration of a therapeutically effective amount of another active agent such as an anti-cancer chemotherapeutic agent or immunotherapeutic agent but is not limited to such. The amount to be given may be readily determined by one skilled in the art based upon therapy with anti-CD3 antibody.

EXAMPLES

The following examples are offered to illustrate, but not to limit the claimed invention.

Example 1

Criteria for the selection of preferred sites of incorporation of non-naturally encoded amino acids into anti-CD3 antibody:—This example demonstrates how preferred sites within the antigen-binding polypeptide, CD3, can be selected for introduction of non-naturally encoded amino acids utilizing the three dimensional structure composed of two molecules of anti-CD3 antibody, or the secondary, tertiary, or quaternary structure of anti-CD3 antibody.

The following criteria is used to evaluate each position of anti-CD3 antibody for the introduction of a non-naturally encoded amino acid: the residue (a) should not interfere with binding of either anti-CD3 antibody based on structural analysis of three dimensional structures, or the secondary, tertiary, or quaternary structure of anti-CD3 antibody, b) should not be affected by alanine or homolog scanning mutagenesis, (c) should be surface exposed and exhibit minimal van der Waals or hydrogen bonding interactions with surrounding residues, (d) may be on one or more of the exposed faces of anti-CD3 antibody, (e) may be a site or sites of anti-CD3 antibody that are juxtaposed to a second anti-CD3 antibody, or other molecule or fragment thereof, (f) should be either deleted or variable in anti-CD3 antibody variants, (g) would result in conservative changes upon substitution with a non-naturally encoded amino acid, (h) may modulate the conformation of the anti-CD3 antibody itself or a dimer or multimer comprising one or more anti-CD3 antibody, by altering the flexibility or rigidity of the complete structure as desired, (i) could be found in either highly flexible regions or structurally rigid regions and (j) are found in complementarity determining regions (CDR) or not. In addition, further calculations were performed on the anti-CD3 antibody molecule, utilizing the Cx program (Pintar et al. *Bioinformatics*, 18, pp 980) to evaluate the extent of protrusion for each protein atom. As a result, in some embodiments, the non-naturally encoded encoded amino acid is substituted atone or more positions of anti-CD3 antibody.

Example 2

Expression of anti-CD3 antibody including a non-naturally encoded amino acid in *E. coli*:—An introduced translation system that comprises an orthogonal tRNA (O-tRNA) and an orthogonal aminoacyl tRNA synthetase (O-RS) is used to express anti-CD3 antibody containing a non-naturally encoded amino acid. The O-RS preferentially aminoacylates the O-tRNA with a non-naturally encoded amino acid. In turn the translation system inserts the non-naturally encoded amino acid into anti-CD3 antibody, in response to an encoded selector codon.

The transformation of *E. coli* with plasmids containing the modified anti-CD3 antibody gene and the orthogonal aminoacyl tRNA synthetase/tRNA pair, (specific for the desired non-naturally encoded amino acid), allows the site-specific incorporation of non-naturally encoded amino acid into the anti-CD3 antibody. The transformed *E. coli*, grown at 37° C. in media containing between 0.01-100 mM of the particular non-naturally encoded amino acid, expresses modified anti-CD3 antibody with high fidelity and efficiency. The anti-CD3 antibody containing a non-naturally encoded amino acid is produced by the *E. coli* host cells as soluble proteins in the periplasmic Methods for purification of anti-CD3 antibody are well known in the art and are confirmed by SDS-PAGE, Western Blot analyses, or electrospray-ionization ion trap mass spectrometry and the like.

Expression/Suppression: Suppression with nonnaturally encoded amino acid—para-acetyl-phenylalanine (pAF): Suppression of the Amber mutations in *E. coli* is achieved using standard protocols known in the art. Briefly, for the periplasmic suppression of antibody fragments in *E. coli* (Fab), the expression vector construct is transformed into *E. coli* host cells with a plasmid encoding an orthogonal tRNA synthetase (for example, orthogonal tyrosyl-tRNA-synthetase from *M. jannaschii* (MjTyrRS)). Overnight bacterial cultures were diluted 1:100 into shake flasks containing either LB media (Luria-Bertani) or Superbroth and grown at 37° C. to an OD of approximately 0.8. Fab expression is induced while suppression of the amber codon is achieved by the addition of para-acetyl-phenylalanine (pAF) to a final concentration of 4 mM. Cultures were incubated at 25° C. overnight.

Suppression with non-naturally encoded amino acid derivatives: Suppression of amber mutations with a derivative of a non-naturally encoded amino acid (for example, pAF (aa 9.2)) is achieved in a similar manner as described above, except that the orthogonal synthetase (for example, tyrosyl-tRNA-synthetase from *M. jannaschii* (MjTyrRS)) used is specific for the amino acid. For example, suppression is achieved by the addition of aa9.2 (4 mM) at the time of induction.

Cells are harvested by centrifugation and resuspended in periplasmic release buffer (50 mM $NaPO_4$, 20% sucrose, 1 mM EDTA, pH 8.0) supplemented with 100 ug/ml of lysozyme and incubated on ice for 30 minutes. After centrifugation, antibody fragments in the supernatant are immobilized on ProBind beads (Invitrogen; Carlsbad, CA) by virtue of their His tag, the beads are washed extensively with binding buffer and the bound fragments eluted from the beads with 0.5 M imidazole. Purified fragments were dialyzed in storage buffer (50 mM HEPES, 150 mM NaCl, 10% glycerol, 5% sucrose, pH 7.8). For small scale analysis of Fab fragments expressed in the periplasm, *E. coli* from 15 ml of culture are collected by centrifugation and re-suspended in 1 ml of lysis buffer (B-PER, Pierce Biotechnology; Rockford, IL) supplemented with 10 ug/ml of DNase. The mixture is incubated at 37° C. for 30 minutes, diluted to 1× in Protein Loading buffer (Invitrogen; Carlsbad, CA) and analyzed by SDS-PAGE.

Example 3

Design and construction of humanized anti-CD3 genes in pFUSE vectors—Mouse monoclonal anti-CD3 antibody SP34 (Harvard BIDMC) was humanized. Based on in-silico analysis and design, synthesis of 3 variable heavy chain (vH1.0, vH1.1 & vH1.2) and 3 variable light chain genes (vL1.0, vL1.1 & vL1.2) (Genewiz, South Plainfield, NJ) containing various mouse framework back mutations in addition to the mouse CDR sequences into the selected human framework scaffold was conducted. Table 2 lists mouse framework residues (back mutations), with their Kabat numbering, that were retained in 3 variable heavy (vH) and 3 variable light (vL) chains of 9 humanized anti-CD3 Fabs mentioned in FIG. 1. Amino acid residues that were reverted back to human framework sequences are shown in bold.

TABLE 2

List of mouse framework residues

| LC ID | LC Back Mutation(s) | HC ID | HC Back Mutation(s) |
|---|---|---|---|
| vL1.0 | V36F/G46T/G49Y/G57W/V58T | vH1.0 | N30/A49G/I77S/V93 |
| vL1.1 | V36/G46/G49/G57/V58 | vH1.1 | N30/A49/I77S/V93 |
| vL1.2 | V36/G46/G49/G57/V58T | vH1.2 | N30/A49/I77/V93 |

As shown in Table 2, there are 5 mouse back mutations in variable light chains (V36, G46, G49, G57 and V58) and 4 mouse back mutations in variable heavy chains (N30, A49, I77 and V93). The 6 short synthetic variable genes shown in Table 2 were cloned into Invivogen's heavy chain (HC) and light chain (LC) expression vectors (pFUSE-CHIg-HG1 and pFUSE-CLig-hk, respectively) resulting in plasmids that express humanized anti-CD3 SP34 antibodies. As shown in FIG. 1 and Table 2, variable light chain vL1.0 with all 5 mouse back mutations converted to human residues lost binding with any variable heavy (vH) chain combinations.

Example 4

Expression of humanized anti-CD3 antibodies in HEK293 transient system: The humanized SP34 antibodies described in the previous Example were transiently expressed into HEK293 cells by combining each vH gene containing plasmid with each vL gene containing plasmid (co-transfection). Protein concentration in cell culture media from each co-transfection experiment was determined, and directly used for PBMC-based CD3 binding assays without further purification. Controls used were chimeric SP34 construct, positive control, and an unrelated PSMA antibody construct, negative control. Humanized anti-CD3 antibodies, without non-natural amino acid incorporation, and with or without HC-DKTHT extension were also expressed in HEK293 cells and characterized (Table 3). These antibodies were used in screening for low-affinity Fab variants. Table 3 shows novel wild-type (WT) amino acid sequences of humanized anti-CD3 heavy (vH+CH1) and light (vL+CL) chain sequences used in varying combinations to generate Fab WT sequences disclosed herein. Also shown in Table 3 are WT amino acid sequences of humanized anti-CD3 heavy (vH+CH1-DKTHT) chain sequences.

TABLE 3

Wild-type (WT) amino acid sequences- anti-CD3 heavy (vH + CH1), (vH + CH1-DKTHT) and light (vL + CL) chains

| SEQ. ID. NO. | CHAIN | SEQUENCE |
|---|---|---|
| 1 | HC (vH1.2 + CH1) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSC |
| 2 | HC (vH1.1 + CH1) | EVQLVESGGGLVQPGGSLRLSCAASGFTFNTYAMNWVRQA PGKGLEWVARIRSKYNNYATYYADSVKDRFTISRDDSKNS LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSC |
| 3 | HC (vH1.0 + CH1) | EVQLVESGGGLVQPGGSLRLSCAASGFTFNTYAMNWVRQA PGKGLEWVGRIRSKYNNYATYYADSVKDRFTISRDDSKNS LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSC |
| 4 | HC (vH1.2 + CH1-DKTHT) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHT |
| 5 | HC (vH1.1 + CH1-DKTHT) | EVQLVESGGGLVQPGGSLRLSCAASGFTFNTYAMNWVRQA PGKGLEWVARIRSKYNNYATYYADSVKDRFTISRDDSKNS LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHT |
| 6 | HC (vH1.0 + CH1-DKTHT) | EVQLVESGGGLVQPGGSLRLSCAASGFTFNTYAMNWVRQA PGKGLEWVGRIRSKYNNYATYYADSVKDRFTISRDDSKNS LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHT |

TABLE 3-continued

Wild-type (WT) amino acid sequences-
anti-CD3 heavy (vH + CH1), (vH + CH1-DKTHT)
and light (vL + CL) chains

| SEQ. ID. NO. | CHAIN | SEQUENCE |
|---|---|---|
| 7 | LC (vL1.2 + CL) | QAVVTQEPSLTVSPGGTVTLTCRSSTGAVTTSNYANWVQQ KPGQAPRGLIGGTNKRAPGTPARFSGSLLGGKAALTLSGA QPEDEAEYYCALWYSNLWVFGGGTKLTVLGRTVAAPSVFI FPPSDEQLKSGTASVVCLLNNFYPREAKVQWKVDNALQSG NSQESVTEQDSKDSTYSLSSTLTLSKADYEKHKVYACEVT HQGLSSPVTKSFNRGEC |
| 8 | LC (vL1.1 + CL) | QAVVTQEPSLTVSPGGTVTLTCRSSTGAVTTSNYANWVQQ KPGQAPRGLIGGTNKRAPGVPARFSGSLLGGKAALTLSGA QPEDEAEYYCALWYSNLWVFGGGTKLTVLGRTVAAPSVFI FPPSDEQLKSGTASVVCLLNNFYPREAKVQWKVDNALQSG NSQESVTEQDSKDSTYSLSSTLTLSKADYEKHKVYACEVT HQGLSSPVTKSFNRGEC |
| 9 | LC (vL1.0 + CL) | QAVVTQEPSLTVSPGGTVTLTCRSSTGAVTTSNYANWFQQ KPGQAPRTLIYGTNKRAPWTPARFSGSLLGGKAALTLSGA QPEDEAEYYCALWYSNLWVFGGGTKLTVLGRTVAAPSVFI FPPSDEQLKSGTASVVCLLNNFYPREAKVQWKVDNALQSG NSQESVTEQDSKDSTYSLSSTLTLSKADYEKHKVYACEVT HQGLSSPVTKSFNRGEC |

Example 5

Testing for CD3 binding with activated human and cyno PBMC: To distinguish between the humanized anti-CD3 antibodies generated, binding to human CD3 was tested using activated human PBMCs (n=2). The activation of PBMCs and subsequent fluorescence-based CD3 binding assays were followed as described previously (see for example, Angew Chem Int Ed Engl, 52(46):12101-12104, 2013). As shown in FIG. 1, three antibodies with vL1.0 light chain lost binding to human CD3 with any vH heavy chain combinations. The binding of the remaining 6 humanized antibodies to both human and cyno CD3 using activated human and cyno PBMCs, respectively, was titrated. As shown in FIGS. 2A-2F, all 6 humanized anti-CD3 antibodies (engineered from 3 vH heavy chains with 2 vL light chain combinations shown in Table 3) retained comparable binding to both human and cyno CD3. The six (6) humanized anti-CD3 antibodies were obtained as follows: Fab1, Fab2 and Fab3 wildtype were generated by combination of LC ((vL1.2+CL); (SEQ.ID. NO:7)) and HC ((vH1.2+CH1); (SEQ.ID. NO:1)), ((vH1.1+CH1); (SEQ.ID. NO:2)) and ((vH1.0+CH1); (SEQ.ID. NO:3)) respectively. Fab4, Fab 5 and Fab6 wildtype were generated by combination of LC ((vL1.1+CL); (SEQ.ID. NO:8)) and HC ((vH1.2+CH1); (SEQ.ID. NO:1)), ((vH1.1+CH1); (SEQ.ID. NO:2)) and ((vH1.0+CH1); (SEQ.ID. NO:3)) respectively.

Since the data showed no significant difference between the 6 humanized antibodies with respect to binding to both CD3 substrates, Fab1 (vH1.2+vL1.2 combination) was selected to further demonstrate the key aspects of the present invention. For example, Fab1 was used for expression in *Escherichia coli* for further optimization employing proprietary unnatural amino acid (UAA) incorporation technology through orthogonal amber suppression system previously described (see for example, WO2017/079272, WO2012/166560 and WO2013/192360). The list of mouse framework back mutations that were necessary for retention of binding activity in these 6 Fabs is shown in Table 4 which provides a list of mouse framework residues (back mutations), with their Kabat numbering, that were retained in 6 humanized anti-CD3 Fabs mentioned in FIGS. 2A-2F. Amino acid residues that were reverted back to human framework sequence are shown in bold. The vL1.2 and vH1.2 variable chain combination resulting in Fab1 (underlined) was chosen as lead for further modification.

TABLE 4

Mouse framework residues retained in 6 humanized anti-CD3 Fabs

| Fab# | LC ID | LC Back Mutation(s) | HC ID | HC Back Mutation(s) |
|---|---|---|---|---|
| <u>Fab1</u> | <u>vL1.2</u> | V36/G46/G49/G57/V58T | <u>vH1.2</u> | N30/A49/I77/V93 |
| Fab2 | vL1.2 | V36/G46/G49/G57/V58T | vH1.1 | N30/A49/I77S/V93 |
| Fab3 | vL1.2 | V36/G46/G49/G57/V58T | vH1.0 | N30/A49G/I77S/V93 |
| Fab4 | vL1.1 | V36/G46/G49/G57/V58 | vH1.2 | N30/A49/I77/V93 |
| Fab5 | vL1.1 | V36/G46/G49/G57/V58 | vH1.1 | N30/A49/I77S/V93 |
| Fab6 | vL1.1 | V36/G46/G49/G57/V58 | vH1.0 | N30/A49G/I77S/V93 |

Example 6

Cloning of synthetic Fab genes into *E. coli* expression vector: The synthetic Fab genes were cloned into proprietary standard *E. coli* expression vector using Gibson Assembly cloning kit (New England Biolabs). After sequence verification of each expression plasmid, each was transformed into standard *E. coli* production host W3110B60 strain and an isolated single colony for each plasmid was purified to make glycerol vials. The glycerol vials served as the production clones for *E. coli* fermentation of these Fab molecules. The amino acid sequences of the 4 heavy and 3 light chains used in engineering these Fabs are shown in Table 5 as SEQ.ID. NOs: 10 to 20.

TABLE 5

Amino acid sequences of humanized anti-CD3 Fab1
(vH1.2 + CH1, vL1.2 + CL) heavy and light
chain sequences with the non-natural amino acid, pAF,
incorporation site underlined that were produced in
*E. coli*.

| SEQ. ID. NO. | CHAIN | SEQUENCE |
|---|---|---|
| 10 | HC (vH1.2 + CH1-HA114pAF) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSpAFSTKGPSVFPLAPSSKSTSGGTAALGCLVKDYF PEPVTVSWNSGALTSGVHTFPAVLQSSGLYSLSSVVTVPS SSLGTQTYICNVNHKPSNTKVDKKVEPKSC |
| 11 | HC (vH1.2 + CH1-HS115pAF) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSApAFTKGPSVFPLAPSSKSTSGGTAALGCLVKDYF PEPVTVSWNSGALTSGVHTFPAVLQSSGLYSLSSVVTVPS SSLGTQTYICNVNHKPSNTKVDKKVEPKSC |
| 12 | HC (vH1.2 + CH1-HK129pAF) | EVQLVESGGGLVQPGGSLRLSCAASGFTFNTYAMNWVRQA PGKGLEWVARIRSKYNNYATYYADSVKDRETISRDDSKNI LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSC |
| 13 | HC (vH1.2 + CH1-HT160pAF) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALpAFSGVHTFPAVLQSSGLYSLSSVVTVPS SSLGTQTYICNVNHKPSNTKVDKKVEPKSC |
| 14 | HC (vH1.2 + CH1-HA114pAF + DKTHT) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSpAFSTKGPSVFPLAPSSKSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 15 | HC (vH1.2 + CH1-HS115pAF + DKTHT) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSApAFTKGPSVFPLAPSSKSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 16 | HC (vH1.2 + CH1-HK129pAF-DKTHT) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 17 | HC (vH1.2 + CH1-HT160pAF + DKTHT) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALpAFSGVHTFPAVLQSSGLYSLSSVVTVPS SSLGTQTYICNVNHKPSNTKVDKKVEPKSCDKTHT |
| 18 | LC (vL1.2 + CL-LL157pAF) | QAVVTQEPSLTVSPGGTVTLTCRSSTGAVTTSNYANWVQQ KPGQAPRGLIGGTNKRAPGTPARFSGSLLGGKAALTLSGA QPEDEAEYYCALWYSNLWVFGGGTKLTVLGRTVAAPSVFI FPPSDEQLKSGTASVVCLLNNFYPREAKVQWKVDNApAFQ SGNSQESVTEQDSKDSTYSLSSTLTLSKADYEKHKVYACE VTHQGLSSPVTKSFNRGEC |
| 19 | LC (vL1.2 + CL-LK172pAF) | QAVVTQEPSLTVSPGGTVTLTCRSSTGAVTTSNYANWVQQ KPGQAPRGLIGGTNKRAPGTPARFSGSLLGGKAALTLSGA QPEDEAEYYCALWYSNLWVFGGGTKLTVLGRTVAAPSVFI FPPSDEQLKSGTASVVCLLNNFYPREAKVQWKVDNALQSG NSQESVTEQDSpAFDSTYSLSSTLTLSKADYEKHKVYACE VTHQGLSSPVTKSFNRGEC |

TABLE 5-continued

Amino acid sequences of humanized anti-CD3 Fab1
(vH1.2 + CH1, vL1.2 + CL) heavy and light
chain sequences with the non-natural amino acid, pAF,
incorporation site underlined that were produced in
E. coli.

| SEQ. ID. NO. | CHAIN | SEQUENCE |
|---|---|---|
| 20 | LC (vL1.2 + CL-LS205pAF) | QAVVTQEPSLTVSPGGTVTLTCRSSTGAVTTSNYANWVQQ KPGQAPRGLIGGTNKRAPGTPARFSGSLLGGKAALTLSGA QPEDEAEYYCALWYSNLWVFGGGTKLTVLGRTVAAPSVFI FPPSDEQLKSGTASVVCLLNNFYPREAKVQWKVDNALQSG NSQESVTEQDSKDSTYSLSSTLTLSKADYEKHKVYACEVT HQGLpAFSPVTKSFNRGEC |

Three light chain (LL157pAF, LK172pAF, and LS205pAF) pAF variants, (SEQ. ID. NOs: 18 to 20), as well as 3 double pAF variants ((HK129pAF+LL157pAF); (SEQ. ID. NOs: 16 and 18)); ((HK129pAF+LK172pAF); (SEQ. ID. NOs: 16 and 19)), and ((HK129pAF+LS205pAF) (SEQ. ID. NOs: 16 and 20)) were engineered. SEQ. ID. NOs: 10 to 13 represent the heavy chain pAF variants without a 5-aa heavy chain C-terminal extension—DKTHT.

E. coli fermentation: The fermentation process for production of anti-CD3 Fab-pAF consists of two stages: (i) inoculum preparation and (ii) fermentor production. The inoculum is started from a single glycerol vial, thawed, diluted 1:1000 (v/v) into 50 mL of defined seed medium in a 250 mL baffled Erlenmeyer flask, and incubated at 37° C. and 250 rpm. Prior to use, the fermentor is cleaned and autoclaved. A specified amount of basal medium is added to the fermentor and steam sterilized. Specified amounts of kanamycin sulfate solution, feed medium and P2000 antifoam are added to the basal medium prior to inoculation. All solutions added to the fermentor after autoclaving are either 0.2 μm filtered or autoclaved prior to aseptic addition.

The production fermentor is inoculated at a target $OD_{600}$ of 0.0004 by aseptic transfer of the contents of the inoculum. After inoculation, the culture is sampled at appropriate intervals for determination of $OD_{600}$. Temperature, pH and dissolved oxygen are monitored and controlled at the specified setpoints of 37° C., 7.0, and ≥30%, respectively. The pH is controlled by the addition of ammonium hydroxide solution or sulfuric acid. Dissolved oxygen is controlled by varying the agitation speed and by increasing the composition of oxygen in the sparged air/oxygen mixture. Antifoam is added during the fermentation process to control foaming.

When the cell density reaches an $OD_{600}$ of >25, a bolus of feed medium is added. When the cell density reaches an $OD_{600}$ of >50, a feed medium is added at constant flow rate of 0.094 mL/L-start volume/minute for 32 hours until it is reduced to 0.052 mL/L-start volume/minute until the end of fermentation. Immediately after feed start, a specified amount of non-naturally encoded amino acid, (for example, pAF), solution is added aseptically to allow incorporation of the non-natural amino acid into the protein amino acid sequence. Simultaneously, the temperature is shifted from 37° C., used during growth, to 27° C. for production. Production is controlled by the phoA promoter and starts when phosphate levels in the medium are depleted. The harvest is initiated approximately 48 hours after induction.

Example 7

Purification and conjugation to Folate and PEG-Folate: The anti-CD3 Fabs of the present invention are produced in E. coli cells and recovered from the whole cell lysate (WCL) supernatant. Cell lysis is performed at 4° C. Cells are lysed in 100 mM acetic acid, 100 mM NaCl, 1 mM EDTA, pH 3.5, in a volume equal to the original fermentation volume, resulting in a post-lysis pH of 4.1-4.2.

Following lysis, the WCL is centrifuged at 15,900×g for 30 minutes at 4° C. and filtered (0.8/0.2 micron) to remove precipitated protein and cell debris. Capto S cation exchange chromatography is then used to capture anti-CD3 Fab from E. coli WCL supernatant. Following Capto S column, Butyl HP hydrophobic interaction chromatography (HIC) is used as a polishing column to isolate intact anti-CD3 Fab from product-related impurities present in the Capto S elution pool. The Butyl HP elution pool containing intact anti-CD3 Fab is then buffer exchanged into 50 mM acetate, 5% Trehalose, pH 4.0 and concentrated to prepare for conjugation with Folate or PEG-Folate. This step is performed at 4° C. and utilizes the Amicon Ultracel 10K regenerated cellulose (15 mL) centrifugal device.

Following buffer exchange and concentration into 50 mM acetate, 5% Trehalose, pH 4, anti-CD3 Fab is conjugated with Folate or PEG-Folate to target folate receptors on cancer cells. The conjugation reaction is performed at 28° C., pH 4 for 24-48 hours. Following conjugation with Folate, the anti-CD3 Fab-Folate is buffer exchanged into formulation buffer, 50 mM Histidine, 100 mM NaCl, 5% Trehalose, pH 6.0. This step is performed at 4° C. and utilizes the Amicon Ultracel 10K regenerated cellulose (15 mL) centrifugal device. Following conjugation with PEG-Folate, Toyo SP 5PW cation exchange chromatography is used to separate unconjugated, single and dual conjugated anti-CD3 Fab-PEG-Folates.

CD3 Fab Folate-5KPEG, CD3 Fab Folate-10KPEG, CD3 Fab Folate-20KPEG, CD3 Fab Folate-$(5K)_2$PEG, CD3 Fab Folate-$(10K)_2$PEG compounds were generated. To CD3 Fab in buffer solution (50 mM acetate, 5% Trehalose at pH 4) the desired Folate-PEG, (5K, 10K, 20K, $5K_2$, or $10K_2$ PEG), was added at 28° C. After an hour, the mixture was purified by cation exchange chromatography (Toyo SP 5PW), and formulated with 50 mM Histidine, 100 mM NaCl, 5% Trehalose, pH 6.0 buffer by using Centrifugal Filter (c/o 10K) to obtain the desired CD3 Fab-Folate-PEGylated compositions. Structures, chemistry, and conjugation of CD3 Fab Folate conjugates are described herein and illustrated in FIGS. 12A-12D.

Additionally, CD3 Fab Folate-PEGylated C-terminal conjugates were generated. To CD3 Folate (8.0 mg) in PBS (2.0 mL), EDTA (6.7 uL, 0.5 M, pH8) and DTT (0.4 mg) were added and the solution incubated at 37° C. for 30 min. The mixtures were purified by a desalting column with 5 mmol EDTA in PBS eluent. To the mixture was added Mal-PEG at various concentrations, (4.2 mg 5K, 8.2 mg 10K, or 16 mg 20K), at room temperature. After 2 hours, the mixture was purified by Toyo SP 5PW cation exchange chromatography to obtain CD3 Fab Folate-(PEG5K)$_2$ C-terminal conjugate, CD3 Fab Folate-(PEG10K)$_2$ C-terminal conjugate, and CD3 Fab Folate-(PEG20K)$_2$ C-terminal conjugate. Structures, chemistry and conjugation of C-terminal PEG conjugates are described herein and illustrated in FIGS. 12E-12F.

Example 8

In-vitro binding and killing assays: The purified humanized anti-CD3 Fabs with Folate conjugated at various heavy chain sites (HA114, HS115, HK129, HT160) were initially tested for binding to both human and cyno CD3 with corresponding unconjugated proteins having pAF at these positions as well as the WT protein as controls. Table 6 depicts the EC$_{50}$ of modified anti-CD3 Fab1 proteins purified from E. coli cells to activated human and cyno PBMCs. As shown in Table 6, neither pAF nor conjugated Folate at the different sites interfered significantly with their CD3 binding.

TABLE 6

Binding of modified anti-CD3 Fab1 proteins

| Modified Fab1 Molecules | Binding EC$_{50}$ (nM) Human PBMC | Binding EC$_{50}$ (nM) Cyno PBMC |
|---|---|---|
| Fab1-WT | 0.93 | 0.75 |
| Fab1-HA114-pAF1 | 1.35 | 1.33 |
| Fab1-HS115-pAF1 | 1.26 | 1.76 |
| Fab1-HK129-pAF1 | 1.14 | 1.15 |
| Fab1-HA114-Folate | 1.27 | 1.37 |
| Fab1-HS115-Folate | 1.41 | 1.37 |
| Fab1-HK129-Folate | 1.69 | 2.05 |

The cytotoxicity of these Folate-conjugated anti-CD3 Fabs were tested with activated human and cyno PBMCs with SKOV-3 cells at E:T=10:1 with and without 50 nM Serum Folic Acid (SFA). The cytotoxicity assay was performed as described previously (See, for example, Angew Chem Int Ed Engl, 52(46):12101-12104, 2013). Briefly, effector cells (either activated PBMC or non-activated PBMC) and target cells (SKOV-3, KB etc.) at various E:T ratios were co-incubated in U-bottomed 96-well plates with varying concentrations of anti-CD3 Fab-Folate overnight or as indicated. The amount of LDH released into the culture medium was used as an index for cytotoxicity and was measured with non-radioactive cytotoxicity assay kit from Promega as per manufacturer's instruction.

As shown in Table 7, there were no significant difference in killing EC$_{50}$ between the Folate conjugation sites. However, about 15-60 fold decrease in cytotoxic EC$_{50}$ was observed when 50 nM SFA was present compared to no SFA due to competitive inhibition by the free SFA. Also, the cyno EC$_{50}$ was about 10-fold higher than the human EC$_{50}$ for each variant.

TABLE 7

Cytotoxicity of modified anti-CD3 Fab1 proteins to SKOV-3 cells

| Modified Fab1 Molecules | Killing EC$_{50}$ (pM) Human PBMC | Killing EC$_{50}$ (pM) Cyno PBMC |
|---|---|---|
| Without Serum Folic Acid (SFA) | | |
| Fab1-HA114-Folate | 0.148 | 2.5 |
| Fab1-HS115-Folate | 0.267 | 4.1 |
| Fab1-HK129-Folate | 0.124 | 1.0 |
| With 50 nM Serum Folic Acid (SFA) | | |
| Fab1-HA114-Folate | 9.9 | 139 |
| Fab1-HS115-Folate | 9.2 | 67 |
| Fab1-HK129-Folate | 3.3 | 33 |

Example 9

Cytotoxicity of anti-CD3-Folate variants against various FOLRα tumor cell lines harboring various Folate Receptor (FRα) levels: The activity of three different anti-CD3 Fab-Folate conjugates was tested at HA114, HS115 and HK129 sites by in vitro cytotoxicity assay with 6 different cell lines having varying levels of FRα over-expression on their cell surface (Table 8). The FRα numbers varied from 5,700 per cell in an alveolar basal epithelial cell carcinoma A549 cell line to 1,630,000 per cell in a nasopharyngeal cancer cell line. Cells were co-cultured with activated human peripheral blood mononuclear cells (PBMCs; ratio 1:10 of target: effector cells) and treated with various concentrations of anti-CD3 Fab-Folate in the presence of 50 nM SFA. Cytotoxicity was quantitated by measuring released LDH levels from lysed cells, and with CellTiter-Glo and FACS based toxicity assays.

TABLE 8

Cytotoxicity of anti-CD3-Folate variants against various FRα tumor cell lines

| Cell Line | Fab1-HA114-Folate, EC$_{50}$ (pM) | Fab1-HS115-Folate, EC$_{50}$ (pM) | Fab1-HK129-Folate, EC$_{50}$ (pM) | FOLRα Receptor # |
|---|---|---|---|---|
| A549 | No activity | No activity | No activity | 5,700 |
| OV-90 | 81.8 | 34.0 | 22.2 | 10,200 |
| OVCAR-3 | 10.6 | 7.5 | 4.9 | 15,400 |
| SKOV-3 | 18.9 | 16.3 | 10.7 | 21,800 |
| N87 | Not tested | Not tested | 26.7 | 21,600 |
| KB | Not tested | Not tested | 0.72 | 1,630,000 |

The anti-CD3 Fab-Folate conjugates at all three different sites of conjugation demonstrated efficient killing of all 5 cell lines having FRα above 10K. However, no killing was observed with A549 cell line with any site conjugates having FRα of 5,700. There seems to be a threshold of about 10,000 FRα for efficient killing; however, killing activity seems to be independent of FRα numbers above that threshold value of 10K. Since in-vitro killing EC$_{50}$ did not vary significantly on the site of Folate conjugation in the antibody, HK129 position was selected as a Folate conjugation site for further experiments.

Example 10

This Example demonstrates the effects on in-vitro binding affinity and cytotoxic activity of various anti-CD3 Fab1-

HK129-pAF molecules upon either Folate-PEG conjugation at a single site or addition of a second Folate (BiFolate).

Effects of Folate-PEG conjugation: Table 9 shows the effects on binding and Table 10 cytotoxicity upon conjugation of either a 5K or 20K linear PEG molecule with Folate using a bi-functional linker as described herein. A modest reduction (1.7 to 8.4-fold) in binding was observed for both activated human and cyno PBMCs depending on 5K or 20K PEG size. But the cytotoxic activity was drastically reduced with 20K PEG compared to 5K PEG (3.7 to 5.6 fold vs 50 to 58 fold) for both human and cyno PBMCs. Based on this experiment, 5K PEG instead of 20K PEG was used for half-life extension.

TABLE 9

CD3 Binding

| Modified Fab1 molecules | Human PBMC Binding $EC_{50}$ (nM) | Fold reduction in binding | Cyno PBMC Binding $EC_{50}$ (nM) | Fold reduction in binding |
|---|---|---|---|---|
| Fab1-HK129-Folate | 2.78 | — | 1.41 | — |
| Fab1-HK129-5KPEG-Folate | 5 | 1.9 | 2.46 | 1.7 |
| Fab1-HK129-20KPEG-Folate | 12 | 4.3 | 11.81 | 8.4 |

TABLE 10

Cytotoxicity

| Modified Fab1 molecules | Human PBMC Killing $EC_{50}$ (pM) | Fold reduction in killing | Cyno PBMC Killing $EC_{50}$ (pM) | Fold reduction in killing |
|---|---|---|---|---|
| Fab1-HK129-Folate | 6.69 | — | 15.6 | — |
| Fab1-HK129-5KPEG-Folate | 37.1 | 5.6 | 57.9 | 3.7 |
| Fab1-HK129-20KPEG-Folate | 335 | 50 | 904 | 58 |

Effects of double Folate (BiFolate) conjugation: Table 11 shows the effects of a second Folate conjugation at two light chain sites (LL157 and LK172) in combination with heavy chain HK129 site on in-vitro binding and Table 12 shows increase in cytotoxicity of double vs single Folate molecules was also evident with the presence or absence of 50 nM SFA. Based on this experiment, LL157 site over LK172 site was used in combination with HK129 site for future studies.

TABLE 11

CD3 Binding

| Modified Fab1 molecules | Human PBMC Binding $EC_{50}$ (nM) | Fold increase binding | SKOV-3 Cells (with 50 nM SFA); Binding $EC_{50}$ (nM) | Fold increase binding |
|---|---|---|---|---|
| Fab1-HK129-Folate | 2.45 | — | 44.5 | — |
| Fab1-HK129-LL157-BiFolate | 1.93 | 1.3 | 19.8 | 2.2 |
| Fab1-HK129-LK172-BiFolate | 2.85 | 0.86 | 10 | 4.4 |

TABLE 12

Cytotoxicity

| Modified Fab1 molecules | Human PBMC, 50 nM SFA; Killing $EC_{50}$ (pM) | Fold increase in potency (single vs double folate) | Human PBMC, no SFA; Killing $EC_{50}$ (pM) | Fold increase in potency (single vs double folate) |
|---|---|---|---|---|
| Fab1-HK129-Folate | 11.41 | — | 0.195 | — |
| Fab1-HK129-LL157-BiFolate | 1.76 | 6.5 | 0.067 | 2.9 |
| Fab1-HK129-LK172-BiFolate | 4 | 2.9 | 0.044 | 4.4 |

Summary of binding affinity and in vitro cytotoxicity: Table 13 summarizes the effects on binding and cytotoxic activities of various anti-CD3 Fabs due to PEGylation and second Folate conjugation. A modest decrease in binding affinity to both CD3 and FRα results in a significant decrease in potency and is correlated with PEG size. Conjugation of BiFolate molecules increased affinity for FRα and thereby cytotoxic potency despite some reduction in CD3 binding affinity. Despite a decrease in affinity to both targets due to PEG conjugation, the in-vitro killing EC50 of all CD3-Fab-Folate molecules maintained high potency in the range of 37 to 335 μM.

TABLE 13

Binding and cytotoxic activities of various anti-CD3 Fabs PEGylated.

| Modified Fab1 molecules | Modification | Killing EC50 pM | Change - potency | CD3 binding affinity (nM) | FRα binding affinity (nM) | Affinity ratio (FRα:CD3) |
|---|---|---|---|---|---|---|
| Fab1-HK129-Folate | Folate lead | 3-15 | — | 1.69 | 59.6 | 35 |
| Fab1-HK129-5KPEG-Folate | 5KPEG | 37 | 5.6-fold decrease | 5 | 129 | 26 |
| Fab1-HK129-20KPEG-Folate | 20KPEG | 335 | 50-fold decrease | 12 | 310 | 26 |
| Fab1-HK129-LL157-BiFolate | BiFolate | 1.8 | 6.5-fold increase | 1.93 | 19.8 | 10 |
| Fab1-HK129-LK172-BiFolate | BiFolate | 4 | 2.9-fold increase | 2.85 | 10 | 3.5 | cytotoxicity. Expectedly, a modest increase in both binding affinity and cytotoxic activity was observed with BiFolate variants over HK 129 single Folate molecule. Modest Effects of various Effector to Target (E:T) cell ratios on the cytotoxicity of SKOV-3 cells by anti-CD3 Fab1 molecules: To test the effects of E:T ratios on cytotoxicity of SKOV-3 cells, cytotoxicity assays of 3 anti-CD3 Fab1 molecules was performed at E:T ratios of 10:1, 5:1, 1:1, 1:5 and 1:10 in the presence of 50 nM SFA. As expected, and shown in Table 14, E:T ratios correlated to in vitro killing potency. At an E:T=1:1, a 2-fold increase in $EC_{50}$ was observed for BiFolate molecule whereas an S-fold decrease was seen with a 5KPEG-Folate molecule. All three molecules remained highly potent with $EC_{50}$ of 1.69 to 175 μM within the E:T ratios of 10:1 to 1:10.

TABLE 14

Effector to Target (E:T) cell ratios on in-vitro cytotoxicity

| E:T ratio | Fab1-HK129-Folate Cytotoxic $EC_{50}$ (pM) | Fab1-HK129-5KPEG-Folate Cytotoxic $EC_{50}$ (pM) | Fab1-HK129-LL157-BiFolate Cytotoxic $EC_{50}$ (pM) |
|---|---|---|---|
| 10:1 | 4.22 | 22.1 | 1.69 |
| 5:1 | 6.68 | 28.4 | 3.08 |
| 1:1 | 10.50 | 83.5 | 5.37 |
| 1:5 | 13.93 | 210.4 | 10.4 |
| 1:10 | 13.82 | 175.2 | 26.16 |

Example 12

PEGylation of anti-CD3 Fab1 molecules to extend plasma half-life: The pharmacokinetic properties of anti-CD3 Fab1-Folate conjugates with and without PEG conjugation in rats was examined. Male Sprague Dawley rats (about 7 weeks old) were used. On the day of administration, the weight of each animal was measured. 1 mg per kg body weight of the non-conjugated and conjugated anti-CD3 antibody samples were each injected intravenously into the tail vein of three rats. At different time points after the injection, 500 μl of blood was withdrawn from each rat while under $CO_2$ anesthesia. The blood samples were stored at room temperature for 1.5 hours followed by isolation of serum by centrifugation (4° C., 18000×g for 5 minutes). The serum samples are stored at −80° C. until the day of analysis. The amount of active anti-CD3 antibody in the serum samples was quantified by the anti-CD3 antibody in vitro activity assay after thawing the samples on ice.

Figure 3:
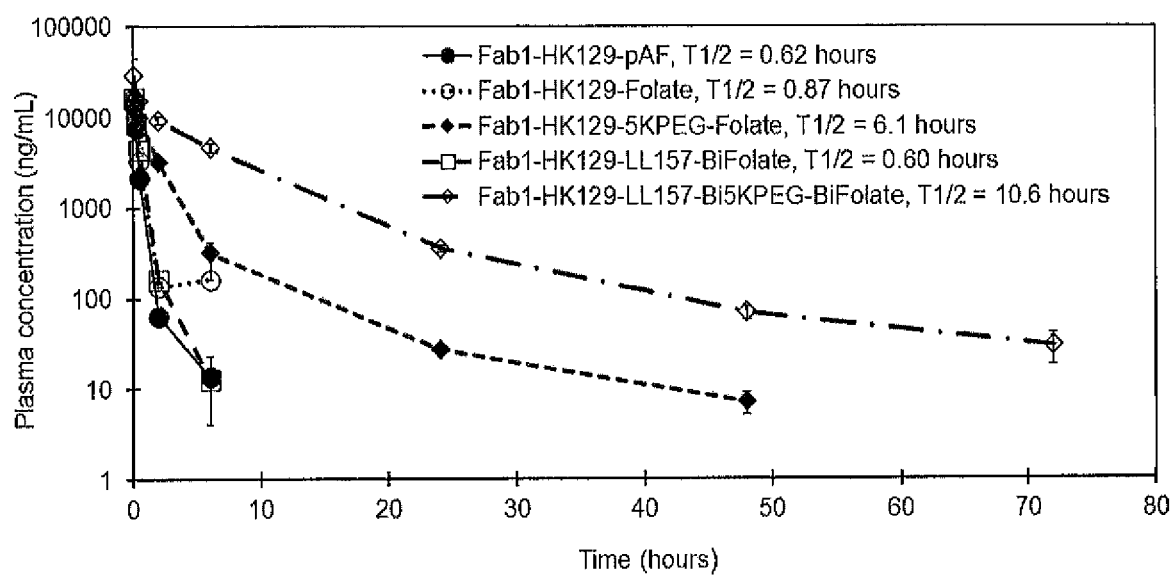
FIG. 3 depicts rat pharmacokinetic (PK) analysis of anti-CD3 Fab1 molecules. PEGylation of humanized anti-CD3 Fab1 molecules extend plasma half-life (T½) in rats.

As shown in FIG. 3, the serum concentration quickly decreased for two anti-CD3 Fab1-Folates and the corresponding unconjugated anti-CD3 Fab1 at the same rate with a serum half-life of less than one hour. In contrast, the serum half-life of two PEG-conjugated anti-CD3 Fab1s was significantly extended to 6.1 hours and 10.6 hours for 5KPEG and Bi5KPEG, respectively. Table 15 shows various PK parameters following IV administration of various anti-CD3 Fab1 molecules in rats. This data illustrates that Bi5KPEG-BiFolate extends T½ and increases AUC significantly (13.2-fold over Fab1-Folate and 3.9-fold over Fab1-5KPEG-Folate), (Table 15).

TABLE 15

Pharmacokinetics of various Fab1 molecule in rats

| | Group | | | | | |
|---|---|---|---|---|---|---|
| | 1 | | 2 | | 3 | |
| | Dose (mg/kg) | | | | | |
| | 1 | | 1 | | 1 | |
| | Molecule | | | | | |
| | Fab1-HK129-pAF | | Fab1-HK129-Folate | | Fab1-HK129-5KPEG-Folate | |
| PK Parameter | Mean | SD | Mean | SD | Mean | SD |
| C0 (ng/mL) | 18500 | 2350 | 18400 | 2940 | 19500 | 3960 |
| Cmax (ng/mL) | 13700 | 1070 | 14100 | 1450 | 17400 | 2610 |
| Tmax (h) | 0.0833 | 0 | 0.0833 | 0 | 0.0833 | 0 |
| AUClast (ng*h/mL) | 6150 | 491 | 7880 | 550 | 27400 | 472 |
| Tlast (h) | 6 | 0 | 6 | 0 | 40 | 13.9 |
| AUCinf (ng*h/mL) | 6160 | 486 | 8180 | 1020 | 27500 | 451 |
| Cl (mL/h/kg) | 163 | 12.4 | 124 | 14.6 | 36.4 | 0.593 |
| Vss (mL/kg) | 55.1 | 5.91 | 92.9 | 70.1 | 81.9 | 11.4 |
| T1/2 (h) | 0.618 | 0.0699 | 0.865 | 0.394 | 6.1 | 2.99 |
| AUC % Extrap | 0.21 | 0.176 | 3.22 | 5.21 | 0.313 | 0.0816 |
| Rsq | 0.819 | 0.0645 | 0.73 | 0.238 | 0.921 | 0.0423 |

| | Group | |
|---|---|---|
| | 4 | 5 |
| | Dose (mg/kg) | |
| | 1 | 1 |
| | Molecule | |
| | Fab1-HK129-LL157-BiFolate | Fab1-HK129-LL157-Bi5KPEG-BiFolate |
| PK Parameter | Mean SD | Mean SD |
| C0 (ng/mL) | 22600  2590 | 40600  31800 |
| Cmax (ng/mL) | 16400  1720 | 28800  15300 |

TABLE 15-continued

| Pharmacokinetics of various Fab1 molecule in rats | | | | |
|---|---|---|---|---|
| Tmax (h) | 0.0833 | 0 | 0.0833 | 0 |
| AUClast (ng*h/mL) | 9050 | 666 | 107000 | 7980 |
| Tlast (h) | 6 | 0 | 72 | 0 |
| AUCinf (ng*h/mL) | 9070 | 667 | 108000 | 8030 |
| Cl (mL/h/kg) | 111 | 8.13 | 9.33 | 0.681 |
| Vss (mL/kg) | 44.6 | 5.02 | 59.2 | 3.86 |
| T1/2 (h) | 0.596 | 0.00115 | 10.6 | 2.64 |
| AUC % Extrap | 0.121 | 0.000553 | 0.398 | 0.0974 |
| Rsq | 0.904 | 0.0119 | 0.964 | 0.0445 |

Example 13

This Example demonstrates generation and screening for anti-CD3 low-affinity antibody variants in HEK293 cells.

D-convolution of mouse back and germ-line mutations: Mouse framework residues (back mutations) for both vH and vL sequences obtained during humanization of anti-CD3 antibody were examined by reverting them back to human germline residues one-at-a-time to see their effects on antigen binding (dc-convolution), For vH sequence, 4 mouse framework residues (back mutations) at Kabat positions 30, 49, 77 and 93 were predicted to play critical roles in antigen binding (Tables 2-3 and 16-17). Similarly, for vL sequence, 5 mouse framework residues (back mutations) at Kabat positions 36, 46, 49, 57 and 58 were also predicted to play critical roles in antigen binding.

TABLE 16

Anti-CD3 Fab1 light chain (LC) back and germ-line mutation positions

| | | Kabat Position | | | | |
|---|---|---|---|---|---|---|
| | Round# | 36 | 46 | 49 | 53 | 57 | 58 |
| Mouse AA | | V | G | G | K | G | V |
| Human AA | | F | T | Y | | W | T |
| Mouse Germline AA | | | | | N | | |
| LC ID# | | | | | | | |
| vL1.0 | R0 | F | T | Y | K | W | T |
| vL1.1 | R0 | V | G | G | K | G | V |
| vL1.2 | R0 | V | G | G | K | G | T |
| vL2.1 | R1 | F | G | G | K | G | V |
| vL2.2 | R1 | V | T | G | K | G | V |
| vL2.3 | R1 | V | G | Y | K | G | V |
| vL2.4 | R1 | V | G | G | K | W | V |
| vL2.5 | R2 | F | G | G | K | W | V |
| vL3.1 | R2 | V | G | G | N | G | T |

TABLE 17

Anti-CD3 Fab1 heavy chain (HC) back and germ-line mutation positions.

| | | Kabat Position | | | | |
|---|---|---|---|---|---|---|
| | Round# | 30 | 35 | 49 | 52c | 77 | 93 |
| Mouse AA | | N | N | A | Y | I | V |
| Human AA | | S | | G | | S | A |
| Mouse Germline AA | | | H | | S | M | |

TABLE 17-continued

Anti-CD3 Fab1 heavy chain (HC) back and germ-line mutation positions.

| | | Kabat Position | | | | |
|---|---|---|---|---|---|---|
| | Round# | 30 | 35 | 49 | 52c | 77 | 93 |
| HC ID# | | | | | | | |
| vH1.0 | R0 | N | N | G | Y | S | V |
| vH1.1 | R0 | N | N | A | Y | S | V |
| vH1.2 | R0 | N | N | A | Y | I | V |
| vH2.1 | R1 | S | N | A | Y | I | V |
| vH2.2 | R1 | N | N | G | Y | I | V |
| vH2.3 | R1 | N | N | A | Y | I | A |
| vH2.4 | R2 | S | N | G | Y | S | V |
| vH2.5 | R2 | N | N | G | Y | S | A |
| vH2.6 | R2 | S | N | G | Y | S | A |
| vH3.1 | R2 | N | H | A | Y | I | V |
| vH3.2 | R2 | N | N | A | S | I | V |
| vH3.3 | R2 | N | H | A | S | I | V |

To assess the effects on antigen binding (de-convolution), 4 new vL (vL2.1 to vL2.4) and 3 new vH (vH2.1 to vH 2.3) plasmids (Round 1 plasmids in Tables 16-17) were generated. These vH and vL plasmids were used with the original vH and vL plasmids described in the above Examples (Round 0 plasmids in Tables 16-17) in a co-transfection experiment with HEK293 cells. A total of 35 transient transfections were performed in Round 1 screening, and the cell culture supernatants were directly used to screen for binding as described below and in the above Examples.

Based on the screening results from Round 1, three (3) additional vH plasmids (vH2.4 to 2.6) (Round 2 plasmids in Tables 16-17) were generated to assess the additive effects of individual back mutations. In a similar fashion, a new plasmid for vL (vL2.5) was generated by combining two mouse back mutations. Additionally, mouse germ-line mutations found within vH and vL CDRs were analyzed for conferring reduced binding in this round. Toward this end, 3 new vH plasmids (vH3.1 to 3.3) (Round 2 plasmids in Tables 16-17) were generated by changing amino acids at Kabat position N35 in HC-CDR1 and at Y52c in HC-CDR2. In a similar fashion, a vL plasmid (vL3.1) (Round 2 plasmids in Tables 16-17) was generated by changing amino acid at Kabat position K53 in LC-CDR2. Round 2 screening experiment was performed with a total of 43 transfections by selectively combining various vL/vH plasmid pairs.

Figure 4A:
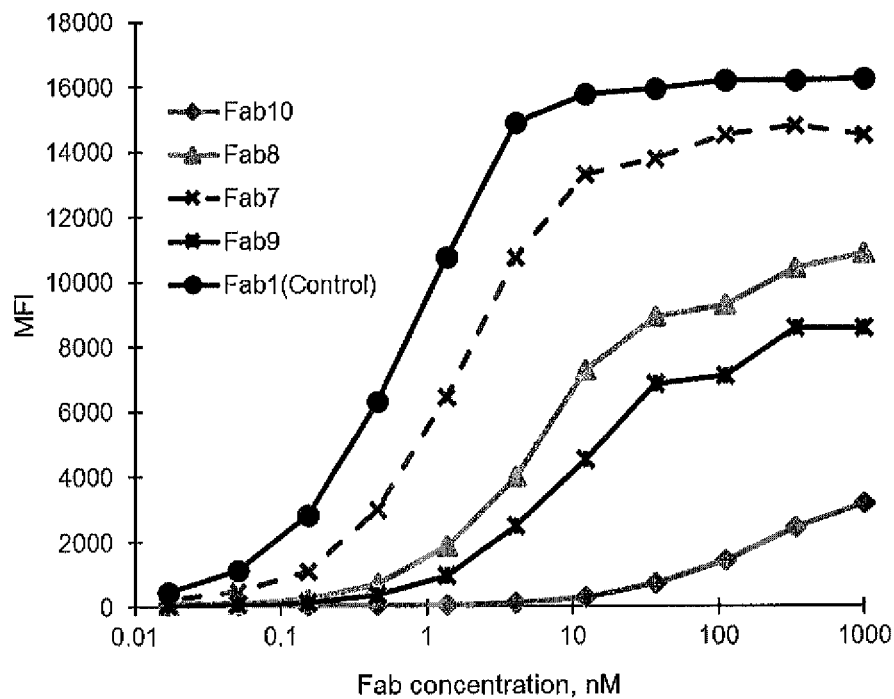
FIGS. 4A-4B depict binding of Round 1 low-affinity Fabs from HEK293 cells. Round 1 anti-CD3 Fab variants produced from HEK293 cells with reduced binding affinities to human (FIG. 4A) and cyno (FIG. 4B) CD3 are shown. Out of 35 new Fab variants tested in Round 1 screening, titration curves for 4 selected (Fabs 7 to 10) reduced-affinity Fabs are shown along with control Fab1.
Figure 4B:
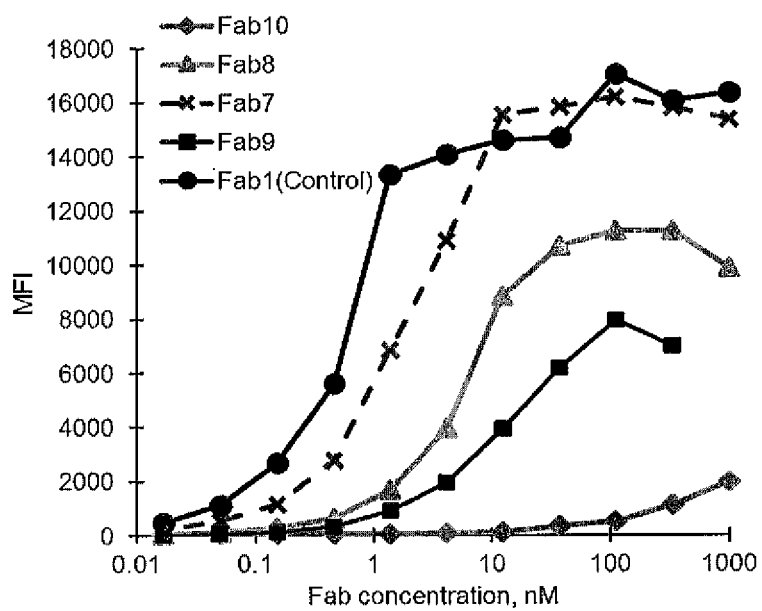
Figure 5A:
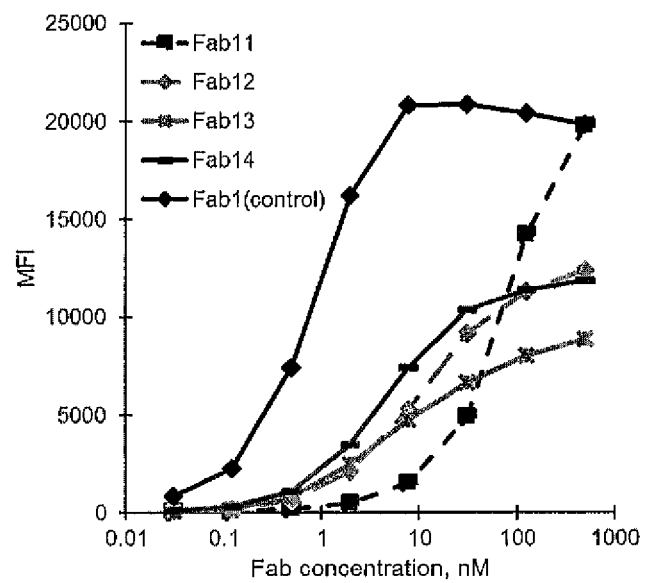
FIGS. 5A-5B depict binding of Round 2 low-affinity Fabs from HEK293 cells to human CD3. Round 2 anti-CD3 Fab variants produced from HEK293 cells with reduced binding affinities to human (FIG. 5A) and cyno (FIG. 5B) CD3 are shown. Out of 43 new Fab variants tested in Round 2 screening, titration curves for 4 selected reduced-affinity Fabs are shown along with parent control Fab1.
Figure 5B:
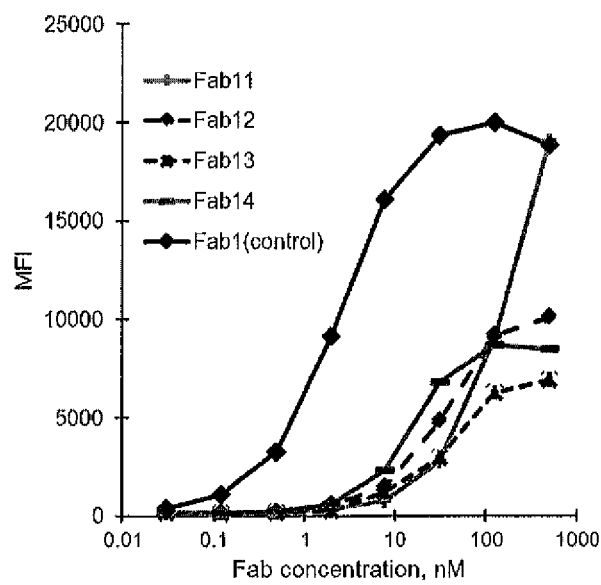
Figure 6A:
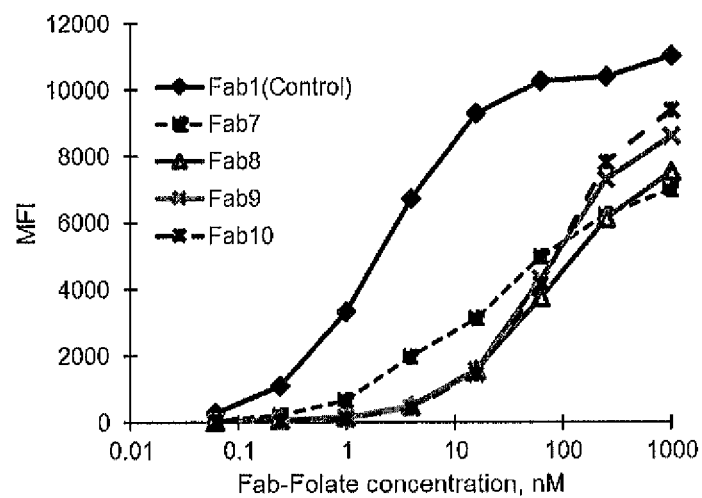
FIGS. 6A-6B depict binding of low-affinity Fab-Folate variants from E. coli cells to human CD3.
Figure 6B:
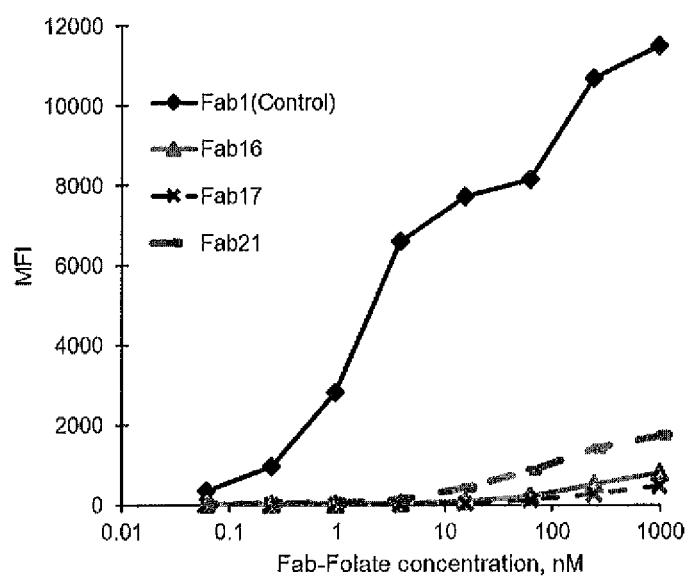

Screening for human and cyno CD3 binding: HEK293 culture supernatants were directly used to test for binding to human CD3 in the screening phase. In Round 1 experiment, initially 35 clones were tested for binding to human CD3 at three different protein concentrations, and 13 were selected for detailed binding assays to both human and cyno CD3. An 11-point binding titration curve was generated to both human (FIG. 4A) and cyno CD3 (FIG. 4B) for each clone. Based on the data, Fabs 7 to 10 were selected as low-affinity candidates for further evaluation (FIGS. 4A-4B). Similarly, 43 clones were screened in Round 2 experiment. After two-stage screening as described above for Round 1, 11 low-affinity variants were obtained, of which 4 are represented as shown in FIGS. 5A-5B These 15 low-affinity anti-CD3 Fab variants (Fabs 7-10 from Round 1 and Fabs 11-21 from Round 2) were then transitioned into E. coli expression system for nonnatural amino acid (UAA) incorporation and further testing as described in Examples below. FIG. 6A shows the Fab-Folate conjugates of the same wild type Fabs as shown in FIG. 4A. Fab-Folate conjugates representative of the wild type Fabs obtained from Round 2 screening are depicted in FIG. 6B. Table 18 shows the list of low-affinity mutations as well as their HC, LC and Fab IDs. As shown, both mouse framework back mutations and germ-line CDR mutations played significant roles in conferring reduced binding to both human and cyno CD3. In variable light chain (vL), 5 mouse back residues at Kabat positions V36, G46, G49, G57 and V58 and one mouse germ-line residue at Kabat position K53 in LC-CDR2 were involved in reduced binding. In variable heavy chain (vH), 4 mouse back residues at Kabat positions N30, A49, I77 and V93 and two mouse germ-line residues at Kabat position N35 in HC-CDR1 and at position Y52c in HC-CDR2 were involved in reduced binding.

TABLE 18

List of mutations in low-affinity humanized anti-CD3 Fab variants

| Fab# | LC ID | LC Mutation(s) | HC ID | HC Mutation(s) |
|---|---|---|---|---|
| Fab1 | vL1.2 | V36/G46/G49/G57/V58T | vH1.2 | N30/A49/I77/V93 |
| Fab7 | vL2.4 | V36/G46/G49/G57W/V58 | vH2.3 | N30/A49/I77/V93A |
| Fab8 | vL2.1 | V36F/G46/G49/G57/V58 | vH2.2 | N30/A49G/I77/V93 |
| Fab9 | vL2.1 | V36F/G46/G49/G57/V58 | vH1.0 | N30/A49G/I77S/V93 |
| Fab10 | vL2.1 | V36F/G46/G49/G57/V58 | vH2.1 | N30S/A49/I77/V93 |
| Fab11 | vL1.0 | V36F/G46T/G49Y/G57W/V58T | vH2.4 | N30S/A49G/I77S/V93 |
| Fab12 | vL2.1 | V36F/G46/G49/G57/V58 | vH2.4 | N30S/A49G/I77S/V93 |
| Fab13 | vL2.5 | V36F/G46/G49/G57W/V58 | vH2.4 | N30S/A49G/I77S/V93 |
| Fab14 | vL2.1 | V36F/G46/G49/G57/V58 | vH2.5 | N30/A49G/I77S/V93A |
| Fab15 | vL2.2 | V36/G46T/G49/G57/V58 | vH2.5 | N30/A49G/I77S/V93A |
| Fab16 | vL2.1 | V36F/G46/G49/G57/V58 | vH2.6 | N30S/A49G/I77S/V93A |
| Fab17 | vL2.5 | V36F/G46/G49/G57W/V58 | vH1.0 | N30/A49G/I77S/V93 |
| Fab18 | vL2.5 | V36F/G46/G49/G57W/V58 | vH2.2 | N30/A49G/I77/V93 |
| Fab19 | vL1.2 | V36/G46/G49/G57/V58T | vH3.1 | N30/N35H/A49/Y52c/I77/V93 |
| Fab20 | vL3.1 | V36/G46/G49/K53N/G57/V58T | vH3.1 | N30/N35H/A49/Y52c/I77/V93 |
| Fab21 | vL3.1 | V36/G46/G49/K53N/G57/V58T | vH3.2 | N30/N35/A49/Y52cS/I77/V93 |

TABLE 19

Amino acid sequences of humanized anti-CD3 heavy
(vH + CH1), (vH + CH1-DKTHT) and light
(vL + CL) chains used in screening for low-affinity
variant of Fabs in HEK293 cells

| SEQ. ID. NO. | CHAIN | SEQUENCE |
|---|---|---|
| 21 | HC (vH2.3 + CH1-DKTHT) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCARHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHT |
| 22 | HC (vH2.2 + CH1-DKTHT) | EVQLVESGGGLVQPGGSLRLSCAASGFTFNTYAMNWVRQA PGKGLEWVGRIRSKYNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHT |
| 23 | HC (vH2.1 + CH1-DKTHT) | EVQLVESGGGLVQPGGSLRLSCAASGFTFSTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHT |
| 24 | HC (vH2.4 + CH1-DKTHT) | EVQLVESGGGLVQPGGSLRLSCAASGFTFSTYAMNWVRQA PGKGLEWVGRIRSKYNNYATYYADSVKDRFTISRDDSKNS LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHT |

TABLE 19-continued

Amino acid sequences of humanized anti-CD3 heavy
(vH + CH1), (vH + CH1-DKTHT) and light
(vL + CL) chains used in screening for low-affinity
variant of Fabs in HEK293 cells

| SEQ. ID. NO. | CHAIN | SEQUENCE |
|---|---|---|
| 25 | HC (vH2.5 + CH1-DKTHT) | EVQLVESGGGLVQPGGSLRLSCAASGFTFNTYAMNWVRQAPGKGLEWVGRIRSKYNNYATYYADSVKDRFTISRDDSKNSLYLQMNSLKTEDTAVYYCARHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT |
| 26 | HC (vH2.6 + CH1-DKTHT) | EVQLVESGGGLVQPGGSLRLSCAASGFTFSTYAMNWVRQAPGKGLEWVGRIRSKYNNYATYYADSVKDRFTISRDDSKNSLYLQMNSLKTEDTAVYYCARHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT |
| 27 | HC (vH3.1 + CH1-DKTHT) | EVQLVESGGGLVQPGGSLRLSCAASGFTFNTYAMHWVRQAPGKGLEWVARIRSKYNNYATYYADSVKDRFTISRDDSKNILYLQMNSLKTEDTAVYYCVRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT |
| 28 | HC (vH3.2 + CH1-DKTHT) | EVQLVESGGGLVQPGGSLRLSCAASGFTFNTYAMNWVRQAPGKGLEWVARIRSKSNNYATYYADSVKDRFTISRDDSKNILYLQMNSLKTEDTAVYYCVRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT |
| 29 | HC (vH3.3 + CH1-DKTHT) | EVQLVESGGGLVQPGGSLRLSCAASGFTFNTYAMHWVRQAPGKGLEWVARIRSKSNNYATYYADSVKDRFTISRDDSKNILYLQMNSLKTEDTAVYYCVRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT |
| 30 | HC (vH2.3 + CH) | EVQLVESGGGLVQPGGSLRLSCAASGFTFNTYAMNWVRQAPGKGLEWVARIRSKYNNYATYYADSVKDRFTISRDDSKNILYLQMNSLKTEDTAVYYCARHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 31 | HC (vH2.2 + CH) | EVQLVESGGGLVQPGGSLRLSCAASGFTFNTYAMNWVRQAPGKGLEWVGRIRSKYNNYATYYADSVKDRFTISRDDSKNILYLQMNSLKTEDTAVYYCVRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 32 | HC (vH2.1 + CH) | EVQLVESGGGLVQPGGSLRLSCAASGFTFSTYAMNWVRQAPGKGLEWVARIRSKYNNYATYYADSVKDRFTISRDDSKNILYLQMNSLKTEDTAVYYCVRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 33 | HC (vH2.4 + CH) | EVQLVESGGGLVQPGGSLRLSCAASGFTFSTYAMNWVRQAPGKGLEWVGRIRSKYNNYATYYADSVKDRFTISRDDSKNSLYLQMNSLKTEDTAVYYCVRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 34 | HC (vH2.5 + CH) | EVQLVESGGGLVQPGGSLRLSCAASGFTFNTYAMNWVRQAPGKGLEWVGRIRSKYNNYATYYADSVKDRFTISRDDSKNSLYLQMNSLKTEDTAVYYCARHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |

TABLE 19-continued

Amino acid sequences of humanized anti-CD3 heavy
(vH + CH1), (vH + CH1-DKTHT) and light
(vL + CL) chains used in screening for low-affinity
variant of Fabs in HEK293 cells

| SEQ. ID. NO. | CHAIN | SEQUENCE |
|---|---|---|
| 35 | HC (vH2.6 + CH) | EVQLVESGGGLVQPGGSLRLSCAASGFTFSTYAMNWVRQA PGKGLEWVGRIRSKYNNYATYYADSVKDRFTISRDDSKNS LYLQMNSLKTEDTAVYYCARHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSC |
| 36 | HC (vH3.1 + CH) | EVQLVESGGGLVQPGGSLRLSCAASGFTFNTYAMHWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSC |
| 37 | HC (vH3.2 + CH) | EVQLVESGGGLVQPGGSLRLSCAASGFTFNTYAMNWVRQA PGKGLEWVARIRSKSNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSC |
| 38 | HC (vH3.3 + CH) | EVQLVESGGGLVQPGGSLRLSCAASGFTFNTYAMHWVRQA PGKGLEWVARIRSKSNNYATYYADSVKDRFTISRDDSKNI LYLQMNSLKTEDTAVYYCVRHGNFGNSYVSWFAYWGQGTL VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSC |
| 39 | LC (vL2.3 + CL) | QAVVTQEPSLTVSPGGTVTLTCRSSTGAVTTSNYANWVQQ KPGQAPRGLIYGTNKRAPGVPARFSGSLLGGKAALTLSGA QPEDEAEYYCALWYSNLWVFGGGTKLTVLGRTVAAPSVFI FPPSDEQLKSGTASVVCLLNNFYPREAKVQWKVDNALQSG NSQESVTEQDSKDSTYSLSSTLTLSKADYEKHKVYACEVT HQGLSSPVTKSFNRGEC |

SEQ. ID. NOs: 21 to 29 represent amino acid sequences of heavy chains with a 5-aa C-terminal extension—DKTHT used in screening for low-affinity variant Fabs. SEQ. ID. NOs: 30 and 38 represent these humanized heavy chain amino acid sequences without a 5-aa heavy chain C-terminal extension. SEQ. ID. NO: 39 represent the amino acid sequence of a light chain used in screening for low-affinity variant Fabs in HEK293 cells.

This Example demonstrates construction, expression, purification and testing of low-affinity humanized anti-CD3 Fab variants produced from *E. coli* cells with heavy chain HK129 amber mutation.

Cloning into *E. coli* expression vector: Synthetic genes were designed for all low-affinity variants disclosed in Table 20, SEQ. ID NOs.: 40-62 with the STII-LC-Spacer-STIM-C expression cassette architecture with Amber TAG stop codon inserted at heavy chain HK129 position and cloned into proprietary *E. coli* expression vector as described in the above Examples. The amino acid sequences of both the heavy and light chains used to engineer these Fabs are shown as SEQ. ID. NOs: 40 through 62. SEQ. ID. NOs: 40 to 48 represent the humanized heavy chain HK129 pAF variants with a 5-aa heavy chain C-terminal extension—DKTHT used in testing. SEQ. ID. NOs: 49 and 57 represent these humanized heavy chain HK129 pAF variants without a 5-aa heavy chain C-terminal extension—DKTHT. SEQ. ID. NOs: 58-62 represent light chain sequences used in combination with the HK129pAF-DKTHT variants of SEQ. ID. NOs: 40 to 48 that were expressed in *E. coli* and further characterized.

TABLE 20

Amino acid sequences of low affinity anti-CD3
Fab-HK129pAF heavy and light chain sequences expressed
in *E. coli*. Also disclosed are all of the sequences in
the table below, where pAF is replaced by any other
non-natural amino acid.

| SEQ. ID. NO. | CHAIN | SEQUENCE |
|---|---|---|
| 40 | HC (vH2.3 + CH1-HK129pAF-DKTHT) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCARHGNFGNSYVSWFAYWGQGTL VTVSSASTKGPSVFPLAPSS<u>p</u>AFSTSGGTAALGCLVKDYF |

TABLE 20-continued

Amino acid sequences of low affinity anti-CD3
Fab-HK129pAF heavy and light chain sequences expressed
in E. coli. Also disclosed are all of the sequences in
the table below, where pAF is replaced by any other
non-natural amino acid.

| SEQ. ID. NO. | CHAIN | SEQUENCE |
|---|---|---|
| | | PEPVTVSWNSGALTSGVHTFPAVLQSSGLYSLSSVVTVPS SSLGTQTYICNVNHKPSNTKVDKKVEPKSCDKTHT |
| 41 | HC (vH2.2 + CH1-HK129pAF-DKTHT) | EVQLVESGGGLVQPGGSLRLSCAASGFTFNTYAMNWVRQA PGKGLEWVGRIRSKYNNYATYYADSVKDRFTISRDDSKNI LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 42 | HC (vH1.0 + CH1-HK129pAF-DKTHT) | EVQLVESGGGLVQPGGSLRLSCAASGFTFNTYAMNWVRQA PGKGLEWVGRIRSKYNNYATYYADSVKDRFTISRDDSKNS LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 43 | HC (vH2.1 + CH1-HK129pAF-DKTHT) | EVQLVESGGGLVQPGGSLRLSCAASGFTFSTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 44 | HC (vH2.4 + CH1-HK129pAF-DKTHT) | EVQLVESGGGLVQPGGSLRLSCAASGFTFSTYAMNWVRQA PGKGLEWVGRIRSKYNNYATYYADSVKDRFTISRDDSKNS LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 45 | HC (vH2.5 + CH1-HK129pAF-DKTHT) | EVQLVESGGGLVQPGGSLRLSCAASGFTFNTYAMNWVRQA PGKGLEWVGRIRSKYNNYATYYADSVKDRFTISRDDSKNS LYLQMNSLKTEDTAVYYCARHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 46 | HC (vH2.6 + CH1-HK129pAF-DKTHT) | EVQLVESGGGLVQPGGSLRLSCAASGFTFSTYAMNWVRQA PGKGLEWVGRIRSKYNNYATYYADSVKDRFTISRDDSKNS LYLQMNSLKTEDTAVYYCARHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 47 | HC (vH3.1 + CH1-HK129pAF-DKTHT) | EVQLVESGGGLVQPGGSLRLSCAASGFTFNTYAMHWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 48 | HC (vH3.2 + CH1-HK129pAF-DKTHT) | EVQLVESGGGLVQPGGSLRLSCAASGFTFNTYAMNWVRQA PGKGLEWVARIRSKSNNYATYYADSVKDRFTISRDDSKNI LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSCDKTHT |
| 49 | HC (vH2.3 + CH1-HK129pAF) | EVQLVESGGGLVQPGGSLRLSCAASGFTFNTYAMNWVRQA PGKGLEWVARIRSKYNNYATYYADSVKDRFTISRDDSKNI LYLQMNSLKTEDTAVYYCARHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSC |

TABLE 20-continued

Amino acid sequences of low affinity anti-CD3 Fab-HK129pAF heavy and light chain sequences expressed in E. coli. Also disclosed are all of the sequences in the table below, where pAF is replaced by any other non-natural amino acid.

| SEQ. ID. NO. | CHAIN | SEQUENCE |
|---|---|---|
| 50 | HC (vH2.2 + CH1-HK129pAF) | EVQLVESGGGLVQPGGSLRLSCAASGFTFNTYAMNWVRQA PGKGLEWVGRIRSKYNNYATYYADSVKDRFTISRDDSKNI LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSC |
| 51 | HC (vH1.0 + CH1-HK129pAF) | EVQLVESGGGLVQPGGSLRLSCAASGFTFNTYAMNWVRQA PGKGLEWVGRIRSKYNNYATYYADSVKDRFTISRDDSKNS LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSC |
| 52 | HC (vH2.1 + CH1-HK129pAF) | EVQLVESGGGLVQPGGSLRLSCAASGFTFSTYAMNWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSC |
| 53 | HC (vH2.4 + CH1-HK129pAF) | EVQLVESGGGLVQPGGSLRLSCAASGFTFSTYAMNWVRQA PGKGLEWVGRIRSKYNNYATYYADSVKDRFTISRDDSKNS LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSC |
| 54 | HC (vH2.5 + CH1-HK129pAF) | EVQLVESGGGLVQPGGSLRLSCAASGFTFNTYAMNWVRQA PGKGLEWVGRIRSKYNNYATYYADSVKDRFTISRDDSKNS LYLQMNSLKTEDTAVYYCARHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSC |
| 55 | HC (vH2.6 + CH1-HK129pAF) | EVQLVESGGGLVQPGGSLRLSCAASGFTFSTYAMNWVRQA PGKGLEWVGRIRSKYNNYATYYADSVKDRFTISRDDSKNS LYLQMNSLKTEDTAVYYCARHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSC |
| 56 | HC (vH3.1 + CH1-HK129pAF) | EVQLVESGGGLVQPGGSLRLSCAASGFTFNTYAMHWVRQA PGKGLEWVARIRSKYNNYATYYADSVKDRFTISRDDSKNI LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSC |
| 57 | HC (vH3.2 + CH1-HK129pAF) | EVQLVESGGGLVQPGGSLRLSCAASGFTFNTYAMNWVRQA PGKGLEWVARIRSKSNNYATYYADSVKDRFTISRDDSKNI LYLQMNSLKTEDTAVYYCVRHGNFGNSYVSWFAYWGQGTL VTVSSASTKGPSVFPLAPSSpAFSTSGGTAALGCLVKDYF PEPVTVSWNSGALTSGVHTFPAVLQSSGLYSLSSVVTVPS SSLGTQTYICNVNHKPSNTKVDKKVEPKSC |
| 58 | LC (vL2.4 + CL) | QAVVTQEPSLTVSPGGTVTLTCRSSTGAVTTSNYANWVQQ KPGQAPRGLIGGTNKRAPWVPARFSGSLLGGKAALTLSGA QPEDEAEYYCALWYSNLWVFGGGTKLTVLGRTVAAPSVFI FPPSDEQLKSGTASVVCLLNNFYPREAKVQWKVDNALQSG NSQESVTEQDSKDSTYSLSSTLTLSKADYEKHKVYACEVT HQGLSSPVTKSFNRGEC |
| 59 | LC (VL2.1 + CL) | QAVVTQEPSLTVSPGGTVTLTCRSSTGAVTTSNYANWFQQ KPGQAPRGLIGGTNKRAPGVPARFSGSLLGGKAALTLSGA QPEDEAEYYCALWYSNLWVFGGGTKLTVLGRTVAAPSVFI FPPSDEQLKSGTASVVCLLNNFYPREAKVQWKVDNALQSG NSQESVTEQDSKDSTYSLSSTLTLSKADYEKHKVYACEVT HQGLSSPVTKSFNRGEC |

TABLE 20-continued

Amino acid sequences of low affinity anti-CD3
Fab-HK129pAF heavy and light chain sequences expressed
in E. coli. Also disclosed are all of the sequences in
the table below, where pAF is replaced by any other
non-natural amino acid.

| SEQ. ID. NO. | CHAIN | SEQUENCE |
|---|---|---|
| 60 | LC (vL2.5 + CL) | QAVVTQEPSLTVSPGGTVTLTCRSSTGAVTTSNYANWFQQ KPGQAPRGLIGGTNKRAPWVPARFSGSLLGGKAALTLSGA QPEDEAEYYCALWYSNLWVFGGGTKLTVLGRTVAAPSVFI FPPSDEQLKSGTASVVCLLNNFYPREAKVQWKVDNALQSG NSQESVTEQDSKDSTYSLSSTLTLSKADYEKHKVYACEVT HQGLSSPVTKSFNRGEC |
| 61 | LC (vL2.2 + CL) | QAVVTQEPSLTVSPGGTVTLTCRSSTGAVTTSNYANWVQQ KPGQAPRTLIGGTNKRAPGVPARFSGSLLGGKAALTLSGA QPEDEAEYYCALWYSNLWVFGGGTKLTVLGRTVAAPSVFI FPPSDEQLKSGTASVVCLLNNFYPREAKVQWKVDNALQSG NSQESVTEQDSKDSTYSLSSTLTLSKADYEKHKVYACEVT HQGLSSPVTKSFNRGEC |
| 62 | LC (vL3.1 + CL) | QAVVTQEPSLTVSPGGTVTLTCRSSTGAVTTSNYANWVQQ KPGQAPRGLIGGTNNRAPGTPARFSGSLLGGKAALTLSGA QPEDEAEYYCALWYSNLWVFGGGTKLTVLGRTVAAPSVFI FPPSDEQLKSGTASVVCLLNNFYPREAKVQWKVDNALQSG NSQESVTEQDSKDSTYSLSSTLTLSKADYEKHKVYACEVT HQGLSSPVTKSFNRGEC |

Fermentation, purification & Folate conjugation: *E. coli* fermentation, purification, Folate conjugation and post-conjugation purification were performed as described in the above Examples.

Figure 7A:
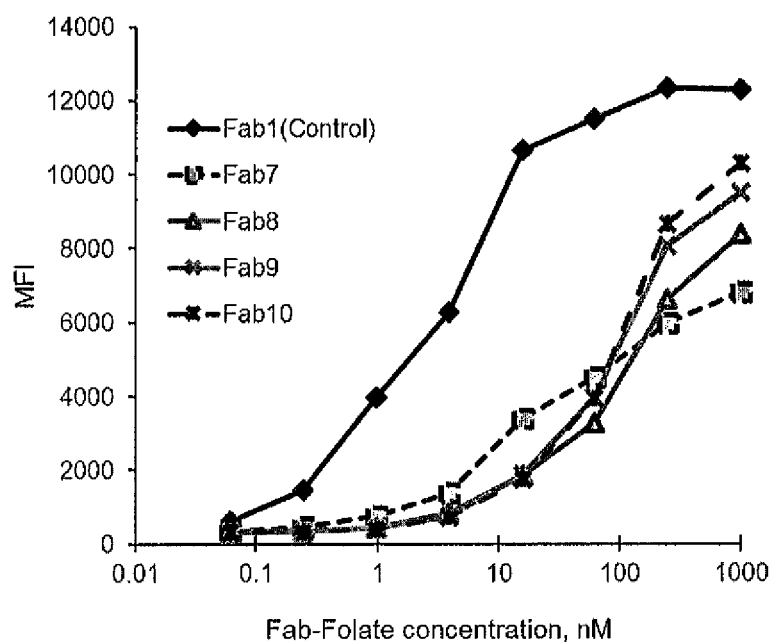
FIGS. 7A-7B depict low affinity variants of anti-CD3 Fab-Folate binding to cyno CD3.
Figure 7B:
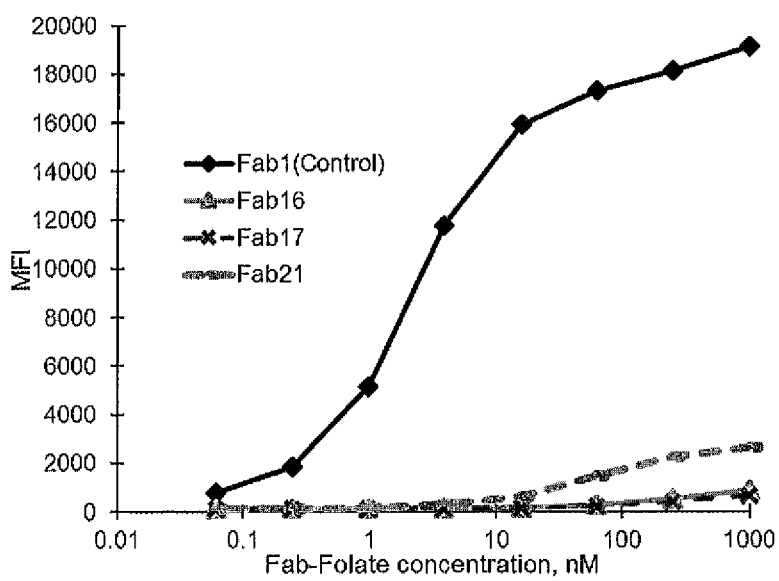

Binding of Folate-conjugated Fabs to human and cyno CD3: Binding of *E. coli* produced and Folate-conjugated low-affinity variants of humanized anti-CD3 Fabs was performed as described in the above Examples. FIGS. 6A-6B shows the binding affinities to human CD3 for two sub-sets of low-affinity Fab variants of anti-CD3 Fab-HK129-Folate along with the positive control Fab1. Out of the low-affinity Fabs tested, 10 failed to significantly bind to human CD3 even at highest concentration tested (1000 nM). The binding $EC_{50}$ of the remaining 4 Fabs (Fabs 7 to 10; described in Table 18) varied from 23.4 nM to 83.6 nM compared to the control Fab1 which is at 2.31 nM. Fab 21 showed weak binding activity which did not saturate even at 1000 nM cone. Very similar binding profile was observed for cyno CD3 binding as shown in FIGS. 7A-7B.

Figure 8:
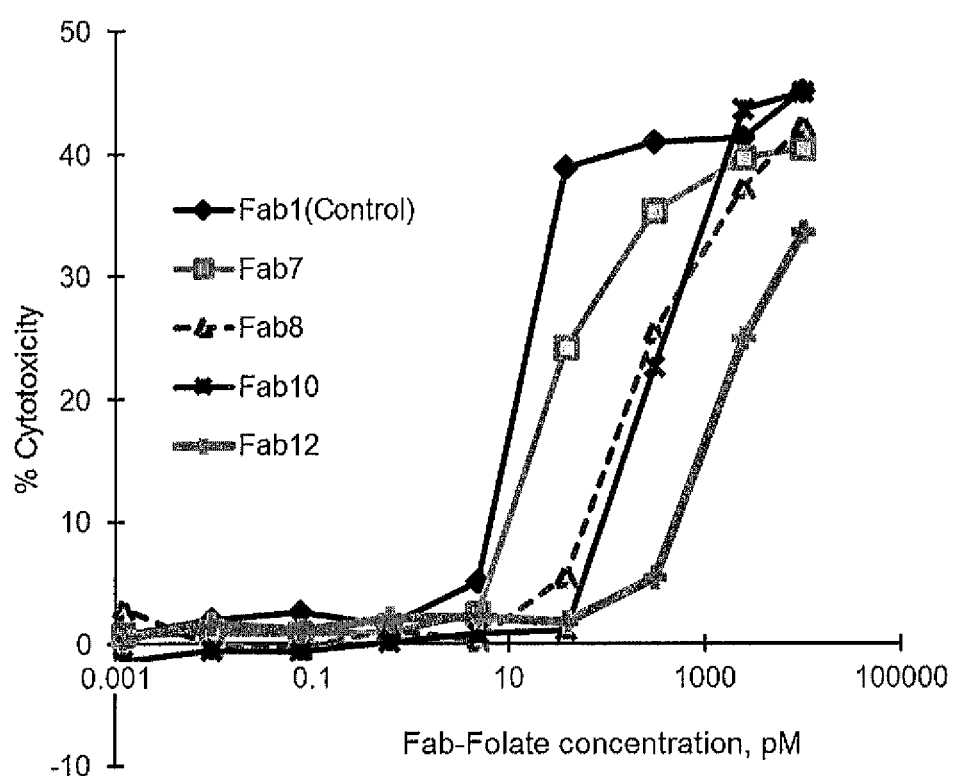
FIG. 8 depicts cytotoxicity to SKOV-3 cells with human PBMC. In-vitro cytotoxicity of 4 low-affinity variants of humanized anti-CD3 Fab-HK129-Folate molecules produced from E. coli cells with human PBMC. Fab1-HK129-Folate, parent control, is included as a positive control.
Figure 9:
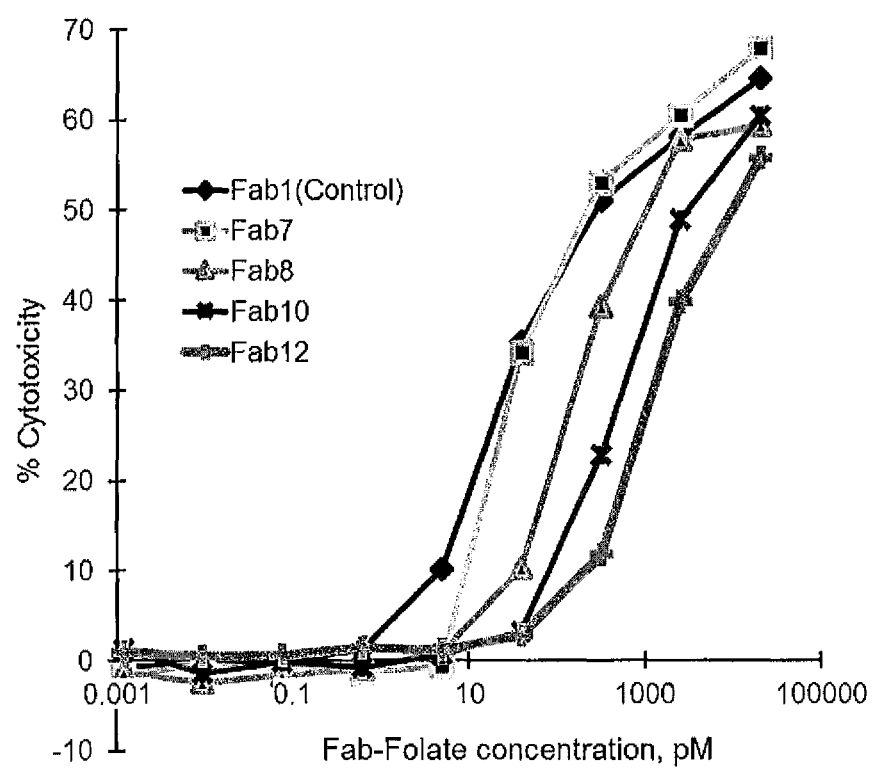
FIG. 9 depicts cytotoxicity to SKOV-3 cells with cyno PBMC. In-vitro cytotoxicity of 4 low-affinity variants of humanized anti-CD3 Fab-HK129-Folate molecules produced from E. coli cells with cyno PBMC. Fab1-HK129-Folate, parent control, is included as a positive control.

Cytotoxicity assay of Folate-conjugated Fabs with human and cyno PBMC: Cytotoxicity of the low-affinity Fabs was performed as described in the above Examples. FIG. 8 shows the cytotoxicity data of activated human PBMC with SKOV-3 cells. As shown, all 4 Fabs with 10 to 36-fold reduced binding affinity to human CD3 (FIGS. 6A-6B) showed comparable killing activity compared to control Fab1 (FIG. 8). Three Fabs (Fabs 11, 19, and 20) did not show any cytotoxic activity (data not shown). All other 8 Fabs showed considerable killing activity although they failed to bind even at 1000 nM concentration. Very similar cytotoxic profile was observed with activated cyno PBMC (FIG. 9).

Example 15

This Example demonstrates T cell activation and cytokine release assays of humanized anti-CD3 low-affinity antibody variants.

T cell activation/cytokine release assays: Purified human T cells and T cell-depleted human PBMCs were isolated from the same volume of whole blood by EasySep Human T cell Enrichment Kit and EasySep Human CD3 Positive Selection Kit (STEMCELL Technologies Inc), respectively. The purity of isolated T cells and accessory cells was confirmed by flow cytometry. To selectively monitor the activation of T cells in the presence of accessory cells, the purified T cells were labeled with Cellvue Lavender cell labeling kit (eBioscience), as per manufacturer protocol, prior to mixing with T cell-depleted human PBMCs. The resulting reconstituted PBMCs were incubated with target cells in the presence of anti-CD3 Fab variants. After 48 h, cells were labeled with APC-Cγ7-conjugated anti-human CD25 (Biolegend) or PE-conjugated anti-human CD69 (BD Biosciences) and analyzed by flow cytometry. The release of IFNγ and TNFα in the cultured supernatant was measured by enzyme-linked immunosorbent assay (ELISA)kit (R&D System).

Figure 10A:
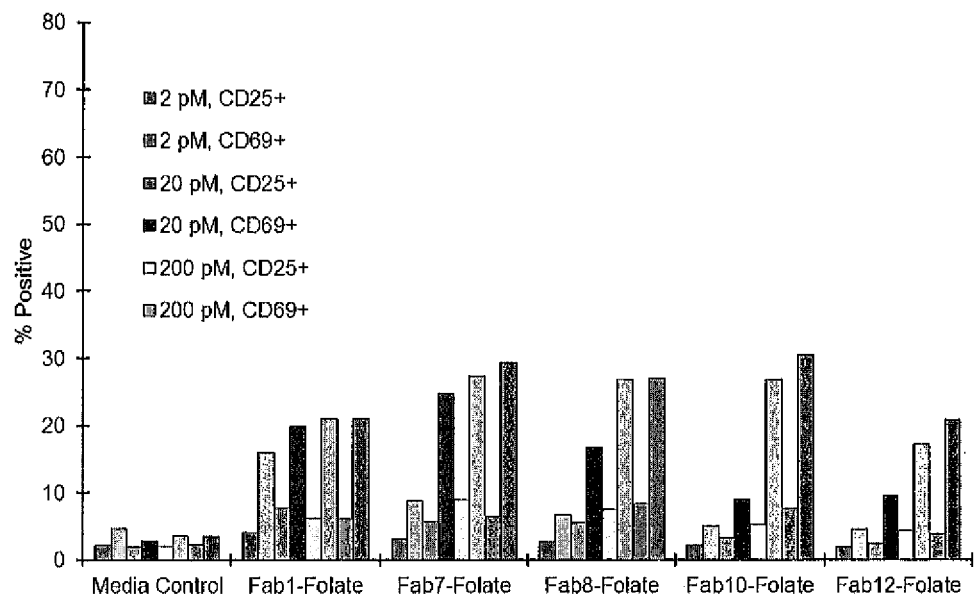
FIGS. 10A-10B depict T-cell activation.
Figure 10B:
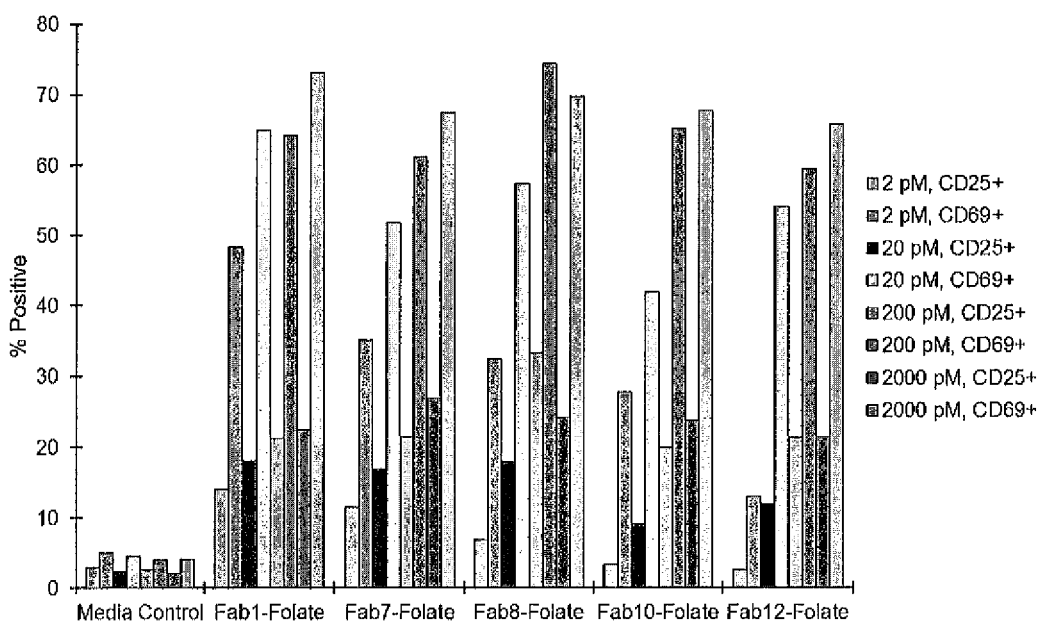
Figure 11B:
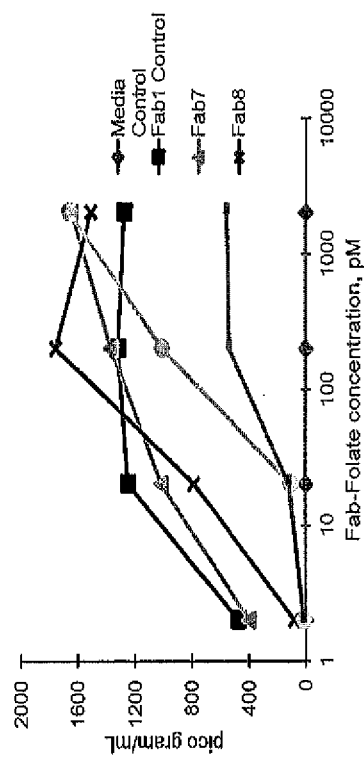
FIGS. 11A-11D depict in-vitro cytokine release with IFNgamma (FIGS. 11A and 11B), and TNFα (FIGS. 11C and 11D) of various low affinity anti-CD3 Fab-HK129-Folate variants in the absence (FIGS. 11A and 11C) or in the presence (FIGS. 11B and 11D) of SKOV-3 tumor cells.
Figure 11D:
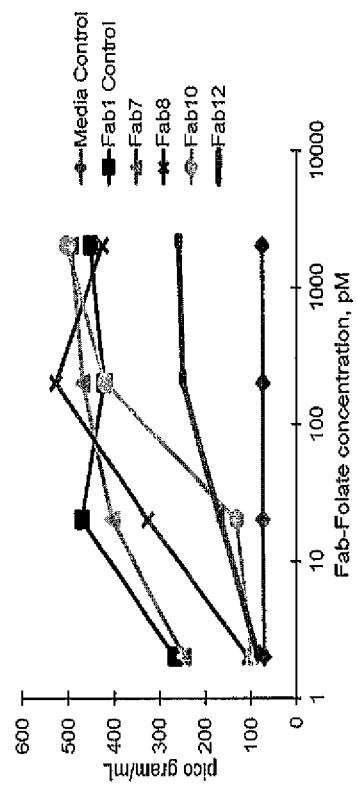
Figure 11A:
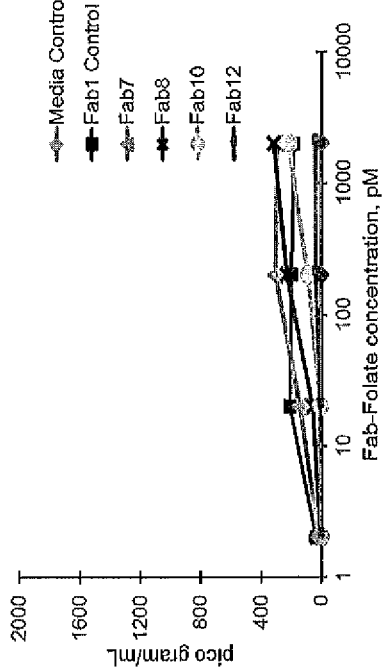
Figure 11C:
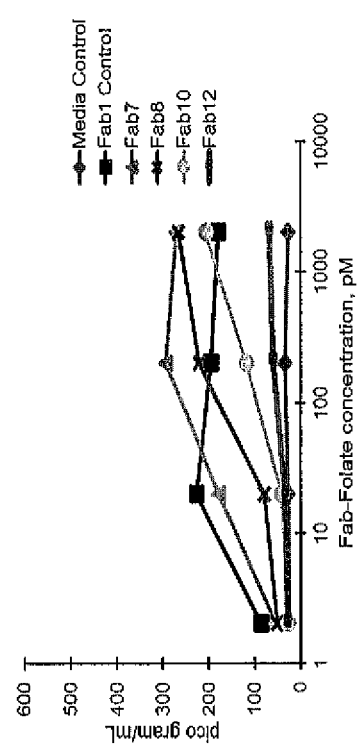
Figure 12A:
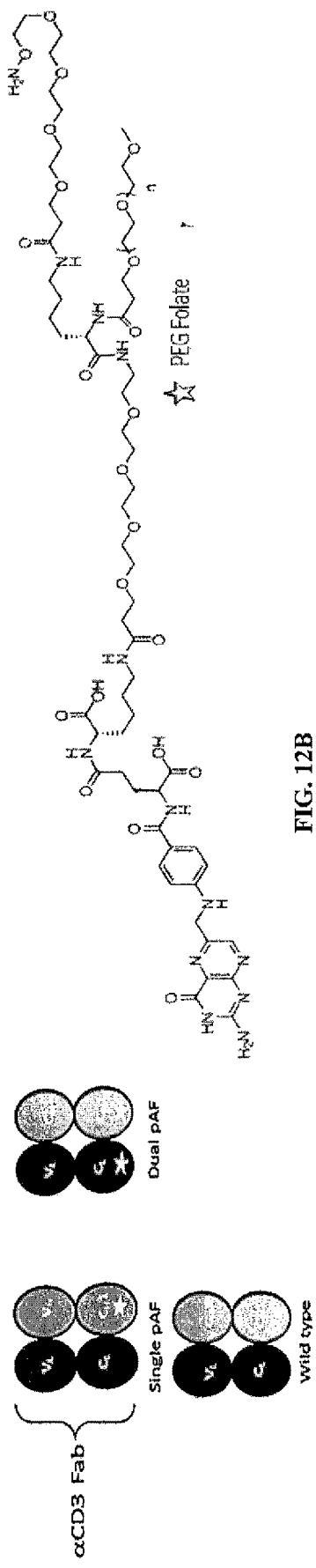
FIGS. 12A-12F depict illustrations of anti-CD3 Fab-Folate bispecific conjugates and PEG linker of the invention.
Figure 12B:
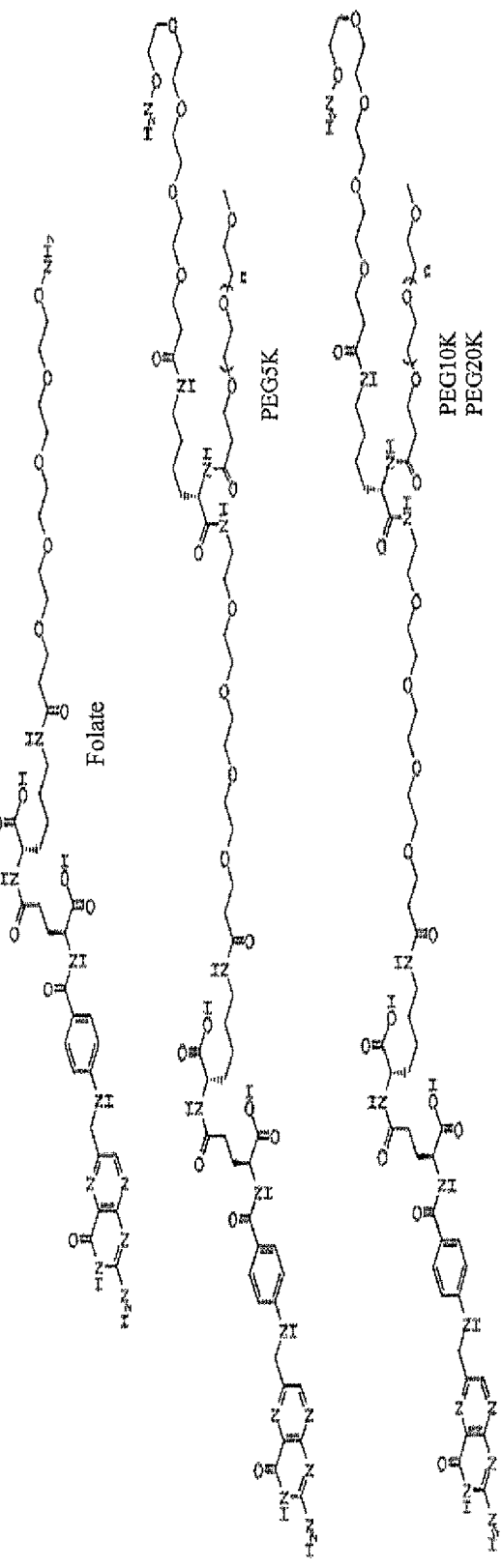
Figure 12C:
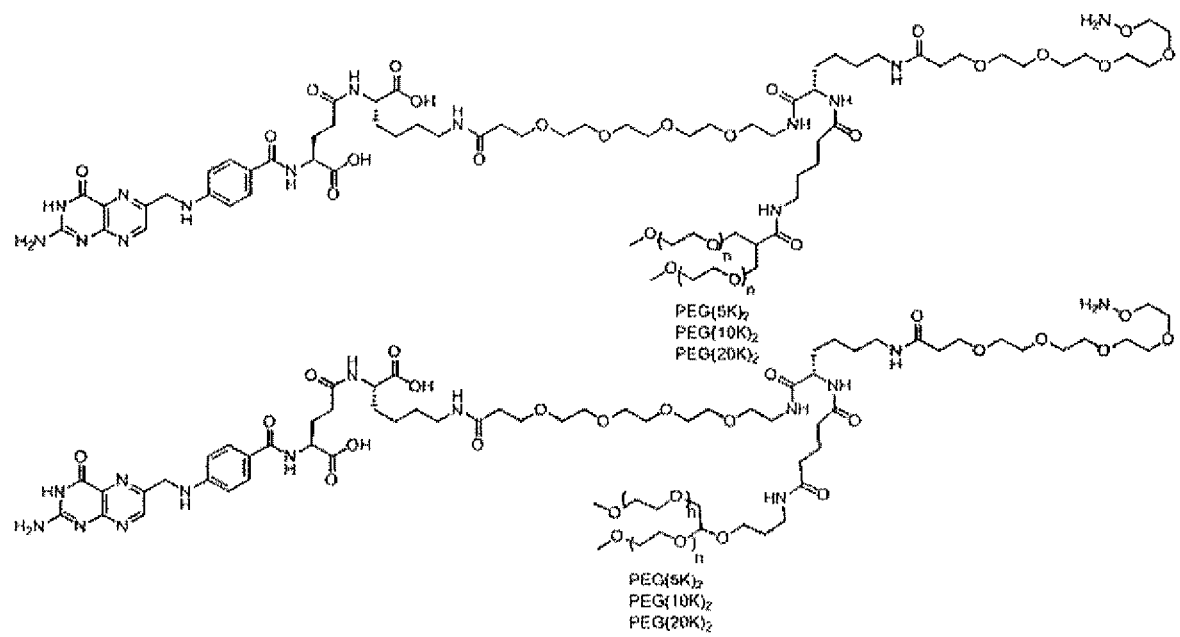
Figure 12D:
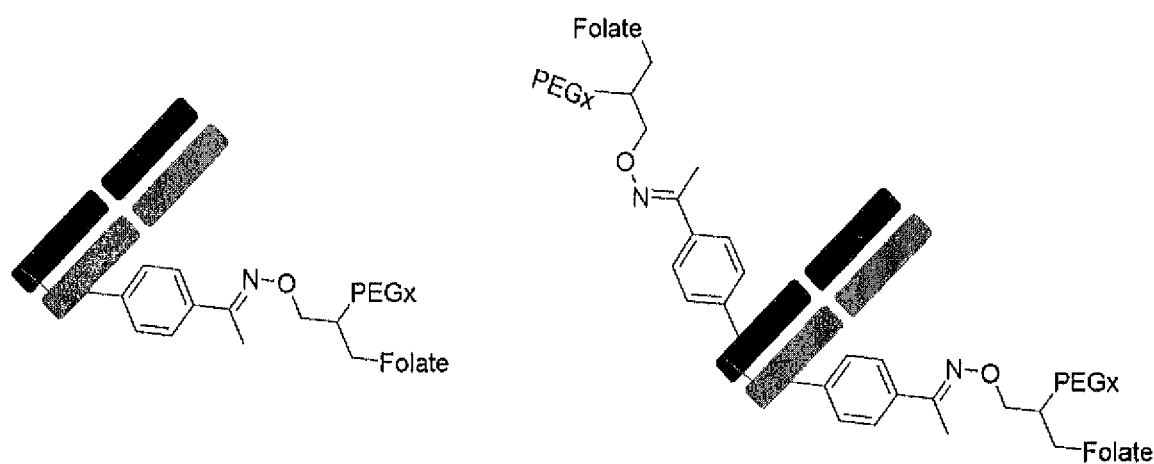
Figure 12E:
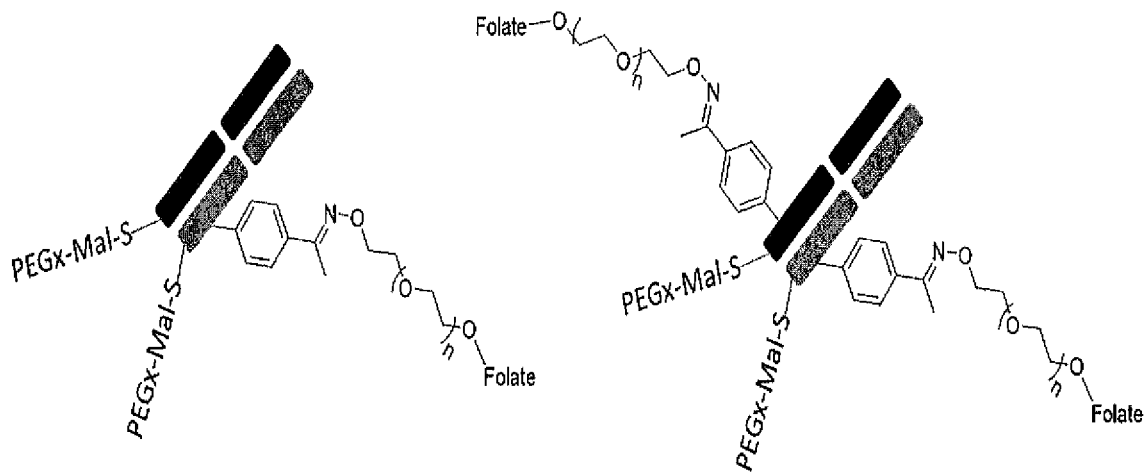
Figure 12F:
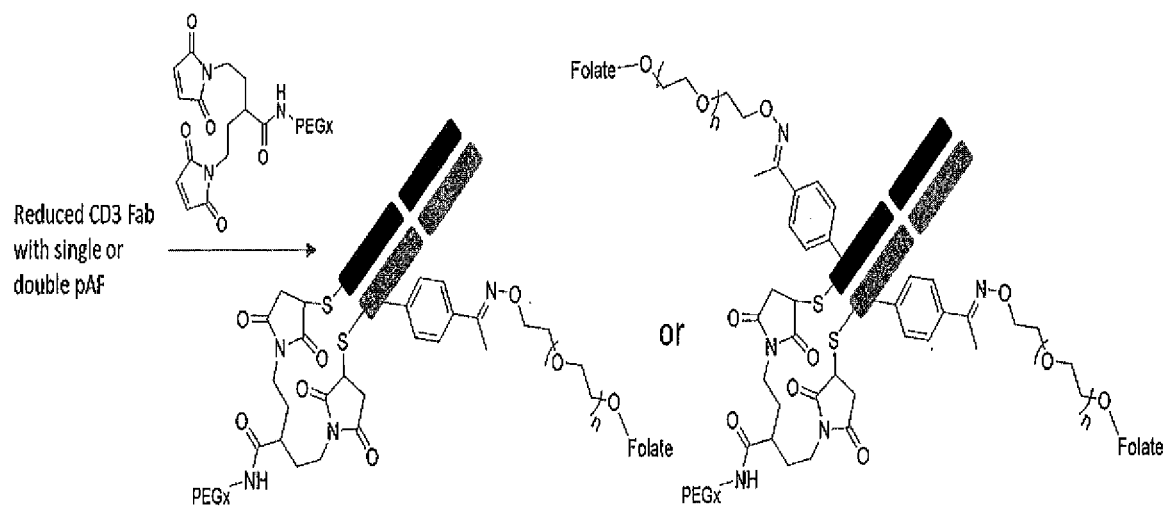

As shown in FIGS. 10A-10B, significant T cell activation (by CD25 and CD 69 T cell markers) achieved in the presence of SKOV-3 cells is strongly dose-dependent on various low-affinity anti-CD3 Fab-HK129-Folate molecules. Similar correlation was observed for cytokine release assays for IFNγ FIGS. 11A-11B in the absence and presence of SKOV-3 tumor cells respectively and TNFα FIGS. 1C-11D in the absence and presence of SKOV-3 tumor cells respectively.

Summary of low-affinity variants characterization: Table 21 summarizes the binding and cytotoxicity data, (human and cyno CD3), as well as T cell activation, (CD25 and CD69 markers), and cytokine release, (IFNγ and TNFα), assays for 12 low-affinity anti-CD3 Fab variants with HK129-Folate modification. As shown, there is a general correlation between the strength of CD3 binding, cytotoxic potential, T cell activation and cytokine release.

TABLE 21

Summary of CD3 binding, in-vitro cytotoxicity, T cell activation and cytokine release by various anti-CD3 Fab-HK129-Folate low affinity variants.

| Modified Fab Molecules | Cytotoxicity with human PBMC EC50 (pM) | Cytotoxicity with human PBMC Fold decrease | Cytotoxicity with cyno PBMC EC50 (pM) | Cytotoxicity with cyno PBMC Fold decrease | Binding CD3, EC50 (nM) Human/Cyno | T-cell activation CD25 & CD69 | Cytokine release IFNγ + TNFα |
|---|---|---|---|---|---|---|---|
| Fab1-HK129-Folate | 14.03 | | 32.95 | | 2.31/3.3 | +++ | +++ |
| Fab7-HK129-Folate | 29.6 | 2.1 | 38.56 | 1.2 | 23.4/20.2 | +++ | +++ |
| Fab8-HK129-Folate | 221 | 15.8 | 173.3 | 5.3 | 78.3/129.9 | +++ | ++ |
| Fab9-HK129-Folate | 250 | 17.8 | 295.4 | 9.0 | 69.1/93.1 | ++ | ++ |
| Fab10-HK129-Folate | 311.1 | 22.2 | 590.15 | 17.9 | 83.6/99.5 | ++ | + |
| Fab12-HK129-Folate | 1299.6 | 92.6 | 1280.4 | 38.9 | Minimal | ++ | + |
| Fab13-HK129-Folate | 339.6 | 24.2 | 647.2 | 19.6 | Minimal | ++ | ++ |
| Fab15-HK129-Folate | 1153.3 | 82.2 | 437.2 | 13.3 | Minimal | ND | +/− |
| Fab16-HK129-Folate | 1019.2 | 72.6 | 261.6 | 7.9 | Minimal | ND | +/− |
| Fab17-HK129-Folate | 2380 | 169.6 | 994.2 | 30.2 | Minimal | ND | +/− |
| Fab18-HK129-Folate | 2161 | 154.0 | 543.6 | 16.5 | Minimal | ND | +/− |
| Fab21-HK129-Folate | 91.32 | 6.5 | 42.9 | 1.3 | ND | ND | +++ |

Based on the data set, three low-affinity variants Fab9, Fab10, Fab21, were selected along with the parental molecule Fab1 for detailed in-vitro characterization including in-vivo testing in mice. Table 22 shows the comparison between these variants with respect to cytotoxicity and production of two cytokines. As shown, cytokine production has much higher $EC_{50}$ than those for T cell activation and killing. Thus, it may be possible to identify a range of anti-CD3 Fab concentrations where cytokine release does not pose significant safety issues but killing potency and T-cell activation are not compromised. This anti-CD3 antibody affinity fine-tuning approach might allow for uncoupling of these two opposing events and achieving better safety profile without compromising efficacy.

TABLE 22

Characterization of 3 selected low-affinity variants with HK129-Folate modification

| Modified Fab Molecules | Cytotoxicity with human PBMC $EC_{50}$ (pM) | Cytotoxicity with cyno PBMC $EC_{50}$ (pM) | IFNγ release $EC_{50}$ (pM) | TFNα release $EC_{50}$ (pM) |
|---|---|---|---|---|
| Fab1-HK129-Folate | 14.03 | 32.95 | 235 | 84.5 |
| Fab9-HK129-Folate | 250 | 295.4 | 1833 | 1164 |
| Fab10-HK129-Folate | 311.1 | 590.15 | 3274 | 797 |
| Fab21-HK129-Folate | 91.32 | 42.9 | 5276 | 691 |

Example 16

In-silico immunogenicity analysis of anti-CD3 Fab1, 9 & 10: To assess potential immunogenicity, the amino acid sequences of anti-CD3 Fab1, Fab9 and Fab10 was scanned in-silico for the presence of putative human leukocyte antigen (HLA) class II restricted epitopes, also known as T helper (Th)-cell epitopes based on Lonza's Epibase platform using the 'HLA class II—Global v4.0' settings (Lonza, UK). HLA binding specificities of all possible 10-mer peptides derived from a target sequence was analyzed. Profiling was performed at the allotype level for 43 DRB1, 8 DRB3/4/5, 22 DQ and 12 DP, i.e., 85 HLA class II allotypes in total. Peptides corresponding to self-peptides were treated separately as 'germline filtered' peptides. As a general overview of the results, Table 23 shows the number of strong binders corresponding to the DRB1, DRB3/4/5, DQ and DP genes (epitope counts). As in the humoral response raised against an antigen, the observed Th cell activation/proliferation is generally interpreted in terms of the DRB1 specificity. The results in Table 23 show that Fab 1, Fab9 and Fab10 corresponded to strong potential DRB1 binders 13, 11 and 13, respectively Table 24 shows DRB1 risk scores for each of these 3 Fabs in the global population are comparable to those of the humanized therapeutic antibodies. Of the 3 Fabs, Fab9 is the least immunogenic.

TABLE 23

HLA binders corresponding to the DRB1, DRB3/4/5, DQ and DP genes (epitope counts).

| Sequence | DRB1 | DRB3/4/5 | DQ | DP |
|---|---|---|---|---|
| Fab1-HC | 6 | 2 | 2 | 2 |
| Fab1-LC | 7 | 0 | 1 | 4 |
| Fab1-Total | 13 | 2 | 3 | 6 |
| Fab9-HC | 4 | 2 | 2 | 2 |
| Fab9-LC | 7 | 0 | 2 | 4 |
| Fab9-Total | 11 | 2 | 4 | 6 |

TABLE 23-continued

HLA binders corresponding to the DRB1, DRB3/4/5, DQ and DP genes (epitope counts).

| Sequence | DRB1 | DRB3/4/5 | DQ | DP |
| --- | --- | --- | --- | --- |
| Fab10-HC | 6 | 1 | 1 | 2 |
| Fab10-LC | 7 | 0 | 2 | 4 |
| Fab10-Total | 13 | 1 | 3 | 6 |

TABLE 24

DRB1 risk scores of the 3 Fabs in the global population.

| Fab | LC | HC | Total |
| --- | --- | --- | --- |
| Fab1 | 477.5 | 748.6 | 1226.1 |
| Fab9 | 521.4 | 488.1 | 1009.5 |
| Fab10 | 521.4 | 720 | 1241.4 |

Example 17

Design and synthesis of bi-functional PEG-Folate linkers illustrated in FIGS. 12A-12F. This example demonstrates the synthetic routes and structures of various PEG-Folate linker compounds.

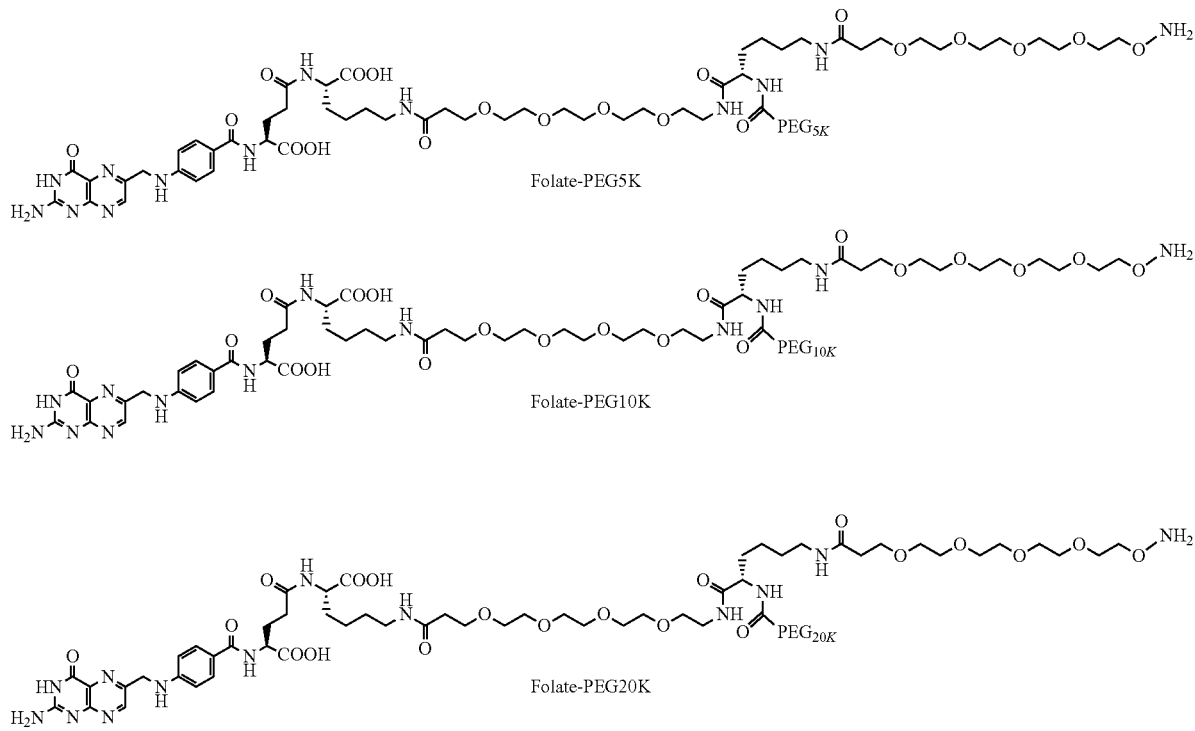

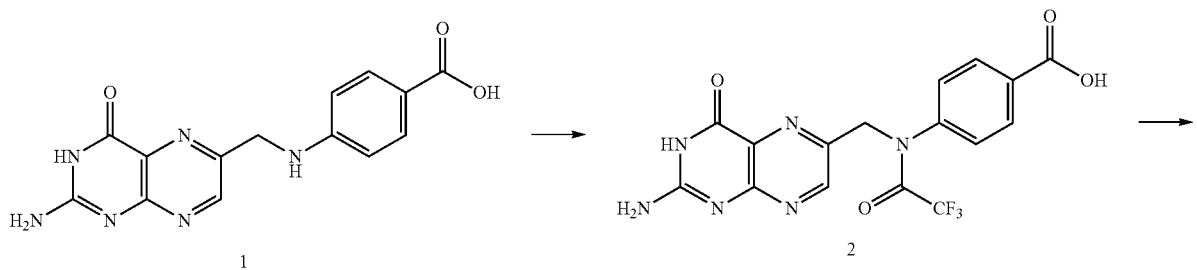

This example demonstrates synthetic routes for the synthesis of compound 10.

-continued
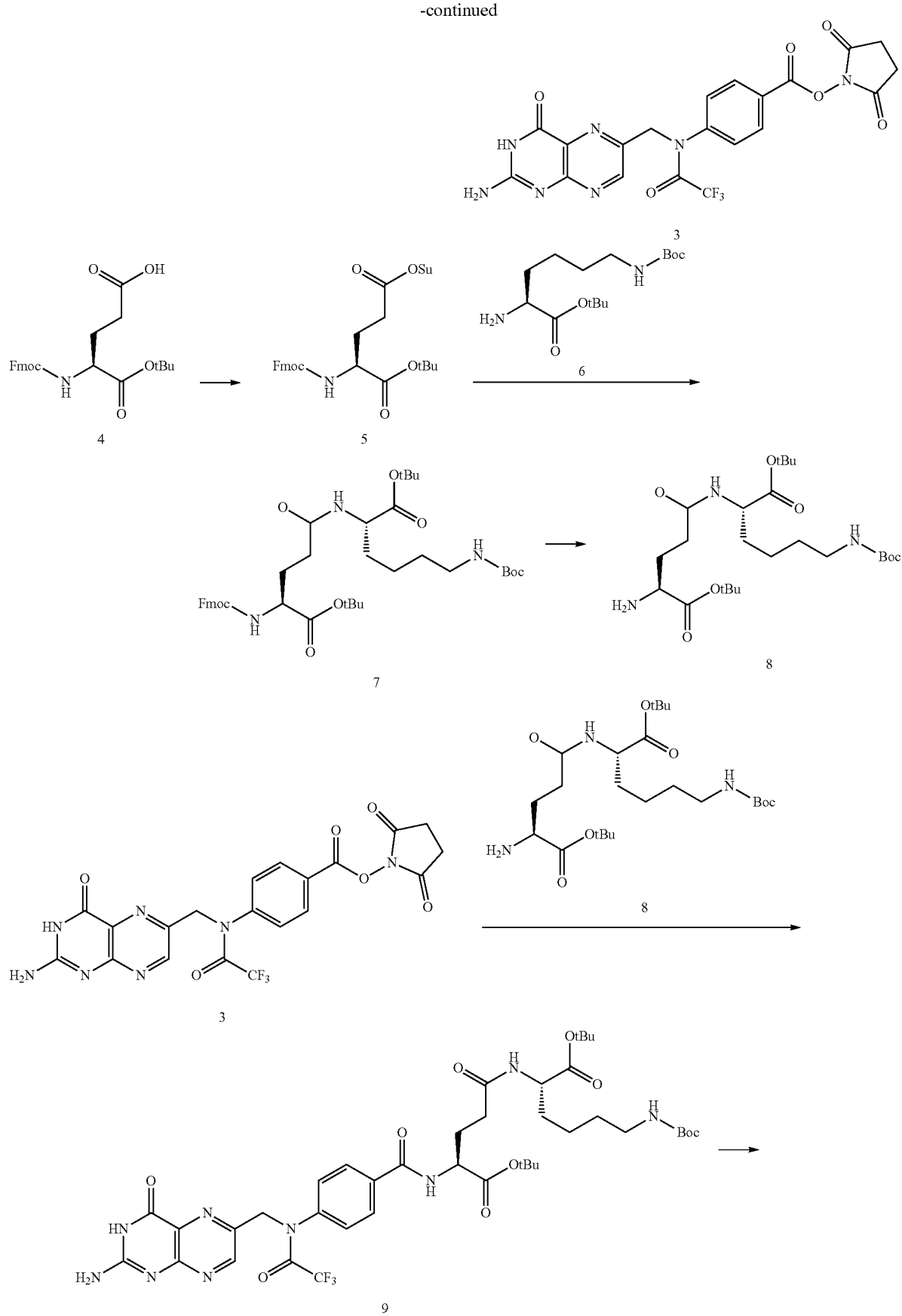

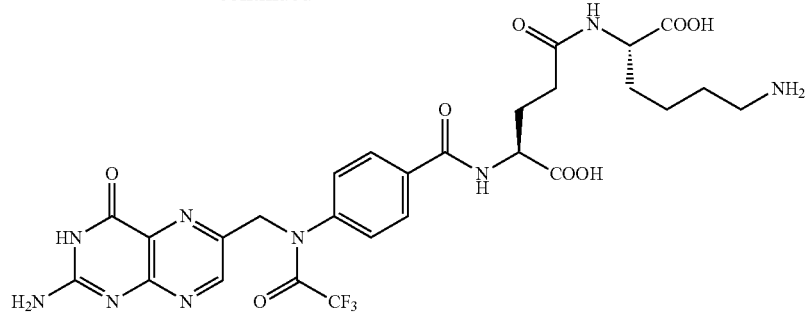

10

$N^{10}$-Trifluoroacetylpteroic acid (2). To 1.0 g Pteroic acid (1) in a round bottom flask was introduced 10 ml of trifluoroacetic anhydride under nitrogen, dropwise, for 10 minutes. The reaction mixture was stirred at room temperature for 24 hours away from light. Dark brown solution was filtered through a pad of celite and evaporated. The resulting viscous brown oil was triturated with ether, and the separated precipitate was collected by filtration washed with ether and dried under vacuum overnight to afford crude intermediate as light brown powder. The crude acylated material was re-suspended in anhydrous THF and treated with ice. The resulting mixture was stirred at room temperature for 10 hours; light brown precipitate separated during this time. The reaction mixture was diluted with ether, and precipitate was collected by filtration, washed with ether, and dried under vacuum overnight to afford $N^{10}$-trifluoroacetylpteroic acid (2) (1.45 g crude) as light brown powder which was used in the next reaction without further purification.

$N^{10}$-Trifluoroacetylpteroic acid OSu ester (3). The solution of $N^{10}$ trifluoroacetylpteroic acid (2) in anhydrous DMSO was treated with N-hydroxysuccinimide (0.43 g), followed by EDCI-HCl (2.04 g) in one portion at room temperature. The resulting dark solution was stirred for 24 hours at ambient temperature and diluted with ice-cold water (40 ml). The separated fine brown precipitate was collected by centrifugation, washed with cold water, air dried overnight and under vacuum for 1 day to obtain compound (3) as brown powder, MS(ESI) m/z 506 (M+H)$^+$.

Fmoc-Glu-O$^t$Bu-Lys(Boc)-O$^t$Bu (7). To a mixture of Fmoc-Glu-O$^t$Bu (4), (4.26 g) and N-hydroxysuccinimide (1.15 g) in anhydrous THF (40 mL) was added DCC (2.06 g) in one portion at room temperature. The resulting solution was stirred overnight at room temperature, and then solids were filtered off and washed with THF. Combined filtrate was evaporated to dryness and dried under vacuum to give crude Fmoc-Glu(OSu)-O$^t$Bu (5), (5.3 g) as white foam This material was re-dissolved in THF (20 mL) and added at room temperature to a mixture of H-Lys(Boc)-O$^t$Bu-HCl (6), (3.39 g), and DIPEA (3.5 mL) in anhydrous THF (50 mL). The resulting mixture was stirred for 4 hours at ambient temperature, until reaction was judged complete by HPLC analysis, and solvent removed under vacuum. The residue was re-dissolved in ethyl acetate (100 mL), washed with 10/aqueous citric acid (50 mL), water (50 mL), and brine (50 mL), and dried over sodium sulfate. After removal of solvents under vacuum, the residue was triturated with 5% ether/hexanes (50 mL). The separated white solid product was filtered, washed with hexanes, and dried under vacuum to afford Fmoc-Glu-O$^t$Bu-Lys(Boc)-O$^t$Bu (7).

H-Glu-O$^t$Bu-Lys(Boc)-O$^t$Bu (8). A solution of Fmoc-Glu-O$^t$Bu-Lys(Boc)-O$^t$Bu (7) in DCM was treated with diethyl amine. The resulting solution was stirred for 4 hours at room temperature, until deprotection was judged complete by HPLC analysis. All solvents were removed under vacuum and the residue was purified by silica gel column chromatography eluting first with dichloromethane, then 5-10% MeOH in dichloromethane to afford H-Glu-O$^t$Bu-Lys(Boc)-O$^t$Bu (8) as colorless oil.

Compound 9: A solution of amine 8 in anhydrous DMF was treated with N-trifluoroacetylpteroic acid OSu ester (3) in one portion. The resulting mixture was stirred at room temperature for 24 hours, while monitored by HPLC analysis for completion. The reaction mixture was diluted with ethyl acetate and filtered through a pad of silica gel eluting with 10% methanol in ethyl acetate. Combined filtrate was evaporated to dryness, re-dissolved in ethyl acetate and washed sequentially with 10% aqueous citric acid, water, saturated NaHCO$_3$, and brine. The extract was dried over sodium sulfate, evaporated, and dried under vacuum to overnight to afford crude 9 as brown solid.

Compound 10: The crude compound 9 was dissolved in a 1:1 (v/v) mixture of trifluoroacetic acid and dichloromethane. The resulting solution was allowed to stand at room temperature for 2 hours until the global deprotection was complete as judged by HPLC analysis. All solvents were removed under vacuum, and the residual brown oil was triturated with diethyl ether and briefly sonicated. The separated pale precipitate was collected by filtration, thoroughly washed with ether, and dried under vacuum for one day to afford product 10 as pale yellow powder.

This example demonstrates synthetic routes for the synthesis of compound 13.

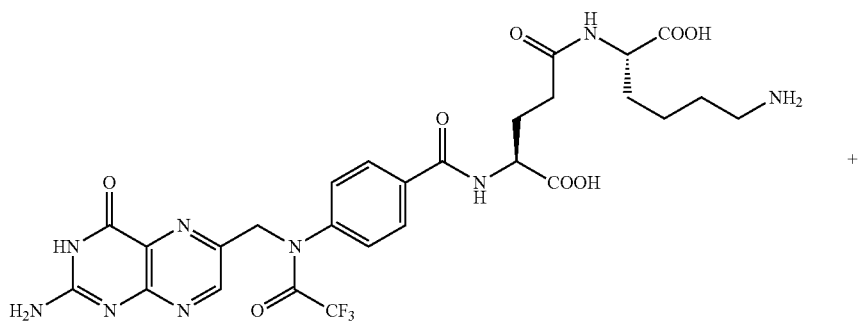

10

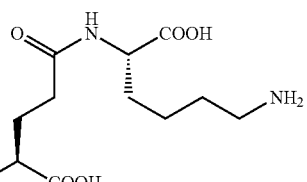

11

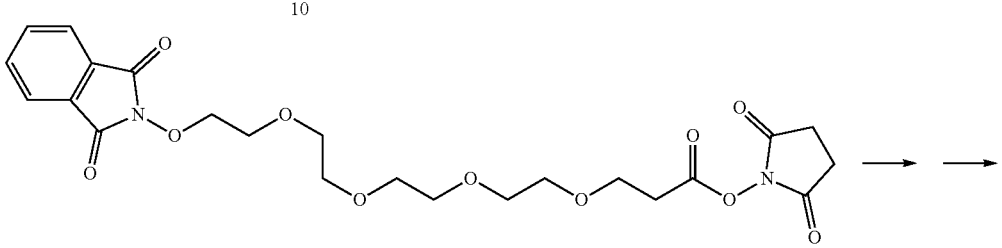

12

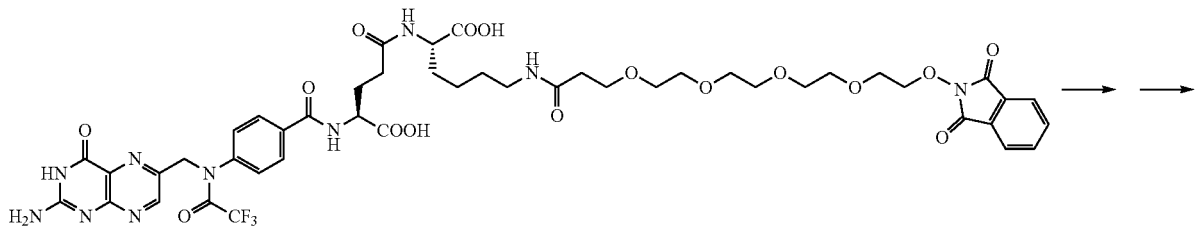

13

Compound 12: To a solution of compound 10 (0.45 g) and compound 11 (0.26 g) in DMF (15 mL) was added DIEA (0.44 mL) at room temperature. Reaction mixture was stirred at room temperature for overnight until complete consumption of 11 was observed by HPLC analysis. Reaction mixture was diluted with pH 5 acetate buffer (0.5M) and 1 mL of acetonitrile and purified by C18 reverse phase HPLC using 20-90/o acetonitrile/0.05% TFA gradient as eluent to obtain compound 12 as white solid after lyophilization.

Compound 13: To a solution of compound 12 (0.31 g) in DMF (1.5 mL) was added hydrazine, $H_2O$ (0.19 mL) at room temperature. Reaction mixture was stirred at room temperature overnight. Reaction mixture was diluted with water (~2 mL) and purified by C18 reverse phase HPLC using 20-90% acetonitrile/0.05% TFA gradient as eluent to obtain compound 13 as a yellow solid after lyophilization. MS(ESI) m/z 831 (M+H)*.

The present invention incorporates linker synthesis as exemplified below by demonstrating synthetic routes for the synthesis of compound 11, (CAS #: 1415328-95-8).

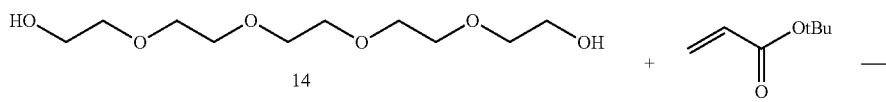

14

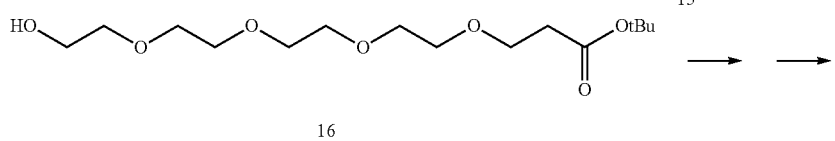

16

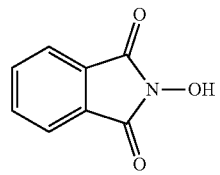

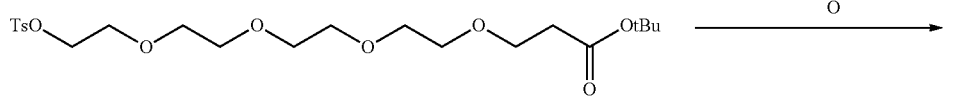

17

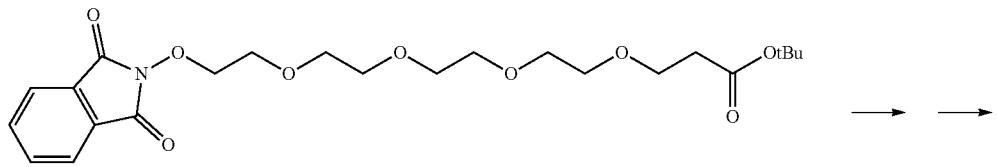

18

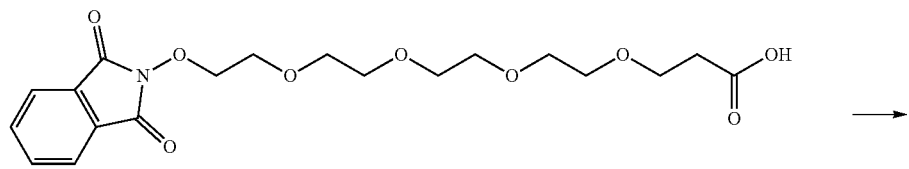

19

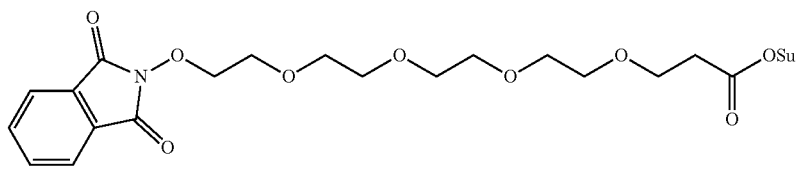

11

Compound 16: To a solution of tetraethylene glycol 14 in anhydrous THF were added sodium in small pieces at room temperature and was stirred until completely dissolved. Acrylate 15 was added slowly over 15 minutes period to the resulting solution. Reaction mixture was allowed to stir at room temperature for 20 hours, then concentrated under vacuum and re-suspended in brine, followed by extraction with ethyl acetate. Combined organic phase was washed with brine and dried over sodium sulfate. Removal of solvents in vacuum afforded compound 16 as clear yellowish oil.

Compound 17: To a mixture of alcohol 16 and pyridine in anhydrous DCM were added tosyl chloride in small portions at 0° C. The resulting mixture was stirred for 30 minutes at 0° C., then at room temperature overnight. Reaction mixture was quenched with 10% citric acid; aqueous layer was extracted with ethyl acetate, combined organics were washed with saturated sodium bicarbonate, water, brine, and dried over sodium sulfate. After removal of solvents the residue was purified on silica gel to afford tosylate 17 as clear colorless oil.

Compound 18: To a mixture of tosylate 17 and N-hydroxyphthalimide in DMF were added DBU at room temperature. The resulting deep red solution was heated to 90° C. for 1 hour, then cooled down, quenched with 10% citric acid and extracted with ethyl acetate. Organic phase was washed thoroughly with saturated aqueous sodium bicarbonate, water, and brine, dried over sodium sulfate. After removal of solvents the residue was purified on silica gel to give compound 18 as colorless oil.

Compound 19: t-Butyl ester 18 was treated with 1:1 mixture of TFA and DCM at room temperature. After 3 hours solvents were removed in vacuum, the residue was taken up into dichloromethane and washed thoroughly with brine and dried over sodium sulfate. After removal of solvent under vacuum, crude carboxylic acid 19 was obtained as yellowish clear oil.

Compound 11: Crude carboxylic acid 19 in anhydrous THF was treated with N-hydroxysuccinimide, followed by DCC at room temperature. Stirring continued for 6 hours, solids were removed by filtration, washed with THF. Filtrate was evaporated, the residue was passed through a silica pad, and washed with EtOAc to give compound 11 as colorless oil, which slowly solidified into white solid upon storage.

This example discloses branched linker synthesis. For example, synthetic routes for the synthesis of compound 25:

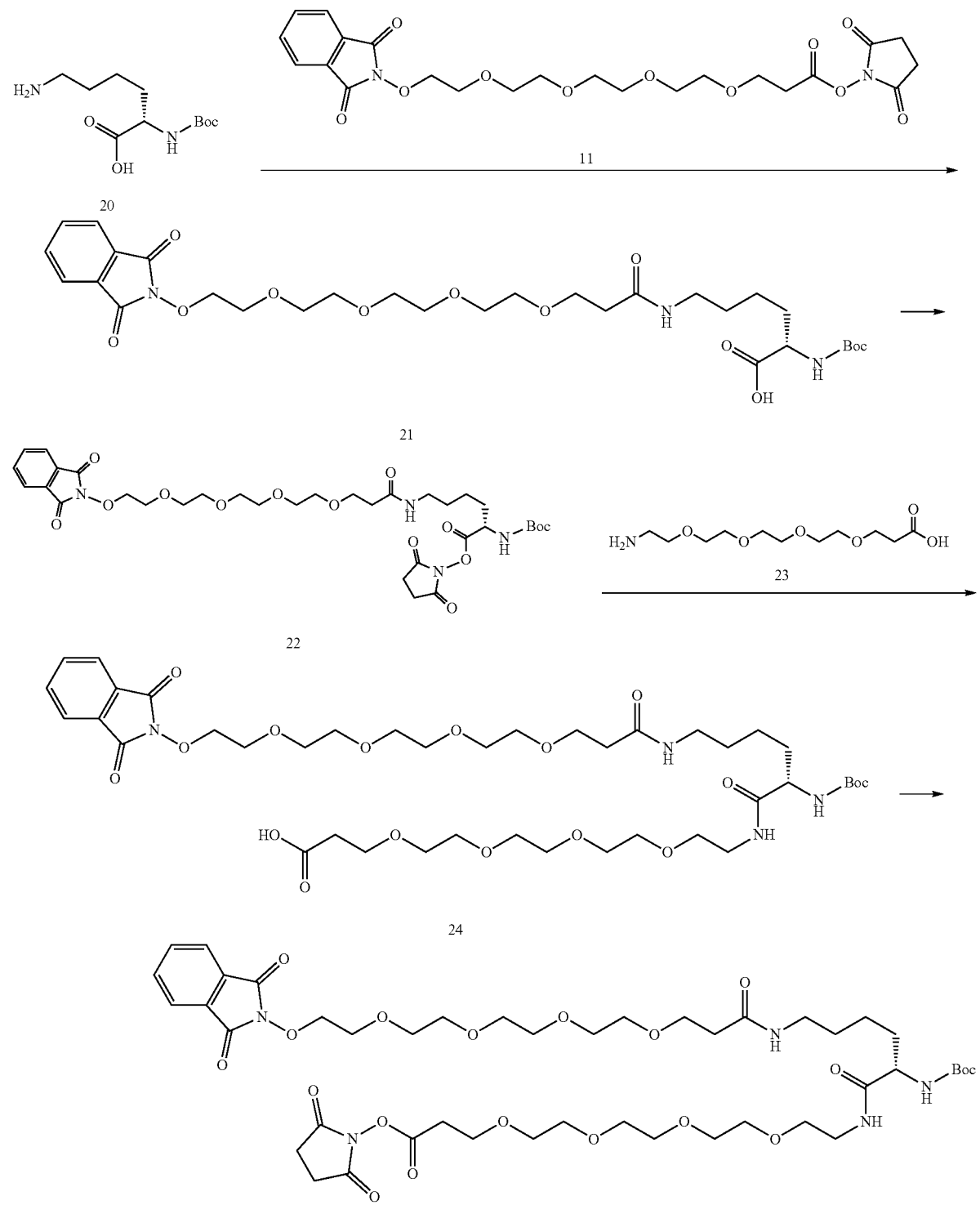

Compound 21: Boc-Lys-OH 20 To a solution of OSu ester 11 (1.55 g) and Boc-Lys-OH 20 (0.72 g) in DCM (50 ml) was added DIEA (1.03 mL) at 23° C. After 10 min, LCMS showed the reaction complete. The mixture was washed with 1N HCl (50 ml), saturated sodium bicarbonate (50 ml) and brine (50 ml). The organic layer was dried with MgSO$_4$. Removal of solvents gave crude acid 21 as a white solid, which was used in the next step without purification.

Compound 22: Crude acid 21 was dissolved in anhydrous THF and treated with N-hydroxysuccinimide, followed by DCC at room temperature. Reaction mixture was stirred overnight at room temperature, and then filtered to remove DCU, washed with THF. The product was isolated by column chromatography on silica gel using 0-10% methanol/DCM gradient as eluent to afford compound 22 as white solid, MS(ESI) m/z 737 (M+H)*.

Compound 24: Compound 22 was dissolved in DCM and treated with compound 23. The resulting mixture was treated with DIEA and stirred at room temperature for 5 hours. The reaction mixture was diluted by DCM and washed by water, brine and dried over sodium sulfate. The crude product was purified by 5% citric acid (20 ml), and brine (50 ml). The organic layer was dried with MgSO$_4$. The solvent was removed in vacuo to give compound 24 as white solid. The crude product was used for next step without further purification. MS(ESI) m/z 887 (M+H)$^+$.

Compound 25: Compound 24 was dissolved in THF and treated with N-hydroxysuccinimide, followed by DCC at room temperature. After 4 hours, the mixture was filtered to remove DCU, concentrated in vacuo. The residue was purified by column chromatography on silica gel using 0-6% methanol/DCM gradient as eluent to afford compound as white solid, MS(ESI) m/z 984 (M+H)*.

This example discloses synthetic routes for the synthesis of compound 30.

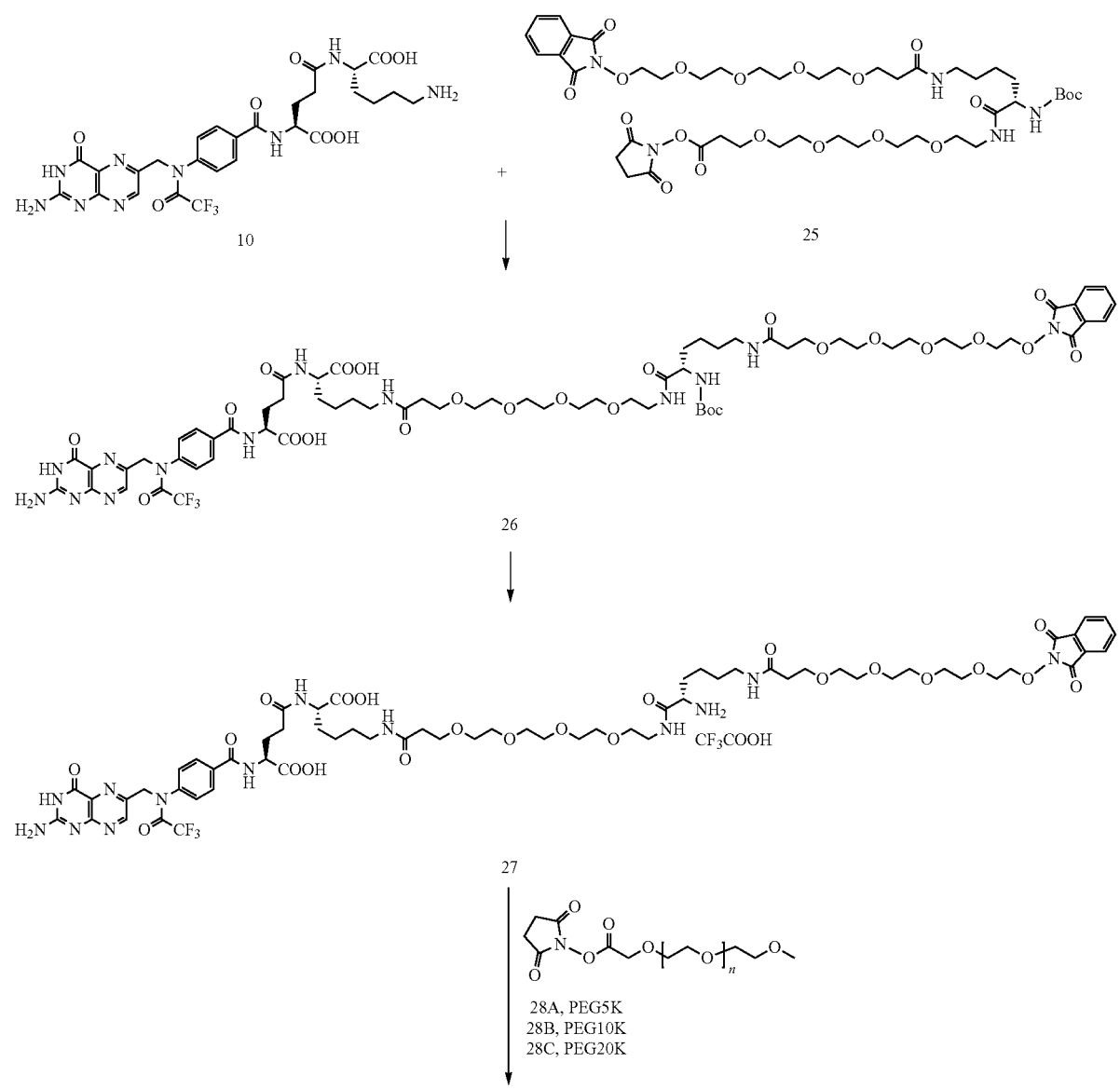

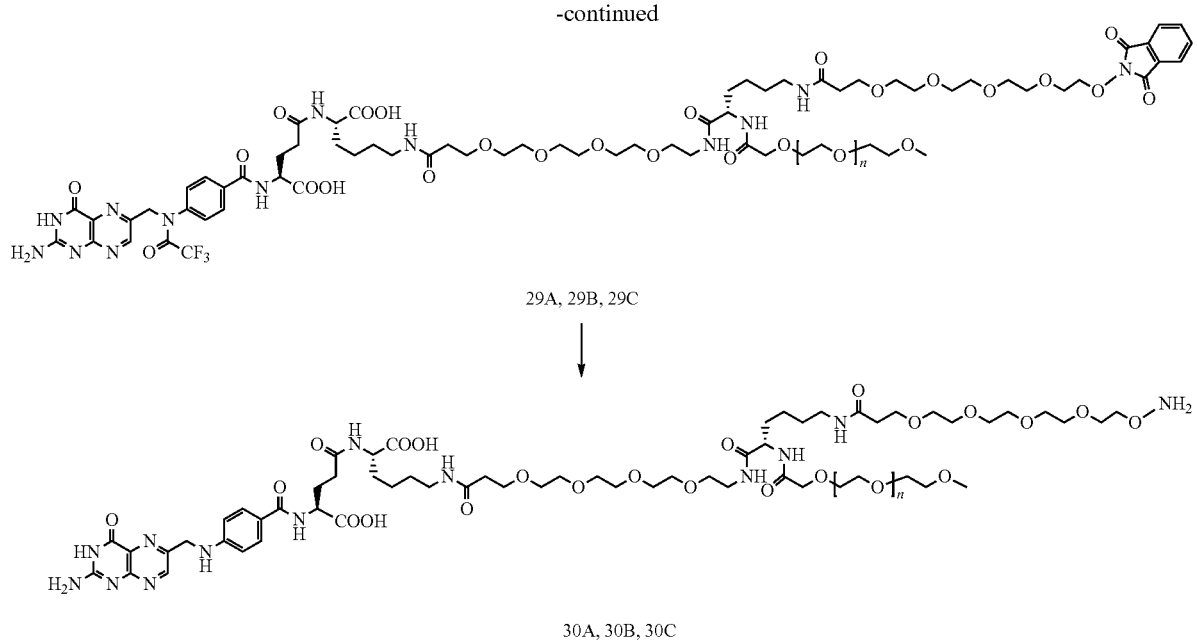
29A, 29B, 29C
30A, 30B, 30C
This example discloses the synthesis of branched PEG-Folate compounds 30.
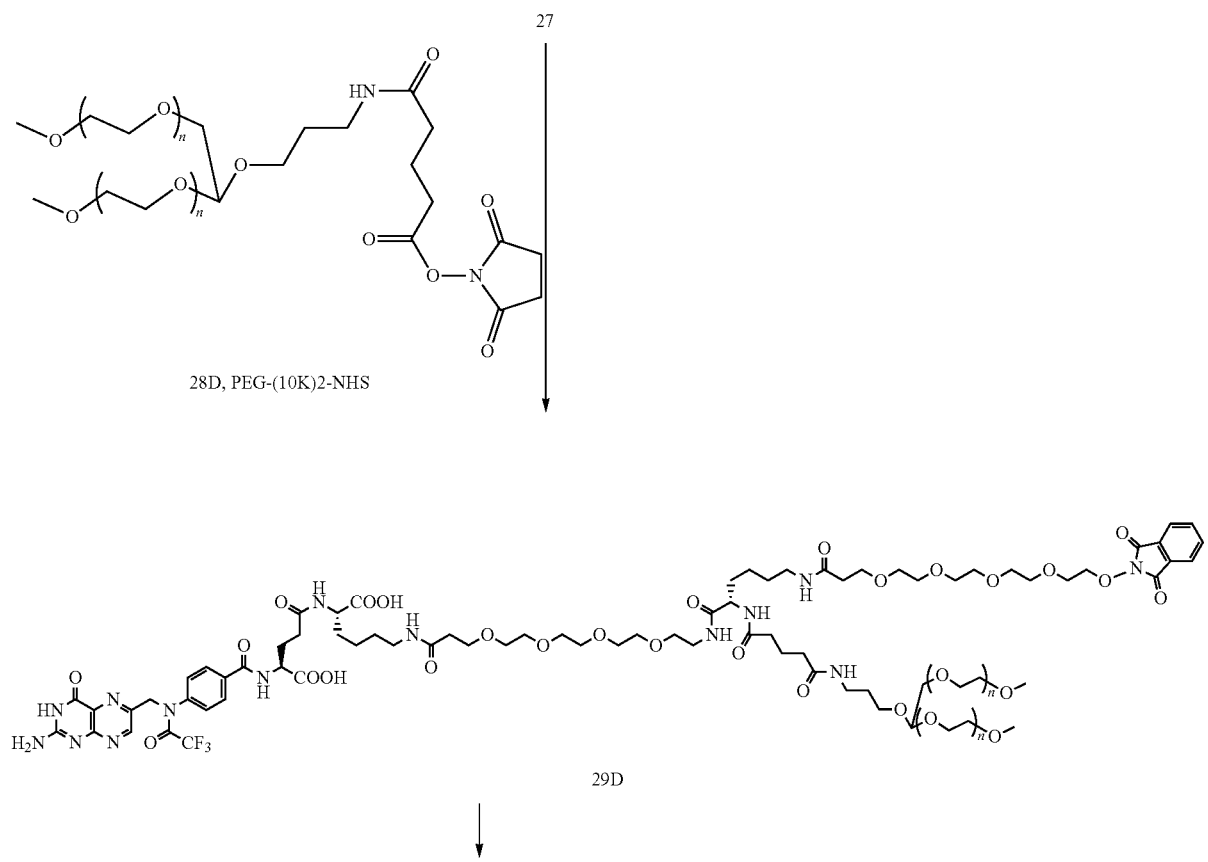
28D, PEG-(10K)2-NHS
29D

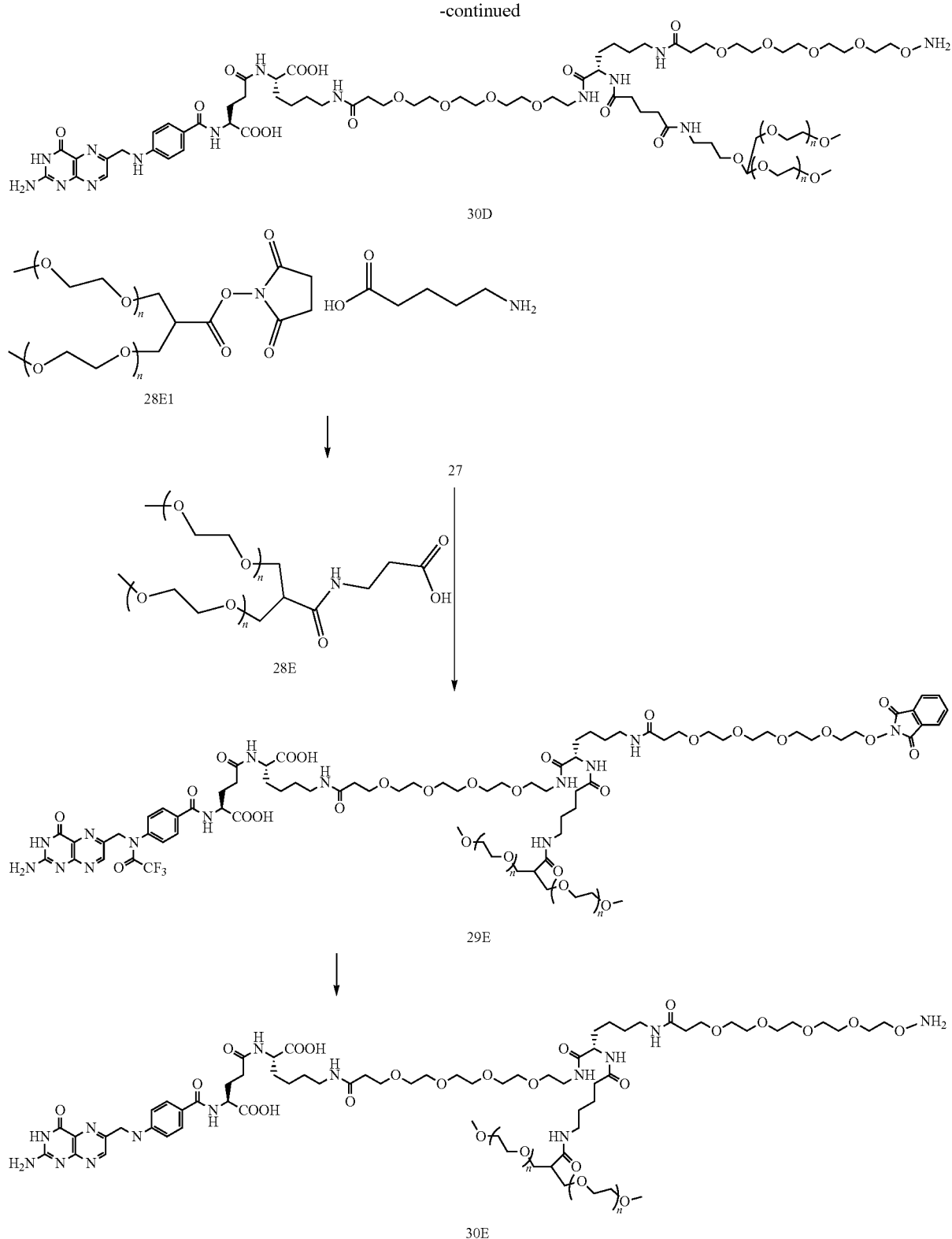

Compound 26: To a solution of Compound 25 (0.6 g, crude) and compound 10 (0.6 g) in DMF (5 ml) was added DIEA (0.47 mL) at 23° C. and stirred for 1 hour. The mixture was purified by Prep-LC with 5% to 60% of water/90% ACN 0.05% TFA gradient for 20 min by using C18 column. The fractions containing product were combined and evaporated in vacuo to give compound 26 as a brown solid; MS(ESI) m/z 1535 (M+H)$^+$.

Compound 27: To compound 26 (0.25 g) was added DCM (3 ml) and TFA (2 ml) at 23° C., and then stirred for 30 min.

The solvent was removed in vacuo. The residue was dissolved in DCM (~5 ml), and the solution was dropped in 45 ml of MTBE in a conical tube. The precipitate was isolated by centrifuge (4000 rpm, 5 min), and dried to give compound 27 as a brown solid; MS(ESI) m/z 1434 (M+H)$^+$.

Compound 29A: To a solution of compound 27 (0.054 g) and compound 28A (PEG5K-C5-NHS, 0.17 g) in DMF (2 ml) was added DIEA (0.034 mL) at 23° C. After being stirred for 5 hours, the mixture was dropped on 40 mL of MTBE, and centrifuged (5 min, 4000 rpm) to separate precipitate. To the precipitate 45 mL of MTBE was added and centrifuged (5 min, 4000 rpm). The solvent was decanted, and the white precipitate dried under high vacuum overnight to give compound 29A as a crude white solid.

Compound 30A: To a solution of Compound 29A (0.24 g) in water (10 ml) was added hydrazine, H$_2$O (0.033 mL) at 23° C. After being stirred 24 hours, the mixture was purified by Prep-LC with 20% to 100% of ACN and 0.05% TFA water gradient for 20 min by using C18 column. The fractions containing product were combined and evaporated. The residue was dissolved in water (10 ml) and lyophilized to give compound 30A as a light yellow solid. (See for example FIG. 12).

Compound 29B: To a solution of compound 27 (0.04 g) and compound 28B (PEG10K-C5-NHS, 0.26 g) in DMF (6 ml) was added DIEA (0.040 mL) at 23° C. After being stirred for 16 hours, the mixture was dropped on 40 mL of MTBE and centrifuged, (5 min, 4000 rpm), to separate precipitate. To the precipitate 45 mL of MTBE was added, and then centrifuged (5 min, 4000 rpm). The solvent was decanted, and the white precipitate dried under high vacuum overnight to give compound 29B as a crude white solid.

Compound 30B: To a solution of Compound 29B (0.47 g) in water (6 ml) was added hydrazine, H$_2$O (0.080 mL) at 23° C. After being stirred 6 hours the mixture was purified by Prep-LC with 20% to 100% of ACN and 0.05% TFA water gradient for 20 min by using C18 column. The fractions containing product were combined and evaporated. The residue was dissolved in water (10 ml) and lyophilized to give compound 30B as a light yellow solid.

Compound 29C: To a solution of compound 27 (0.040 g) and compound 28C (PEG20K-C5-NHS, 0.51 g) in DMF (8 ml) was added DIEA (0.040 mL) at 23° C. After being stirred for 16 hours, the mixture was dropped on 40 mL of MTBE, and centrifuged (5 min, 4000 rpm) to separate precipitate. To the precipitate 45 mL of MTBE was added, and centrifuged (5 min, 4000 rpm) again. The solvent was decanted, and the white precipitate dried under high vacuum overnight to give compound 29C as a crude white solid.

Compound 30C: To a solution of Compound 29C (0.67 g, <0.031 mmol) in water (8 ml) was added hydrazine, H$_2$O (0.060 mL) at 23° C. After being stirred for 6 hours, the mixture was purified by Prep-LC with 20% to 100% of ACN and 0.05% TFA water gradient for 20 min by using C18 column. The fractions containing product were combined and evaporated. The residue was dissolved in water (10 ml) and lyophilized to give compound 30C as a light yellow solid.

Compound 29D: To a solution of compound 27 (0.033 g, 0.023 mmol) and compound 28D ((PEG10K)$_2$-C2-NHS, 0.4 g) in DMF (4 ml) was added DIEA (0.020 mL) at 23° C. After being stirred for 18 hours, the mixture was dropped on 40 mL of MTBE, and centrifuged (5 min, 4000 rpm) to separate precipitate. To the precipitate was added 45 mL of MTBE, and centrifuged (5 min, 4000 rpm). The solvent was decanted, and the white precipitate dried under high vacuum overnight to give compound 29D as a crude white solid.

Compound 30D: To a solution of Compound 29D (0.45 g, <0.021 mmol) in water (8 ml) was added hydrazine, H$_2$O (0.080 mL) at 23° C. After being stirred 48 hours, the mixture was purified by Prep-LC with 20% to 100% of ACN and 0.05% TFA water gradient for 20 min by using C18 column. The fractions containing product were combined and evaporated. The residue was dissolved in water (10 ml) and lyophilized to give compound 30D as a light yellow solid.

Compound 28E: To a solution of compound 28E1 ((PEG5K)$_2$-NHS, 0.1 g) and aminovaleric acid (0.003 g) in DMF (0.5 ml) was added DIEA (0.010 mL) at 23° C. After being stirred for 1 hour, the mixture was diluted to 1 mL with water, and purified by desalting column. The collected fraction was lyophilized to give compound 28E as a white solid.

Compound 30E: To a solution of compound 28E (0.04 g), DMTMMT (0.003 g) and DIEA (0.005 mL) in DMF (2 mL) was added compound 27 (0.009 g) at 23° C. After being stirred for 1 hour, LCMS showed the reaction complete. To this mixture (crude compound 29E) was added hydrazine, H$_2$O (2 ul) is situ. After being stirred for 1 hour, the mixture was purified by Prep-LC with 20% to 100% of ACN and 0.05% TFA water gradient for 20 min by using C18 column. The fractions containing product were combined and evaporated. The residue was dissolved in water (10 ml) and lyophilized to give compound 30E as a light yellow solid.

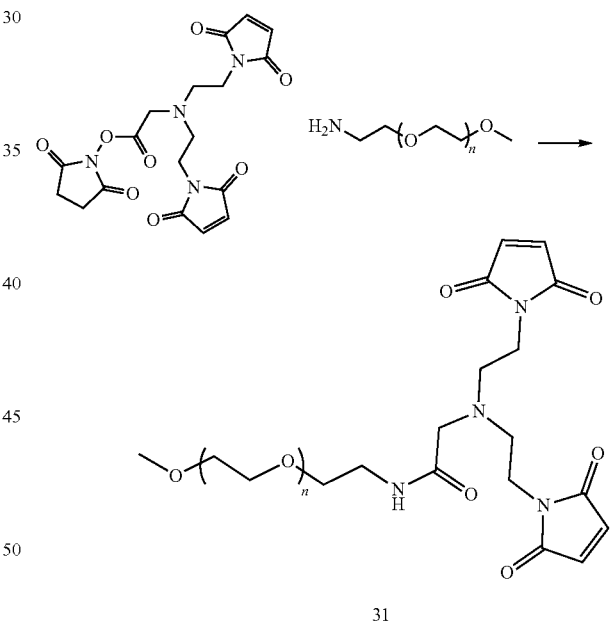

31

Compound 31: To a solution of 20K-PEG-amine (0.31 g) and 2,5-Dioxopyrrolidin-1-yl 2-(bis(2-(2,5-dioxo-2,5-dihydro-1H-pyrrol-1-yl)ethyl)amino)acetate (0.003 g) in DMF (1.0 ml) was added DIEA (0.006 mL) at 23° C. After 30 min, the mixture was purified with desalting column (PD-10) and lyophilized overnight to give compound 31 as a white solid. Other PEG variants can be prepared using the same procedure described herein.

Example 18

This Example demonstrates construction, expression and purification of double amber containing humanized anti- CD3 Fab lead molecules. A second pAF incorporation site was added at anti-CD3 Fab light chain position LL157 in Fab1-HK129pAF, Fab9-HK129pAF and Fab10-HK129pAF, resulting in new Fab molecules as Fab1-HK129pAF-LL157pAF, Fab9-HK129pAF-LL157pAF and Fab10-HK129pAF-LL157pAF, respectively. This allowed for conjugation of two Folate plus two 5KPEG molecules in each Fab using any of the bifunctional linkers as described in the previous Example.

CD3-PEG-folate purified protein used for in vitro activity, in vivo efficacy and PK studies were analyzed by SDS gel electrophoresis (SDS PAGE). Purified CD3 was conjugated with 5K or 10K PEG-folate at the pAF site using oxime chemistry and then purified, post-conjugation, utilizing cation exchange chromatography to isolate unconjugated, single site and dual site conjugated forms (FIGS. 13A-13B). Following purification, the compositions were formulated in 50 mM Histidine, 100 mM NaCl, 5% Trehalose pH 6 and sterile filtered.

FIG. 13A shows 5 µg of each purified CD3-Folate bispecific antibodies with 5K PEG conjugates. Lanes 3 and 6 represent unconjugated CD3 Fab compositions with single and dual pAF incorporation respectively. Lanes 4 and 7 represents CD3 Fab compositions with single and dual pAF and Folate respectively. Lanes 5 and 8 represent conjugated 5KPEG-Folate and Bi5KPEG-BiFolate respectively.

FIG. 13B shows SDS-PAGE results under non-reducing conditions with 10 µg protein loaded per well. Lanes 2 and 7 represent unconjugated CD3 Fab compositions, lanes 3 and 4 each represent different dual conjugated Bi5KPEG-BiFolate CD3 Fab compositions, and lanes 5 and 6 represent dual conjugated Bi10KPEG-BiFolate and 10KPEG-Folate respectively. The data, (FIGS. 13A-B), illustrates high purity (>90%) for all samples with the expected increase in molecular weight based on PEG size.

Figure 13C:
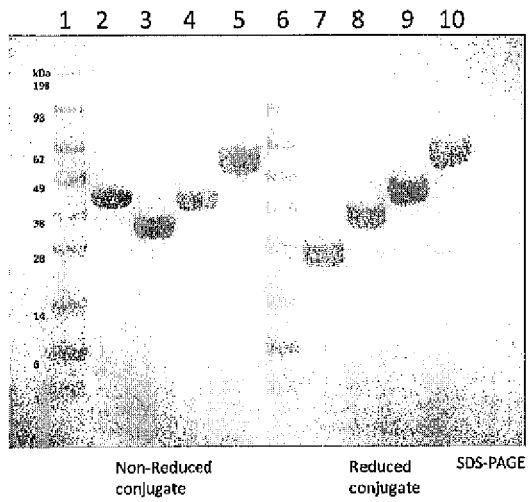

To increase conjugation efficiency purified CD3 Fab compositions were conjugated with PEG-folate using a two-step conjugation process. Folate was conjugated at the pAF sites using oxime chemistry followed by PEG conjugation with 5K, 10K or 20K PEG at the C-terminal cysteine of both the heavy and light chain using maleimide-thiol click chemistry. FIG. 13C shows SDS-PAGE under non-reducing (lanes 2-5) and reducing (lanes 7-10) conditions with 10 µg of protein loaded per well. Lanes 2 and 7 represent BiFolate unconjugated compositions, lanes 3 and 8, 4 and 9, 5 and 10 each represent BiFolate-C-terminal Bi5KPEG, Bi10KPEG and Bi20KPEG compositions, respectively. The data in FIG. 13C illustrates high purity (>95%) for all samples with the expected increase in molecular weight based on PEG size.

Example 19

This Example demonstrates the effects of Bi-Folate and Bi-PEG conjugation on CD3 Fab1 compositions and two low-affinity variants Fab9 and Fab10. Human CD3 binding and cytotoxicity: Table 25 shows the effects of various modifications including the conjugation of Bi5KPEG-BiFolate on the binding affinity and cytotoxicity of Fab1 molecule in the presence of 50 nM SFA.

TABLE 25

In-vitro binding and cytotoxic activities of anti-CD3 Fab1 modifications

| Modified Fab1 Molecules | Binding EC50 (nM) | Cytotoxicity EC50 (pM) |
| --- | --- | --- |
| Fab1-HK129-pAF | 1.92 | No activity |
| Fab1-HK129-Folate | 2.00 | 1.63 |
| Fab1-HK129-5KPEG-Folate | 5.27 | 3.98 |
| Fab1-HK129-LL157-BiFolate | 2.37 | 0.56 |
| Fab1-HK129-LL157-BiFolate-Bi5KPEG | 7.50 | 1.55 |

Figure 13D:
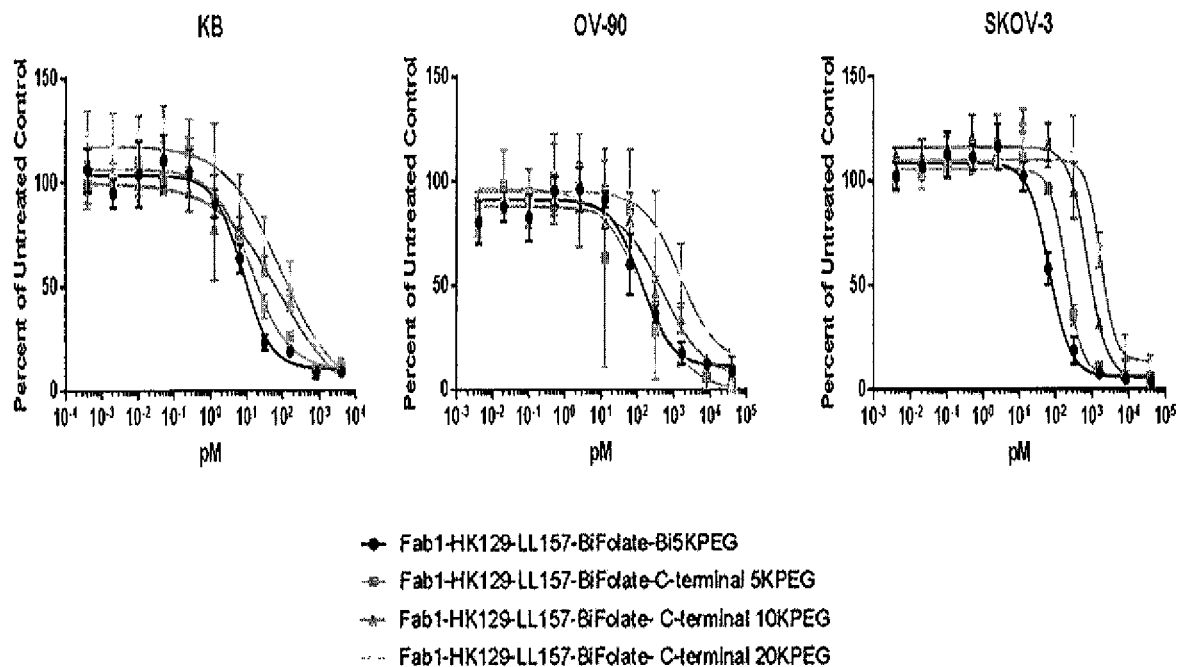

In vitro cytotoxicity studies were also conducted using CD3-Folate bispecific antibodies with 5K, 10K or 20K PEG C-terminal conjugates, in the presence of 50 nM ScA, in KB, OV-90 and SKOV-3 cells (FIG. 13D, Table 26. Though potency decreased slightly with increasing PEG length, all constructs tested retained potent cytotoxic activity. The results and trend were consistent between all cell lines tested. Based on these studies it is postulated that the slight decrease in potency observed with increase PEG size would be offset by increased exposure from half life extension.

TABLE 26

In-vitro cytotoxicity of anti-CD3-Folate C-terminal modifications in various cells

| Modified Fab1 Molecules | Cytotoxicity KB cells EC50 (pM) | Cytotoxicity OV-90 cells EC50 (pM) | Cytotoxicity SKOV3 cells EC50 (pM) |
| --- | --- | --- | --- |
| Fab1-HK129-LL157-BiFolate-Bi5KPEG | 7.8 | 130.9 | 67.9 |
| Fab1-HK129-LL157-BiFolate-C-terminal Bi5KPEG | 13.6 | 155.9 | 205.5 |
| Fab1-HK129-LL157-BiFolate-C-terminal Bi10KPEG | 88.9 | 508.2 | 789.4 |
| Fab1-HK129-LL157-BiFolate-C-terminal Bi20KPEG | 90.5 | 1529.0 | 1782.0 |

Table 27 compares the binding affinities of the parent Fab1 as well as two low-affinity variants, Fabs 9 and 10, to human CD3 in the presence of 20 nM SFA. As shown, conjugation of Bi5KPEG-BiFolate using PEG-Folate bifunctional linker, as described in the above Examples, led to a decrease in human CD3 binding and corresponding cytotoxic potential for all 3 Fabs compared to their un-conjugated controls.

TABLE 27

Characterization of low-affinity Fabs 9 and 10

| Modified Fab Molecules | Binding human PBMC EC50 (nM) | Cytotoxicity human PBMC EC50 (pM) | CD69 induction EC50 (pM) | IFNγ release EC50 (pM) | TFNα release EC50 (pM) |
| --- | --- | --- | --- | --- | --- |
| Fab1-HK129-LL157-BiFolate-Bi5KPEG | 5.7 | 8.03 | 0.38 | 2.7 | 5.7 |
| Fab9-HK129-LL157-BiFolate-Bi5KPEG | 340 | 66.8 | 73 | 326 | 228 |
| Fab10-HK129-LL157-BiFolate-Bi5KPEG | 6312 | 1553 | 724 | 2420 | 1960 |

T-cell activation and cytokine release: Table 27 shows the activation of T cell marker CD69 and the release of two cytokines, IFNgamma and TNFα, by the 3 modified Fabs. As shown in the above Examples, the general correlation between the strength of CD3 binding, cytotoxic potential, activation of T cells and subsequent release of cytokines hold true across all Fabs even after significant modification by BiFolate-Bi5KPEG conjugation. This suggests efficacy can be retained while minimizing toxicity due to cytokine release syndrome by simultaneously lowering CD3 affinity and increasing tumor-associated antigen (TAA) affinity. Furthermore, PK properties, including half-life (T½) extension, were improved by site-specific PEGylation using proprietary UAA (unnatural amino acid) incorporation technology.

Example 20

Figure 14:
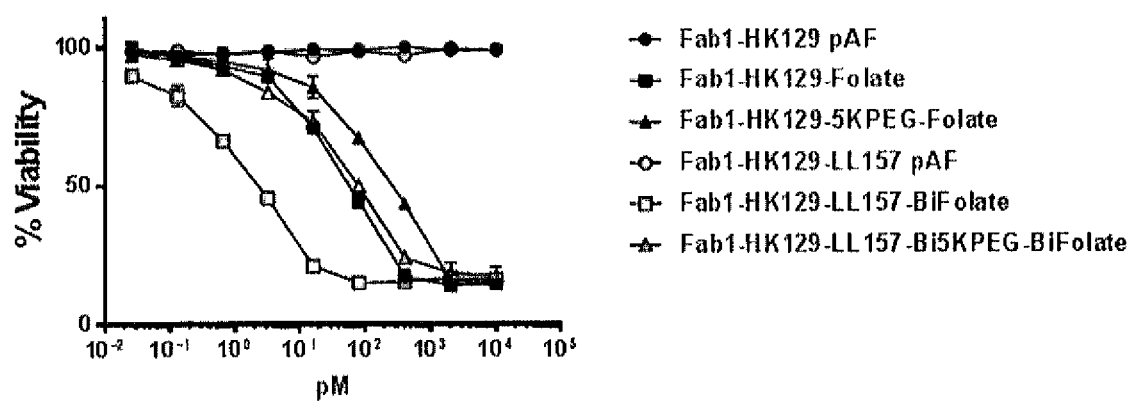
FIG. 14 depicts in vitro cytotoxicity and shows the anti-CD3 Fab-Folate bispecific antibodies selectively kill FOLRα expressing KB cells.

In vitro cytotoxicity data shows CD3-Folate bispecific antibodies selectively kill FOLRα expressing KB cells. KB cells were treated with increasing concentration of CD3-Folate bispecific antibodies in the presence of 50 nM folic acid, a physiologically relevant concentration of folate. The most potent CD3-Folate bispecific antibody, Fab1-HK129-LL157-BiFolate, containing two molecules of folate, showed an $IC_{50}$ value of 1.3 pM (FIG. 14). The single folate containing CD3-Folate bispecific antibody, Fab1-HK129-Folate, showed an IC50 value of 40.3 pM, 31-fold less potent than Fab1-HK129-LL157-BiFolate. This data that two folates increases the potency of CD3-Folate bispecific antibodies. The addition of 5KPEG decreased the potency. A 4.9-fold decrease in potency was observed between the single CD3-Folate bispecific antibody, Fab1-HK129-Folate, and Fab1-HK129-5KPEG-Folate with an $IC_{50}$ value of 198 pM. A 37.3 fold decrease in the potency between Fab1-HK129-LL157-BiFolate and Fab1-HK129-LL157-Bi5KPEG-BiFolate with an $IC_{50}$ value of 48.5 pM was observed. These data show that the CD3-Folate bispecific antibodies maintain potent in vitro cytotoxicity at physiologically relevant concentrations of folate.

Example 21

Figure 15A:
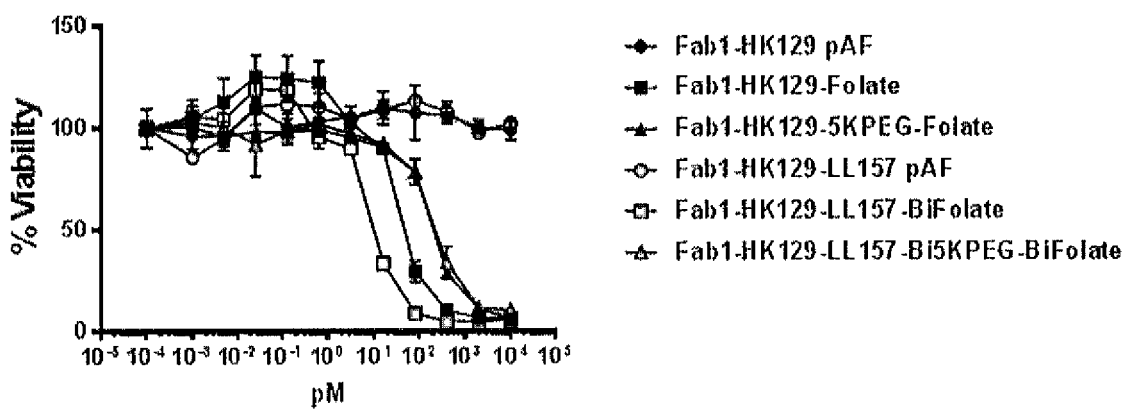
FIGS. 15A-15B depict in vitro cytotoxicity.
Figure 15B:
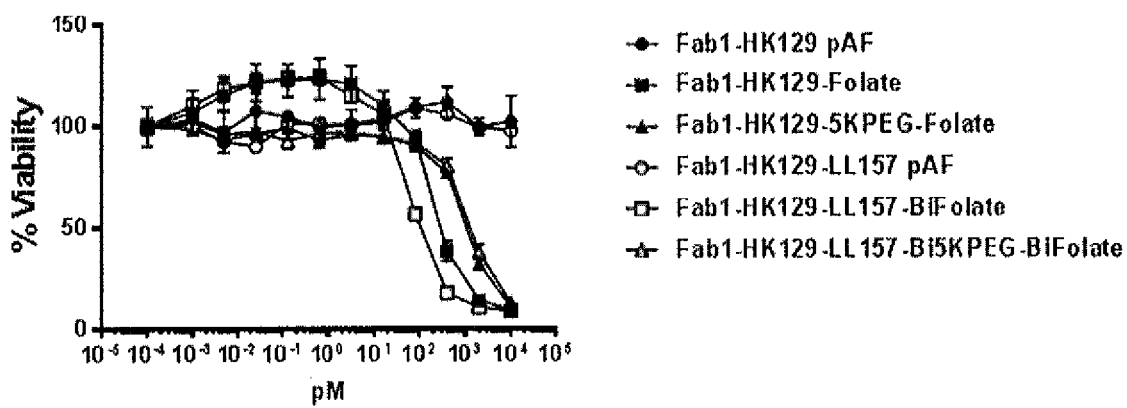

In vitro cytotoxicity data shows CD3-Folate bispecific antibodies selectively kill FOLRα expressing SKOV3 cells in the presence of 20 or 50 nM folic acid. SKOV3 cells were treated with increasing concentration of CD3-Folate bispecific antibodies in 20 or 50 nM of folic acid, physiologically relevant concentrations of folate (FIGS. 15A and 15B). The CD3-Folate bispecific antibodies showed decreased potency, 5.6-fold to 8-fold, when the folic acid concentration increased from 20 nM to 50 nM, which is near the top of the normal physiologically relevant concentration for folate. The addition of 5KPEG also resulted in decrease potency of CD3-Folate bispecific antibodies. A 5.4-fold decrease between single folate and single 5KPEG folate bispecific antibody and a 22.9-fold decrease between the double folate and the double 5KPEG folate bispecific antibody was observed. No significant difference in potency was observed between the single and double pegylated CD3-Folate bispecific antibodies. The data, Table 28, shows that CD3-Folate bispecific antibodies can kill FOLRα expressing cells in the presence of physiologically relevant concentrations of folate and although the pegylated antibodies have decreased potency compared to the non-pegylated antibodies, the CD3-Folate bispecific antibodies can kill the FOLRα expressing cells.

TABLE 28

In vitro cytotoxicity in SKOV3 cells

In vitro cytotoxicity $IC_{50}$ Values (pM) using SKOV3 cells

| Drug | Fab1-HK129-Folate | Fab1-HK129-5KPEG-Folate | Fab1-HK129-LL157-BiFolate | Fab1-HK129-LL157-Bi5KPEG-BiFolate |
| --- | --- | --- | --- | --- |
| 20 nM Folic Acid | 34.5 | 186.3 | 8.5 | 194.7 |
| 50 nM Folic Acid | 204 | 1053 | 69.2 | 1239 |

Example 22

Figure 16A:
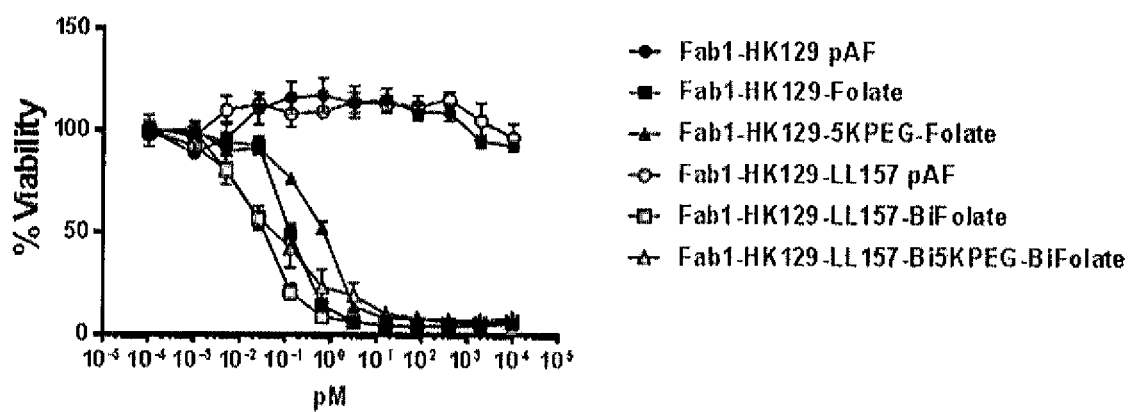
FIGS. 16A-16B depict in vitro cytotoxicity data and show the anti-CD3 Fab-Folate bispecific antibodies selectively kill FOLRα expressing SKOV3 cells in the presence of 20 nM (FIG. 16A) or 50 nM (FIG. 16B) 5-mTHF.
Figure 16B:
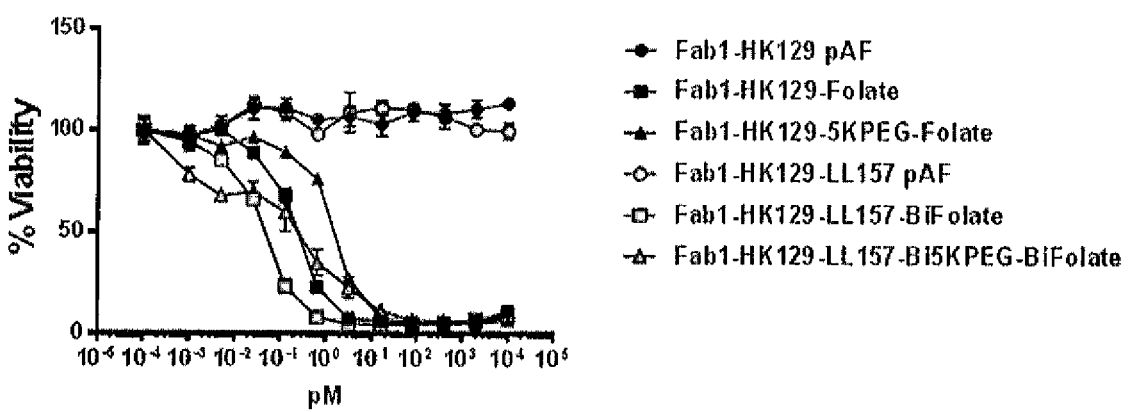

Further in vitro cytotoxicity studies were conducted in the presence of 20 or 50 nM 5-mTHF. SKOV3 cells were treated with increasing concentrations of CD3-Folate bispecific antibodies in the presence of 20 or 50 nM, (physiologically relevant concentrations of the predominant form of folate found in human serum), 5-methyltetrahydrofolate (5-mTHF), (FIGS. 16A and 16B). 5-mTHF has a binding affinity of 1-10 nM to FOLRα and does not bind as well to FOLRα as folate, which has a binding affinity less than 1 nM. CD3-Folate bispecific antibodies maintained very potent IC50 values between 0.03 to 0.16 pM and between 0.1 to 1.5 pM for double and single CD3-Folate bispecific antibodies respectively. The data, Table 29, show CD3-Folate bispecific antibodies have potent in vitro cytotoxicity against FOLRα expressing SKOV3 cells in the presence of physiologically relevant concentrations of 5-mTHF.

TABLE 29

In vitro cytotoxicity in the presence of 5-mTHF
In vitro cytotoxicity $IC_{50}$ Values (pM) using SKOV3 cells

| Drug | Fab1-HK129-Folate | Fab1-HK129-5KPEG-Folate | Fab1-HK129-LL157-BiFolate | Fab1-HK129-LL157-Bi5KPEG-BiFolate |
|---|---|---|---|---|
| 20 nM 5-mTHF | 0.1 | 0.5 | 0.03 | 0.04 |
| 50 nM 5-mTHF | 0.2 | 1.5 | 0.04 | 0.16 |

Example 23

Figure 17:
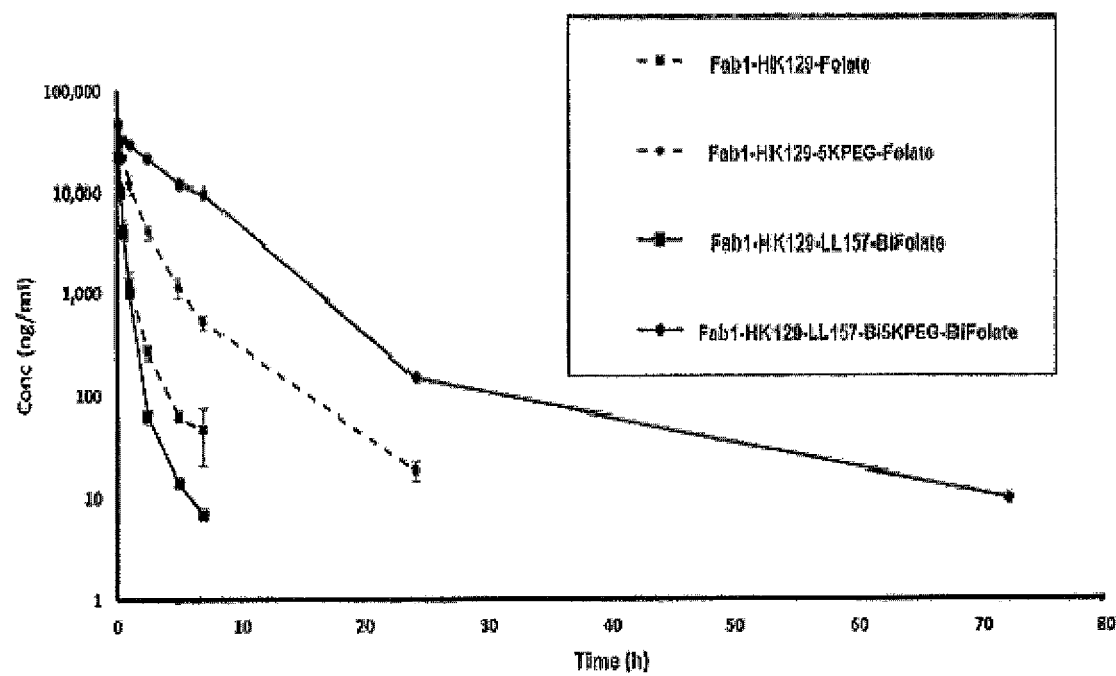
FIG. 17 depicts mouse pharmacokinetic study in CD1 mice.

Mouse pharmacokinetic study in CD1 mice: CD3-Folate bispecific antibodies were injected, i.v. via the mouse tail vein of CD-1 mice at 1 or 5 mg/kg. Blood samples were collected at nine time points and analyzed via ELISA. The data clearly showed that the addition of 5KPEG increases the serum exposures (AUClast), (Tables 30-31 and FIG. 17). Fab1-HK129-5KPEG-Folate at 1 mg/kg showed 4.3-fold improvement over Fab1-HK129-Folate and Fab1-HK129-5KPEG-Folate at 5 mg/kg showed 5-fold improvement over Fab1-HK129-Folate. Fab1-HK129-LL157-Bi5KPEG-BiFolate showed 16.25-fold improvement over Fab1-HK129-LL157-BiFolate at 1 mg/kg and Fab1-HK129-LL157-Bi5KPEG-BiFolate showed 21.7-fold improvement over Fab1-HK129-LL157-BiFolate at 5 mg/kg. The data show 3.9-fold difference between Fab1-HK129-5KPEG-Folate and Fab1-HK129-LL157-Bi5KPEG-BiFolate. Also observed was an improvement in the serum half-life (T½) when 5KPEG is added to CD3-Folate bispecific antibodies. The largest improvement in serum half-life was observed with two 5KPEGs incorporated in CD3-Folate bispecific antibodies. Fab1-HK129-LL157-Bi5KPEG-BiFolate shows 4.2-fold improvement in serum half-life over Fab1-HK129-LL157-BiFolate at 1 mg/kg while Fab1-HK129-LL157-Bi5KPEG-BiFolate shows 6.25-fold improvement in serum half-life over Fab1-HK129-LL157-BiFolate at 5 mg/kg. The data show that addition of 5KPEG improves serum exposure and serum half-life of CD3-Folate bispecific antibodies which leads to less frequent dosing to achieve efficacious serum exposures in vivo.

TABLE 30

CD3-Folate bispecific single Amber antibody mouse pharmacokinetic analysis

| PK Parameters | Fab1-HK129-Folate 1 mg/kg | | Fab1-HK129-Folate 5 mg/kg | | Fab1-HK129-5KPEG-Folate 1 mg/kg | | Fab1-HK129-5KPEG-Folate 5 mg/kg | |
|---|---|---|---|---|---|---|---|---|
| | Mean | SD | Mean | SD | Mean | SD | Mean | SD |
| $C_0$ (ng/mL) | 7110 | 589 | 27600 | 7240 | 9120 | 1100 | 50300 | 5960 |
| $C_{max}$ (ng/mL) | 4240 | 457 | 20100 | 3480 | 7440 | 866 | 41900 | 4330 |
| $C_{max}\_D$ (ng/mL)/(mg/kg) | 4240 | 457 | 4020 | 697 | 7440 | 866 | 8390 | 866 |
| AUClast (ng*h/mL) | 1530 | 209 | 8890 | 2060 | 6640 | 1000 | 45000 | 5420 |
| AUClast_D (ng*h/mL)/(mg/kg) | 1530 | 209 | 1780 | 411 | 6640 | 1000 | 8990 | 1080 |
| $T_{1/2}$ (h) | 1.05 | 0.484 | 1.38 | 0.411 | 1.8 | 1.19 | 3.32 | 0.141 |
| MRTlast (h) | 0.444 | 0.0647 | 0.557 | 0.155 | 1.28 | 0.253 | 1.9 | 0.0841 |
| Cl (mL/h/kg) | 660 | 91 | 579 | 120 | 151 | 20.9 | 112 | 14.3 |
| Vss (mL/kg) | 317 | 65.8 | 352 | 29.5 | 208 | 34.1 | 219 | 26.6 |

TABLE 31

CD3-Folate bispecific double Amber antibody mouse pharmacokinetic analysis

| PK Parameters | Fab1-HK129-LL157-BiFolate 1 mg/kg | | Fab1-HK129-LL157-BiFolate; 5 mg/kg | | Fab1-HK129-LL157-Bi5KPEG-BiFolate 1 mg/kg | | Fab1-HK129-LL157-Bi5KPEG-BiFolate 5 mg/kg | |
|---|---|---|---|---|---|---|---|---|
| | Mean | SD | Mean | SD | Mean | SD | Mean | SD |
| $C_0$ (ng/mL) | 4650 | 889 | 34100 | 12300 | 6040 | 925 | 54900 | 11900 |
| $C_{max}$ (ng/mL) | 3280 | 381 | 22700 | 7790 | 8140 | 3580 | 46400 | 7280 |
| $C_{max}\_D$ (ng/mL)/(mg/kg) | 3280 | 381 | 4530 | 1560 | 8140 | 3580 | 9280 | 1460 |
| AUClast (ng*h/mL) | 1360 | 200 | 8140 | 2710 | 22100 | 3060 | 177000 | 28000 |
| AUClast_D (ng*h/mL)/(mg/kg) | 1360 | 200 | 1630 | 542 | 22100 | 3060 | 35300 | 5610 |
| $T_{1/2}$ (h) | 0.715 | 0.454 | 0.93 | 0.355 | 3.02 | 0.0597 | 5.82 | 0.0842 |
| MRTlast (h) | 0.445 | 0.168 | 0.358 | 0.0325 | 3.92 | 0.219 | 4.91 | 0.222 |
| Cl (mL/h/kg) | 764 | 120 | 708 | 366 | 45.7 | 5.53 | 28.9 | 4.58 |
| Vss (mL/kg) | 359 | 109 | 269 | 172 | 183 | 17.6 | 142 | 16.6 |

This Example demonstrates CD3-folate-Folate bispecific antibodies kill Human M2 macrophages: Macrophages are heterogeneous cell population that play roles in host defense. Classically activated macrophages (M1 macrophages) have pro-inflammatory function, recruiting tumor-infiltrating lymphocytes, and anti-tumor activity, whereas M2 macrophages are anti-inflammatory and are involved in tissue remodeling, cancer cell migration, invasion, and metastasis. Human M2 macrophages are associated with cancer cell proliferations and have been associated with poor prognosis in ovarian cancer. Inhibition of M2 macrophage may enhance the activity of immune-oncology therapies, such as checkpoint inhibitors. Human M2 macrophages express FOLRβ or FRβ, which or FR has similar binding affinities to folate as FOLRα or FRα. Therefore, strategies to increase the ratio of M1 to M2 macrophages either by repolarization to M1 macrophages or by selectively killing M2 macrophages provide potential therapeutic approaches in cancer treatment.

Study 1: To assess the effects of CD3-Folate bispecific antibodies on macrophages, the following experiments were conducted: Fab1-HK129-LL157-pAF, Fab1-HK129-LL157-Folate and Fab1-HK129-LL157-5KPEG folate were incubated with human M2 macrophage and human T-cells in the presence of 50 nM folic acid. The data show that Fab1-HK129-LL157-Folate and Fab1-HK129-LL157-5KPEG-Folate kill human M2 macrophage with $IC_{50}$ values of 1.2 pM and 112.1 pM respectively (data not shown). Fab1-HK129-LL157-pAF which lacks folate does not cause human M2 macrophage kill. The data supports that Fab1-HK129-LL157-Folate and Fab1-HK129-LL157-5KPEG-Folate cytotoxicity is specific to binding to FOLRβ. Further, the data suggest that in addition to killing FOLRα expressing tumor cells, CD3-Folate bispecific antibodies can kill M2 macrophage cells and possibly other FOLRα/β expressing immune-inhibitory cells.

Study 2: In these studies, monocytes-derived macrophages were generated from human blood of healthy donors and treated with either granulocyte-macrophage colony-stimulating factor (GM-CSF) for M1 macrophage differentiation or macrophage colony-stimulating factor (M-CSF) for M2 macrophage differentiation.

Prior to conducted the studies the Folate receptor beta (FOLRβ or FR-beta) expression was initially measured by flow cytometry and found to increase by an average of 26-fold in M2 than M1 macrophages in terms of median fluorescence intensity (MFI).

Human M1 or M2 macrophages were seeded on 96-well clear-bottom, white plates at 9,000 cells/well and incubated overnight. Next day, 90,000 cells of human T cells were added as effector cells at effector: target (E:T) cell ratio of 10:1 to the macrophage containing wells and incubated with serial dilutions of CD3-Folate bispecific antibodies, (from 0.001 pM to 100 nM), in the presence of 20 nM folic acid, at 37° C., 5% $CO_2$ for 3 days. The relative viability of macrophages was measured by CellTiter-Glo (100 uL/well) after removal of floating cells and calculated as the percentage of untreated control.

Effect of PEGylation on CD3-folate bispecific antibody: Table 32 shows $IC_{50}$ data for in vitro macrophage cytotoxicity by single folate containing CD3-folate bispecific antibodies in the presence of 20 nM folic acid. Fab1-HK129-Folate has an average $IC_{50}$ of 85.0 pM (range 53.5-120.0 pM) in M1 macrophage and an average $IC_{50}$ of 5.6 pM (range 1.4-15.0 pM) in M2 macrophage. Based on the $IC_{50}$ ratio, M2 macrophages is on average 26-fold improved, (range 5-42-fold), over M1) with Fab1-HK129-Folate. Fab1-HK129-5KPEG-Folate shows average $IC_{50}$ of 616.8 pM (range 198.0-908.9 pM) in M1 macrophages and an average $IC_{50}$ of 13.4 pM (range 2.3-33.2 pM) in M2 macrophages with an improved average $IC_{50}$ ratio between M1 and M2 macrophages improved average of 69-fold (range 23-126-fold) in M2 macrophages. These results indicate that single folate containing CD3-folate bispecific antibodies are specific to M2 macrophage killing and PEGylation of single folate containing CD3-folate bispecific antibody (Fab1-HK129-5KPEG-Folate) is more selective to M2 macrophage killing than Fab1-HK129-Folate

TABLE 32

In vitro macrophage cytotoxicity by single folate containing CD3-Folate bispecific antibodies in the presence of 20 nM folic acid

| | Fab1-HK129-Folate | | | Fab1-HK129-5KPEG-Folate | | |
|---|---|---|---|---|---|---|
| Donors | $IC_{50}$ (pM) in M1 | $IC_{50}$ (pM) in M2 | $IC_{50}$ ratio | $IC_{50}$ (pM) in M1 | $IC_{50}$ (pM) in M2 | $IC_{50}$ ratio |
| 6007 | 116.0 | 2.8 | 42 | 607.6 | 10.8 | 57 |
| 4943 | 120.0 | 4.1 | 30 | 908.9 | 23.2 | 39 |
| 6213 | 79.2 | 15.0 | 5 | 904.9 | 33.2 | 27 |
| 6081 | 53.5 | 4.9 | 11 | 288.4 | 2.3 | 126 |
| 5540 | 56.5 | 1.4 | 41 | 757.7 | 11.0 | 69 |
| Average | 85.0 | 5.6 | 26 | 693.5 | 16.1 | 64 |

Figure 18A:
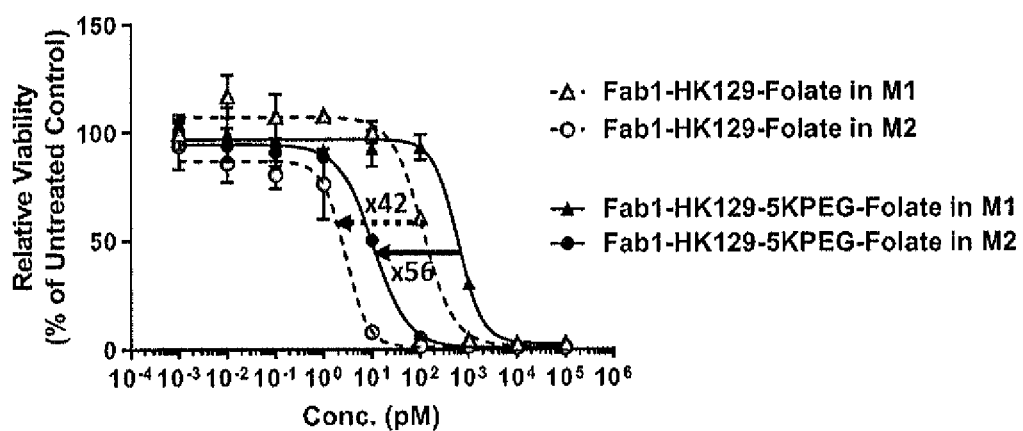
FIGS. 18A-18B depict anti-CD3 Fab-Folate bispecific antibodies selectively kill human M2 macrophages.

The results of in vitro macrophage cytotoxicity by single folate containing CD3-Folate bispecific antibodies from a representative donor, donor 6007 are depicted in FIG. 18A. The arrow and number denote $IC_{50}$ fold differences between M1 and M2 macrophages. The dotted lines indicate Fab1-HK129-Folate in M1 and M2 and solid lines indicate Fab1-HK129-5KPEG-Folate in M1 and M2.

Table 33 shows $IC_{50}$ data for in vitro macrophage cytotoxicity by double folate containing CD3-folate bispecific antibodies in the presence of 20 nM folic acid. Fab1-HK129-LL157-BiFolate has an average $IC_{50}$ of 29.2 pM (range 10.9-42.8 pM) in M1 macrophage and an average $IC_{50}$ of 1.5 pM (range 0.1 pM-5.5 pM) in M2 macrophage with an average $IC_{50}$ ratio between M1 and M2 macrophages of 72-fold difference (range 6-212-fold). Fab1-HK129-LL157-BiFolate-Bi5KPEG shows average 1620.8 pM of $IC_{50}$ (range 834.7-2651 pM) in M1 macrophages and average $IC_{50}$ of 15.7 pM (range 3.6-52.4 pM) in M2 macrophages with an improved average-$IC_{50}$ ratio between M1 and M2 macrophages of 181-fold (range 49-501-fold) in M2 macrophages. These results indicate that double folate containing CD3-folate bispecific antibodies are specific to M2 macrophage killing. Although PEGylation of double folate containing CD3-folate bispecific antibody (Fab1-HK129-LL157-BiFolate-Bi5KPEG) is shown to be less potency, and more selective to M2 macrophage killing than Fab1-HK129-LL157-BiFolate or Fab1-HK129-5KPEG-Folate as shown in Table XXX.

TABLE 33

In vitro macrophage cytotoxicity by double folate containing CD3-Folate bispecific antibodies in the presence of 20 nM folic acid

| | Fab1-HK129-LL157-BiFolate | | | Fab1-HK129-LL157-BiFolate-Bi5KPEG | | |
|---|---|---|---|---|---|---|
| Donors | $IC_{50}$ (pM) in M1 | $IC_{50}$ (pM) in M2 | $IC_{50}$ ratio | $IC_{50}$ (pM) in M1 | $IC_{50}$ (pM) in M2 | $IC_{50}$ ratio |
| 6007 | 31.9 | 0.7 | 44 | 1393.0 | 8.2 | 170 |
| 4943 | 42.8 | 0.8 | 54 | 2651 | 22.3 | 119 |

TABLE 33-continued

In vitro macrophage cytotoxicity by double folate containing CD3-
Folate bispecific antibodies in the presence of 20 nM folic acid

| Donors | Fab1-HK129-LL157-BiFolate | | | Fab1-HK129-LL157-BiFolate-Bi5KPEG | | |
|---|---|---|---|---|---|---|
| | $IC_{50}$ (pM) in M1 | $IC_{50}$ (pM) in M2 | $IC_{50}$ ratio | $IC_{50}$ (pM) in M1 | $IC_{50}$ (pM) in M2 | $IC_{50}$ ratio |
| 6213 | 34.3 | 5.5 | 6 | 2543 | 52.4 | 49 |
| 6081 | 26.1 | 0.1 | 212 | 834.7 | 3.6 | 235 |
| 5540 | 10.9 | 0.2 | 45 | 1027 | 14.8 | 69 |
| Average | 29.2 | 1.5 | 72 | 1689.7 | 20.2 | 128 |

Figure 18B:
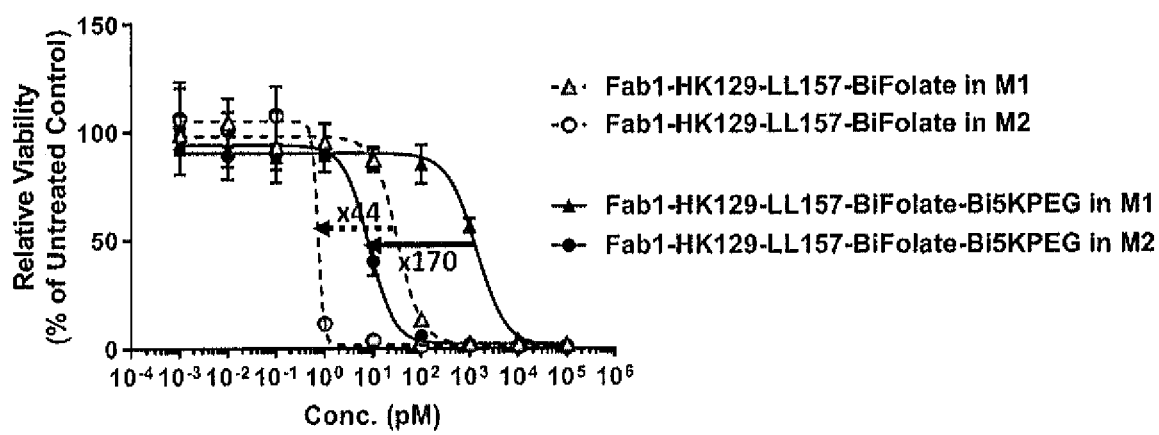

FIG. 18B shows the results of in vitro macrophage cytotoxicity by double folate containing CD3-Folate bispecific antibodies from a representative donor, donor 6007. The arrow and number denote $IC_{50}$ fold differences between M1 and M2 macrophages. The dotted lines indicate Fab1-HK129-LL157-BiFolate in M1 and M2 and solid lines indicate Fab1-HK129-LL157-BiFolate-Bi5KPEG in M1 and M2.

Further studies were conducted to mimic physiological relevant concentrations of the predominant form of folate found in human serum, which range between 9.1-45.1 nM. Of this physiological range, 86.7% (37.5 nM) is 5-methyl-tetrahydrofolate (5-mTHF), the primary folic acid metabolite, and only 4% (1.2 nM) is unmetabolized folic acid (Pfeiffer et al., Br. J. Nutr., 2015 Jun. 28: 113(12):1965-1977). As well known in the art, the binding affinity of folic acid to FR-beta is less than 1 nM, and the affinity of 5-mTHF to FR-beta is 1-10 nM. Based on this information, it was hypothesized that the concentration or composition of folic acid and 5-mTHF can impact the activity of CD3-Folate bispecific antibodies. To asses this, the following experiment was conducted: In vitro macrophage cytotoxicity data in the presence of 45 nM 5-mTHF are shown in Table 34 and Table 35. $IC_{50}$ of Fab1-HK129-Folate averaged 9.1 pM and 0.31 pM and $IC_{50}$ of Fab1-HK129-5KPEG-Folate averaged 48.5 pM and 1.26 pM in M1 or M2 macrophages, respectively. $IC_{50}$ of Fab1-HK129-LL157-BiFolate averaged 4.0 pM in M1 and 0.05 pM in M2, and $IC_{50}$ of Fab1-HK129-LL157-BiFolate-Bi5KPEG averaged 99.4 pM in M1 and 0.85 pM in M2. These data show CD3-Folate bispecific antibodies are more potent in the presence of 5-mTHF than with folic acid (Table 32 and Table 33). $IC_{50}$ ratios between M1 and M2 averaged 43-fold and 57-fold by single folate containing CD3-Folate bispecific antibodies and 89-fold and 212-fold by double folate containing CD3-Folate bispecific antibodies. These data indicate CD3-Folate containing bispecific antibodies maintain M2 macrophage specific killing and PEGylation provides more specificity in physiologically relevant of 5-mTHF concentration.

TABLE 34

In vitro macrophage cytotoxicity by single folate containing CD3-
Folate bispecific antibodies in the presence of 45 nM 5-mTHF

| Donors | Fab1-HK129-Folate | | | Fab1-HK129-5KPEG-Folate | | |
|---|---|---|---|---|---|---|
| | $IC_{50}$ (pM) in M1 | $IC_{50}$ (pM) in M2 | $IC_{50}$ ratio | $IC_{50}$ (pM) in M1 | $IC_{50}$ (pM) in M2 | $IC_{50}$ ratio |
| 6106 | 8.3 | 0.26 | 33 | 37.6 | 0.88 | 43 |
| 1474 | 11.3 | 0.11 | 102 | 93.6 | 0.71 | 132 |
| 6081 | 9.2 | 0.45 | 21 | 43.3 | 0.94 | 46 |
| 5540 | 7.7 | 0.44 | 18 | 19.5 | 2.5 | 8 |
| Average | 9.1 | 0.31 | 43 | 48.5 | 1.26 | 57 |

TABLE 35

In vitro macrophage cytotoxicity by double folate containing CD3-
Folate bispecific antibodies in the presence of 45 nM 5-mTHF

| Donors | Fab1-HK129-LL157-BiFolate | | | Fab1-HK129-LL157-BiFolate-Bi5KPEG | | |
|---|---|---|---|---|---|---|
| | $IC_{50}$ (pM) in M1 | $IC_{50}$ (pM) in M2 | $IC_{50}$ ratio | $IC_{50}$ (pM) in M1 | $IC_{50}$ (pM) in M2 | $IC_{50}$ ratio |
| 6106 | 2.0 | 0.03 | 74 | 37.4 | 0.47 | 80 |
| 1474 | 8.9 | 0.04 | 206 | 276.5 | 0.41 | 681 |
| 6081 | 2.8 | 0.09 | 32 | 65.4 | 0.87 | 75 |
| 5540 | 2.4 | 0.05 | 44 | 18.3 | 1.67 | 11 |
| Average | 4.0 | 0.05 | 89 | 99.4 | 0.85 | 212 |

Overall the data indicates that in the presence of folic acid or 5mTHF metabolite, double PEGylated CD3-Folate compositions showed greater specificity to M2 macrophage kill than single PEGylated CD3-Folate compositions. Thus, improved selectivity was observed with more PEGylation.

Further studies with CD3-Folate bispecific antibodies were also conducted in human myeloid derived suppressor cells (MDSCs) to investigate FR expression. Human peripheral blood mononuclear cells (PBMCs) from healthy donors were treated with Fab1-HK129-5KPEG-Folate and Fab1-LL157-Bi5KPEG-BiFolate to test their cytotoxic activity against mononuclear MDSCs (mMDSCs) 0, 1, 10, and 100 pM, for each CD3-Folate bispecific antibodies, were added into PBMCs and incubated at 37° C. and 5% $CO_2$ incubator for 24 hrs. After incubation, mMDSCs were gated by $CD3^-/CD33^+/CD11b^+/CD14^+/HLA-DR^{low}$ population using flow cytometry and the percentage (%) of live cells from untreated control was measured.

Based on the observation the percentage of mMDSCs decreased in a dose dependent manner. Fab1-HK129-5KPEG-Folate showed a dose dependent decrease from 72% to 24% at 10 pM versus 100 pM respectively. Similarly, Fab1-HK129-LL157-Bi5KPEG-BiFolate showed a dose dependent decrease from 88% to 22% at 10 pM versus 100 pM respectively. These results demonstrate that treatment with CD3-Folate bispecific antibodies selectively eliminated mMDSCs given that non-MDSCs having high HLA-DR were preserved.

Given that these inhibitory cells may express folate receptor and are involved in the inhibition of activity of immune-oncology drugs, suggest that combination therapy using checkpoint inhibitors and other immuno-oncology drugs can be utilized as therapeutics for various cancers or conditions/diseases/disorders in which folate receptor may be expressed. This supports the use of the CD3-Folate compositions of the present invention as valuable therapeutics that is significantly different from other immuno-oncology therapies.

Example 25

This Example demonstrate CD3-Folate bispecific antibody binding affinity to FOLRα in several cell types. CD3-Folate bispecific antibody binding affinity to FOLRα expressing KB cells: As shown in Table 36, Fab1-HK129-Folate binds to FOLRα expressing KB cells with an affinity of 1.97 nM and, Fab1-HK129-5KPEG-Folate, binds with an affinity of 3.69 nM. Fab1-HK129-LL157-BiFolate binds to KB cells with an affinity of 0.85 nM and Fab1-HK129-LL157-Bi5KPEG-BiFolate with an affinity of 2.28 nM. PEGylated antibodies retained similar binding affinities as to the non-PEGylated antibodies which is in the low nM range to the FOLRα expressing KB cells.

TABLE 36

CD3-Folate bispecific antibody binding affinity to KB cells

| Bispecific Antibody | Cell Line | Kd (nM) | Bmax |
|---|---|---|---|
| Fab1-HK129-Folate | KB | 1.97 | 100552 |
| Fab1-HK129-5KPEG-Folate | KB | 3.69 | 134422 |
| Fab1-HK129-LL157-BiFolate | KB | 0.85 | 74439 |
| Fab1-HK129-LL157-Bi5KPEG-BiFolate | KB | 2.28 | 83056 |

CD3-Folate bispecific antibody binding affinities to human T-cells: Fab1-HK129-pAF, (anti-CD3 Fab), does not contain folate or PEG and binds to human T-cells with an affinity of 1.59 nM (Table 37). Fab1-HK129-Folate binds to CD3 expressing human T-cells with an affinity of 1.53 nM and Fab1-HK129-5KPEG-Folate binds with an affinity of 2.34 nM. These CD3-Folate bispecific antibodies have similar binding affinities to human T-cells. Fab1-HK129-LL157-pAF binds to human T-cells with an affinity of 0.604 nM. Fab1-HK129-LL157-BiFolate binds to human T-cells with an affinity of 0.669 nM and Fab1-HK129-LL157-Bi5KPEG-BiFolate has an affinity of 3.34 nM. These data show that pegylated CD3-Folate bispecific antibodies have about 5-fold lower binding affinity to human T-cells than the non-pegylated version. These data also show that the CD3-Folate bispecific antibodies have low nM binding affinities to human T-cells.

TABLE 37

CD3-Folate Bispecific antibody binding affinities to human T-cells

| Bispecific Antibody | T-Cell Species | Kd (nM) | Bmax |
|---|---|---|---|
| Fab1-HK129-pAF | Human T-cells | 1.59 | 31998 |
| Fab1-HK129-Folate | Human T-cells | 1.53 | 30106 |
| Fab1-HK129-5KPEG-Folate | Human T-cells | 2.34 | 23391 |
| Fab1-HK129-LL157-pAF | Human T-cells | 0.604 | 27908 |
| Fab1-HK129-LL157-BiFolate | Human T-cells | 0.669 | 24553 |
| Fab1-HK129-LL157-Bi5KPEG-BiFolate | Human T-cells | 3.34 | 15253 |

TABLE 38

CD3-Folate Bispecific antibody binding affinities to Cynomolgus monkey T-cells

| Bispecific Antibody | T-Cell Species | Kd (nM) | Bmax |
|---|---|---|---|
| Fab1-HK129-pAF | Cynomolgus T-cells | 2.67 | 26636 |
| Fab1-HK129-Folate | Cynomolgus T-cells | 2.69 | 25704 |
| Fab1-HK129-5KPEG-Folate | Cynomolgus T-cells | 3.31 | 19924 |
| Fab1-HK129-LL157-pAF | Cynomolgus T-cells | 0.955 | 23436 |
| Fab1-HK129-LL157-BiFolate | Cynomolgus T-cells | 1 | 19589 |
| Fab1-HK129-LL157-Bi5KPEG-BiFolate | Cynomolgus T-cells | 5.01 | 13175 |

Example 26

The following Studies demonstrate in-vivo safety and efficacy studies in mice using CD3 Folate antibodies of the present invention.

Figure 19A:
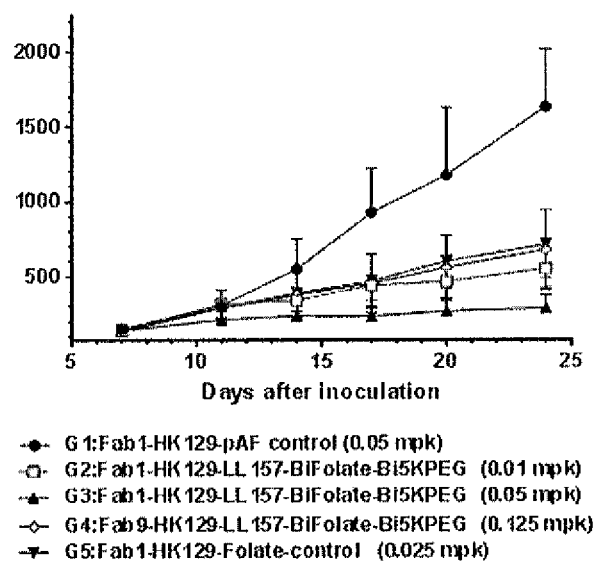
FIGS. 19A-19B depict anti-tumor efficacy of anti-CD3-Folate bispecific antibodies.
Figure 19B:
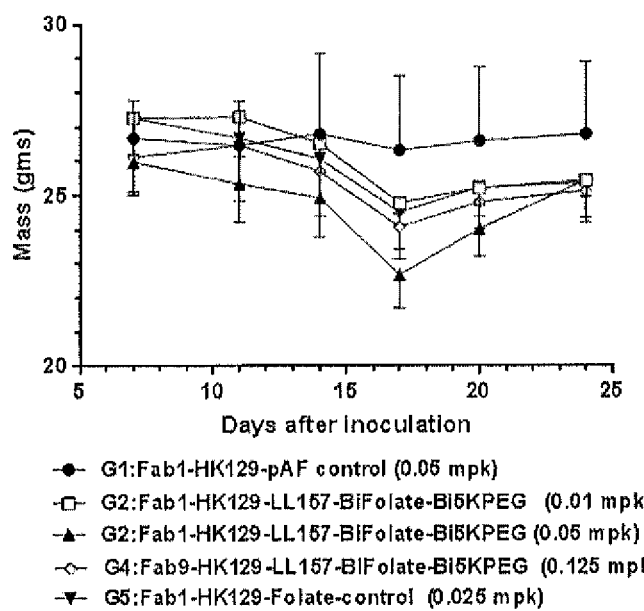

Study 1: Anti-CD3-Folate bispecific antibodies were tested for anti-tumor efficacy by multiple dose administration in female immuno-compromised mice bearing human cervical tumors derived from the KB cell line. Non-targeting anti-CD3 antibodies were included as control. Female NSG mice bearing KB cervical tumors, (inoculated with $2.0 \times 10^6$ cells from passage 7, initially grown from frozen passage 3), were sorted into 5 groups of 8 animals each. When tumors were approximately 100 mm³ in size, $7.5 \times 10^6$ PanT cells were inoculated into mice intraperitoneally. Twenty four hours later mice were randomized into the following treatment groups: G1: anti-CD3 Fab1-HK129-pAF control (0.05 mpk), G2 and G3 each having 0.01 mpk and 0.05 mpk, respectively, of CD3 Fab1-HK129-LL157-BiFolate-Bi5KPEG, G4: Fab9-HK129-LL157-BiFolate-Bi5KPEG (0.125 mpk), and G5: CD3 Fab1-HK129-Folate control (0.25 mpk); and tumor volume (FIG. 19A) and mass/body weight (FIG. 19B) were determined. All mice were dosed intravenously (IV) on day 7 when tumors averaged approximately ~125 mm³. Animals were monitored for tumor growth by caliper measurement and body weight, twice weekly. All CD3-Folate bispecific compositions showed efficacy, with group 3 (Fab1-HK129-LL157-BiFolate-Bi5KPEG, 0.05 mpk), having the greatest impact on impeding tumor growth (TGI=82%), as shown in FIG. 19A. All compositions, except control, CD3 Fab-HK129-pAF antibody, caused body weight loss (FIG. 19B).

Figure 19C:
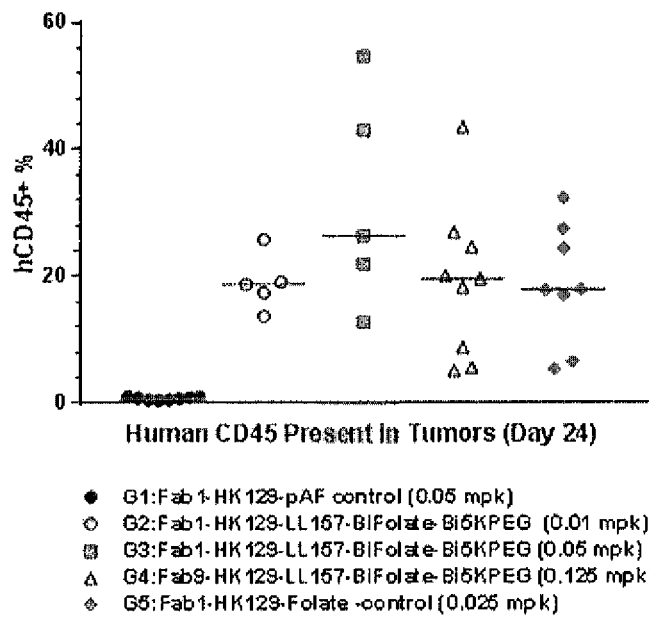
Figure 19D:
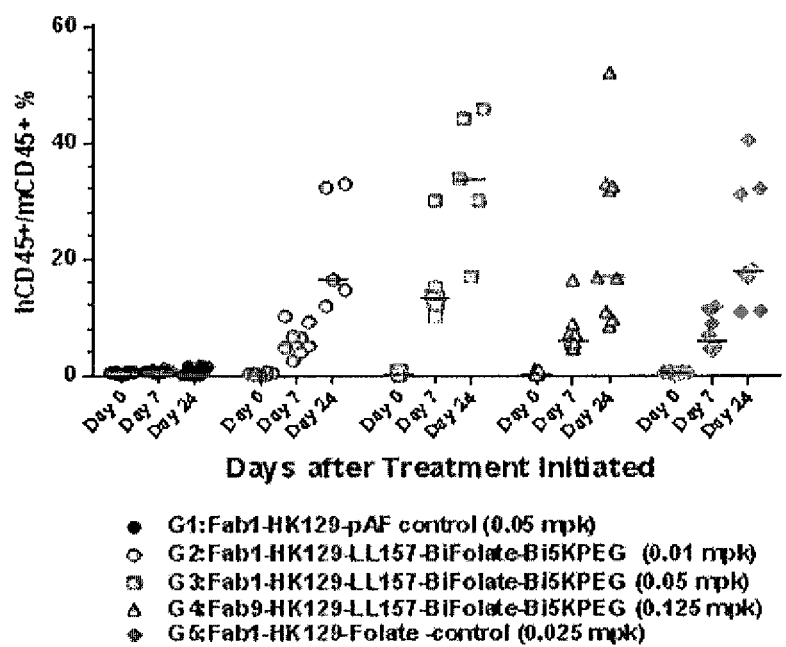

Biomarker analysis: blood samples were drawn from each animal prior to the initiation of treatments and at days 7 and 24 days following treatment initiation. The samples were analyzed for percentages of human CD45/mouse CD45 by FACs analysis to determine if treatments increase peripheral human T-cell populations as proposed by CD3-folate activation/targeting. At conclusion of the study tumors were analyzed by FACs for the presence of tumor infiltrating lymphocytes (TILs), using the human lymphocyte marker hCD45. All CD3-Folate treatment groups showed anti-tumor efficacy and the ability to increase blood levels of human CD45 to varying degrees—with the highest levels of human CD45 and being attributed to treatment by the bispecific antibody, Fab1-HK129-LL157-BiFolate-Bi5KPEG, at 0.05 mpk (FIG. 19C). This study also examined tumor growth inhibition and the ability of the invented CD3-Folate compositions to promote tumor infiltrating lymphocytes (TILs) In addition, the presence of TILs—a hallmark of tumor immune surveillance activation, was found to be increased in all treatment over control groups with group 3, (Fab1-HK129-LL157-BiFolate-Bi5KPEG, 0.05 mpk), having the highest induction of TILs (FIG. 19D).

Figure 20A:
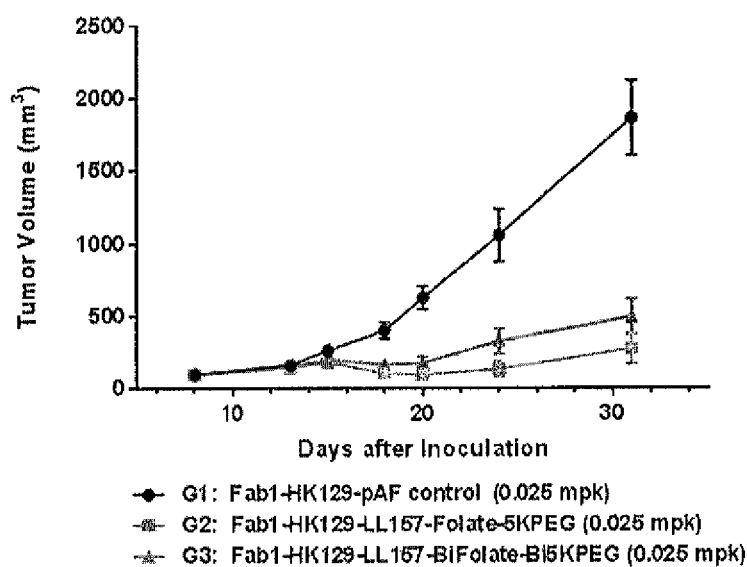
FIGS. 20A-20B depict anti-tumor efficacy of anti-CD3-Folate bispecific antibodies.
Figure 20B:
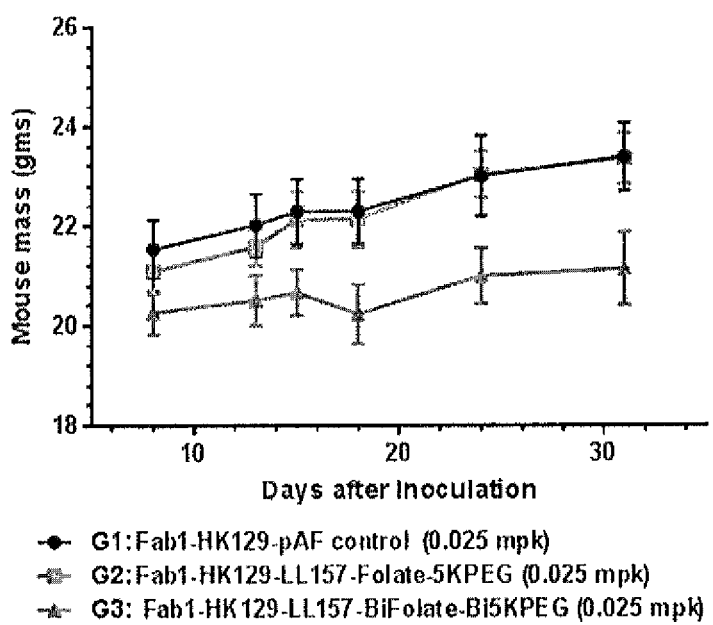

Study 2: This study examined tumor growth inhibition (TGI) and changes in percentages of human CD45 in the mice blood/tumor infiltration in NCG mice bearing KB tumors. Single, (Fab1-HK129-LL157-Folate-5KPEG), and double, (Fab1-HK129-LL157-BiFolate-Bi5KPEG), PEGylated anti-CD3-Folate bispecific antibodies were tested for anti-tumor efficacy by multiple dose administration in female immuno-compromised mice bearing human cervical tumors derived from the KB cell line. Non-targeting CD3 antibodies were included as control. 35 female NCG mice bearing KB cervical tumors, (inoculated with $2.0 \times 10^6$ cells from passage 5, initially grow from frozen passage 3), were sorted into 3 groups of 10 animals each. When tumors were approximately 85-100 mm$^3$ mice were inoculated intraperitoneally with $6.0 \times 10^6$ PanT cells. Twenty-four hours later mice were randomized into the following treatment groups: G1: CD3 Fab1-HK129-pAF control, G2: Fab1-HK129-LL157-Folate-5KPEG, G3: Fab1-HK129-LL157-BiFolate-Bi5KPEG, each at 0.025 mpk every 5 days (FIGS. 20A and 20B). All mice were inoculated with $6.0 \times 10^6$ Pan-T cells on day 7 and dosed intravenously (IV) on day 8 when tumors averaged approximately ~100 mm$^3$. Animals were monitored for tumor growth (FIG. 20A) by caliper measurement and body weight (FIG. 20B), twice weekly. All CD3-Folate targeting compositions showed varying degrees of efficacy, with G2: Fab1-HK129-LL157-Folate-5KPEG (single PEG composition) having the greatest impact on impeding tumor growth (TGI=85%) and in 5 of 10 mice causing complete tumor regressions (CR)—compared to G3: Fab1-HK129-LL157-BiFolate-Bi5KPEG (double PEG composition) which had a TGI of 76% and 3 of 10 animals having CR (FIG. 20A). All test articles were tolerated, G3 (double PEG composition) showed a slight weight loss in a few mice however, these did not exceed 15% loss (FIG. 20B).

Figure 20C:
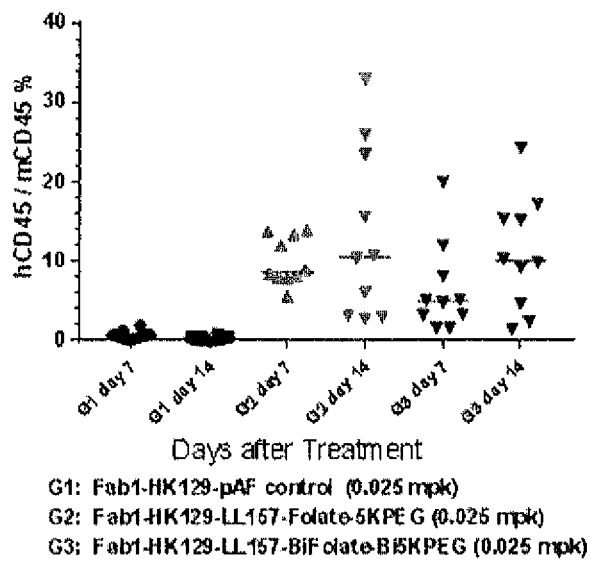
Figure 20D:
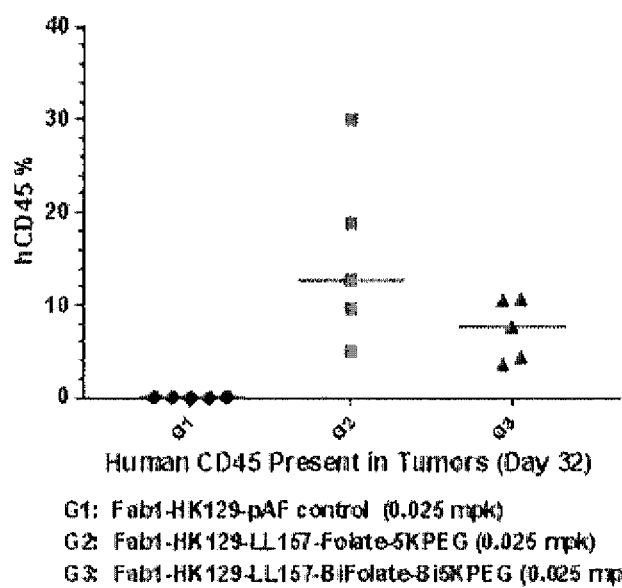
Figure 21A:
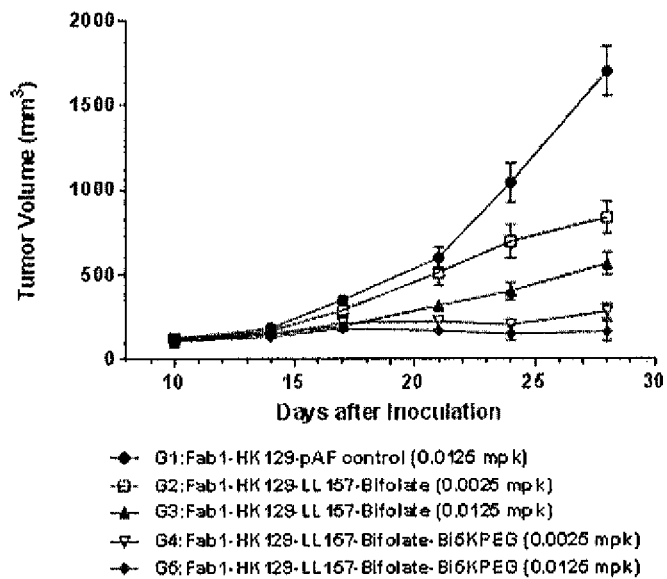
Figure 21B:
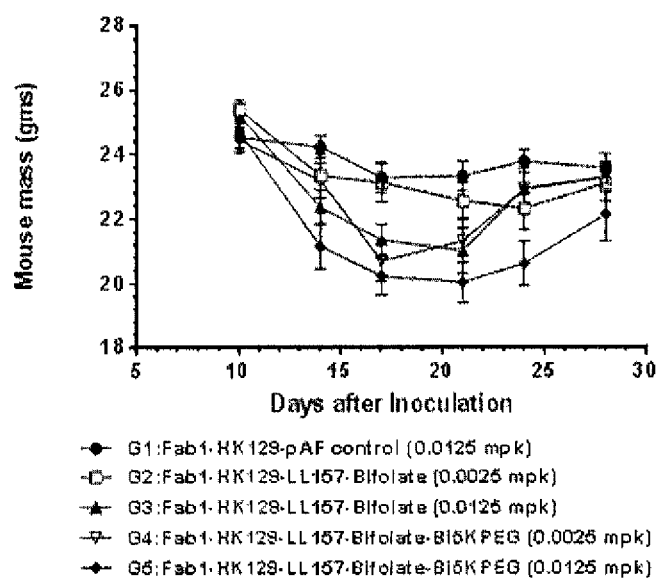

Biomarker analysis: Blood samples was drawn from each animal at Day 7 and Day 14 following the start of treatments as outlined above. Blood samples were analyzed for changes in percentages of human CD45 to determine if treatments increase peripheral human T-cell populations through CD3-Folate activation/targeting. At conclusion of the study tumors were analyzed by FACs for tumor infiltrating lymphocytes (TILs), using the human lymphocyte marker hCD45. All CD3-Folate treatment groups showed anti-tumor efficacy and the ability to increase blood (FIG. 20C), and tumor (FIG. 20D), levels of human CD45 to varying degrees—with the highest levels of human CD45 and TGI being attributed to treatment with the single PEGylated CD3-Folate targeting composition. Study 3: Shows similar results as in Study 1 and 2. 50 female NSG-humanized mice (CD34+ from Jackson laboratories) bearing KB cervical tumors, (inoculated with $2.0 \times 10^6$ cells from passage 5, initially grow from frozen passage 3), were sorted into 5 groups of 10 animals. When tumors were approx. 80-100 mm$^3$ treatments began. G1: Fab1-HK129-pAF control (0.0125 mpk) G2: Fab1-HK129-BiFolate (0.0025 mpk), G3:Fab1-HK129-BiFolate (0.0125 mpk), G4: Fab1-HK129-BiFolate-Bi5KPEG (0.0025 mpk), G5: Fab1-HK129-BiFolate-Bi5KPEG (0.0125 mpk). All mice were dosed intravenously (IV) twice weekly. Animals were monitored for tumor growth, (FIG. 21A), by caliper measurement and body weight, (FIG. 21B), twice weekly. T-Cell activation was analyzed in blood samples drawn from animals at day 5 of treatments, (one day after the second dose). Blood samples were analyzed for percentages of human CD45, CD3, CD25 and CD69 by FACs analysis to determine if the CD3-Folate targeting compositions increase expression of T-cell activation markers (FIGS. 21C-21F). Tumor infiltrating lymphocytes (TILs) were also analyzed at conclusion of the study, with 5 tumors from each group being analyzed for TILs (CD45, CD3 and CD8) by FACs. All CD3-Folate targeting compositions showed varying degrees of efficacy—however at similar doses all PEGylated CD3-Folate targeting compositions, (groups G4 at 87% TGI and G5 at 91% TGI), out-performed their non-PEGylated isoforms at equal dosing, (groups G2 at 51% TGI and G3 at 67% TGI), including the induction of T-cell activation markers CD25/CD69, increased TILs, and having a greater anti-tumor growth inhibition. All test articles caused marginal weight loss in the mice but did not exceed 15%.

Figure 22A:
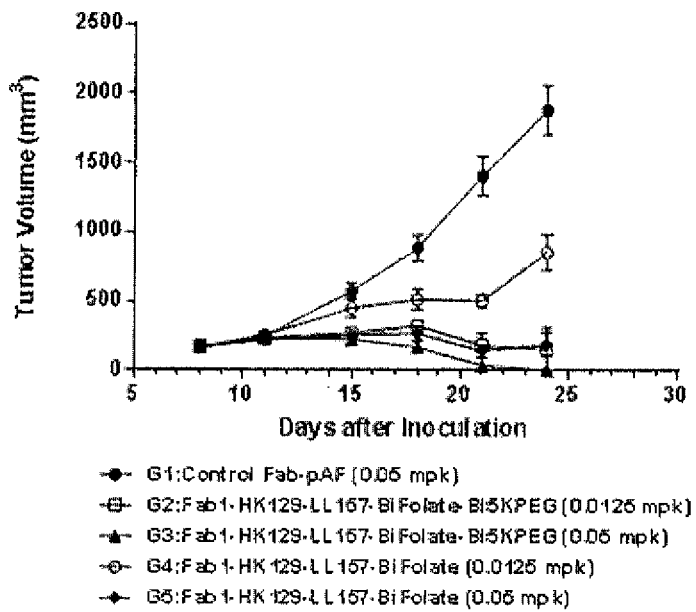
FIGS. 22A-22B depict anti-tumor efficacy of CD3-Folate bispecific antibodies in human cervical tumors derived from the KB cell line.
Figure 22B:
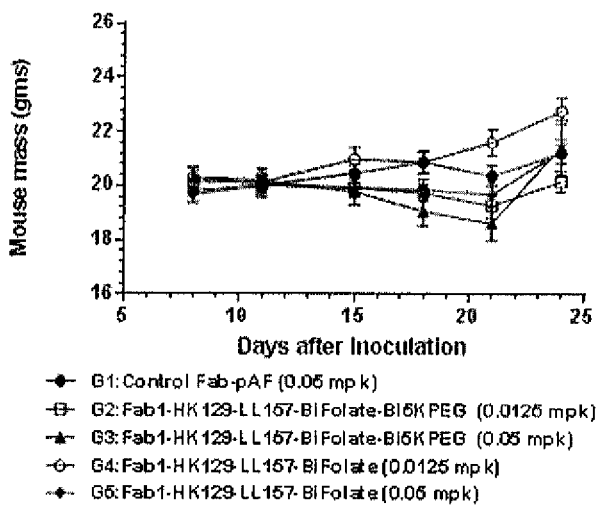

Study 4: CD3-Folate bispecific antibodies, Fab1-HK129-LL157-BiFolate and Fab1-HK129-LL157-BiFolate-Bi5KPEG were tested for anti-tumor efficacy by multiple dose administration in female immuno-compromised mice bearing human cervical tumors derived from the KB cell line. Non-targeting CD3 antibodies, (Fab1-HK129-pAF), were included as control. Sixty-five (65) female NSG mice bearing KB cervical tumors, (inoculated with $2.0 \times 10^6$ cells from passage 7, initially grow from frozen passage 3), were sorted into 6 groups of 10 animals each. When tumors were approximately 85-100 mm$^3$, $7.5 \times 10^6$ PanT cells were inoculated into mice intraperitoneally. Twenty four hours later mice were randomized into the following treatment groups: G1: CD3 Fab1-HK129-pAF control, G2: Fab1-HK129-LL157-BiFolate-Bi5KPEG (0.0125 mpk), G3: Fab1-HK129-LL157-BiFolate-Bi5KPEG (0.05 mpk), G4: Fab1-HK129-LL157-BiFolate (0.0125 mpk), G5: Fab1-HK129-LL157-BiFolate (0.05 mpk). All mice were dosed intravenously (IV) on day 8 when tumors averaged approximately ~100 mm$^3$. Animals were monitored for tumor growth by caliper measurement and body weight, twice weekly. As shown in FIG. 22A, all CD3-Folate targeting compositions showed anti-tumor activity, (TGI=G2:92%, G4:55%, G5:90%), with group G3, (Fab1-HK129-LL157-BiFolate-Bi5KPEG at 0.05 mpk), having the greatest impact on impeding tumor growth (TGI=99%), and resulting in 6 of 8 mice experiencing complete tumor regressions (CR). All test compositions, except control CD3 Fab antibody, caused some body weight loss but did not exceed 15% loss, (FIG. 22B). The results of this study show there is a dose dependent response which can be attributed to the biophysical properties of PEG addition to CD3 Fab-Folate compounds.

Figure 23A:
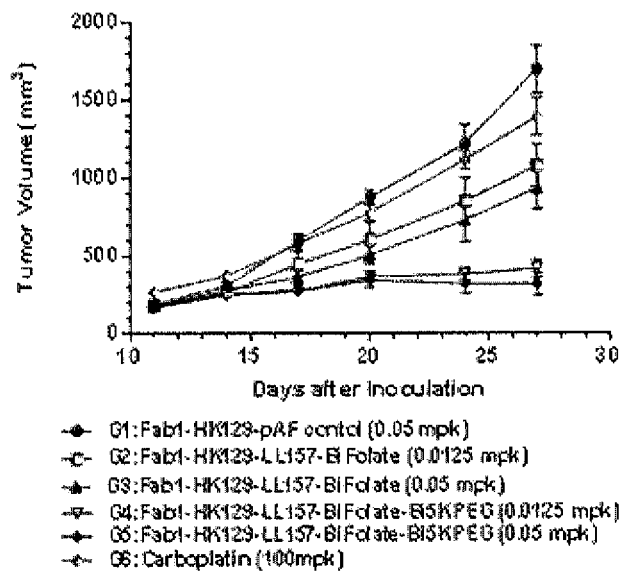
FIGS. 23A-23B depict anti-tumor efficacy of CD3-Folate bispecific antibodies compared to carboplatin in human ovarian tumors derived from OV-90 cell line.
Figure 23B:
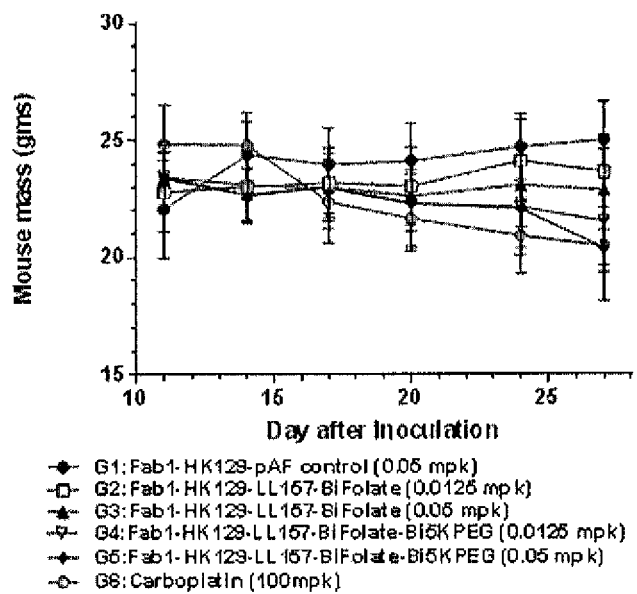

Study 5: CD3-Folate bispecific antibodies, Fab1-HK129-LL157-BiFolate and Fab1-HK129-LL157-BiFolate-Bi5KPEG, were tested for anti-tumor efficacy by multiple dose administration in female immuno-compromised mice bearing human ovarian tumors derived from the OV-90 cell line (FIGS. 23A and 23B). The OV-90 was selected to determine if the invented CD3 Fab-Folate compositions have activity in a model resistance to the standard of care for ovarian cancers, i.e., platin based therapies. Non-targeting CD3 antibodies, (Fab1-HK129-pAF), were included as control. Seventy (70) female NSG mice bearing OV-90 ovarian tumors, (inoculated with $7.5 \times 10^6$ cells from passage 5, initially grow from frozen passage 2), were sorted into 6 groups of 10 animals each. When tumors were approximately 100-200 mm$^3$ $7.5 \times 10^6$ PanT cells were inoculated into mice intraperitoneally. Twenty four hours later mice were randomized into the following treatment groups: G1:

Fab1-HK129-pAF control, G2: Fab1-HK129-LL157-BiFolate (0.0125 mpk), G3: Fab1-HK129-LL157-BiFolate (0.05 mpk), G4: Fab1-HK129-LL157-BiFolate-Bi5KPEG (0.0125 mpk), G5: Fab1-HK129-LL157-BiFolate-Bi5KPEG (0.05 mpk), and G6: Carboplatin (100 mpk). All mice were dosed intravenously (IV) on day 8 when tumors averaged approximately ~100 mm$^3$. Groups 1 through 5 were dosed every 5 days for a total of three doses, while group 6 was dosed 7 days later, (Day 15), for a total of 2 doses. Animals were monitored for tumor growth by caliper measurement and body weight, twice weekly. Although the OV-90 model is resistant to the standard of care use of carboplatin for treating ovarian cancers (group G6), all CD3-Fab Folates targeting compositions tested showed varying degrees of efficacy, with G5 group (Fab1-HK129-LL157-BiFolate-Bi5KPEG at 0.05 mpk), having the greatest impact on impeding tumor growth (TGI=81%); FIG. 23A. All test compositions, except the control CD3 Fab antibody, caused body weight loss but did not exceed 20% weight loss in each group (FIG. 23B).

Similar to the results of Study 4, Study 5 shows that the groups treated with Fab1-HK129-LL157-BiFolate-Bi5KPEG have better anti-tumor activity when dosed at equal concentrations than the groups treated with Fab1-HK129-LL157-BiFolate. This can be attributed to the enhanced biophysical properties resulting from PEG addition to CD3 Fab-Folate compositions. It is further noted that in ovarian cancer cells with low folate receptor copy, (such as OV-90 with ~10K copy per cell), strong antitumor effect is still observed. This supports use of the invented CD3 Fab-Folate compositions as front line therapeutics for treating patient populations, without the prerequisite of high copy numbers of the folate receptor. This is further affirmed by the in vitro cytotoxicity analyses herein, showing that cells with low folate receptor copy numbers still have $EC_{50}$ values in the picomolar range.

Example 27

Human Clinical Trial of the Safety and Efficacy of anti-CD3 Fab-Folate Bispecific Antibody, (Fab-BiFolate, Fab-Folate-PEG, and Fab-BiFolate-BiPEG), compositions comprising a non-naturally encoded amino acid.

Objective: To compare the safety and pharmacokinetics of subcutaneously administered anti-CD3 Fab-Folate bispecific recombinant human antibody comprising a non-naturally encoded amino acid with a commercially available product specific for the same target antigen.

Patients: Eighteen healthy volunteers ranging between 20-40 years of age and weighing between 60-90 kg are enrolled in the study. The subjects will have no clinically significant abnormal laboratory values for hematology or serum chemistry, and a negative urine toxicology screen, HIV screen, and hepatitis B surface antigen. They should not have any evidence of the following: hypertension; a history of any primary hematologic disease; history of significant hepatic, renal, cardiovascular, gastrointestinal, genitourinary, metabolic, neurologic disease; a history of anemia or seizure disorder, a known sensitivity to bacterial or mammalian-derived products, PEG, or human serum albumin; habitual and heavy consumer to beverages containing caffeine; participation in any other clinical trial or had blood transfused or donated within 30 days of study entry; had exposure to anti-CD3 antibody within three months of study entry; had an illness within seven days of study entry; and have significant abnormalities on the pre-study physical examination or the clinical laboratory evaluations within 14 days of study entry. All subjects are evaluable for safety and all blood collections for pharmacokinetic analysis are collected as scheduled. All studies are performed with institutional ethics committee approval and patient consent.

This will be a Phase I, single-center, open-label, randomized, two-period crossover study in healthy female volunteers. Eighteen subjects are randomly assigned to one of two treatment sequence groups (nine subjects/group). Anti-CD3 antibody is administered via dosing periods either locally or systemically by any of the routes normally used for introducing an antibody to a subject, in need thereof, by the skilled artisan. The anti-CD3 antibody compositions according to the present invention can be administered subcutaneously, intramuscularly, intradermally, intraarticularly, intrapleurally, intraperitoneally, intraarterially, or intravenously, although the most suitable route in any given case will depend on the nature and severity of the disease and/or condition being treated. For example, administration can be over two separate dosing periods as a bolus subcutaneous (s.c.) or intravenous injection using equivalent doses of the bispecific anti-CD3 Fab-Folate antibody comprising a non-naturally encoded amino acid and the commercially available product chosen. The dose and frequency of administration of the commercially available product is as instructed in the package label. Additional dosing, dosing frequency, or other parameter as desired, using the commercially available products may be added to the study by including additional groups of subjects. Each dosing period is separated by a 14-day washout period. Subjects are confined to the study center at least 12 hours prior to and 72 hours following dosing for each of the two dosing periods, but not between dosing periods. Additional groups of subjects may be added if there are to be additional dosing, frequency, or other parameters, to be tested for the PEGylated bispecific anti-CD3 antibody as well. The experimental formulation of anti-CD3 antibody is the bispecific anti-CD3 Fab-Folate antibody comprising a non-naturally encoded amino acid.

Blood Sampling: Serial blood is drawn by direct vein puncture before and after administration of anti-CD3 Fab-Folate bispecific antibody. Venous blood samples (5 mL) for determination of serum anti-CD3 antibody concentrations are obtained at about 30, 20, and 10 minutes prior to dosing (3 baseline samples) and at approximately the following times after dosing: 30 minutes and at 1, 2, 5, 8, 12, 15, 18, 24, 30, 36, 48, 60 and 72 hours. Each serum sample is divided into two aliquots. All serum samples are stored at −20° C. Serum samples are shipped on dry ice. Fasting clinical laboratory tests (hematology, serum chemistry, and urinalysis) are performed immediately prior to the initial dose on day 1, the morning of day 4, immediately prior to dosing on day 16, and the morning of day 19.

Bioanalytical Methods: A radioimmunoassay (RA) or ELISA kit procedure is used for the determination of serum bispecific anti-CD3 Fab-Folate antibody concentrations.

Safety Determinations: Vital signs are recorded immediately prior to each dosing (Days 1 and 16), and at 6, 24, 48, and 72 hours after each dosing. Safety determinations are based on the incidence and type of adverse events and the changes in clinical laboratory tests from baseline. In addition, changes from pre-study in vital sign measurements, including blood pressure, and physical examination results are evaluated.

Data Analysis: Post-dose serum concentration values are corrected for pre-dose baseline anti-CD3 antibody concentrations by subtracting from each of the post-dose values the mean baseline anti-CD3 antibody concentration determined from averaging the anti-CD3 antibody levels from the three samples collected at 30, 20, and 10 minutes before dosing. Pre-dose serum anti-CD3 antibody concentrations are not included in the calculation of the mean value if they are below the quantification level of the assay. Pharmacokinetic parameters are determined from serum concentration data corrected for baseline anti-CD3 antibody concentrations. Pharmacokinetic parameters are calculated by model independent methods on a Digital Equipment Corporation VAX 8600 computer system using the latest version of the BIO-AVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Safety Results: The incidence of adverse events is equally distributed across the treatment groups. There are no clinically significant changes from baseline or pre-study clinical laboratory tests or blood pressures, and no notable changes from pre-study in physical examination results and vital sign measurements. The safety profiles for the two treatment groups should appear similar.

Pharmacokinetic Results: Mean serum anti-CD3 antibody Fab-Folate bispecific concentration-time profiles (uncorrected for baseline anti-CD3 antibody levels) in all 18 subjects after receiving a single dose of one or more of commercially available products specific for the same target antigen are compared to the bispecific anti-CD3 antibody comprising a non-naturally encoded amino acid at each time point measured. All subjects should have pre-dose baseline anti-CD3 antibody concentrations within the normal physiologic range. Pharmacokinetic parameters are determined from serum data corrected for pre-dose mean baseline anti-CD3 antibody concentrations and the $C_{max}$ and $t_{max}$ are determined. The mean $t_{max}$ for the clinical comparator(s) chosen is significantly shorter than the $t_{max}$ for the bispecific anti-CD3 antibody comprising the non-naturally encoded amino acid. Terminal half-life values are significantly shorter for the commerically available anti-CD3 antibody products tested compared with the terminal half-life for the bispecific anti-CD3 antibody comprising a non-naturally encoded amino acid of the present invention.

In conclusion, subcutaneously administered single doses of bispecific anti-CD3 antibody comprising non-naturally encoded amino acid will be safe and well tolerated by healthy female subjects. Based on a comparative incidence of adverse events, clinical laboratory values, vital signs, and physical examination results, the safety profiles of the commercially available forms of anti-CD3 antibody and bispecific anti-CD3 fab folate antibody comprising non-naturally encoded amino acid will be equivalent. The bispecific anti-CD3 antibody comprising non-naturally encoded amino acid potentially provides large clinical utility to patients and health care providers.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference herein in their entirety for all purposes.

The present invention is further described by the following numbered embodiments:

1. An anti-CD3 Fab antibody comprising at least one of SEQ ID NO: 1-61.
2. The anti-CD3 Fab antibody of claim 1 comprising two of SEQ ID NO: 1-61.
3. A bispecific binding molecule comprising i) a first binding domain and ii) a second binding domain wherein the second binding domain is selected from the group consisting of SEQ ID NO: 1-61.
4. A cytotoxically active CD3 Fab specific binding construct comprising the amino acid sequence set forth in one or more of SEQ ID NO: 1-61.
5. An anti-CD3 Fab antibody, wherein the anti-CD3 antibody comprises a binding domain comprising (a) a VH domain comprising an amino acid sequence selected from the group consisting of SEQ ID NO: 1-3 and (b) a VL domain comprising an amino acid sequence selected from the group consisting of SEQ ID NO: 4-5.
6. The anti-CD3 Fab antibody of claim 4, wherein the antibody is linked to a linker, polymer, or biologically active molecule.
7. The anti-CD3 antibody of claim 6, wherein the biologically active molecule is folate.
8. The anti-CD3 Fab antibody of claim 1 having a non-naturally encoded amino acid incorporated.
9. An anti-CD3 Fab variant of claim 6, wherein the heavy chain further comprises an amino acid extension at the C-terminus.
10. The anti-CD3 Fab variant of claim 9, wherein the amino acid extension comprises amino acids DKTHT.
11. The anti-CD3 Fab antibody of claim 5, wherein the heavy chain and light chain sequence comprise framework residues or germline mutations at one or more positions for antigen binding.
12. The anti-CD3 Fab antibody of claim 6, wherein the linker is a water-soluble polymer.
13. The anti-CD3 Fab antibody of claim 12, wherein the water-soluble polymer is linear or branched.
14. The anti-CD3 Fab antibody of claim 6, comprising one or more folate and one or more poly(ethylene glycol).
15. A method for optimizing cell kill in a cell expressing high folate receptor numbers comprising an anti-CD3 Fab antibody of claim 5 wherein the antibody comprises one or more folate; and wherein one or more non-naturally encoded amino acid is incorporated into the antibody.
16. The method of claim 15, wherein the folate receptor number is equal or greater than 10,000.
17. The anti-CD3 Fab antibody of claim 5, further comprising a PEG folate linker having the structure according to compound 30.
18. A method of treating a patient having a disease or condition in a cell expressing high folate receptor number comprising administering to the patient a therapeutically-effective amount of the anti-CD3 Fab antibody of claim 17.
19. The bispecific anti-CD3 Fab antibody of claim 3 comprising two folate and two PEGylated molecules.
20. The bispecific anti-CD3 Fab antibody of claim 19, further comprising a non-naturally encoded amino acid site specifically incorporated.

What is claimed is:

1. An anti-CD3 antibody or a fragment thereof, comprising a heavy chain and a light chain, wherein:
   (i) the heavy chain comprises the amino acid sequence of SEQ ID NO: 32, and the light chain comprises the amino acid sequence of SEQ ID NO: 59;
   wherein said anti-CD3 antibody or fragment thereof comprises one to two non-natural amino acids incorporated at positions selected from the group consisting of: positions A114, S115, K129 and T160 of the heavy chain and positions L157, K172 and S205 of the light chain;
   wherein the numbering is according to the Kabat numbering system;
   wherein neither the light chain nor the heavy chain comprise multiple non-natural amino acids; or
   (ii) the heavy chain comprises the amino acid sequence of SEQ ID NO: 3, and the light chain comprises the amino acid sequence of SEQ ID NO: 59;
   wherein said anti-CD3 antibody or fragment thereof comprises one to two non-natural amino acids incorporated at positions selected from the group consisting of: positions A114, S115, K129 and T160 of the heavy chain and positions L157, K172 and S205 of the light chain;
   wherein the numbering is according to the Kabat numbering system;
   wherein neither the light chain nor the heavy chain comprise multiple non-natural amino acids.

2. The anti-CD3 antibody or the fragment thereof of claim 1, wherein the antibody or fragment thereof comprises an IgG, Fab, or (Fab')$_2$.

3. The anti-CD3 antibody or the fragment thereof of claim 1, wherein each said non-natural amino acid is para-acetyl phenylalanine, p-nitrophenylalanine, p-sulfotyrosine, p-carboxyphenylalanine, o-nitrophenylalanine, m-nitrophenylalanine, p-boronyl phenylalanine, o-boronylphenylalanine, m-boronylphenylalanine, p-aminophenylalanine, o-aminophenylalanine, maminophenylalanine, p-acylphenylalanine, o-acylphenylalanine, m-acylphenylalanine, p-OMe phenylalanine, o-OMe phenylalanine, m-OMe phenylalanine, p-sulfophenylalanine, o-sulfophenylalanine, m-sulfophenylalanine, 5-nitro His, 3-nitro Tyr, 2-nitro Tyr, nitro substituted Leu, nitro substituted His, nitro substituted De, nitro substituted Trp, 2-nitro Trp, 4-nitro Trp, 5-nitro Trp, 6-nitro Trp, 7-nitro Trp, 3-aminotyrosine, 2-aminotyrosine, O-sulfotyrosine, 2-sulfooxyphenylalanine, 3-sulfooxyphenylalanine, o-carboxyphenylalanine, m-carboxyphenylalanine, p-acetyl-L-phenylalanine, p-propargyl-phenylalanine, O-methyl-L-tyrosine, L-3-(2-naphthyl) alanine, 3-methylphenylalanine, O-4-allyl-L-tyrosine, 4-propyl-L-tyrosine, tri-O-acetyl-GlcNAcB-serine, L-Dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-iodophenylalanine, p-bromophenylanine, p-amino-L-phenylalanine, isopropyl-L-phenylalanine, or p-propargyloxy-L-phenylalanine.

4. The anti-CD3 antibody or the fragment thereof of claim 3, wherein each said non-natural amino acid is para-acetyl phenylalanine.

5. An anti-CD3 antibody bioconjugate comprising:
(i) an anti-CD3 antibody or a fragment thereof, comprising a heavy chain and a light chain, wherein:
(a) the heavy chain comprises the amino acid sequence of SEQ ID NO: 32, and the light chain comprises the amino acid sequence of SEQ ID NO: 59;
wherein said anti-CD3 antibody or fragment thereof comprises one to two non-natural amino acids incorporated at positions selected from the group consisting of: positions A114, S115, K129 and T160 of the heavy chain and positions L157, K172 and S205 of the light chain;
wherein the numbering is according to the Kabat numbering system;
wherein neither the light chain nor the heavy chain comprise multiple non-natural amino acids; or
(b) the heavy chain comprises the amino acid sequence of SEQ ID NO: 3, and the light chain comprises the amino acid sequence of SEQ ID NO: 59;
wherein said anti-CD3 antibody or fragment thereof comprises one to two non-natural amino acids incorporated at positions selected from the group consisting of: positions A114, S115, K129 and T160 of the heavy chain and positions L157, K172 and S205 of the light chain;
wherein the numbering is according to the Kabat numbering system;
wherein neither the light chain nor the heavy chain comprise multiple non-natural amino acids; and
(ii) a linker, a polymer a biologically active molecule or a combination thereof; wherein the anti-CD3 antibody or the fragment thereof is linked to the linker, the polymer, the biologically active molecule or the combination thereof.

6. The anti-CD3 antibody or the fragment thereof of claim 1, wherein the heavy chain comprises one non-natural amino acid, and wherein the one non-natural amino acid is at position K129.

7. The anti-CD3 antibody or the fragment thereof of claim 1, wherein the light chain comprises one non-natural amino acid, and wherein the one non-natural amino acid is at position L157.

8. The anti-CD3 antibody bioconjugate of claim 5, wherein the biologically active molecule comprises a folate moiety.

9. The anti-CD3 antibody bioconjugate of claim 5, wherein the polymer is a water-soluble polymer, and the non-natural amino acid is linked to the water-soluble polymer.

10. The anti-CD3 antibody bioconjugate of claim 9, wherein the water-soluble polymer comprises a poly(ethylene glycol) (PEG) moiety.

11. The anti-CD3 antibody bioconjugate or antibody fragment of claim 10, wherein the PEG moiety comprises a linear PEG moiety.

12. The anti-CD3 bioconjugate of claim 5, wherein the anti-CD3 antibody or fragment thereof is linked to the polymer and the biologically active molecule via the linker, wherein the polymer is a water-soluble polymer, and the biologically active molecule is a folate moiety.

13. The anti-CD3 antibody bioconjugate of claim 11, wherein the linear PEG moiety has an average molecular weight of between about 5 kDa and about 20 kDa.

14. The anti-CD3 bioconjugate of claim 12, wherein the anti-CD3 antibody is linked to a structure of Formula (I):

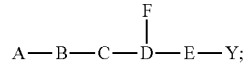

wherein:
A is the folate moiety having the following structure:

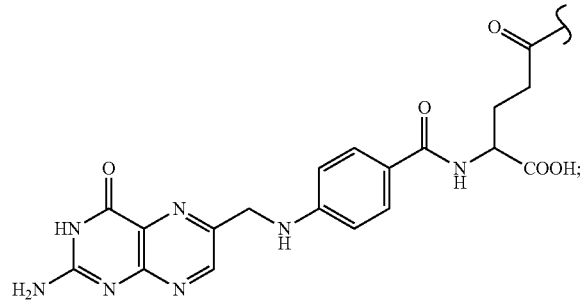 [SMILES: CC(=O)CCC(NC(=O)c1ccc(NCc2cnc3nc(N)[nH]c(=O)c3n2)cc1)C(=O)O]

B-C-D-E-Y is the linker, wherein
B is a bivalent group connecting A and C, wherein B has the following structure:

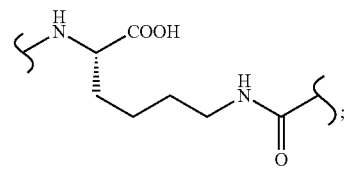

C and E are each independently selected from the group consisting of -alkylene-, -alkylene-C(O)—, -(alkylene-O)$_{n'}$-alkylene-, and -(alkylene-O)$_{n'}$-alkylene-C(O)—; wherein n' is independently an integer greater than or equal to one;

D is a trivalent group connecting C, E and F; and

Y is selected from the group consisting of: —ONH$_2$, aldehyde, protected aldehyde, ketone, protected ketone, thioester, ester, dicarbonyl, hydrazine, amidine, imine, diamine, azide, keto-amine, keto-alkyne, alkyne, cycloalkyne and ene-dione; and F is the water-soluble polymer;

wherein Y forms a linkage to the non-natural amino acid of the anti-CD3 antibody or the fragment thereof.

15. The anti-CD3 bioconjugate of claim 14, wherein the non-natural amino acid is para-acetyl phenylalanine; Y is —ONH$_2$; and Y forms a linkage to the para-acetyl phenylalanine to form an oxime linkage.

16. The anti-CD3 antibody bioconjugate of claim 14, wherein the water-soluble polymer E comprises a linear poly(ethylene glycol) moiety having an average molecular weight of about 5 kDa, about 10 kDa, or about 20 kDa.

17. The anti-CD3 antibody or the fragment thereof of claim 1, wherein:
(i) the heavy chain comprises the amino acid sequence of SEQ ID NO: 32 with one non-natural amino acid incorporated at position K129; and
(ii) the light chain comprises the amino acid sequence of SEQ ID NO: 59 with one non-natural amino acid incorporated at position L157;
wherein each said non-natural amino acid is a para-acetyl phenylalanine (pAf), and wherein the numbering system is according to the Kabat numbering system.

18. The anti-CD3 bioconjugate comprising the anti-CD3 antibody or the fragment thereof of claim 17, wherein each pAF is conjugated to a linear poly(ethylene glycol) (PEG) moiety, and wherein each linear PEG moiety has an average molecular weight of about 10 kDa.

19. The anti-CD3 antibody or the fragment thereof of claim 1, wherein:
(i) the heavy chain comprises the amino acid sequence of SEQ ID NO: 3 with one non-natural amino acid incorporated at position K129; and
(ii) the light chain comprising the amino acid sequence of SEQ ID NO: 59 with one non-natural amino acid incorporated at position L157;
wherein each said non-natural amino acid is a para-acetyl phenylalanine (pAf), and wherein the numbering system is according to the Kabat numbering system.

20. The anti-CD3 bioconjugate comprising the anti-CD3 antibody or the fragment thereof of claim 19, wherein each pAF is conjugated to a linear poly(ethylene glycol) (PEG) moiety, and wherein each linear PEG moiety has an average molecular weight of about 10 kDa.

21. The anti-CD3 antibody bioconjugate of claim 5, wherein each said non-natural amino acid is para-acetyl phenylalanine.

* * * * *